US007241876B2

(12) United States Patent
Frudakis et al.

(10) Patent No.: US 7,241,876 B2
(45) Date of Patent: Jul. 10, 2007

(54) COMPOSITIONS AND METHODS FOR THE THERAPY AND DIAGNOSIS OF BREAST CANCER

(75) Inventors: Tony N. Frudakis, Sarasota, FL (US); Steven G. Reed, Bellevue, WA (US); John M. Smith, Columbia Heights, MN (US); Lynda E. Misher, Seattle, WA (US); Davin C. Dillon, Issaquah, WA (US); Marc W. Retter, Carnation, WA (US); Aijun Wang, Issaquah, WA (US); Yasir A. W. Skeiky, Bellevue, WA (US); Susan L. Harlocker, Seattle, WA (US); Craig H. Day, Shoreline, WA (US); Samuel X. Li, Redmond, WA (US); Ta Deng, Edmonds, WA (US)

(73) Assignee: Corixa Corporation, Hamilton, MT (US)

( * ) Notice: Subject to any disclaimer, the term of this patent is extended or adjusted under 35 U.S.C. 154(b) by 0 days.

(21) Appl. No.: 09/924,400

(22) Filed: Aug. 7, 2001

(65) Prior Publication Data

US 2002/0165371 A1 Nov. 7, 2002

Related U.S. Application Data

(63) Continuation-in-part of application No. 09/810,936, filed on Mar. 16, 2001, now abandoned, which is a continuation-in-part of application No. 09/699,295, filed on Oct. 26, 2000, now Pat. No. 6,828,431, which is a continuation-in-part of application No. 09/590,583, filed on Jun. 8, 2000, now abandoned, which is a continuation-in-part of application No. 09/577,505, filed on May 24, 2000, now abandoned, which is a continuation-in-part of application No. 09/534,825, filed on Mar. 23, 2000, which is a continuation-in-part of application No. 09/429,755, filed on Oct. 28, 1999, now Pat. No. 6,656,480, which is a continuation-in-part of application No. 09/289,198, filed on Apr. 9, 1999, now Pat. No. 6,586,570.

(51) Int. Cl.
*C07H 21/02* (2006.01)

(52) U.S. Cl. .................. 536/23.1; 536/23.5; 536/24.3; 536/24.31; 514/44; 435/6; 435/320.1; 436/501

(58) Field of Classification Search ...... 536/23.1–24.5; 435/6, 92.2; 514/44; 436/6, 69.1, 320.1, 436/501

See application file for complete search history.

(56) References Cited

U.S. PATENT DOCUMENTS

| 5,082,767 A * | 1/1992 | Hatfield et al. ................. 435/6 |
| 5,231,012 A | 7/1993 | Mosmann et al. ....... 435/69.52 |
| 5,428,145 A | 6/1995 | Okamoto et al. ........ 536/23.72 |
| 5,516,650 A | 5/1996 | Foster et al. ............... 435/68.1 |
| 5,523,225 A | 6/1996 | Kraus ...................... 435/240.1 |
| 5,585,270 A | 12/1996 | Grotendorst et al. ...... 435/252.3 |
| 5,811,535 A | 9/1998 | Adamou et al. ........... 536/23.5 |
| 5,872,237 A | 2/1999 | Feder et al. ............... 536/23.5 |
| 5,912,143 A | 6/1999 | Bandman et al. .......... 435/69.1 |
| 6,225,054 B1 | 5/2001 | Frudakis et al. ............... 435/6 |
| 6,329,505 B1 * | 12/2001 | Xu et al. ..................... 530/350 |
| 6,344,550 B1 * | 2/2002 | Frudakis et al. ........... 536/23.5 |
| 6,395,278 B1 * | 5/2002 | Xu et al. .................. 424/192.1 |
| 6,423,496 B1 | 7/2002 | Frudakis et al. |
| 6,586,570 B1 | 7/2003 | Frudakis et al. |
| 6,620,922 B1 | 9/2003 | Xu et al. |
| 6,630,305 B1 | 10/2003 | Xu et al. |
| 6,656,480 B2 | 12/2003 | Retter et al. |
| 6,828,431 B1 | 12/2004 | Frudakis et al. |
| 6,861,506 B1 | 3/2005 | Frudakis et al. |
| 2002/0009738 A1 | 1/2002 | Houghton et al. .............. 435/6 |
| 2002/0022248 A1 | 2/2002 | Xu et al. .................... 435/69.1 |
| 2002/0051977 A1 | 5/2002 | Xu et al. ........................ 435/6 |
| 2002/0068285 A1 | 6/2002 | Frudakis et al. ................ 435/6 |
| 2002/0165371 A1 | 11/2002 | Frudakis et al. ........... 536/23.1 |
| 2002/0183251 A1 | 12/2002 | Xu et al. ....................... 514/12 |
| 2002/0192763 A1 | 12/2002 | Xu et al. ................... 435/69.7 |
| 2002/0193296 A1 | 12/2002 | Xu et al. ....................... 514/12 |
| 2003/0088062 A1 | 5/2003 | Xu et al. ..................... 530/350 |

FOREIGN PATENT DOCUMENTS

CA    2044940 A1    12/1992

(Continued)

OTHER PUBLICATIONS

Genbank Accession No. AA533501, Aug. 21, 1997.*

(Continued)

*Primary Examiner*—Mary K. Zeman
(74) *Attorney, Agent, or Firm*—Seed IP Law Group PLLC

(57) ABSTRACT

Compositions and methods for the therapy and diagnosis of cancer, particularly breast cancer, are disclosed. Illustrative compositions comprise one or more breast tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly breast cancer.

4 Claims, 22 Drawing Sheets

FOREIGN PATENT DOCUMENTS

| | | |
|---|---|---|
| EP | 0475623 A1 | 3/1992 |
| EP | 1033401 A2 | 9/2000 |
| GB | 2 273 099 A | 6/1994 |
| WO | WO 91/02062 | 2/1991 |
| WO | WO 92/10573 | 6/1992 |
| WO | WO 92/15680 | 9/1992 |
| WO | WO 94/11514 | 5/1994 |
| WO | WO 95/10777 | 4/1995 |
| WO | WO 95/19369 | 7/1995 |
| WO | WO 95/32311 | 11/1995 |
| WO | WO 96/38463 | 12/1996 |
| WO | WO 97/06256 | 2/1997 |
| WO | WO 97/06260 | 2/1997 |
| WO | WO 97/25426 | 7/1997 |
| WO | WO 97/25431 | 7/1997 |
| WO | WO 98/06399 | 2/1998 |
| WO | 98/45328 | * 10/1998 |
| WO | WO 98/45328 | 10/1998 |
| WO | WO 99/06550 | 2/1999 |
| WO | WO 99/31236 | 6/1999 |
| WO | WO 00/04149 | 1/2000 |
| WO | WO 00/61753 | 10/2000 |
| WO | WO 01/25272 | 4/2001 |
| WO | WO 01/34802 | 5/2001 |
| WO | WO 01/51628 | 7/2001 |
| WO | WO 01/51633 | 7/2001 |
| WO | WO 01/75171 | 10/2001 |
| WO | WO 01/90152 | 11/2001 |
| WO | WO 03/013431 | 2/2003 |

OTHER PUBLICATIONS

Genbank Accession No. AQ063365, Jul. 31, 1998.*
Genbank Accession No. AQ124119, Sep. 22, 1998.*
Genbank Accession No. AQ204617, Sep. 17 1998.*
Lehninger, A. Biochemistry. 1970. Worth Publisher, Inc. NY, NY.*
Nagata et al. (1999) Biochem. Biophys. Res. Commun. 261: 445-451.*
Adams et al., Genbank Accession No. Q60347, 1993.
Adams et al., Genbank Accession No. Q61250, 1993.
Ahmed et al., "Characterization of retrovirus isolated form normal mink cells co-cultivated with a dog mammary tumour," *J. Gen. Virol.* 42:179-184, 1979.
Anderson et al., "Sequence and organization of the human mitochondrial genome," *Nature* 290:457-465, 1981.
Bakker et al., "Generation of antimelanoma cytotoxic T lymphocytes for healthy donors after presentation of melanoma-associated antigen-derived epitopes by dendritic cells in vivo," *Cancer Research* 55:5330-5334, Nov. 15, 1995.
Bauer et al., "Identification of differentially expressed mRNA species by an improved display technique (DDRT-PCR)," *Nucleic Acids Research* 21(18):4272-4280, 1993.
Bernard et al., "Cloning and Sequencing of Pro-α1(XI) Collagen cDNA Demonstrates That Type XI Belongs to the Fibrillar Class of Collagens and Reveals That the Expression of the Gene Is Not Restricted to Cartilagenous Tissue," *J. Biol. Chem.* 263(32):17159-17166, 1988.
Bratthauer et al., "Expression of LINE-1 Retrotransposons in Human Breast Cancer," *Cancer* 73:2333-2336, 1994.
Byrne et al., "A Screening Method to Identify Genes Commonly Overexpressed in Carcinomas and the Identification of a Novel Complementary DNA Sequence," *Cancer Research* 55:2869-2903, 1995.
Cease et al., "T cell clones specific for an amphipathic α-helical region of sperm whale myoglobin show differing fine specificities for synthetic peptides," *Journal of Experimental Medicine* 164:1779-1784, Nov. 1986.
Chai et al., Genbank Accession No. U03644, 1994.
Charnock-Jones et al., "Extension of incomplete cDNAs (ESTs) by biotin./streptavidin- mediated walking using polymerase chain reaction," *J. Biotechno.* 35:205-215, Jun. 1994.

Chen and Sager, "Differential Expression of Human Tissue Factor in Normal Mammary Epithelial Cells and in Carcinomas," *Molecular Medicine* 1(2): 153-160, 1995.
Cordonnier et al., "Isolation of Novel Human Endogenous Retrovirus-Like Elements with Foamy Virus-Related *pol* Sequence," *Journal of Virology* 69(9):5890-5897, 1995.
Databank Genebank Accession No. Z34289, 1995.
Derks et al., "Synthesis of a viral protein with molecular weight of 30,000 (p30) by leukemic cells and antibodies cross-reacting with simian sarcoma virus p30 in serum of a chronic myeloid leukemia patient," *Cancer Research* 42:681-686, Feb. 1982.
Ezzell, "Cancer "Vaccines": An Idea Whose Time Has Come?," *The Journal of NIH Research* 7:46-49, 1995.
Frank et al., Genbank Accession No. Q70049, 1994.
Gura, "Systems for Identifying New Drugs Are Often Faulty," *Science* 278:1041-1042, 1997.
Haltmeier et al., "Identification of S71-Related Human Endogenous Retroviral Sequences with Full-Length *pol* Genes," *Virology* 209:550-560, 1995.
Hehlmann et al., "Detection and biochemical characterization of antigens in human leukemic sera that cross-react with primate C-type viral proteins (M 30,000)[1]," *Cancer Research* 43:392-399, Jan. 1983.
Herbrink et al., "Detection antibodies cross-reactive with type C RNA tumor viral p30 protein in human sera and exudate fluids," *Cancer Research* 40:166-173, Jan. 1980.
Hillier et al., Genbank Accession No. H80165, 1995.
Hillier et al., Genbank Accession No. R19532, 1995.
Hillier et al., Genbank Accession No. R55637, 1995.
Hillier et al., Genbank Accession No. R60426, 1995.
Hillier et al., Genbank Accession No. T83348, 1995.
Hillier et al., Genbank Accession No. R35308, 1995.
Hopp, T., "Computer prediction of protein surface features and antigenic determinants," *Molecular Basis of Cancer* Part B: Macromolecular Recognition, Chemotherapy, and Immunology:367-377, 1985.
Jerabek et al., "Detection and immunochemical characterization of a primate type C retrovirus-related p30 protein in normal human placentas," *Proc. Natl. Acad. Sci. USA* 81:6501-6505, Oct. 1984.
Kast et al., "Role of HLA-A motifs in identification of potential CTL epitopes in human papillmavirus type 16 E6 and E7 proteins," *J. Immunol.* 152:3904-3912, 1994.
Kawakami et al., "Recognition of multiple epitopes in the human melanoma antigen gp100 by tumor-infiltrating T lymphocytes associated with in vivo tumor regression," *J. Immunol.* 154:3961-3968, 1995.
Keydar et al., "Properties of retrovirus-like particles produced by a human breast carcinoma cell line: Immunological relationship with mouse mammary tumor virus proteins," *Proc. Natl. Acad. Sci. USA* 81:4188-92, 1984.
Leib-Mösch and Seifarth, "Evolution and Biological Significance of Human Retroelements," *Virus Genes* 11(2/3):133-145, 1996.
Leib-Mösch et al., "Endogenous Retroviral Elements in Human DNA," *Cancer Research* 50:5636s-5642s, 1994.
Leib-Mösch et al., "Genomic Distribution and Transcription of Solitary HERV-K LTRs," *Genomics* 18:261-269, 1993.
Liang et al., "Differential Display of Eukaryotic Messenger RNA by Means of the Polymerase Chain Reaction," *Science* 257:967-971, 1992.
Maeda et al., "Serum antibody reacting with placental syncytiotrophoblast in sera of patients with autoimmune diseases—a possible relation to type C RNA retroviruses," *Clin. Exp. Immunol.* 60:645-653, 1985.
Margalit et al., "Prediction of immunodominant helper T cell antigenic sites from the primary sequence," *The Journal of Immunology* 138(7):2213-2229, Apr. 1, 1987.
Matsubara et al., Genbank Accession No. T24124, 1995.
McCombs, R., "Role of oncornaviruses in carcinoma of the prostate," *Cancer Treatment Reports* 61(2):131-132, Mar./Apr. 1977.
Porter-Jordan and Lippman et al., "Overview of the biologic markers of breast cancer," *Breast Cancer* 8(1):73-100, Feb. 1994.
Rammensee et al., "MHC ligands and peptide motifs: first listing," *Immunogenetics* 41:178-228, 1995.

Rothbard and Taylor, "A sequence pattern common to T cell epitopes," *The EMBO Journal* 7(1):93-100, Jan. 1988.
Sette et al., "The relationship between class I binding affinity and immunogenicity of potential cytotoxic T cell epitopes," *J. Immunol.* 153:5586-5592, 1994.
Smith et al., "Expression of antigenic crossreactivity to RD114 p30 protein in a human fibrosarcoma cell line," *Proc. Natl. Acad. Sci. USA* 74(2):744-748, Feb. 1977.
Spouge et al., "Strong conformational propensities enhance T cell antigenicity," *The Journal of Immunology* 138(1):204-212, Jan. 1987.
Tsai et al., "In vitro immunization and expansion of antigen-specific cytotoxic T-lymphocytes for adoptive immunotherapy using peptide pulsed dendritic cells," *Critical Reviews in Immunology* 18:65-75, 1998.
Vaczi and Toth, "Studies on antigens of C-type primate viruses and antibodies to them at patients wit myeloid leukemia and potentially preleukemic hematological disorders," *Arch. Geschwulstforsch* 50(8):769-777, 1980.
Visseren et al., "CTL specific for the tyrosinase autoantigen can be induced form healthy donor blood to lyse melanoma cells," *J. Immunol* 154:3991-3998, 1995.
Vitiello et al., "Analysis of the HLA-restricted influenza specific cytotoxic T lymphcyte response in transgenic mice carrying a chimeric human-mouse class I major histocompatability complex," *J. Exp. Med.* 173:1007-1015, Apr. 1991.
Wang et al., "Detection of Mammary Tumor Virus ENV Gene-like Sequences in Human Breast Cancer," *Cancer Research* 55:5173-5179, 1995.
Watson and Fleming, "Isolation of Differentially Expressed Sequence Tags from Human Breast Cancer," *Cancer Research* 54(17):4598-4602, 1994.
Werner et al., "S71 Is a Phylogenetically Distinct Human Endogenous Retroviral Element with Structural and Sequence Homology to Simian Sarcoma Virus (SSV)," *Virology* 174:225-238, 1990.
Wiley and Cunningham, "A steady state model for analyzing the cellular binding, internalization and degradation of polypeptide ligands," *Cell* 25:433-440, Aug. 1981.
Yoshioka et al., "Pro-α1(XI) Collagen. Structure Of The Amino-Terminal Propeptide And Expression Of The Gene In Tumor Cell Lines," *J. Biol. Chem.* 265(11):6423-6426, 1990.
Critical Synergy: The Biotechnology Industry and Intellectual Property Protection, Presentation of the Intellectual Property Committee of the Biotechnology Industry Organization at the Oct. 17, 1994, Hearing of the U.S. Patent and Trademark Office, San Diego, CA, published by the Biotechnology Industry Organization, Washington, D.C., pp. 75, 100-107.
GenBank Accession No. Z34289, "*H. sapiens* mRNA for nucleolar phosphoprotein p130," Jun. 1, 1995.
GenBank Accession No. AP001465, May 9, 2000.
Ahn and Kunkel, "The Structural and functional diversity of dystrophin," *Nature Genetics* 3:283-291, Apr. 1993.
Attwood, T.K., "The Babel of Bioinformatics," *Science* 290: 471-473, Oct. 20, 2000.
Boon, T., "Toward a Genetic Analysis of Tumor Rejection Antigens," *Adv. Cancer Res.* 58:177-210.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology* 111:2129-2138, Nov. 1990.
Cawthon et al., "cDNA Sequence and Genomic Structure of *EV12B*, a Gene Lying with an Intron of the Neurofibromatosis Type 1 gene," *Genomics* 9: 446-460, 1991.
Curti, B.D., "Physical barriers to drug delivery in tumors," *Critical Reviews in Oncology/Hematology* 14:29-39, 1993.
Dermer, G.B., "Another Anniversary for the War on Cancer," *Bio/Technology* 12: 320, Mar. 1994.
Drexler, H. "Recent Results on the Biology of Hodgkin and Reed-Sternberg cells. II. Continuous Cell Lines," *Leukemia and Lymphoma* 9: 1-25, 1993.

Embleton, M.J., "Monoclonal Antibodies to Osteogenic Sarcoma Antigens," in Monoclonal Antibodies and Cancer, *Immunology Series 23*, Wright, Jr. G.L. (ed.), Marcel Dekker, New York, NY, 1984, pp. 181-207.
Freshney, R.I., *Culture of Animal Cells: A Manual of Basic Technique*, Alan T. Liss, Inc., New York, 1983, pp. 3-4.
GenBank Accession No. AA533501, Aug. 1, 1997.
GenBank Accession No. AC018804, Feb. 11, 2003.
GenBank Accession No. AI804733, Jul. 6, 1999.
GenBank Accession No. AQ063365, Jul. 30, 1998.
GenBank Accession No. AQ124119, Aug. 31, 1998.
Genseq (Derwent) Accession No. AAV68996, Jan. 22, 1999.
Genseq (Derwent) Accession No. AAL10921, Dec. 7, 2001.
Genseq (Derwent) Accession No. AAL11383, Dec. 7, 2001.
Genseq (Derwent) Accession No. AAL11455, Dec. 7, 2001.
Genseq (Derwent) Accession No. AAL13620, Dec. 7, 2001.
Genseq (Derwent) Accession No. AAL18685, Dec. 7, 2001.
Genseq (Derwent) Accession No. AAL20282, Dec. 7, 2001.
Genseq (Derwent) Accession No. AAL20354, Dec. 7, 2001.
Genseq (Derwent) Accession No. AAL22489, Dec. 7, 2001.
Gerhold and Caskey, "It's the genes! EST access to human genome content," *BioEssays* 18(12):973-981, 1996.
Geysen et al., "Cognitive Features of Continuous Antigenic Determinants," *Journal of Molecular Recognition* 1(1):32-41, 1988.
Gillies and Wesolowski et al., "Antigen binding and biological activities of engineered mutant chimeric antibodies with human tumor specificities," *Hum. Antibod. Hybridomas* 1(1):47-54, 1990.
Harris et al., "Polycystic Kidney Disease 1: Identification and Analysis of the Primary Defect," *Journal of the American Society of Nephrology* 6(4): 1125-1133, Oct. 1995.
Hartwell et al., "Integrating Genetic Approaches into the Discovery of Anticancer Drugs," *Science* 278: 1064-1068, Nov. 7, 1997.
Hsu, T.C., "Karyology of Cells in Culture," in Tissue Culture: Methods and Applications, Kurse, Jr et al. (eds.), Academic Press, New York, 1973, pp. 764-767.
Jain, R. K., "Barriers to Drug Delivery in Solid Tumors," *Scientific American* 271(1): 58-65, Jul. 1994.
Johnstone and Thorpe (eds.), *Immunochemistry in Practice*, Second Edition, Blackwell Scientific Publications, Oxford England, 1987, pp. 49-50.
Lazar et al., "Transforming Growth Factor α: Mutation of Aspartic Acid 47 and Leucine 48 Results in Different Biological Activities," *Molecular and Cellular Biology* 8: 1247-1252, Mar. 1988.
Russell and Barton, "Structural Features can be Unconserved in Proteins with Similar Folds," *J. Mol. Biol.* 244: 332-350, 1994.
Tao and Morrison, "Studies of Aglycosylated Chimeric Mouse-Human IgG. Role of Carbohydrate in the Structure and Effector Functions Mediated by the Human IgG Constant Region," *Journal of Immunity* 143(8): 2595-2601, Oct. 15, 1989.
Venter et al., "Genome sequence analysis: scientific objectives and practical strategies," *Trends in Biotechnology* 10: 8-11, Jan./Feb. 1992.
Walter, G., "Production of use of antibodies against synthetic peptides," *Journal of Immunological Methods* 88: 149-161, 1986.
Wei, W.-Z. et al., "Production Against Mammary Tumor Growth By Vaccination with Full-Length, Modified Human *ErB-2* DNA," *Int. J. Cancer* 81: 748-754, 1999.
Wells and Peitsch, "The chemokine information source: identification and characterization of novel chemokines using the WorldWideWeb and Expressed Sequence Tag Databases," *Journal of Leukocyte Biology* 61: 545-550, May 1997.
Houghton, R.L. et al., "Transcriptional Complementarity in Breast Cancer: Application to Detection of Circulating Tumor Cells," *Molecular Diagnosis* 6(2): 79-91, Jun. 2001.
Anderson et al., "A comparison of selected mRNA and protein abundances in human liver," *Electrophoresis*, 18:533-537, 1997.
Cox et al., "Sequencing, Expression Analysis, and Mapping of Three Unique Human Tropomodulin Genes and Their Mouse Orthologs," *Genomics*, 63:97-107, Jan. 1, 2000.
Csoka et al., "Expression Analysis of Six Paralogous Human Hyaluronidase Genes Clustered on Chromosomes 3p21 and 7q31," *Genomics*, 60:356-361, Sep. 15, 1999.
EMBL Database, Accession No. A1127438, Mar. 3, 2000.

GenBank Accession No. BF329652, Nov. 22, 2000.
GenBank Accession No. B48260, Apr. 8, 1999.
GenBank Accession No. BF676987, Dec. 21, 2000.
GenBank Accession No. AQ204617 Sep. 17, 1998.
GenBank Accession No. AI804733, Mar. 7, 2000.
Genseq (Derwent) Accession No. AAT96475, Feb. 26, 1998.
Gibson et al., "A Novel Method for Real Time Quantitative RT-PCR," *Genome Research* 6(10):995-1001, Oct. 1996.
Gygi et al., "Correlation between Protein and mRNA Abundance in Yeast," *Molecular and Cellular Biology,* 19(3):1720-1730, Mar. 1999.
Heid et al., "Real time quantitative PCR," *Genome Research* 6(10):986-994, Oct. 1996.
Liu et al., "Evolution of *cis*-Acting Elements in 5' Flanking Regions of Vertebrate Actin Genes," *J. Mol. Evol.,* 50(1):22-30, January 2000.

Nagata et al., "Codon Optimization Effect on Translational Efficiency of DNA Vaccine in Mammalian Cells: Analysis of Plasmid DNA Encoding a CTL Epitope Derived from Microorganisms," *Biochemical and Biophysical Research Communications* 261(2):445-451, Jun. 25, 1999.
Schena et al., "Quantitative monitoring of Gene Expression Patterns with a Complementary DNA Microarray," *Science* 270:467-470, Oct. 20, 1995.
*Stratagene Catalogue,* 1988.
Yee et al., "Isolation of Tyrosinase-Specific CD8+ and CD4+ T Cell Clones from the Peripheral Blood of Melanoma Patients Following In Vitro Stimulation with Recombinant Vaccinia Virus," *The Journal of Immunology* 157:(9):4079-4086, Nov. 1, 1996.

* cited by examiner

NUCLEOTIDE SEQUENCE OF THE REPRESENTATIVE
BREAST-TUMOR SPECIFIC cDNA B18Ag1

```
TTA GAG ACC CAA TTG GGA CCT AAT TGG GAC CCA AAT TTC TCA AGT GGA    48
Leu Glu Thr Gln Leu Gly Pro Asn Trp Asp Pro Asn Phe Ser Ser Gly
 1           5                  10                  15

GGG AGA ACT TTT GAC GAT TTC CAC CGG TAT CTC CTC GTG GGT ATT CAG    96
Gly Arg Thr Phe Asp Asp Phe His Arg Tyr Leu Leu Val Gly Ile Gln
         20                  25                  30

GGA GCT GCC CAG AAA CCT ATA AAC TTG TCT AAG GCG ATT GAA GTC GTC   144
Gly Ala Ala Gln Lys Pro Ile Asn Leu Ser Lys Ala Ile Glu Val Val
             35                  40                  45

CAG GGG CAT GAT GAG TCA CCA GGA GTG TTT TTA GAG CAC CTC CAG GAG   192
Gln Gly His Asp Glu Ser Pro Gly Val Phe Leu Glu His Leu Gln Glu
         50                  55                  60

GCT TAT CGG ATT TAC ACC CCT TTT GAC CTG GCA GCC CCC GAA AAT AGC   240
Ala Tyr Arg Ile Tyr Thr Pro Phe Asp Leu Ala Ala Pro Glu Asn Ser
 65              70                  75                  80

CAT GCT CTT AAT TTG GCA TTT GTG GCT CAG GCA GCC CCA GAT AGT AAA   288
His Ala Leu Asn Leu Ala Phe Val Ala Gln Ala Ala Pro Asp Ser Lys
             85                  90                  95

AGG AAA CTC CAA AAA CTA GAG GGA TTT TGC TGG AAT GAA TAC CAG TCA   336
Arg Lys Leu Gln Lys Leu Glu Gly Phe Cys Trp Asn Glu Tyr Gln Ser
             100                 105                 110

GCT TTT AGA GAT AGC CTA AAA GGT TTT                               363
Ala Phe Arg Asp Ser Leu Lys Gly Phe
             115                 120
```

*Fig. 6*

NUCLEOTIDE SEQUENCE OF THE REPRESENTATIVE
BREAST-TUMOR SPECIFIC cDNA B17Ag1

```
GC TGGGCACAGT GGCTCATACC TGTAATCCTG ACCGTTTCAG AGGCTCAGGT     60

CG CTTGAGCCCA AGATTTCAAG ACTAGTCTGG GTAACATAGT GAGACCCTAT    120

AA AAATAAAAAA ATGAGCCTGG TGTAGTGGCA CACACCAGCT GAGGAGGGAG    180

CT AGGAGA                                                    196
```

*Fig. 7*

NUCLEOTIDE SEQUENCE OF THE REPRESENTATIVE
BREAST-TUMOR SPECIFIC cDNA B17Ag2

```
GC TTGGGGGCTC TGACTAGAAA TTCAAGGAAC CTGGGATTCA AGTCCAACTG   60
AC TTACACTGTG GNCTCCAATA AACTGCTTCT TTCCTATTCC CTCTCTATTA  120
AA GGAAAACGAT GTCTGTGTAT AGCCAAGTCA GNTATCCTAA AAGGAGATAC  180
AT TAAATATCAG AATGTAAAAC CTGGGAACCA GGTTCCCAGC CTGGGATTAA  240
CA AGAAGACTGA ACAGTACTAC TGTGAAAAGC CCGAAGNGGC AATATGTTCA  300
TT GAAGGATGGC TGGGAGAATG AATGCTCTGT CCCCCAGTCC CAAGCTCACT  360
CT CCTTTATAGC CTAGGAGA                                     388
```

Fig. 8

NUCLEOTIDE SEQUENCE OF THE REPRESENTATIVE
BREAST-TUMOR SPECIFIC cDNA B13Ag2a

```
GC CTATAATCAT GTTTCTCATT ATTTTCACAT TTTATTAACC AATTTCTGTT   60
AA AATATGAGGG AAATATATGA AACAGGGAGG CAATGTTCAG ATAATTGATC  120
TG ATTTCTACAT CAGATGCTCT TTCCTTTCCT GTTTATTTCC TTTTTATTTC  180
GG TCGAATGTAA TAGCTTTGTT TCAAGAGAGA GTTTGGCAG TTTCTGTAGC   240
CT GCTCATGTCT CCAGGCATCT ATTTGCACTT TAGGAGGTGT CGTGGGAGAC  300
CT ATTTTTTCCA TATTTGGGCA ACTACTA                          337
```

Fig. 9

NUCLEOTIDE SEQUENCE OF THE REPRESENTATIVE BREAST-TUMOR SPECIFIC cDNA B13Ag1b

| | |
|---|---|
| GC CATACAGTGC CTTTCCATTT ATTTAACCCC CACCTGAACG GCATAAACTG | 60 |
| GC TGGTGTTTTT TACTGTAAAC AATAAGGAGA CTTTGCTCTT CATTTAAACC | 120 |
| AT TTCATATTTT ACGCTCGAGG GTTTTTACCG GTTCCTTTTT ACACTCCTTA | 180 |
| TT TAAGTCGTTT GGAACAAGAT ATTTTTTCTT TCCTGGCAGC TTTTAACATT | 240 |
| TT TGTGTCTGGG GGACTGCTGG TCACTGTTTC TCACAGTTGC AAATCAAGGC | 300 |
| CC AAGAAAAAAA AATTTTTTTG TTTTATTTGA AACTGGACCG GATAAACGGT | 360 |
| CG GCTGCTGTAT ATAGTTTTAA ATGGTTTATT GCACCTCCTT AAGTTGCACT | 420 |
| GG GGGGNTTTTG NATAGAAAGT NTTTANTCAC ANAGTCACAG GGACTTTTNT | 480 |
| NA CTGAGCTAAA AAGGGCTGNT TTTCGGGTGG GGGCAGATGA AGGCTCACAG | 540 |
| TC TCTTAGAGGG GGGAACTNCT A | 571 |

*Fig. 10*

NUCLEOTIDE SEQUENCE OF THE REPRESENTATIVE
BREAST-TUMOR SPECIFIC cDNA B13Ag1a

TA ATAACTTAAA TATATTTTGA TCACCCACTG GGGTGATAAG ACAATAGATA    60

TT TCCAAAAAGC ATAAAACCAA AGTATCATAC CAAACCAAAT TCATACTGCT   120

CC GCACTGAAAC TTCACCTTCT AACTGTCTAC CTAACCAAAT TCTACCCTTC   180

GG TGCGTGCTCA CTACTCTTTT TTTTTTTTTT TTTNTTTTGG AGATGGAGTC   240

CA GCCCAGGGGT GGAGTACAAT GGCACAACCT CAGCTCACTG NAACCTCCGC   300

TT CATGAGATTC TCCTGNTTCA GCCTTCCCAG TAGCTGGGAC TACAGGTGTG   360

TG CCTGGNTAAT CTTTTTTNGT TTTNGGGTAG AGATGGGGGT TTTACATGTT   420

TG GTNTCGAACT CCTGACCTCA AGTGATCCAC CCACCTCAGG CTCCCAAAGT   480

TA CAGACATGAG CCACTGNGCC CAGNCCTGGT GCATGCTCAC TTCTCTAGGC   540

*Fig. 11*

NUCLEOTIDE SEQUENCE OF THE REPRESENTATIVE
BREAST-TUMOR SPECIFIC cDNA B11Ag1

| | |
|---|---|
| TG CACATGCAGA ATATTCTATC GGTACTTCAG CTATTACTCA TTTTGATGGC | 60 |
| AG CCTATCCTCA AGATGAGTAT TTAGAAAGAA TTGATTTAGC GATAGACCAA | 120 |
| GC ACTCTGACTA CACGAAATTG TTCAGATGTG ATGGATTTAT GACAGTTGAT | 180 |
| GA GATTATTAAG TGATTATTTT AAAGGGAATC CATTAATTCC AGAATATCTT | 240 |
| TC AAGATGATAT AGAAATAGAA CAGAAAGAGA CTACAAATGA AGATGTATCA | 300 |
| TA TTGAAGAGCC TATAGTAGAA AATGAATTAG CTGCATTTAT TAGCCTTACA | 360 |
| TT TTCCTGATGA ATCTTATATT CAGCCATCGA CATAGCATTA CCTGATGGGC | 420 |
| GA ATAATAGAAA CTGGGTGCGG GGCTATTGAT GAATTCATCC NCAGTAAATT | 480 |
| AC AAAATATAAC TCGATTGCAT TTGGATGATG GAATACTAAA TCTGGCAAAA | 540 |
| GG AGCTACTAGT AACCTCTCTT TTTGAGATGC AAAATTTTCT TTTAGGGTTT | 600 |
| CT ACTTTACGGA TATTGGAGCA TAACGGGA | 638 |

*Fig. 12*

NUCLEOTIDE SEQUENCE OF THE REPRESENTATIVE
BREAST-TUMOR SPECIFIC cDNA B3CA3c

| | | | | | | |
|---|---|---|---|---|---|---|
| ACTGATGGAT | GTCGCCGGAG | GCGAGGGGCC | TTATCTGATG | CTCGGCTGCC | TGTTCGTGAT | 60 |
| GTGCGCGGCG | ATTGGGCTGT | TTATCTCAAA | CACCGCCACG | GCGGTGCTGA | TGGCGCCTAT | 120 |
| TGCCTTAGCG | GCGGCGAAGT | CAATGGGCGT | CTCACCCTAT | CCTTTTGCCA | TGGTGGTGGC | 180 |
| GATGGCGGCT | TCGGCGGCGT | TTATGACCCC | GGTCTCCTCG | CCGGTTAACA | CCCTGGTGCT | 240 |
| TGGCCCTGGC | AAGTACTCAT | TTAGCGATTT | TGTCAAAATA | GGCGTG | | 286 |

*Fig. 13*

NUCLEOTIDE SEQUENCE OF THE REPRESENTATIVE
BREAST-TUMOR SPECIFIC cDNA B9CG1

| | | | | | |
|---|---|---|---|---|---|
| AG CAGCCCCTTC | TTCTCAATTT | CATCTGTCAC | TACCCTGGTG | TAGTATCTCA | 60 |
| CA TTTTTATAGC | CTCCTCCCTG | GTCTGTCTTT | TGATTTTCCT | GCCTGTAATC | 120 |
| AC ATAACTGCAA | GTAAACATTT | CTAAAGTGTG | GTTATGCTCA | TGTCACTCCT | 180 |
| AA ATAGTTTCCA | TTACCGTCTT | AATAAAATTC | GGATTTGTTC | TTTNCTATTN | 240 |
| CA CCTATGACCG AA | | | | | 262 |

*Fig. 14*

NUCLEOTIDE SEQUENCE OF THE REPRESENTATIVE
BREAST-TUMOR SPECIFIC cDNA B9CG3

AG CAAAGCCAGT GGTTTGAGCT CTCTACTGTG TAAACTCCTA AACCAAGGCC    60

TA AATGGTGGCA GGATTTTTAT TATAAACATG TACCCATGCA AATTTCCTAT   120

GA TATATTCTTC TACATTTAAA CAATAAAAAT AATCTATTTT TAAAAGCCTA   180

AG TTAGGTAAGA GTGTTTAATG AGAGGGTATA AGGTATAAAT CACCAGTCAA   240

TG CCTATGACCG A                                            261

*Fig. 15*

NUCLEOTIDE SEQUENCE OF THE REPRESENTATIVE BREAST-TUMOR SPECIFIC cDNA B2CA2

```
CGACGTCGGT AAAATCGGAC ATGAAGCCAC CGCTGGTCTT TTCGTCCGAG CGATAGGCGC    60

CGGCCAGCCA GCGGAACGGT TGCCCGGATG GCGAAGCGAG CCGGAGTTCT TCGGACTGAG   120

TATGAATCTT GTTGTGAAAA TACTCGCCGC CTTCGTTCGA CGACGTCGCG TCGAAATCTT   180

CGAACTCCTT ACGATCGAAG TCTTCGTGGG CGACGATCGC GGTCAGTTCC GCCCCACCGA   240

AATCATGGTT GAGCCGGATG CTGCCCCCGA AGCCCT                             276
```

Fig. 16

NUCLEOTIDE SEQUENCE OF THE REPRESENTATIVE
BREAST-TUMOR SPECIFIC cDNA B3CA1

| | | | | | |
|---|---|---|---|---|---|
| CCCAGGTCAA | CCAGGCTGCA | ACACGCAGGT | CCTTGGATTG | GGCACGAAGC | AGCGCTTCGC | 60 |
| TGTTTTCCAG | GATTTTCAAC | CAGTCGGTCT | GGCCGTTCTC | ATGGAGCGAG | AGCGCCTTGC | 120 |
| CCAGCTCATT | TTCCAGCGCC | TCGTATTCGC | TGGAAAAACG | CACATCCTCA | CCCGCAAAGA | 180 |
| CATCCTTTGA | AATCGGCTGT | TCCGCGAGTT | CCAGATANTG | CGAGGAGAGC | TTGCTCGAAT | 240 |
| AGGTCATCCT | AACCCTTCAA | TGCACACCAT | GTGCGCCAAT | GAATATCTTA | ACAATTCAAC | 300 |
| TAGTTGGCAT | AANAACCGAA | CGAAAATCCC | AATAGTCTGA | AGAGCTCTTT | TG | 352 |

Fig. 17

NUCLEOTIDE SEQUENCE OF THE REPRESENTATIVE
BREAST-TUMOR SPECIFIC cDNA B3CA2

| | | | | | |
|---|---|---|---|---|---:|
| CTGCATGTCC | ACGGCCTGGA | TTTACGGGTG | GTCGGCGTTC | ACCCCTGGCA | GCTGGCGCTC | 60 |
| TTCCCGACCA | GGCCCAGCAG | GATGTGTGGG | GCAAGGATAA | CGGCGTGCGC | ATCGCCTCGA | 120 |
| CCTATATGCC | TACTGGCAAG | GCCGAGCCCG | TGGAAGGCGG | ATTCAGGTTC | ANCGGTCGCT | 180 |
| GGAGCTTTTC | CACCGGCTCC | ATGCATTGTG | ACTGGCTGTT | TCTAGGCGGT | CTGTTGCCCA | 240 |
| AGCGTGATGG | TACGTCTGGC | CTGGAGCATG | TGACTTTCTG | | | 280 |

Fig. 18

NUCLEOTIDE SEQUENCE OF THE REPRESENTATIVE
BREAST-TUMOR SPECIFIC cDNA B3CA3

```
AG GGAGCAAGGA GAAGGCATGG AGAGGCTCAN GCTGGTCCTG GCCTACGACT     60

CT GTCGCCGGGG ATGGTGGAGA ACTGAAGCGG GACCTCCTCG AGGTCCTCCG    120

TC NCCGTCCAGG AGGAGGGTCT TTCCGTGGTC TNGGAGGAGC GGGGGGAGAA    180

TC ATGGTCNACA TCCC                                           204
```

Fig. 19

NUCLEOTIDE SEQUENCE OF THE REPRESENTATIVE
BREAST-TUMOR SPECIFIC cDNA B4CA1

TC AGGAGCGGGT AGAGTGGCAC CATTGAGGGG ATATTCAAAA ATATTATTTT   60

TG ATAGTTGCTG AGTTTTTCTT TGACCCATGA GTTATATTGG AGTTTATTTT  120

CC AATCGCATGG ACATGTTAGA CTTATTTTCT GTTAATGATT NCTATTTTA   180

GA TTTGAGAAAT TGGTTNTTAT TATATCAATT TTTGGTATTT GTTGAGTTTG  240

GC TTAGTATGTG ACCA                                         264

*Fig. 20*

SEQUENCE LISTING

<160> NUMBER OF SEQ ID NOS: 340

<210> SEQ ID NO 1
<211> LENGTH: 363
<212> TYPE: DNA
<213> ORGANISM: Homo sapiens

<400> SEQUENCE: 1
ttagagaccc aattgggacc taattgggac ccaaatttct caagtggagg gagaactttt      60
gacgatttcc accggtatct cctcgtgggt attcagggag ctgcccagaa acctataaac     120
ttgtctaagg cgattgaagt cgtccagggg catgatgagt caccaggagt gttttagag     180 cacctccagg aggcttatcg gatttacacc ccttttgacc tggcagcccc cgaaaatagc    240
catgctctta atttggcatt tgtggctcag gcagcccag atagtaaaag gaaactccaa    300
aaactagagg gattttgctg gaatgaatac cagtcagctt ttagagatag cctaaaaggt   360
ttt                                                                   363

<210> SEQ ID NO 2
<211> LENGTH: 121
<212> TYPE: PRT
<213> ORGANISM: Homo sapiens

<400> SEQUENCE: 2

Leu Glu Thr Gln Leu Gly Pro Asn Trp Asp Pro Asn Phe Ser Ser Gly
 1               5                  10                  15

Gly Arg Thr Phe Asp Asp Phe His Arg Tyr Leu Leu Val Gly Ile Gln
             20                  25                  30

Gly Ala Ala Gln Lys Pro Ile Asn Leu Ser Lys Ala Ile Glu Val Val
         35                  40                  45

Gln Gly His Asp Glu Ser Pro Gly Val Phe Leu Glu His Leu Gln Glu
     50                  55                  60

Ala Tyr Arg Ile Tyr Thr Pro Phe Asp Leu Ala Ala Pro Glu Asn Ser
 65                  70                  75                  80

His Ala Leu Asn Leu Ala Phe Val Ala Gln Ala Ala Pro Asp Ser Lys
                 85                  90                  95

Arg Lys Leu Gln Lys Leu Glu Gly Phe Cys Trp Asn Glu Tyr Gln Ser
            100                 105                 110

Ala Phe Arg Asp Ser Leu Lys Gly Phe
        115                 120

<210> SEQ ID NO 3
<211> LENGTH: 1080
<212> TYPE: DNA
<213> ORGANISM: Homo sapiens
<220> FEATURE:
<221> NAME/KEY: misc_feature
<222> LOCATION: 681, 685, 706, 720, 741, 752, 758, 780, 789, 824, 840,
      859, 866, 884, 890, 905, 917, 926, 930, 951, 957, 959, 962, 974,
      980, 982, 988, 995, 996, 1007, 1010, 1025, 1040, 1051, 1052,
      1056, 1057, 1078
<223> OTHER INFORMATION: n = A,T,C or G

<400> SEQUENCE: 3
tcttagaatc ttcataccccc gaactcttgg gaaaacttta atcagtcacc tacagtctac     60

```
cacccattta ggaggagcaa agctacctca gctcctccgg agccgtttta agatccccca    120
tcttcaaagc ctaacagatc aagcagctct ccggtgcaca acctgcgccc aggtaaatgc    180
caaaaaaggt cctaaaccca gcccaggcca ccgtctccaa gaaaactcac caggagaaaa    240
gtgggaaatt gactttacag aagtaaaacc acaccgggct gggtacaaat accttctagt    300
actggtagac accttctctg gatggactga agcatttgct accaaaaacg aaactgtcaa    360
tatggtagtt aagtttttac tcaatgaaat catccctcga cgtgggctgc ctgttgccat    420
agggtctgat aatggaacgg ccttcgcctt gtctatagtt taatcagtca gtaaggcgtt    480
aaacattcaa tggaagctcc attgtgccta tcgacccaga gctctgggca agtagaacgc    540
atgaactgca ccctaaaaaa acactcttac aaaattaatc ttaaaaaccg gtgttaattg    600
tgttagtctc cttcccttag ccctacttag agttaaggtg caccccttac tgggctgggt    660
tctttacctt ttgaaatcat ntttnggaag gggctgccta tctttncttt actaaaaaan    720
gcccatttgg caaaaatttc ncaactaatt tntacgtncc tacgtctccc caacaggtan    780
aaaaatctnc tgccctttc aaggaaccat cccatccatt cctnaacaaa aggcctgccn    840 ttcttcccc agttaactnt tttttnttaa aattcccaaa aaangaaccn cctgctggaa    900 aaacncccc ctccaancc cggccnaagn ggaaggttcc cttgaatccc ncccccncna    960
anggcccgga accnttaaan tngttccngg gggtnnggcc taaaagnccn atttggtaaa    1020
cctanaaatt ttttcttttn taaaaaccac nnttttnnttt ttcttaaaca aaaccctntt    1080
```

<210> SEQ ID NO 4
<211> LENGTH: 1087
<212> TYPE: DNA
<213> ORGANISM: Homo sapiens
<220> FEATURE:
<221> NAME/KEY: misc_feature
<222> LOCATION: 559, 574, 576, 581, 582, 587, 589, 593, 594, 609, 627,
    640, 659, 668, 672, 677, 691, 713, 714, 732, 741, 812, 813, 823,
    825, 829, 838, 845, 849, 852, 855, 856, 859, 874, 876, 877,
    892, 902, 907, 916, 917, 938, 950, 951, 952, 953, 960
<223> OTHER INFORMATION: n = A,T,C or G
<221> NAME/KEY: misc_feature
<222> LOCATION: 965, 974, 976, 978, 982, 996, 1005, 1012, 1049, 1058,
    1073, 1074, 1082, 1084, 1086
<223> OTHER INFORMATION: n = A,T,C or G

<400> SEQUENCE: 4

```
tctagagctg cgcctggatc ccgccacagt gaggagacct gaagaccaga gaaaacacag    60
caagtaggcc ctttaaacta ctcacctgtg ttgtcttcta atttattctg ttttattttg    120
tttccatcat tttaaggggt taaaatcatc ttgttcagac ctcagcatat aaaatgaccc    180
atctgtagac ctcaggctcc aaccataccc caagagttgt ctggttttgt ttaaattact    240
gccaggtttc agctgcagat atccctggaa ggaatattcc agattccctg agtagtttcc    300
aggttaaaat cctataggct tcttctgttt tgaggaagag ttcctgtcag agaaaaacat    360
gattttggat ttttaacttt aatgcttgtg aaacgctata aaaaaatttt ctaccccta    420 gctttaaagt actgttagtg agaaattaaa attccttcag gaggattaaa ctgccatttc    480
agttacccta attccaaatg ttttggtggt tagaatcttc tttaatgttc ttgaagaagt    540
gttttatatt ttcccatcna gataaaattct ctcncnccctt nnttttntnt ctnnttttttt    600 aaaacggant cttgctccgt tgtccangct gggaattttn ttttggccaa tctccgctnc    660
cttgcaanaa tnctgcntcc caaaattacc nccttttcc cacctccacc ccnnggaatt    720
acctggaatt anaggccccc nccccccccc cggctaattt gttttgtttt ttagtaaaaa    780
```

```
acgggtttcc tgttttagtt aggatggccc anntctgacc ccntnatcnt cccccctcngc      840 cctcnaatnt tnggnntang gcttaccccc cccngnngtt tttcctccat tnaaattttc      900
tntggantct tgaatnncgg gttttcccctt ttaaaccnat tttttttttn nnnccccccan    960 ttttncctcc cccntntnta anggggttt cccaanccgg gtccnccccc angtccccaa       1020
tttttctccc ccccccctctt ttttctttnc cccaaaantc ctatcttttc ctnnaaatat    1080 cnantnt                                                                1087
```

<210> SEQ ID NO 5
<211> LENGTH: 1010
<212> TYPE: DNA
<213> ORGANISM: Homo sapiens
<220> FEATURE:
<221> NAME/KEY: misc_feature
<222> LOCATION: 311, 315, 318, 339, 341, 347, 361, 379, 391, 415, 417,
   419, 424, 430, 433, 454, 463, 465, 467, 476, 497, 499, 550, 562,
   564, 587, 591, 595, 597, 598, 612, 625, 631, 640, 641, 645,
   648, 656, 661, 665, 666, 670, 674, 675, 681, 682, 683
<223> OTHER INFORMATION: n = A,T,C or G
<221> NAME/KEY: misc_feature
<222> LOCATION: 687, 688, 692, 710, 721, 778, 788, 811, 820, 830, 860,
   867, 868, 871, 872, 889, 892, 896, 897, 899, 904, 915, 936, 951,
   960, 970, 986, 990, 1000
<223> OTHER INFORMATION: n = A,T,C or G

<400> SEQUENCE: 5

```
tctagaccaa gaaatgggag gattttagag tgactgatga tttctctatc atctgcagtt      60
agtaaacatt ctccacagtt tatgcaaaaa gtaacaaaac cactgcagat gacaaacact     120
aggtaacaca catactatct cccaaatacc tacccacaag ctcaacaatt ttaaactgtt     180
aggatcactg gctctaatca ccatgacatg aggtcaccac caaaccatca agcgctaaac     240
agacagaatg tttccactcc tgatccactg tgtgggaaga agcaccgaac ttacccactg     300
gggggcctgc ntcanaanaa aagcccatgc ccccgggtnt nccttnaac cggaacgaat      360 naacccacca tccccacanc tcctctgttc ntgggccctg catcttgtgg cctcntntnc     420
tttnggggan acntggggaa ggtaccccat ttcnttgacc ccncnanaaa accccngtgg     480
cccctttgcc ctgattcncnt gggcttttc tcttttccct tttgggttgt ttaaattccc     540
aatgtccccn gaaccctctc cntnctgccc aaaacctacc taaattnctc nctangnntt     600
ttcttggtgt tncttttcaa aggtnacctt ncctgttcan nccnacnaa aattnttcc       660 ntatnntggn cccnnaaaaa nnnatcnncc cnaattgccc gaattggttn ggttttttcct    720 nctgggggaa acccttttaaa tttcccccctt ggccggcccc cctttttttcc ccccttttnga 780 aggcaggngg ttcttcccga acttccaatt ncaacagccn tgcccattgn tgaaaccctt     840
ttcctaaaat taaaaaaatan ccggttnngg nnggcctctt tccccctccng gngggnngng   900 aaantcctta ccccnaaaaa ggttgcttag ccccngtcc ccactccccc nggaaaaatn      960
aaccttttcn aaaaaaggaa tataanttttn ccactccttn gttctcttcc                1010
```

<210> SEQ ID NO 6
<211> LENGTH: 950
<212> TYPE: DNA
<213> ORGANISM: Homo sapiens
<220> FEATURE:
<221> NAME/KEY: misc_feature
<222> LOCATION: 199, 200, 209, 223, 224, 236, 240, 241, 244, 248, 249,
   262, 263, 267, 268, 269, 270, 271, 272, 273, 280, 281, 283, 285,
   286, 287, 288, 289, 290, 291, 293, 295, 296, 300, 302, 303,
   309, 313, 314, 315, 316, 317, 318, 319, 320, 322, 323
<223> OTHER INFORMATION: n = A,T,C or G
<221> NAME/KEY: misc_feature
<222> LOCATION: 326, 327, 331, 332, 339, 342, 343, 344, 346, 349, 352,
       353, 355, 356, 359, 360, 362, 363, 364, 367, 369, 371, 375, 377,
       378, 379, 383, 385, 387, 389, 390, 392, 396, 397, 399, 400,
       401, 402, 405, 406, 408, 409, 410, 412, 413, 414, 415
<223> OTHER INFORMATION: n = A,T,C or G
<221> NAME/KEY: misc_feature
<222> LOCATION: 417, 419, 420, 423, 424, 428, 431, 433, 434, 435, 437,
       438, 439, 443, 447, 449, 450, 455, 456, 458, 459, 462, 465, 467,
       469, 472, 480, 481, 483, 484, 485, 486, 487, 488, 493, 494,
       495, 496, 497, 502, 505, 507, 508, 510, 512, 517, 518
<223> OTHER INFORMATION: n = A,T,C or G
<221> NAME/KEY: misc_feature
<222> LOCATION: 520, 521, 524, 526, 531, 536, 538, 539, 543, 544, 548,
       549, 550, 552, 553, 555, 556, 557, 561, 563, 566, 570, 571, 572,
       576, 577, 579, 580, 582, 583, 585, 588, 590, 591, 592, 594,
       597, 603, 606, 607, 614, 616, 618, 620, 621, 622, 623
<223> OTHER INFORMATION: n = A,T,C or G
<221> NAME/KEY: misc_feature
<222> LOCATION: 625, 628, 629, 630, 632, 634, 637, 638, 641, 645, 651,
       652, 653, 658, 659, 663, 664, 668, 672, 673, 674, 678, 685, 689,
       696, 700, 701, 702, 704, 705, 706, 708, 710, 711, 712, 713,
       715, 719, 722, 725, 727, 731, 734, 735, 737, 739, 742
<223> OTHER INFORMATION: n = A,T,C or G
<221> NAME/KEY: misc_feature
<222> LOCATION: 745, 748, 749, 751, 752, 754, 755, 757, 759, 762, 765,
       767, 769, 773, 774, 775, 778, 780, 783, 785, 787, 790, 793, 797,
       800, 803, 810, 812, 824, 828, 832, 836, 839, 843, 844, 846,
       848, 850, 852, 853, 855, 858, 859, 861, 864, 865, 866
<223> OTHER INFORMATION: n = A,T,C or G
<221> NAME/KEY: misc_feature
<222> LOCATION: 868, 869, 872, 875, 880, 886, 889, 890, 891, 892, 893,
       895, 896, 901, 902, 906, 908, 913, 914, 916, 918, 921, 924, 925,
       930, 932, 935, 940
<223> OTHER INFORMATION: n = A,T,C or G

<400> SEQUENCE: 6

```
tctagagctc gcggccgcga gctctaatac gactcactat agggcgtcga ctcgatctca    60
gctcactgca atctctgccc ccggggtcat gcgattctcc tgcctcagcc ttccaagtag   120
ctgggattac aggcgtgcaa caccacaccc ggctaatttt gtattttaa tagagatggg   180
gtttccctt gttggccann atggtctcna acccctgacc tcnngtgatc ccccncccn    240
nganctcnna ctgctgggga tnccgnnnn nncctcccn ncncnnnnnn ncncnntccn    300
tnntccttnc tcnnnnnnnn cnntcnntcc nncttctcnc cnntntttnt cnncnnccnn   360
cnnnccncnt ncccncnnnt tcncntncnn tntccnncnn nntcnncnnn cnnnncntnn   420
ccnntacntc ntnnncnnnt cnntctntnn cctcnncnnt cnctncncnt tntctcctcn   480
ntnnnnnnct ccnnnnntct cntcncnncn tncctcnntn nccncnccc ncctcncnnc   540
ctnntttnnn cnncnnntcc ntnccnttcn nntccnntnn cnncntcncn nncnttnttc   600
ccncnnttc cttncncntn nnntntcnnn cncntcnntc ntttnctcct nnntccnnc    660
tcnnttcncc cnnntccncc cccncctnt ctctcncccn nntnnntntn nnncntccnc   720
tntcncnttc ntcnnntncnt tnctntcnnc nncnntncnc tnccntntnt ctnnntcncn   780
tcncntntcn cntcncnttn ctntctcctn tntccttccc ctcncctnct cnttcnccnc   840
ccnntntntn tnncnccnnt nctnnncnnc cntcntttcn tctctnctnn nnntnncctc   900
nnccntncc ctnntcncct nctnntaccn tnctnctccn tcttccttcc              950
```

<210> SEQ ID NO 7
<211> LENGTH: 1086
<212> TYPE: DNA
<213> ORGANISM: Homo sapiens
<220> FEATURE:
<221> NAME/KEY: misc_feature
<222> LOCATION: 501, 691, 711, 735, 751, 780, 810, 819, 826, 832, 849,
       889, 890, 904, 913, 920, 926, 937, 940, 953, 957, 960, 985, 993, 994, 1000, 1012, 1044, 1060, 1063, 1080, 1081
<223> OTHER INFORMATION: n = A,T,C or G

<400> SEQUENCE: 7

| | | |
|---|---|---|
| tctagagctc gcggccgcga gctcaattaa ccctcactaa agggagtcga ctcgatcaga | 60 |
| ctgttactgt gtctatgtag aaagaagtag acataagaga ttccattttg ttctgtacta | 120 |
| agaaaaattc ttctgccttg agatgctgtt aatctgtaac cctagcccca accctgtgct | 180 |
| cacagagaca tgtgctgtgt tgactcaagg ttcaatggat ttagggctat gctttgttaa | 240 |
| aaaagtgctt gaagataata tgcttgttaa aagtcatcac cattctctaa tctcaagtac | 300 |
| ccagggacac aatacactgc ggaaggccgc agggacctct gtctaggaaa gccaggtatt | 360 |
| gtccaagatt ctccccatg tgatagcctg agatatggcc tcatgggaag ggtaagacct | 420 |
| gactgtcccc cagcccgaca tcccccagcc cgacatcccc cagcccgaca cccgaaaagg | 480 |
| gtctgtgctg aggaagatta ntaaagagg aaggctcttt gcattgaagt aagaagaagg | 540 |
| ctctgtctcc tgctcgtccc tgggcaataa aatgtcttgg tgttaaaccc gaatgtatgt | 600 |
| tctacttact gagaatagga gaaaacatcc ttagggctgg aggtgagaca ccctggcggc | 660 |
| atactgctct ttaatgcacg agatgtttgt ntaattgcca tccagggcca ncccctttcc | 720 |
| ttaactttt atganacaaa aactttgttc nctttcctg cgaacctctc ccctattan | 780 |
| cctattggcc tgcccatccc ctccccaaan ggtgaaaana tgttcntaaa tncgagggaa | 840 |
| tccaaaacnt tttcccgttg gtccccttc caaccccgtc cctgggccnn tttcctcccc | 900 |
| aacntgtccc ggntccttcn ttcccncccc cttcccngan aaaaaacccc gtntganggn | 960 |
| gccccctcaa attataacct ttccnaaaca aannggttcn aaggtggttt gnttccggtg | 1020 |
| cggctggcct tgaggtcccc cctncacccc aatttggaan ccngtttttt ttattgcccn | 1080 |
| ntcccc | 1086 |

<210> SEQ ID NO 8
<211> LENGTH: 1177
<212> TYPE: DNA
<213> ORGANISM: Homo sapiens
<220> FEATURE:
<221> NAME/KEY: misc_feature
<222> LOCATION: 1, 4, 20, 21, 31, 278, 314, 332, 359, 371, 373, 375,
    376, 524, 537, 556, 557, 579, 583, 590, 591, 598, 623, 625, 648,
    700, 703, 719, 738, 742, 746, 749, 751, 752, 800, 808, 820,
    821, 824, 835, 838, 845, 851, 856, 864, 865, 879, 888
<223> OTHER INFORMATION: n = A,T,C or G
<221> NAME/KEY: misc_feature
<222> LOCATION: 911, 920, 926, 935, 945, 950, 952, 956, 969, 972, 977,
    981, 992, 999, 1023, 1024, 1032, 1038, 1039, 1040, 1062, 1069,
    1075, 1084, 1089, 1104, 1119, 1123, 1131, 1143, 1146, 1152,
    1165, 1169, 1172, 1176
<223> OTHER INFORMATION: n = A,T,C or G

<400> SEQUENCE: 8

| | | |
|---|---|---|
| nccntttaga tgttgacaan ntaaacaagc ngctcaggca gctgaaaaaa gccactgata | 60 |
| aagcatcctg gagtatcaga gtttactgtt agatcagcct catttgactt cccctcccac | 120 |
| atggtgttta aatccagcta cactacttcc tgactcaaac tccactattc ctgttcatga | 180 |
| ctgtcaggaa ctgttggaaa ctactgaaac tggccgacct gatcttcaaa atgtgcccct | 240 |
| aggaaaggtg gatgccaccg tgttcacaga cagtaccncc ttcctcgaga agggactacg | 300 |
| aggggccggt gcanctgtta ccaaggagac tnatgtgttg tgggctcagg ctttaccanc | 360 |
| aaacacctca ncncnnaagg ctgaattgat cgccctcact caggctctcg gatgggtaa | 420 |
| gggatattaa cgttaacact gacagcaggt acgcctttgc tactgtgcat gtacgtggag | 480 |

```
ccatctacca ggagcgtggg ctactcactc ggcaggtggc tgtnatccac tgtaaangga      540
catcaaaagg aaaacnnggc tgttgcccgt ggtaaccana aanctgatcn ncagctcnaa      600
gatgctgtgt tgactttcac tcncncctct aaaacttgct gcccacantc tcctttccca      660
accagatctg cctgacaatc cccatactca aaaaaaaaan aanactggcc ccgaacccna      720
accaataaaa acggggangg tnggtnganc nncctgaccc aaaaataatg gatccccgg       780 gctgcaggaa ttcaattcan ccttatcnat accccccaacn nggnggggg ggccngtncc      840 cattncccct ntattnattc tttnnccccc ccccggcnt ccttttttnaa ctcgtgaaag      900 ggaaaacctg ncttaccaan ttatcncctg gaccntcccc ttccncggtn gnttanaaaa      960
aaaagcccnc antcccntcc naaatttgca cngaaaggna aggaatttaa cctttatttt     1020
ttnntccttt antttgtnnn ccccctttta cccaggcgaa cngccatcnt ttaanaaaaa     1080
aaanagaang tttattttc cttngaacca tcccaatana aancacccgc ngggggaacgg     1140 ggnggnaggc cnctcacccc ctttntgtng gngggnc                             1177

<210> SEQ ID NO 9
<211> LENGTH: 1146
<212> TYPE: DNA
<213> ORGANISM: Homo sapiens
<220> FEATURE:
<221> NAME/KEY: misc_feature
<222> LOCATION: 1, 4, 5, 8, 9, 348, 706, 742, 745, 751, 758, 772, 793,
      819, 842, 846, 860, 866, 886, 889, 911, 939, 945, 955, 960, 982,
      999, 1002, 1005, 1009, 1010, 1033, 1047, 1049, 1055, 1058,
      1069, 1074, 1079, 1081, 1104, 1105, 1111, 1116, 1118
<223> OTHER INFORMATION: n = A,T,C or G
<221> NAME/KEY: misc_feature
<222> LOCATION: 1121, 1130, 1135, 1136, 1146
<223> OTHER INFORMATION: n = A,T,C or G

<400> SEQUENCE: 9
nccnnttnnt gatgttgtct ttttggcctc tctttggata ctttccctct cttcagaggt       60
gaaaagggtc aaaaggagct gttgacagtc atcccaggtg ggccaatgtg tccagagtac      120
agactccatc agtgaggtca aagcctgggg cttttcagag aagggaggat tatgggtttt      180
ccaattatac aagtcagaag tagaaagaag ggacataaac caggaagggg gtggagcact      240
catcacccag agggacttgt gcctctctca gtggtagtag aggggctact tcctcccacc      300
acggttgcaa ccaagaggca atgggtgatg agcctacagg ggacatancc gaggagacat      360
gggatgaccc taagggagta ggctggtttt aaggcggtgg gactgggtga gggaaactct      420
cctcttcttc agagagaagc agtacagggc gagctgaacc ggctgaaggt cgaggcgaaa      480
acacggtctg gctcaggaag accttggaag taaaattatg aatggtgcat gaatggagcc      540
atggaagggg tgctcctgac caaactcagc cattgatcaa tgttagggaa actgatcagg      600
gaagccggga atttcattaa caacccgcca cacagcttga acattgtgag gttcagtgac      660
ccttcaaggg gccactccac tccaactttg gccattctac tttgcnaaat ttccaaaact      720 tccttttta aggccgaatc cntantccct naaaaacnaa aaaaaatctg cnccctattct      780 ggaaaaggcc canccttac caggctggaa gaaatttttnc cttttttttt ttttttgaagg     840 cntttnttaa attgaacctn aattcncccc cccaaaaaaa aacccnccng ggggcggat       900 ttccaaaaac naattcccctt accaaaaaac aaaacccnc ccttnttccc ttccncccctn     960 ttcttttaat tagggagaga tnaagccccc caatttccng gnctngatnn gtttccccc      1020 cccccatttt ccnaaacttt tcccancna ggaancncc cttttttttg gtcngattna      1080
```

```
ncaaccttcc aaaccattt tccnnaaaaa ntttgntngg ngggaaaaan acctnntttt    1140 atagan                                                              1146

<210> SEQ ID NO 10
<211> LENGTH: 545
<212> TYPE: DNA
<213> ORGANISM: Homo sapiens

<400> SEQUENCE: 10
cttcattggg tacgggcccc ctcgaggtcg acggtatcga taagcttgat atcgaattcc     60
tgcagcccgg gggatccact agttctagag tcaggaagaa ccaccaacct tcctgatttt    120
tattggctct gagttctgag gccagttttc ttcttctgtt gagtatgcgg gattgtcagg    180
cagatctggc tgtggaaagg agactgtggg cagcaagttt agaggcgtga ctgaaagtca    240
cactgcatct tgagctgctg aatcagcttt ctggttacca cgggcaacag ccgtgttttc    300
cttttgatgt cctttacagt ggattacagc cacctgctga ggtgagtagc ccacgctcct    360
ggtagatggc tccacgtaca tgcacagtag caaaggcgta cctgctgtca gtgttaacgt    420
taatatcctt accccatcgg agagcctgag tgagggcgat caattcagcc cttttgtgct    480
gaggtgtttg ctggttaagc cctgaaccca caacacatct gtctccatgg taacagctgc    540
accgg                                                                545

<210> SEQ ID NO 11
<211> LENGTH: 196
<212> TYPE: DNA
<213> ORGANISM: Homo sapiens

<400> SEQUENCE: 11
tctcctaggc tgggcacagt ggctcatacc tgtaatcctg accgtttcag aggctcaggt     60 gggggggatcg cttgagccca agatttcaag actagtctgg gtaacatagt gagaccctat    120
ctctacgaaa aataaaaaaa atgagcctgg tgtagtggca caccagct gaggagggag    180 aatcgagcct aggaga                                                    196

<210> SEQ ID NO 12
<211> LENGTH: 388
<212> TYPE: DNA
<213> ORGANISM: Homo sapiens
<220> FEATURE:
<221> NAME/KEY: misc_feature
<222> LOCATION: 82, 162, 287
<223> OTHER INFORMATION: n = A,T,C or G

<400> SEQUENCE: 12
tctcctaggc ttgggggctc tgactagaaa ttcaaggaac ctgggattca agtccaactg     60
tgacaccaac ttacactgtg gnctccaata aactgcttct ttcctattcc ctctctatta    120
aataaaataa ggaaaacgat gtctgtgtat agccaagtca gntatcctaa aaggagatac    180
taagtgacat taaatatcag aatgtaaaac ctgggaacca ggttcccagc ctgggattaa    240
actgacagca agaagactga acagtactac tgtgaaaagc ccgaagnggc aatatgttca    300
ctctaccgtt gaaggatggc tgggagaatg aatgctctgt cccccagtcc caagctcact    360 tactataccct cctttatagc ctaggaga                                      388

<210> SEQ ID NO 13
<211> LENGTH: 337
<212> TYPE: DNA
<213> ORGANISM: Homo sapiens
```

<400> SEQUENCE: 13

| tagtagttgc ctataatcat gtttctcatt attttcacat tttattaacc aatttctgtt | 60 |
| taccctgaaa atatgaggg aaatatatga acagggagg caatgttcag ataattgatc | 120 |
| acaagatatg atttctacat cagatgctct ttcctttcct gtttatttcc ttttttattc | 180 |
| ggttgtgggg tcgaatgtaa tagctttgtt tcaagagaga gttttggcag tttctgtagc | 240 |
| ttctgacact gctcatgtct ccaggcatct atttgcactt taggaggtgt cgtgggagac | 300 |
| tgagaggtct attttttcca tatttgggca actacta | 337 |

<210> SEQ ID NO 14
<211> LENGTH: 571
<212> TYPE: DNA
<213> ORGANISM: Homo sapiens
<220> FEATURE:
<221> NAME/KEY: misc_feature
<222> LOCATION: 435, 441, 451, 456, 462, 479, 488, 489, 509, 568
<223> OTHER INFORMATION: n = A,T,C or G

<400> SEQUENCE: 14

| tagtagttgc catacagtgc ctttccattt atttaacccc cacctgaacg gcataaactg | 60 |
| agtgttcagc tggtgttttt tactgtaaac aataaggaga ctttgctctt catttaaacc | 120 |
| aaaatcatat ttcatatttt acgctcgagg gttttttaccg gttccttttt acactcctta | 180 |
| aaacagtttt taagtcgttt ggaacaagat attttttctt tcctggcagc ttttaacatt | 240 |
| atagcaaatt tgtgtctggg ggactgctgg tcactgtttc tcacagttgc aaatcaaggc | 300 |
| atttgcaacc aagaaaaaaa aatttttttg ttttatttga aactggaccg gataaacggt | 360 |
| gtttggagcg gctgctgtat atagtttaa atggtttatt gcacctcctt aagttgcact | 420 |
| tatgtggggg ggggnttttg natagaaagt ntttantcac anagtcacag ggactttnt | 480 |
| cttttggnna ctgagctaaa aagggctgnt tttcgggtgg gggcagatga aggctcacag | 540 |
| gaggcctttc tcttagaggg gggaactnct a | 571 |

<210> SEQ ID NO 15
<211> LENGTH: 548
<212> TYPE: DNA
<213> ORGANISM: Homo sapiens
<220> FEATURE:
<221> NAME/KEY: misc_feature
<222> LOCATION: 224, 291, 326, 376, 388, 394, 428, 433, 507, 514
<223> OTHER INFORMATION: n = A,T,C or G

<400> SEQUENCE: 15

| tatatattta ataacttaaa tatattttga tcacccactg gggtgataag acaatagata | 60 |
| taaaagtatt tccaaaaagc ataaaaccaa agtatcatac caaaccaaat tcatactgct | 120 |
| tcccccaccc gcactgaaac ttcaccttct aactgtctac ctaaccaaat tctacccttc | 180 |
| aagtctttgg tgcgtgctca ctactctttt ttttttttt tttnttttgg agatggagtc | 240 |
| tggctgtgca gcccaggggt ggagtacaat ggcacaacct cagctcactg naacctccgc | 300 |
| ctcccaggtt catgagattc tcctgnttca gccttcccag tagctgggac tacaggtgtg | 360 |
| catcaccatg cctggntaat cttttttngt tttngggtag agatgggggt tttacatgtt | 420 |
| ggccaggntg gtntcgaact cctgacctca agtgatccac ccacctcagg ctcccaaagt | 480 |
| gctaggatta cagacatgag ccactgngcc cagncctggt gcatgctcac ttctctaggc | 540 |
| aactacta | 548 |

```
<210> SEQ ID NO 16
<211> LENGTH: 638
<212> TYPE: DNA
<213> ORGANISM: Homo sapiens
<220> FEATURE:
<221> NAME/KEY: misc_feature
<222> LOCATION: 471, 488
<223> OTHER INFORMATION: n = A,T,C or G

<400> SEQUENCE: 16
ttccgttatg cacatgcaga atattctatc ggtacttcag ctattactca ttttgatggc      60
gcaatccgag cctatcctca agatgagtat ttagaaagaa ttgatttagc gatagaccaa     120
gctggtaagc actctgacta cacgaaattg ttcagatgtg atggatttat gacagttgat     180 cttggaaga gattattaag tgattatttt aaagggaatc cattaattcc agaatatctt      240
ggtttagctc aagatgatat agaaatagaa cagaaagaga ctacaaatga agatgtatca     300
ccaactgata ttgaagagcc tatagtagaa atgaattag ctgcatttat tagccttaca     360
catagcgatt ttcctgatga atcttatatt cagccatcga catagcatta cctgatgggc     420
aaccttacga ataatagaaa ctgggtgcgg ggctattgat gaattcatcc ncagtaaatt     480
tggatatnac aaaatataac tcgattgcat ttggatgatg aatactaaa tctggcaaaa     540 gtaactttgg agctactagt aacctctctt tttgagatgc aaaattttct tttagggttt     600
cttattctct actttacgga tattggagca taacggga                             638

<210> SEQ ID NO 17
<211> LENGTH: 286
<212> TYPE: DNA
<213> ORGANISM: Homo sapiens

<400> SEQUENCE: 17
actgatggat gtcgccggag gcgaggggcc ttatctgatg ctcggctgcc tgttcgtgat      60
gtgcgcggcg attgggctgt ttatctcaaa caccgccacg gcggtgctga tggcgcctat     120
tgccttagcg gcggcgaagt caatgggcgt ctcaccctat cctttgcca tggtggtggc      180 gatggcggct tcggcggcgt ttatgacccc ggtctcctcg ccggttaaca ccctggtgct     240
tggccctggc aagtactcat ttagcgattt tgtcaaaata ggcgtg                    286

<210> SEQ ID NO 18
<211> LENGTH: 262
<212> TYPE: DNA
<213> ORGANISM: Homo sapiens
<220> FEATURE:
<221> NAME/KEY: misc_feature
<222> LOCATION: 184, 234, 240
<223> OTHER INFORMATION: n = A,T,C or G

<400> SEQUENCE: 18
tcggtcatag cagccccttc ttctcaattt catctgtcac taccctggtg tagtatctca      60
tagccttaca ttttatagc ctcctccctg gtctgtcttt tgattttcct gcctgtaatc     120
catatcacac ataactgcaa gtaaacattt ctaaagtgtg ttatgctca tgtcactcct     180 gtgncaagaa atagtttcca ttaccgtctt aataaaattc ggatttgttc tttnctattn     240
tcactcttca cctatgaccg aa                                              262

<210> SEQ ID NO 19
<211> LENGTH: 261
<212> TYPE: DNA
<213> ORGANISM: Homo sapiens
```

<400> SEQUENCE: 19

```
tcggtcatag caaagccagt ggtttgagct ctctactgtg taaactccta aaccaaggcc      60
atttatgata aatggtggca ggatttttat tataaacatg tacccatgca aatttcctat     120
aactctgaga tatattcttc tacatttaaa caataaaaat aatctatttt taaaagccta     180
atttgcgtag ttaggtaaga gtgtttaatg agagggtata aggtataaat caccagtcaa     240
cgtttctctg cctatgaccg a                                               261
```

<210> SEQ ID NO 20
<211> LENGTH: 294
<212> TYPE: DNA
<213> ORGANISM: Homo sapiens
<220> FEATURE:
<221> NAME/KEY: misc_feature
<222> LOCATION: 194, 274, 283, 294
<223> OTHER INFORMATION: n = A,T,C or G

<400> SEQUENCE: 20

```
tacaacgagg cgacgtcggt aaaatcggac atgaagccac cgctggtctt ttcgtccgag      60
cgataggcgc cggccagcca gcggaacggt tgcccggatg gcgaagcgag ccggagttct     120
tcggactgag tatgaatctt gttgtgaaaa tactcgccgc cttcgttcga cgacgtcgcg     180
tcgaaatctt cganctcctt acgatcgaag tcttcgtggg cgacgatcgc ggtcagttcc     240
gccccaccga aatcatggtt gagccggatg ctgnccccga agncctcgtt tgtn           294
```

<210> SEQ ID NO 21
<211> LENGTH: 208
<212> TYPE: DNA
<213> ORGANISM: Homo sapiens
<220> FEATURE:
<221> NAME/KEY: misc_feature
<222> LOCATION: 116, 132, 140, 160, 164, 191, 197, 199
<223> OTHER INFORMATION: n = A,T,C or G

<400> SEQUENCE: 21

```
ttggtaaagg gcatggacgc agacgcctga cgtttggctg aaaatctttc attgattcgt      60
atcaatgaat aggaaaattc ccaaagaggg aatgtcctgt tgctcgccag tttttntgtt     120
gttctcatgg anaaggcaan gagctcttca gactattggn attntcgttc ggtcttctgc     180
caactagtcg ncttgcnang atcttcat                                        208
```

<210> SEQ ID NO 22
<211> LENGTH: 287
<212> TYPE: DNA
<213> ORGANISM: Homo sapiens
<220> FEATURE:
<221> NAME/KEY: misc_feature
<222> LOCATION: 1, 4, 25, 121, 168, 207, 212
<223> OTHER INFORMATION: n = A,T,C or G

<400> SEQUENCE: 22

```
nccnttgagc tgagtgattg agatntgtaa tggttgtaag ggtgattcag gcggattagg      60
gtggcgggtc acccggcagt gggtctcccg acaggccagc aggatttggg gcaggtacgg     120
ngtgcgcatc gctcgactat atgctatggc aggcgagccg tggaaggngg atcaggtcac     180
ggcgctggag cttttccacgg tccatgnatt gngatgctt ttctaggcgg ctgttgccaa     240
gcgtgatggt acgctggctg gagcattgat ttctggtgcc aagtgg                    287
```

<210> SEQ ID NO 23

```
<211> LENGTH: 204
<212> TYPE: DNA
<213> ORGANISM: Homo sapiens
<220> FEATURE:
<221> NAME/KEY: misc_feature
<222> LOCATION: 40, 121, 131, 162, 184, 197
<223> OTHER INFORMATION: n = A,T,C or G

<400> SEQUENCE: 23
ttgggtaaag ggagcaagga gaaggcatgg agaggctcan gctggtcctg gcctacgact    60
gggccaagct gtcgccgggg atggtggaga actgaagcgg gacctcctcg aggtcctccg   120
ncgttacttc nccgtccagg aggagggtct ttccgtggtc tnggaggagc ggggggagaa   180
gatnctcctc atggtcnaca tccc                                           204

<210> SEQ ID NO 24
<211> LENGTH: 264
<212> TYPE: DNA
<213> ORGANISM: Homo sapiens
<220> FEATURE:
<221> NAME/KEY: misc_feature
<222> LOCATION: 171, 206
<223> OTHER INFORMATION: n = A,T,C or G

<400> SEQUENCE: 24
tggattggtc aggagcgggt agagtggcac cattgagggg atattcaaaa atattatttt    60
gtcctaaatg atagttgctg agttttttctt tgacccatga gttatattgg agtttatttt  120
ttaactttcc aatcgcatgg acatgttaga cttattttct gttaatgatt nctattttta  180
ttaaattgga tttgagaaat tggttnttat tatatcaatt tttggtattt gttgagtttg  240
acattatagc ttagtatgtg acca                                           264

<210> SEQ ID NO 25
<211> LENGTH: 376
<212> TYPE: DNA
<213> ORGANISM: Homo sapiens
<220> FEATURE:
<221> NAME/KEY: misc_feature
<222> LOCATION: 103, 111, 192, 196, 199, 220, 224, 230, 251, 268, 283,
      317, 352, 370, 374
<223> OTHER INFORMATION: n = A,T,C or G

<400> SEQUENCE: 25
ttacaacgag gggaaactcc gtctctacaa aaattaaaaa attagccagg tgtggtggtg    60
tgcacccgca atcccagcta cttgggaggt tgagacacaa gantcaccta natgtgggag  120
gtcaaggttg catgagtcat gattgtgcca ctgcactcca gcctgggtga cagaccgaga  180
ccctgcctca anaganaang aataggaagt tcagaaatcn tggntgtggn gcccagcaat  240
ctgcatctat ncaacccctg caggcaangc tgatgcagcc tangttcaag agctgctgtt  300
tctggaggca gcagttnggg cttccatcca gtatcacggc cacactcgca cnagccatct  360
gtcctccgtn tgtnac                                                    376

<210> SEQ ID NO 26
<211> LENGTH: 372
<212> TYPE: DNA
<213> ORGANISM: Homo sapiens
<220> FEATURE:
<221> NAME/KEY: misc_feature
<222> LOCATION: 231, 312, 340
<223> OTHER INFORMATION: n = A,T,C or G

<400> SEQUENCE: 26
```

-continued

```
ttacaacgag gggaaactcc gtctctacaa aaattaaaaa attagccagg tgtggtggtg      60
tgcacctgta atcccagcta cttgggcggc tgagacacaa gaaccaccta aatgtgggag     120
ggtcaaggtt gcatgagtca tgatcgcgcc actgcactcc agcctgggtg acagactgag    180
accctgcctc aaagaaaaa gaataggaag ttcagaaacc ctgggtgtgg ngcccagcaa     240
tctgcattta aacaatccct gcaggcaatg ctgatgcagc ctaagttcaa gagctgctgt    300
tctggaggca gnagtaaggg cttccatcca gcatcacggn caacactgca aaagcacctg    360
tcctcgttgg ta                                                         372
```

<210> SEQ ID NO 27
<211> LENGTH: 477
<212> TYPE: DNA
<213> ORGANISM: Homo sapiens

<400> SEQUENCE: 27

```
ttctgtccac atctacaagt tttatttatt ttgtgggttt tcagggtgac taagtttttc     60
cctacattga aagagaagt tgctaaaagg tgcacaggaa atcatttttt taagtgaata    120
tgataatatg ggtccgtgct taatacaact gagacatatt tgttctctgt ttttttagag    180
tcacctctta aagtccaatc ccacaatggt gaaaaaaaa tagaaagtat tgttctacc     240 tttaaggaga ctgcagggat tctccttgaa acggagtat ggaatcaatc ttaaataaat    300
atgaaattgg ttggtcttct gggataagaa attcccaact cagtgtgctg aaattcacct    360 gactttttt gggaaaaaat agtcgaaaat gtcaatttgg tccataaaat acatgttact    420
attaaaagat atttaaagac aaattctttc agagctctaa gattggtgtg gacagaa      477
```

<210> SEQ ID NO 28
<211> LENGTH: 438
<212> TYPE: DNA
<213> ORGANISM: Homo sapiens
<220> FEATURE:
<221> NAME/KEY: misc_feature
<222> LOCATION: 4, 16, 30, 255, 413
<223> OTHER INFORMATION: n = A,T,C or G

<400> SEQUENCE: 28

```
tctncaacct cttgantgtc aaaaaccttn taggctatct ctaaaagctg actggtattc     60
attccagcaa aatccctcta gttttttggag tttccttta ctatctgggg ctgcctgagc    120
cacaaatgcc aaattaagag catggctatt tcgggggct gacaggtcaa aagggggtgta   180 aatccgataa gcctcctgga ggtgctctaa aaacactcct ggtgactcat catgcccctg    240
gacgacttca atcgncttag acaagtttat aggtttctgg gcagctccct gaatacccac    300
gaggagatac cggtggaaat cgtcaaaagt tctccctcca cttgagaaat ttgggtccca    360
attaggtccc aattgggtct ctaatcacta ttcctctagc ttcctcctcc ggnctattgg    420
ttgatgtgag gttgaaga                                                   438
```

<210> SEQ ID NO 29
<211> LENGTH: 620
<212> TYPE: DNA
<213> ORGANISM: Homo sapiens
<220> FEATURE:
<221> NAME/KEY: misc_feature
<222> LOCATION: 391, 481, 483, 490, 497, 510, 527, 532, 540, 545, 593,
       612
<223> OTHER INFORMATION: n = A,T,C or G

<400> SEQUENCE: 29

```
aagagggtac cagccccaag ccttgacaac ttccataggg tgtcaagcct gtgggtgcac     60
agaagtcaaa aattgagttt tgggatcctc agcctagatt tcagaggata taaagaaaca    120
cctaacacct agatattcag acaaaagttt actacaggga tgaagctttc acggaaaacc    180
tctactagga aagtacagaa gagaaatgtg ggtttggagc ccccaaacag aatcccctct    240
agaacactgc ctaatgaaac tgtgagaaga tggccactgt catccagaca ccagaatgat    300
agacccacca aaaacttatg ccatattgcc tataaaacct acagacactc aatgccagcc    360
ccatgaaaaa aaaactgaga agaagactgt ncectacaat gccaccggag cagaactgcc    420
ccaggccatg aagcacagc tcttatatca atgtgacctg gatgttgaga catggaatcc    480
nangaaatcn ttttaanact tccacggttn aatgactgcc ctattanatt cngaacttan    540
atccnggcct gtgacctctt tgctttggcc attcccctt tttggaatgg ctnttttttt    600
cccatgcctg tncctcetta                                                620
```

<210> SEQ ID NO 30
<211> LENGTH: 100
<212> TYPE: DNA
<213> ORGANISM: Homo sapiens

<400> SEQUENCE: 30

```
ttacaacgag ggggtcaatg tcataaatgt cacaataaaa caatctcttc tttttttttt     60
tttttttttt tttttttttt tttttttttt tttttttttt                         100
```

<210> SEQ ID NO 31
<211> LENGTH: 762
<212> TYPE: DNA
<213> ORGANISM: Homo sapiens
<220> FEATURE:
<221> NAME/KEY: misc_feature
<222> LOCATION: 626, 652, 662, 715, 736
<223> OTHER INFORMATION: n = A,T,C or G

<400> SEQUENCE: 31

```
tagtctatgc gccggacaga gcagaattaa attggaagtt gccctccgga ctttctaccc     60
acactcttcc tgaaaagaga aagaaaagag gcaggaaaga ggttaggatt tcattttcaa    120
gagtcagcta attaggagag cagagtttag acagcagtag gcaccccatg atacaaacca    180
tggacaaagt ccctgtttag taactgccag acatgatcct gctcaggttt tgaaatctct    240
ctgcccataa aagatggaga gcaggagtgc catccacatc aacacgtgtc caagaaagag    300
tctcagggag acaagggtat caaaaaacaa gattcttaat gggaaggaaa tcaaaccaaa    360
aaattagatt tttctctaca tatatataat atacagatat ttaacacatt attccagagg    420
tggctccagt ccttggggct tgagagatgg tgaaaacttt tgttccacat taacttctgc    480
tctcaaattc tgaagtatat cagaatggga caggcaatgt tttgctccac actggggcac    540
agacccaaat ggttctgtgc cgaagaaga gaagcccgaa agacatgaag gatgcttaag    600
gggggttggg aaagccaaat tggtantatc ttttcctcct gcctgtgttc cngaagtctc    660
cnctgaagga attcttaaaa ccctttgtga ggaaatgccc ccttaccatg acaantggtc    720
ccattgcttt tagggngatg gaaacaccaa gggttttgat cc                       762
```

<210> SEQ ID NO 32
<211> LENGTH: 276
<212> TYPE: DNA
<213> ORGANISM: Homo sapiens

<400> SEQUENCE: 32

```
tagtctatgc gtgtattaac ctcccctccc tcagtaacaa ccaaagaggc aggagctgtt    60
attaccaacc ccattttaca gatgcatcaa taatgacaga gaagtgaagt gacttgcgca   120
cacaaccagt aaattggcag agtcagattt gaatccatgg agtctggtct gcactttcaa   180
tcaccgaata ccctttctaa gaaacgtgtg ctgaatgagt gcatggataa atcagtgtct   240
actcaacatc tttgcctaga tatcccgcat agacta                             276

<210> SEQ ID NO 33
<211> LENGTH: 477
<212> TYPE: DNA
<213> ORGANISM: Homo sapiens

<400> SEQUENCE: 33
tagtagttgc caaatatttg aaaatttacc cagaagtgat tgaaaacttt ttggaaacaa    60
aaacaaataa agccaaaagg taaaataaaa atatctttgc actctcgtta ttacctatcc   120
ataacttttt caccgtaagc tctcctgctt gttagtgtag tgtggttata ttaaactttt   180
tagttattat tttttattca cttttccact agaaagtcat tattgattta gcacacatgt   240
tgatctcatt tcatttttc tttttatagg caaaatttga tgctatgcaa caaaaatact   300
caagcccatt atctttttc cccccgaaat ctgaaaattg caggggacag agggaagtta   360
tcccattaaa aaattgtaaa tatgttcagt ttatgtttaa aaatgcacaa aacataagaa   420
aattgtgttt acttgagctg ctgattgtaa gcagttttat ctcagggca actacta       477

<210> SEQ ID NO 34
<211> LENGTH: 631
<212> TYPE: DNA
<213> ORGANISM: Homo sapiens

<400> SEQUENCE: 34
tagtagttgc caattcagat gatcagaaat gctgctttcc tcagcattgt cttgttaaac    60
cgcatgccat ttggaacttt ggcagtgaga agccaaaagg aagaggtgaa tgacatatat   120
atatatatat attcaatgaa agtaaaatgt atatgctcat atactttcta gttatcagaa   180
tgagttaagc tttatgccat tgggctgctg catattttaa tcagaagata aagaaaatc    240 tgggcatttt tagaatgtga tacatgtttt tttaaaactg ttaaatatta tttcgatatt   300
tgtctaagaa ccggaatgtt cttaaaattt actaaaacag tattgtttga ggaagagaaa   360
actgtactgt ttgccattat tacagtcgta caagtgcatg tcaagtcacc cactctctca   420
ggcatcagta tccacctcat agctttacac attttgacgg ggaatattgc agcatcctca   480
ggcctgacat ctgggaaagg ctcagatcca cctactgctc cttgctcgtt gatttgtttt   540
aaaatattgt gcctggtgtc acttttaagc cacagccctg cctaaaagcc agcagagaac   600
agaacccgca ccattctata ggcaactact a                                   631

<210> SEQ ID NO 35
<211> LENGTH: 578
<212> TYPE: DNA
<213> ORGANISM: Homo sapiens

<400> SEQUENCE: 35
tagtagttgc catcccatat tacagaaggc tctgtataca tgacttattt ggaagtgatc    60
tgttttctct ccaaacccat ttatcgtaat ttcaccagtc ttggatcaat cttggtttcc   120
actgatacca tgaaacctac ttggagcaga cattgcacag ttttctgtgg taaaaactaa   180
```

```
aggtttatttt gctaagctgt catcttatgc ttagtatttt ttttttacag tggggaattg    240
ctgagattac attttgttat tcattagata ctttgggata acttgacact gtcttctttt    300
tttcgctttt aattgctatc atcatgcttt tgaaacaaga acacattagt cctcaagtat    360
tacataagct tgcttgttac gcctggtggt ttaaaggact atctttggcc tcaggttcac    420
aagaatgggc aaagtgtttc cttatgttct gtagttctca ataaaagatt gccagggggcc   480 gggtactgtg gctcgcactg taatcccagc actttgggaa gctgaggctg gcggatcatg    540
ttagggcagg tgttcgaaac cagcctgggc aactacta                            578
```

```
<210> SEQ ID NO 36
<211> LENGTH: 583
<212> TYPE: DNA
<213> ORGANISM: Homo sapiens

<400> SEQUENCE: 36
tagtagttgc ctgtaatccc agcaactcag gaggctgggg caggagaatc agttgaacct    60
gggaggcaga agttgtaatt agcaaagatc gcaccattgc acttcagcct gggcaacaag   120
agtgagattc catctcaaaa acaaaaaaaa gaaaaagaaa agaaaaggaa aaacgtata    180 aacccagcca aaacaaaatg atcattcttt taataagcaa gactaattta atgtgtttat   240
ttaatcaaag cagttgaatc ttctgagtta ttggtgaaaa tacccatgta gttaatttag   300
ggttcttact tgggtgaacg tttgatgttc acaggttata aaatggttaa caaggaaaat   360
gatgcataaa gaatcttata aactactaaa aataaataaa atataaatgg ataggtgcta   420
tggatggagt ttttgtgtaa tttaaaatct tgaagtcatt ttggatgctc attggttgtc   480
tggtaatttc cattaggaaa aggttatgat atggggaaac tgtttctgga aattgcggaa   540
tgtttctcat ctgtaaaatg ctagtatctc agggcaacta cta                     583
```

```
<210> SEQ ID NO 37
<211> LENGTH: 716
<212> TYPE: DNA
<213> ORGANISM: Homo sapiens
<220> FEATURE:
<221> NAME/KEY: misc_feature
<222> LOCATION: 15, 669, 673, 678, 686, 704
<223> OTHER INFORMATION: n = A,T,C or G

<400> SEQUENCE: 37
gatctactag tcatntggat tctatccatg gcagctaagc ctttctgaat ggattctact    60
gctttcttgt tctttaatcc agaccctat atatgtttat gttcacaggc agggcaatgt   120
ttagtgaaaa caattctaaa tttttttattt tgcattttca tgctaatttc cgtcacactc   180
cagcaggctt cctgggagaa taaggagaaa tacagctaaa gacattgtcc ctgcttactt   240
acagcctaat ggtatgcaaa accacttcaa taaagtaaca ggaaaagtac taaccaggta   300
gaatggacca aaactgatat agaaaaatca gaggaagaga ggaacaaata tttactgagt   360
cctagaatgt acaaggcttt ttaattacat attttatgta aggcctgcaa aaaacaggtg   420
agtaatcaac atttgtccca ttttacatat aaggaaactg aagcttaaat tgaataattt   480
aatgcataga ttttatagtt agaccatgtt caggtcccta tgttatactt actagctgta   540
tgaatatgag aaaataattt tgttattttc ttggcatcag tattttcatc tgcaaaataa   600
agctaaagtt atttagcaaa cagtcagcat agtgcctgat acatagtagg tgctccaaac   660
atgattacnc tantattngg tattanaaaa atccaatata ggcntggata aaaccg       716
```

-continued

<210> SEQ ID NO 38
<211> LENGTH: 688
<212> TYPE: DNA
<213> ORGANISM: Homo sapiens
<220> FEATURE:
<221> NAME/KEY: misc_feature
<222> LOCATION: 260
<223> OTHER INFORMATION: n = A,T,C or G

<400> SEQUENCE: 38

```
ttctgtccac atatcatccc actttaattg ttaatcagca aaactttcaa tgaaaaatca      60
tccattttaa ccaggatcac accaggaaac tgaaggtgta tttttttta ccttaaaaaa     120
aaaaaaaaaa accaaacaaa ccaaaacaga ttaacagcaa agagttctaa aaaatttaca    180
tttctcttac aactgtcatt cagagaacaa tagttcttaa gtctgttaaa tcttggcatt    240
aacagagaaa cttgatgaan agttgtactt ggaatattgt ggatttttt tttgtctaa     300
tctcccccta ttgttttgcc aacagtaatt taagtttgtg tggaacatcc ccgtagttga    360
agtgtaaaca atgtatagga aggaatatat gataagatga tgcatcacat atgcattaca    420
tgtagggacc ttcacaactt catgcactca gaaaacatgc ttgaagagga ggagaggacg    480
gcccagggtc accatccagg tgccttgagg acagagaatg cagaagtggc actgttgaaa    540
tttagaagac catgtgtgaa tggtttcagg cctgggatgt ttgccaccaa gaagtgcctc    600
cgagaaattt ctttcccatt tggaatacag ggtggcttga tgggtacggt gggtgaccca    660
acgaagaaaa tgaaattctg ccctttcc                                       688
```

<210> SEQ ID NO 39
<211> LENGTH: 585
<212> TYPE: DNA
<213> ORGANISM: Homo sapiens
<220> FEATURE:
<221> NAME/KEY: misc_feature
<222> LOCATION: 14, 15, 24, 53, 108, 135, 465, 477, 495, 499, 504, 517,
      530, 580, 581
<223> OTHER INFORMATION: n = A,T,C or G

<400> SEQUENCE: 39

```
tagtagttgc cgcnnaccta aaanttggaa agcatgatgt ctaggaaaca tantaaaata      60
gggtatgcct atgtgctaca gagagatgtt agcatttaaa gtgcatantt ttatgtattt    120
tgacaaatgc atatncctct ataatccaca actgattacg aagctattac aattaaaaag    180
tttggccggg cgtggtgggc ggtggctgac gcctgtaatc ccagcacttt gggaggccga    240
ggcacgcgga tcacgaggtc gggagttcaa gaccatcctg gctaacacgg tgaaagtcca    300
tctctactaa aaatacgaaa aaattacccc ggcgtggtgg cgggcgcctg tagtcccagc    360
tactccggag gctgaggcag gagaatggcg tgaacccagg acacgagct tgcagtgtgc     420
caacatcacg tcactgccct ccagcctggg ggacaggaac aagantcccg tcctcanaaa    480
agaaaaatac tactnatant ttcnacttta ttttaantta cacagaactn cctcttggta    540
cccccttacc attcatctca cccacctcct atagggcacn nctaa                   585
```

<210> SEQ ID NO 40
<211> LENGTH: 475
<212> TYPE: DNA
<213> ORGANISM: Homo sapiens

<400> SEQUENCE: 40

```
tctgtccaca ccaatcttag aagctctgaa aagaatttgt ctttaaatat cttttaatag     60
taacatgtat tttatggacc aaattgacat tttcgactgt ttttttccaaa aaagtcaggt   120
```

```
gaatttcagc acactgagtt gggaatttct tatcccagaa gaccaaccaa tttcatattt      180
atttaagatt gattccatac tccgttttca aggagaatcc ctgcagtctc cttaaaggta      240
gaacaaatac ttcctatttt tttttcacca ttgtgggatt ggactttaag aggtgactct      300
aaaaaaacag agaacaaata tgtctcagtt gtattaagca cggacccata ttatcatatt      360
cacttaaaaa aatgatttcc tgtgcacctt ttggcaactt ctcttttcaa tgtagggaaa      420
aacttagtca ccctgaaaac ccacaaaata aataaaactt gtagatgtgg acaga           475
```

```
<210> SEQ ID NO 41
<211> LENGTH: 423
<212> TYPE: DNA
<213> ORGANISM: Homo sapiens

<400> SEQUENCE: 41
taagagggta catcgggtaa gaacgtaggc acatctagag cttagagaag tctggggtag       60
gaaaaaaatc taagtattta taagggtata ggtaacattt aaaagtaggg ctagctgaca      120
ttatttagaa agaacacata cggagagata agggcaaagg actaagacca gaggaacact      180
aatatttagt gatcacttcc attcttggta aaaatagtaa cttttaagtt agcttcaagg      240 aagattttg gccatgatta gttgtcaaaa gttagttctc ttgggtttat attactaatt       300
ttgttttaag atccttgtta gtgctttaat aaagtcatgt tatatcaaac gctctaaaac      360
attgtagcat gttaaatgtc acaatatact taccatttgt tgtatatggc tgtaccctct      420
cta                                                                     423
```

```
<210> SEQ ID NO 42
<211> LENGTH: 527
<212> TYPE: DNA
<213> ORGANISM: Homo sapiens
<220> FEATURE:
<221> NAME/KEY: misc_feature
<222> LOCATION: 470, 475, 515, 522
<223> OTHER INFORMATION: n = A,T,C or G

<400> SEQUENCE: 42
tctcctaggc taatgtgtgt gtttctgtaa aagtaaaaag ttaaaaattt taaaaataga       60
aaaaagctta tagaataaga atatgaagaa agaaaatatt tttgtacatt tgcacaatga      120
gtttatgttt taagctaagt gttattacaa aagagccaaa aaggttttaa aaattaaaac      180
gtttgtaaag ttacagtacc cttatgttaa tttataattg aagaaagaaa aactttttt       240 tataaatgta gtgtagccta agcatacagt atttataaag tctggcagtg ttcaataatg      300
tcctaggcct tcacattcac tcactgactc acccagagca acttccagtc ctgtaagctc      360
cattcgtggt aagtgcccta tacaggtgca ccatttattt tacagtattt ttactgtacc      420
ttctctatgt ttccatatgt ttcgatatac aaataccact ggttactatn gcccnacagg      480
taattccagt aacacggcct gtatacgtct ggtancccta gngaaga                    527
```

```
<210> SEQ ID NO 43
<211> LENGTH: 331
<212> TYPE: DNA
<213> ORGANISM: Homo sapiens

<400> SEQUENCE: 43
tcttcaacct cgtaggacaa ctctcatatg cctgggcact attttaggt tactaccttg        60 gctgcccttc tttaagaaaa aaaaaagaag aaaaaagaac ttttccacaa gtttctcttc      120
```

```
ctctagttgg aaaattagag aaatcatgtt tttaattttg tgttatttca gatcacaaat      180
tcaaacactt gtaaacatta agcttctgtt caatcccctg ggaagaggat tcattctgat      240
atttacggtt caaaagaagt tgtaatattg tgcttggaac acagagaacc agttattaac      300
ttcctactac tattatataa taaataataa c                                     331
```

<210> SEQ ID NO 44
<211> LENGTH: 592
<212> TYPE: DNA
<213> ORGANISM: Homo sapiens
<220> FEATURE:
<221> NAME/KEY: misc_feature
<222> LOCATION: 473
<223> OTHER INFORMATION: n = A,T,C or G

<400> SEQUENCE: 44

```
ggcttagtag ttgccaggca aaatarcgtt gattctcctc aggagccacc cccaacaccc       60
ctgtttgctt ctagacctat acctagacta aagtcccagc agaccctag aggtgaggtt       120 cagagtgacc cttgaggaga tgtgctacac tagaaaagaa ctgcttgagt tttctaattt      180
atataagcag aaatctggag aagagtcata ggaatggata ttaagggtgt gagataatgg      240
cggaaggaat atagagttgg atcaggctgg acttattgat ttgaacccac taagtagaga      300
ttctgctttt gatgttgcag ctcagggagt taaaaaggt tttaatggtt ctaatagttt      360
atttgcttgg ttagctgaaa tatggataaa agatggccca ctgtgagcaa gctggaaatg      420
cctgatctct ctcagtttaa tgtagaggaa gggatccaaa agtttaggga ganttggatg      480
ctggraktgg attggtcact ttgrgaccta cccwtcccag ctgggagggt ccagaagata      540
cacccttgac caacgctttg cgaaatggat ttgtgatggc ggcaactact aa              592
```

<210> SEQ ID NO 45
<211> LENGTH: 567
<212> TYPE: DNA
<213> ORGANISM: Homo sapiens
<220> FEATURE:
<221> NAME/KEY: misc_feature
<222> LOCATION: 522, 561, 566
<223> OTHER INFORMATION: n = A,T,C or G

<400> SEQUENCE: 45

```
ggcttagtag ttgccattgc gagtgcttgc tcaacgagcg ttgaacatgg cggattgtct       60
agattcaacg gatttgagtt ttaccagcaa agcgaaccaa gcgcggccca gagaattatg      120
ggttggttgg ctttgaaaag atggaaatcc tgtaggccta gtcagaaaag ccttcttgca      180
gaacagttgg ttctcgggcg aacgctcatc aagatgccca ttggaaaggc tagcgtgtat      240
ttgggagagc ctgatagcgt gtcttctgat gatgtttgtg cttggacagt gacaaaagat      300
atgcaaagca gtccgaact agacgtcaag cttcgtgagc aaattattgt agactcctac      360
ttatactgtg aggaatgata gccaagggtg gggactttaa gactaaggtg gttttgtactt     420 gcgccgatga tcccaggcag aaagamctga tcgctagttt tatacgggca actactaagc      480
cgaattccag cacactggcg gccgttacta attggatccg anctcggtac cagcttgatg      540
catascttga gttwtctata ntgtcnc                                          567
```

<210> SEQ ID NO 46
<211> LENGTH: 908
<212> TYPE: DNA
<213> ORGANISM: Homo sapiens
<220> FEATURE:
<221> NAME/KEY: misc_feature
<222> LOCATION: 21, 23, 24, 27, 29, 34
<223> OTHER INFORMATION: n = A,T,C or G

<400> SEQUENCE: 46

| | | | | | |
|---|---|---|---|---|---|
| gagcgaaaga | ccgagggcag | ngnntangng | cgangaagcg | gagagggcca | aaaagcaacc | 60 |
| gctttccccg | ggggtgccg | attcattaag | gcaggtggag | gacaggtttc | ccgatggaag | 120 |
| gcggcagggg | cgcaagcaat | taatgtgagt | aggccattca | ttagcacccg | ggcttaacat | 180 |
| ttaagcttcg | ggttggtatg | tggtgggaat | tgtgagcgga | taacaatttc | acacaggaaa | 240 |
| cagctatgac | catgattacg | ccaagctatt | taggtgacat | tatagaataa | ctcaagttat | 300 |
| gcatcaagct | tggtaccgag | ttcggatcca | ctagtaacgg | ccgccagtgt | gtggaattcg | 360 |
| gcttagtagt | tgccgaccat | ggagtgctac | ctaggctaga | atacctgagy | tcctccctag | 420 |
| cctcactcac | attaaattgt | atcttttcta | cattagatgt | cctcagcgcc | ttatttctgc | 480 |
| tggacwatcg | ataaattaat | cctgatagga | tgatagcagc | agattaatta | ctgagagtat | 540 |
| gttaatgtgt | catccctcct | atataacgta | tttgcatttt | aatggagcaa | ttctggagat | 600 |
| aatccctgaa | ggcaaaggaa | tgaatcttga | gggtgagaaa | gccagaatca | gtgtccagct | 660 |
| gcagttgtgg | gagaaggtga | tattatgtat | gtctcagaag | tgacaccata | tgggcaacta | 720 |
| ctaagcccga | attccagcac | actggcgggc | gttactaatg | gatccgagct | cggtaccaag | 780 |
| cttgatgcat | agcttgagta | tctatagtgt | cactaaatag | cctggcgtta | tcatggtcat | 840 |
| agctgttttcc | tgtgtgaaat | tgttatccgc | tcccaattcc | ccccaccata | cgagccggaa | 900 |
| cataaagt | | | | | | 908 |

<210> SEQ ID NO 47
<211> LENGTH: 480
<212> TYPE: DNA
<213> ORGANISM: Homo sapiens
<220> FEATURE:
<221> NAME/KEY: misc_feature
<222> LOCATION: 408, 461
<223> OTHER INFORMATION: n = A,T,C or G

<400> SEQUENCE: 47

| | | | | | |
|---|---|---|---|---|---|
| tgccaacaag | gaaagttttta | aatttcccct | tgaggattct | tggtgatcat | caaattcagt | 60 |
| ggttttttaag | gttgttttct | gtcaaataac | tctaacttta | agccaaacag | tatatggaag | 120 |
| cacagataka | atattacaca | gataaaagag | gagttgatct | aaagtaraga | tagttggggg | 180 |
| ctttaatttc | tggaacctag | gtctccccat | cttcttctgt | gctgaggaac | ttcttggaag | 240 |
| cggggattct | aaagttcttt | ggaagacagt | ttgaaaacca | ccatgttgtt | ctcagtacct | 300 |
| ttatttttaa | aaagtaggtg | aacattttga | gagagaaaag | ggcttggttg | agatgaagtc | 360 |
| ccccccccc | ctttttttttt | ttttagctga | aatagatacc | ctatgttnaa | rgaarggatt | 420 |
| attatttacc | atgccaytar | scacatgctc | tttgatgggc | nyctccstac | cctccttaag | 480 |

<210> SEQ ID NO 48
<211> LENGTH: 591
<212> TYPE: DNA
<213> ORGANISM: Homo sapiens

<400> SEQUENCE: 48

| | | | | | |
|---|---|---|---|---|---|
| aagagggtac | cgagtggaat | tccgcttca | ctagtctggt | gtggctagtc | ggtttcgtgg | 60 |
| tggccaacat | tacgaacttc | caactcaacc | gttcttggac | gttcaagcgg | gagtaccggc | 120 |
| gaggatggtg | gcgtgaattc | tggcctttct | ttgccgtggg | atcggtagcc | gccatcatcg | 180 |

```
gtatgtttat caagatcttc tttactaacc cgacctctcc gatttacctg cccgagccgt        240
ggtttaacga ggggagggg atccagtcac gcgagtactg gtcccagatc ttcgccatcg        300
tcgtgacaat gccctatcaac ttcgtcgtca ataagttgtg gaccttccga acggtgaagc      360
actccgaaaa cgtccggtgg ctgctgtgcg gtgactccca aaatcttgat aacaacaagg        420
taaccgaatc gcgctaagga acccggcat ctcgggtact ctgcatatgc gtacccctta        480
agccgaattc cagcacactg gcggccgtta ctaattggat ccgaactccg taaccaagcc        540
tgatgcgtaa cttgagttat tctatagtgt ccctaaaata acctggcgtt a                591

<210> SEQ ID NO 49
<211> LENGTH: 454
<212> TYPE: DNA
<213> ORGANISM: Homo sapiens

<400> SEQUENCE: 49
aagagggtac ctgccttgaa atttaaatgt ctaaggaaar tgggagatga ttaagagttg        60
gtgtggcyta gtcacaccaa atgtatttta ttacatcctg ctcctttcta gttgacagga      120
aagaaagctg ctgtggggaa aggagggata aatactgaag ggatttacta aacaaatgtc      180
catcacagag ttttcctttt ttttttttg agacagagtc ttgctctgtc acccaggctg        240
gaatgaagwg gtatgatctc agttgaatgc aacctctacc tcctaggttc aagcgattct      300
catgcctcag cctcctgagc agctgggact ataggcgcat gctaccatgc caggctaatt      360
tttatatttt tattagagac ggggtgttgc catgttggcc aggcaggtct cgaactcctg      420
ggcctcagat gatctgcccc accgtaccct ctta                                    454

<210> SEQ ID NO 50
<211> LENGTH: 463
<212> TYPE: DNA
<213> ORGANISM: Homo sapiens

<400> SEQUENCE: 50
aagagggtac caaaaaaaag aaaaaggaaa aaagaaaaa caacttgtat aaggctttct        60
gctgcataca gcttttttt tttaaataaa tggtgccaac aaatgttttt gcattcacac      120
caattgctgg ttttgaaatc gtactcttca aaggtatttg tgcagatcaa tccaatagtg      180
atgccccgta ggttttgtgg actgcccacg ttgtctacct tctcatgtag gagccattga      240
gagactgttt ggacatgcct gtgttcatgt agccgtgatg tccggggggcc gtgtacatca      300 tgttaccgtg gggtggggtc tgcattggct gctgggcata tggctgggtg cccatcatgc      360
ccatctgcat ctgcataggg tattgggggcg tttgatccat atagccatga ttgctgtggt      420
agccactgtt catcattggc tgggacatgc tgttaccctc tta                         463

<210> SEQ ID NO 51
<211> LENGTH: 399
<212> TYPE: DNA
<213> ORGANISM: Homo sapiens

<400> SEQUENCE: 51
cttcaacctc ccaaagtgct gggattacag gactgagcca ccacgctcag cctaagcctc        60 ttttcacta ccctctaagc gatctaccac agtgatgagg ggctaaagag cagtgcaatt        120
tgattacaat aatggaactt agatttatta attaacaatt tttccttagc atgttggttc      180
cataattatt aagagtatgg acttacttag aaatgagctt tcattttaag aatttcatct      240
ttgaccttct ctattagtct gagcagtatg acactatacg tattttattt aactaaccta      300
```

```
ccttgagcta ttactttta aaaggctata tacatgaatg tgtattgtca actgtaaagc    360
cccacagtat ttaattatat catgatgtct ttgaggttg                         399
```

<210> SEQ ID NO 52
<211> LENGTH: 392
<212> TYPE: DNA
<213> ORGANISM: Homo sapiens

<400> SEQUENCE: 52

```
cttcaacctc aatcaacctt ggtaattgat aaaatcatca cttaactttc tgatataatg    60
gcaataatta tctgagaaaa aaagtggtg aaagattaaa cttgcatttc tctcagaatc    120
ttgaaggata tttgaataat tcaaaagcgg aatcagtagt atcagccgaa gaaactcact    180
tagctagaac gttggaccca tggatctaag tccctgccct tccactaacc agctgattgg    240
ttttgtgtaa acctcctaca cgcttgggct tggtcgcctc atttgtcaaa gtaaaggctg    300
aaataggaag ataatgaacc gtgtcttttt ggtctctttt ccatccatta ctctgatttt    360
acaaagaggc ctgtattccc ctggtgaggt tg                                 392
```

<210> SEQ ID NO 53
<211> LENGTH: 179
<212> TYPE: DNA
<213> ORGANISM: Homo sapiens
<220> FEATURE:
<221> NAME/KEY: misc_feature
<222> LOCATION: 135, 143, 179
<223> OTHER INFORMATION: n = A,T,C or G

<400> SEQUENCE: 53

```
ttcgggtgat gcctcctcag gctacagtga agactggatt acagaaaggt gccagcgaga    60
tttcagattc ctgtaaacct ctaaagaaaa ggagtcgcgc ctcaactgat gtagaaatga    120
ctagttcagc atacngagac acntctgact ccgattctag aggactgagt gacctgcan    179
```

<210> SEQ ID NO 54
<211> LENGTH: 112
<212> TYPE: DNA
<213> ORGANISM: Homo sapiens
<220> FEATURE:
<221> NAME/KEY: misc_feature
<222> LOCATION: 31, 49, 54, 55, 75, 91, 107
<223> OTHER INFORMATION: n = A,T,C or G

<400> SEQUENCE: 54

```
ttcgggtgat gcctcctcag gctacatcat natagaagca aagtagaana atcnngtttg    60
tgcattttcc cacanacaaa attcaaatga ntggaagaaa ttggganagt at           112
```

<210> SEQ ID NO 55
<211> LENGTH: 225
<212> TYPE: DNA
<213> ORGANISM: Homo sapiens

<400> SEQUENCE: 55

```
tgagcttccg cttctgacaa ctcaatagat aatcaaagga caactttaac agggattcac    60
aaaggagtat atccaaatgc caataaacat ataaaaagga attcagcttc atcatcatca    120
gaagwatgca aattaaaacc ataatgagaa accactatgt cccactagaa tagataaaat    180
cttaaaagac tggtaaaacc aagtgttggt aaggcaagag gagca                  225
```

<210> SEQ ID NO 56

<211> LENGTH: 175
<212> TYPE: DNA
<213> ORGANISM: Homo sapiens

<400> SEQUENCE: 56

```
gctcctcttg ccttaccaac acattctcaa aaacctgtta gagtcctaag cattctcctg      60
ttagtattgg gattttaccc ctgtcctata aagatgttat gtaccaaaaa tgaagtggag     120
ggccataccc tgagggaggg gagggatctc tagtgttgtc agaagcggaa gctca          175
```

<210> SEQ ID NO 57
<211> LENGTH: 223
<212> TYPE: DNA
<213> ORGANISM: Homo sapiens

<400> SEQUENCE: 57

```
agccatttac cacccatgga tgaatggatt ttgtaattct agctgttgta ttttgtgaat      60
ttgttaattt tgttgttttt ctgtgaaaca catacattgg atatgggagg taaggagtg     120
tcccagttgc tcctggtcac tcctttata gccattactg tcttgtttct tgtaactcag     180
gttaggtttt ggtctctctt gctccactgc aaaaaaaaaa aaa                      223
```

<210> SEQ ID NO 58
<211> LENGTH: 211
<212> TYPE: DNA
<213> ORGANISM: Homo sapiens

<400> SEQUENCE: 58

```
gttcgaaggt gaacgtgtag gtagcggatc tcacaactgg ggaactgtca aagacgaatt      60
aactgacttg gatcaatcaa atgtgactga ggaaacacct gaaggtgaag aacatcatcc     120
agtggcagac actgaaaata aggagaatga agttgaagag gtaaagaggg agggtccaaa     180
agagatgact ttggatgggt ggtaaatggc t                                    211
```

<210> SEQ ID NO 59
<211> LENGTH: 208
<212> TYPE: DNA
<213> ORGANISM: Homo sapiens

<400> SEQUENCE: 59

```
gctcctcttg ccttaccaac tttgcaccca tcatcaacca tgtggccagg tttgcagccc      60
aggctgcaca tcaggggact gcctcgcaat acttcatgct gttgctgctg actgatggtg     120
ctgtgacgga tgtggaagcc acacgtgagg ctgtggtgcg tgcctcgaac ctgcccatgt     180
cagtgatcat tatgggtggt aaatggct                                        208
```

<210> SEQ ID NO 60
<211> LENGTH: 171
<212> TYPE: DNA
<213> ORGANISM: Homo sapiens

<400> SEQUENCE: 60

```
agccatttac cacccatact aaattctagt tcaaactcca acttcttcca taaaacatct      60
aaccactgac accagttggc aatagcttct tccttcttta acctcttaga gtatttatgg     120
tcaatgccac acatttctgc aactgaataa agttggtaag gcaagaggag c              171
```

<210> SEQ ID NO 61
<211> LENGTH: 134
<212> TYPE: DNA
<213> ORGANISM: Homo sapiens

```
<220> FEATURE:
<221> NAME/KEY: misc_feature
<222> LOCATION: 37, 70, 80, 86, 88, 97, 117, 123, 131
<223> OTHER INFORMATION: n = A,T,C or G

<400> SEQUENCE: 61
cgggtgatgc ctcctcaggc tttggtgtgt ccactcnact cactggcctc ttctccagca      60
actggtgaan atgtcctcan gaaaancncc acacgcngct cagggtgggg tgggaancat     120
canaatcatc nggc                                                       134

<210> SEQ ID NO 62
<211> LENGTH: 145
<212> TYPE: DNA
<213> ORGANISM: Homo sapiens

<400> SEQUENCE: 62
agagggtaca tatgcaacag tatataaagg aagaagtgca ctgagaggaa cttcatcaag      60
gccatttaat caataagtga tagagtcaag gctcaaccca ggtgtgacgg attccaggtc     120
ccaagctcct tactggtacc ctctt                                           145

<210> SEQ ID NO 63
<211> LENGTH: 297
<212> TYPE: DNA
<213> ORGANISM: Homo sapiens

<400> SEQUENCE: 63
tgcactgaga ggaattcaaa gggtttatgc caaagaacaa accagtcctc tgcagcctaa      60
ctcatttgtt tttgggctgc gaagccatgt agagggcgat caggcagtag atggtccctc     120
ccacagtcag cgccatggtg gtccggtaaa gcatttggtc aggcaggcct cgtttcaggt     180
agacgggcac acatcagctt tctggaaaaa cttttgtagc tctggagctt tgttttccc     240 agcataatca tacactgtgg aatcggaggt cagtttagtt ggtaaggcaa gaggagc       297

<210> SEQ ID NO 64
<211> LENGTH: 300
<212> TYPE: DNA
<213> ORGANISM: Homo sapiens

<400> SEQUENCE: 64
gcactgagag gaacttccaa tactatgttg aataggagtg gtgagagagg gcatccttgt      60
cttgtgccgg ttttcaaagg gaatgcttcc agcttttgcc cattcagtat aatattaaag     120
aatgttttac cattttctgt cttgcctgtt tttctgtgtt tttgttggtc tcttcattct     180
ccatttttag gcctttacat gttaggaata tatttctttt aatgatactt cacctttggt     240
atcttttgtg agactctact catagtgtga taagcactgg gttggtaagg caagaggagc     300

<210> SEQ ID NO 65
<211> LENGTH: 203
<212> TYPE: DNA
<213> ORGANISM: Homo sapiens

<400> SEQUENCE: 65
gctcctcttg ccttaccaac tcacccagta tgtcagcaat ttatcrgct ttacctacga      60 aacagcctgt atccaaacac ttaacacact cacctgaaaa gttcaggcaa caatcgcctt     120
ctcatgggtc tctctgctcc agttctgaac ctttctcttt cctagaaca tgcatttarg     180 tcgatagaag ttcctctcag tgc                                             203
```

<210> SEQ ID NO 66
<211> LENGTH: 344
<212> TYPE: DNA
<213> ORGANISM: Homo sapiens

<400> SEQUENCE: 66

| tacggggacc cctgcattga gaaagcgaga ctcactctga agctgaaatg ctgttgccct | 60 |
| tgcagtgctg gtagcaggag ttctgtgctt tgtgggctaa ggctcctgga tgaccccctga | 120 |
| catggagaag gcagagttgt gtgccccttc tcatggcctc gtcaaggcat catggactgc | 180 |
| cacacacaaa atgccgtttt tattaacgac atgaaattga aggagagaac acaattcact | 240 |
| gatgtggctc gtaaccatgg atatggtcac atacagaggt gtgattatgt aaaggttaat | 300 |
| tccacccacc tcatgtggaa actagcctca atgcagggt ccca | 344 |

<210> SEQ ID NO 67
<211> LENGTH: 157
<212> TYPE: DNA
<213> ORGANISM: Homo sapiens

<400> SEQUENCE: 67

| gcactgagag gaacttcgta gggaggttga actggctgct gaggaggggg aacaacaggg | 60 |
| taaccagact gatagccatt ggatggataa tatggtggtt gaggagggac actacttata | 120 |
| gcagagggtt gtgtatagcc tgaggaggca tcacccg | 157 |

<210> SEQ ID NO 68
<211> LENGTH: 137
<212> TYPE: DNA
<213> ORGANISM: Homo sapiens

<400> SEQUENCE: 68

| gcactgagag gaacttctag aaagtgaaag tctagacata aaataaaata aaaatttaaa | 60 |
| actcaggaga gacagcccag cacggtggct cacgcctgta atcccagaac tttgggagcc | 120 |
| tgaggaggca tcacccg | 137 |

<210> SEQ ID NO 69
<211> LENGTH: 137
<212> TYPE: DNA
<213> ORGANISM: Homo sapiens

<400> SEQUENCE: 69

| cgggtgatgc ctcctcaggc tgtattttga agactatcga ctggacttct tatcaactga | 60 |
| agaatccgtt aaaaatacca gttgtattat ttctacctgt caaaatccat ttcaaatgtt | 120 |
| gaagttcctc tcagtgc | 137 |

<210> SEQ ID NO 70
<211> LENGTH: 220
<212> TYPE: DNA
<213> ORGANISM: Homo sapiens
<220> FEATURE:
<221> NAME/KEY: misc_feature
<222> LOCATION: 89, 112, 129, 171, 172
<223> OTHER INFORMATION: n = A,T,C or G

<400> SEQUENCE: 70

| agcatgttga gcccagacac gcaatctgaa tgagtgtgca cctcaagtaa atgtctacac | 60 |
| gctgcctggt ctgacatggc acaccatcnc gtggagggca casctctgct cngcctacwa | 120 |
| cgagggcant ctcatwgaca ggttccaccc accaaactgc aagaggctca nnaagtactr | 180 |

```
ccagggtmya sggacmasgg tgggaytyca ycacwcatct                    220
```

<210> SEQ ID NO 71
<211> LENGTH: 353
<212> TYPE: DNA
<213> ORGANISM: Homo sapiens
<220> FEATURE:
<221> NAME/KEY: misc_feature
<222> LOCATION: 66, 160, 204, 246, 267, 334, 339, 342
<223> OTHER INFORMATION: n = A,T,C or G

<400> SEQUENCE: 71

```
cgttagggtc tctatccact gctaaaccat acacctgggt aaacagggac catttaacat    60
tcccanctaa atatgccaag tgacttcaca tgtttatctt aaagatgtcc aaaacgcaac   120
tgattttctc ccctaaacct gtgatggtgg gatgattaan cctgagtggt ctacagcaag   180
ttaagtgcaa ggtgctaaat gaangtgacc tgagatacag catctacaag gcagtacctc   240
tcaacncagg gcaactttgc ttctcanagg gcatttagca gtgtctgaag taatttctgt   300
attacaactc acggggcggg gggtgaatat ctantggana gnagaccccta acg         353
```

<210> SEQ ID NO 72
<211> LENGTH: 343
<212> TYPE: DNA
<213> ORGANISM: Homo sapiens

<400> SEQUENCE: 72

```
gcactgagag gaacttccaa tacyatkatc agagtgaaca rgcarccyac agaacaggag    60
aaaatgttyg caatctctcc atctgacaaa aggctaatat ccagawtcta awaggaactt   120
aaacaaattt atgagaaaag aacaracaac ctcawcaaaa agtgggtgaa ggawatgcts   180
aaargaagac atytattcag ccagtaaaca yatgaaaaaa aggctcatsa tcactgawca   240
ttagagaaat gcaaatcaaa accacaatga gataccatct yayrccagtt agaayggtga   300
tcattaaaar stcaggaaac aacagatgct ggacaaggtg tca                    343
```

<210> SEQ ID NO 73
<211> LENGTH: 321
<212> TYPE: DNA
<213> ORGANISM: Homo sapiens
<220> FEATURE:
<221> NAME/KEY: misc_feature
<222> LOCATION: 288
<223> OTHER INFORMATION: n = A,T,C or G

<400> SEQUENCE: 73

```
gcactgagag gaacttcaga gagagagaga gagttccacc ctgtacttgg ggagagaaac    60
agaaggtgag aaagtctttg gttctgaagc agcttctaag atcttttcat ttgcttcatt   120
tcaaagttcc catgctgcca agtgccatc ctttgggta ctgttttctg agctccagtg    180
ataactcatt tatacaaggg agatacccag aaaaaaagtg agcaaatctt aaaaaggtgg   240
cttgagttca gccttaaata ccatcttgaa atgacacaga gaaagaanga tgttgggtgg   300
gagtggatag agaccctaac g                                            321
```

<210> SEQ ID NO 74
<211> LENGTH: 321
<212> TYPE: DNA
<213> ORGANISM: Homo sapiens

<400> SEQUENCE: 74

```
gcactgagag gaacttcaga gagagagaga gagttccacc ctgtacttgg ggagagaaac      60
agaaggtgag aaagtctttg gttctgaagc agcttctaag atcttttcat ttgcttcatt     120
tcaaagttcc catgctgcca aagtgccatc ctttggggta ctgttttctg agctccagtg     180
ataactcatt tatacaaggg agatacccag aaaaaaagtg agcaaatctt aaaaaggtgg     240
cttgagttca gycttaaata ccatcttgaa atgamacaga gaaagaagga tgttgggtgg     300
gagtggatag agaccctaac g                                               321

<210> SEQ ID NO 75
<211> LENGTH: 317
<212> TYPE: DNA
<213> ORGANISM: Homo sapiens

<400> SEQUENCE: 75
gcactgagag gaacttccac atgcactgag aaatgcatgt tcacaaggac tgaagtctgg      60
aactcagttt ctcagttcca atcctgattc aggtgtttac cagctacaca accttaagca     120
agtcagataa ccttagcttc ctcatatgca aaatgagaat gaaaagtact catcgctgaa     180
ttgttttgag gattagaaaa acatctggca tgcagtagaa attcaattag tattcatttt     240
cattcttcta aattaaacaa ataggatttt tagtggtgga acttcagaca ccagaaatgg     300
gagtggatag agaccct                                                    317

<210> SEQ ID NO 76
<211> LENGTH: 244
<212> TYPE: DNA
<213> ORGANISM: Homo sapiens

<400> SEQUENCE: 76
cgttagggtc tctatccact cccactactg atcaaactct atttatttaa ttattttttat     60 catactttaa gttctgggat acacgtgcag catgcgcagg tttgttgcat aggtatacac     120
ttgccatggt ggtttgctgc acccatcagt ccatcatcta cattaggtat ttctcctaat     180
gctatccctc ccctagcccc ttacaccccc aacaggctct agtgtgtgaa gttcctctca     240
gtgc                                                                  244

<210> SEQ ID NO 77
<211> LENGTH: 254
<212> TYPE: DNA
<213> ORGANISM: Homo sapiens

<400> SEQUENCE: 77
cgttagggtc tctatccact gaaatctgaa gcacaggagg aagagaagca gtyctagtga      60
gatggcaagt tcwtttacca cactctttaa catttygttt agttttaacc tttatttatg     120
gataataaag gttaatatta ataatgattt attttaaggc attcccraat ttgcataatt     180
ctccttttgg agatacccct ttatctccag tgcaagtctg gatcaaagtg atasamagaa     240
gttcctctca gtgc                                                       254

<210> SEQ ID NO 78
<211> LENGTH: 355
<212> TYPE: DNA
<213> ORGANISM: Homo sapiens
<220> FEATURE:
<221> NAME/KEY: misc_feature
<222> LOCATION: 69, 87, 186, 192, 220, 227, 251, 278, 339, 346, 350
<223> OTHER INFORMATION: n = A,T,C or G

<400> SEQUENCE: 78
```

```
ttcgatacag gcaaacatga actgcaggag ggtggtgacg atcatgatgt tgccgatggt    60
ccggatggnc acgaagacgc actggancac gtgcttacgt ccttttgctc tgttgatggc   120
cctgagggga cgcaggaccc ttatgaccct cagaatcttc acaacgggag atggcactgg   180
attgantccc antgacacca gagacacccc aaccaccagn atatcantat attgatgtag   240
ttcctgtaga nggccccctt gtggaggaaa gctccatnag ttggtcatct tcaacaggat   300
ctcaacagtt tccgatggct gtgatgggca tagtcatant taaccntgtn tcgaa        355
```

<210> SEQ ID NO 79
<211> LENGTH: 406
<212> TYPE: DNA
<213> ORGANISM: Homo sapiens

<400> SEQUENCE: 79

```
taagagggta ccagcagaaa ggttagtatc atcagatagc atcttatacg agtaatatgc    60
ctgctatttg aagtgtaatt gagaaggaaa attttagcgt gctcactgac ctgcctgtag   120
ccccagtgac agctaggatg tgcattctcc agccatcaag agactgagtc aagttgttcc   180
ttaagtcaga acagcagact cagctctgac attctgattc gaatgacact gttcaggaat   240
cggaatcctg tcgattagac tggacagctt gtggcaagtg aatttgcctg taacaagcca   300 gatttttta aatttatatt gtaaataatg tgtgtgtgtg tgtgtgtata tatatatata   360
tgtacagtta tctaagttaa tttaaaagtt gtttggtacc ctctta               406
```

<210> SEQ ID NO 80
<211> LENGTH: 327
<212> TYPE: DNA
<213> ORGANISM: Homo sapiens

<400> SEQUENCE: 80

```
tttttttttt tttactcggc tcagtctaat ccttttttgta gtcactcata ggccagactt    60
agggctagga tgatgattaa taagagggat gacataacta ttagtggcag gttagttgtt   120
tgtagggctc atggtagggg taaaaggagg gcaattctca gatcaaataa taagaaggta   180
atagctacta agaagaattt tatggagaaa gggacgcggg cggggatat agggtcgaag   240 ccgcactcgt aagggtgga ttttctatg tagccgttga gttgtggtag tcaaaatgta   300
ataattatta gtagtaagcc taggaga                                      327
```

<210> SEQ ID NO 81
<211> LENGTH: 318
<212> TYPE: DNA
<213> ORGANISM: Homo sapiens

<400> SEQUENCE: 81

```
tagtctatgc ggttgattcg gcaatccatt atttgctgga ttttgtcatg tgttttgcca    60
attgcattca taatttatta tgcatttatg cttgtatctc ctaagtcatg gtatataatc   120
catgcttttt atgttttgtc tgacataaac tcttatcaga gccctttgca cacagggatt   180
caataaatat taacacagtc tacatttatt tggtgaatat tgcatatctg ctgtactgaa   240
agcacattaa gtaacaaagg caagtgagaa gaatgaaaag cactactcac aacagttatc   300
atgattgcgc atagacta                                                318
```

<210> SEQ ID NO 82
<211> LENGTH: 338
<212> TYPE: DNA

```
<213> ORGANISM: Homo sapiens

<400> SEQUENCE: 82
tcttcaacct ctactcccac taatagcttt ttgatgactt ctagcaagcc tcgctaacct      60
cgccttaccc cccactatta acctactggg agaactctct gtgctagtaa ccacgttctc     120
ctgatcaaat atcactctcc tacttacagg actcaacata ctagtcacag ccctatactc     180
cctctacata tttaccacaa cacaatgggg ctcactcacc cacccatta acaacataaa      240 accctcattc acacgagaaa acaccctcat gttcatacac ctatccccca ttctcctcct     300
atccctcaac cccgacatca ttaccgggtt ttcctctt                             338

<210> SEQ ID NO 83
<211> LENGTH: 111
<212> TYPE: DNA
<213> ORGANISM: Homo sapiens

<400> SEQUENCE: 83
agccatttac cacccatcca caaaaaaaaa aaaaaaaag aaaatatca aggaataaaa       60 atagactttg aacaaaaagg aacatttgct ggcctgagga ggcatcaccc g             111

<210> SEQ ID NO 84
<211> LENGTH: 224
<212> TYPE: DNA
<213> ORGANISM: Homo sapiens

<400> SEQUENCE: 84
tcgggtgatg cctcctcagg ccaagaagat aaagcttcag acccctaaca catttccaaa     60
aaggaagaaa ggagaaaaaa gggcatcatc cccgttccga agggtcaggg aggaggaaat    120
tgaggtggat tcacgagttg cggacaactc ctttgatgcc aagcgaggtg cagccggaga    180
ctggggagag cgagccaatc aggttttgaa gttcctctca gtgc                     224

<210> SEQ ID NO 85
<211> LENGTH: 348
<212> TYPE: DNA
<213> ORGANISM: Homo sapiens

<400> SEQUENCE: 85
gcactgagag gaacttcgtt ggaaacgggt ttttttcatg taaggctaga cagaagaatt      60
ctcagtaact tccttgtgtt gtgtgtattc aactcacasa gttgaacgat cctttacaca    120
gagcagactt gtaacactct twttgtggaa tttgcaagtg gagatttcag scgctttgaa    180
gtsaaaggta gaaaggaaa tatcttccta taaaaactag acagaatgat tctcagaaac    240
tcctttgtga tgtgtgcgtt caactcacag agtttaacct ttcwtttcat agaagcagtt    300
aggaaacact ctgtttgtaa agtctgcaag tggatagaga ccctaacg                 348

<210> SEQ ID NO 86
<211> LENGTH: 293
<212> TYPE: DNA
<213> ORGANISM: Homo sapiens

<400> SEQUENCE: 86
gcactgagag gaacttcytt gtgwtgtktg yattcaactc acagagttga asswtsmttt      60
acabagwkca ggcttkcaaa cactctttt gtmgaatytg caagwggaka tttsrrccrc    120
tttgwggycw wysktmgaaw mggrwatatc ttcwyatmra amctagacag aaksattctc    180
akaawstyyy ytgtgawgws tgcrttcaac tcacagagkt kaacmwtyct kytsatrgag    240
```
cagttwkgaa actctmtttc tttggattct gcaagtggat agagaccta acg          293

<210> SEQ ID NO 87
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 87
ctcctaggct                                                         10

<210> SEQ ID NO 88
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 88
agtagttgcc                                                         10

<210> SEQ ID NO 89
<211> LENGTH: 11
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 89
ttccgttatg c                                                       11

<210> SEQ ID NO 90
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 90
tggtaaaggg                                                         10

<210> SEQ ID NO 91
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 91
tcggtcatag                                                         10

<210> SEQ ID NO 92
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 92
tacaacgagg                                                          10

<210> SEQ ID NO 93
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 93
tggattggtc                                                          10

<210> SEQ ID NO 94
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 94
ctttctaccc                                                          10

<210> SEQ ID NO 95
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 95
ttttggctcc                                                          10

<210> SEQ ID NO 96
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 96
ggaaccaatc                                                          10

<210> SEQ ID NO 97
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 97
tcgatacagg                                                          10

<210> SEQ ID NO 98
<211> LENGTH: 10
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 98
ggtactaagg                                                          10

<210> SEQ ID NO 99
<211> LENGTH: 10
<212> TYPE: DNA
<213> ORGANISM: Artificial Sequence
<220> FEATURE:
<223> OTHER INFORMATION: PCR primer for amplification from breast cancer tumor cDNA

<400> SEQUENCE: 99
agtctatgcg                                                          10

<210> SEQ ID NO 100
<211> LENGTH: 10
<212> TYPE: DNA
<213> ORGANISM: Artificial Sequence
<220> FEATURE:
<223> OTHER INFORMATION: PCR primer for amplification from breast cancer tumor cDNA

<400> SEQUENCE: 100
ctatccatgg                                                          10

<210> SEQ ID NO 101
<211> LENGTH: 10
<212> TYPE: DNA
<213> ORGANISM: Artificial Sequence
<220> FEATURE:
<223> OTHER INFORMATION: PCR primer for amplification from breast cancer tumor cDNA

<400> SEQUENCE: 101
tctgtccaca                                                          10

<210> SEQ ID NO 102
<211> LENGTH: 10
<212> TYPE: DNA
<213> ORGANISM: Artificial Sequence
<220> FEATURE:
<223> OTHER INFORMATION: PCR primer for amplification from breast cancer tumor cDNA

<400> SEQUENCE: 102
aagagggtac                                                          10

<210> SEQ ID NO 103
<211> LENGTH: 10
<212> TYPE: DNA
<213> ORGANISM: Artificial Sequence
<220> FEATURE:
<223> OTHER INFORMATION: PCR primer for amplification from breast cancer tumor cDNA

<400> SEQUENCE: 103
cttcaacctc                                                          10

<210> SEQ ID NO 104
<211> LENGTH: 20
<212> TYPE: DNA
<213> ORGANISM: Artificial Sequence
<220> FEATURE:
<223> OTHER INFORMATION: PCR primer for amplification from breast cancer tumor cDNA

<400> SEQUENCE: 104
gctcctcttg ccttaccaac                                               20

```
<210> SEQ ID NO 105
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 105
gtaagtcgag cagtgtgatg                                                    20

<210> SEQ ID NO 106
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 106
gtaagtcgag cagtctgatg                                                    20

<210> SEQ ID NO 107
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 107
gacttagtgg aaagaatgta                                                    20

<210> SEQ ID NO 108
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 108
gtaattccgc caaccgtagt                                                    20

<210> SEQ ID NO 109
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 109
atggttgatc gatagtggaa                                                    20

<210> SEQ ID NO 110
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 110
acggggaccc ctgcattgag                                                    20
```

```
<210> SEQ ID NO 111
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 111
tattctagac cattcgctac                                                 20

<210> SEQ ID NO 112
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 112
acataaccac tttagcgttc                                                 20

<210> SEQ ID NO 113
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 113
cgggtgatgc ctcctcaggc                                                 20

<210> SEQ ID NO 114
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 114
agcatgttga gcccagacac                                                 20

<210> SEQ ID NO 115
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 115
gacaccttgt ccagcatctg                                                 20

<210> SEQ ID NO 116
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 116
tacgctgcaa cactgtggag                                                 20

<210> SEQ ID NO 117
```

```
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 117
cgttagggtc tctatccact                                              20

<210> SEQ ID NO 118
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 118
agactgactc atgtcccta                                               20

<210> SEQ ID NO 119
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 119
tcatcgctcg gtgactcaag                                              20

<210> SEQ ID NO 120
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 120
caagattcca taggctgacc                                              20

<210> SEQ ID NO 121
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 121
acgtactggt cttgaaggtc                                              20

<210> SEQ ID NO 122
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 122
gacgcttggc cacttgacac                                              20

<210> SEQ ID NO 123
<211> LENGTH: 20
```

```
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 123
gtatcgacgt agtggtctcc                                                   20

<210> SEQ ID NO 124
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 124
tagtgacatt acgacgctgg                                                   20

<210> SEQ ID NO 125
<211> LENGTH: 20
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 125
cgggtgatgc ctcctcaggc                                                   20

<210> SEQ ID NO 126
<211> LENGTH: 23
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 126
atggctattt tcgggggctg aca                                               23

<210> SEQ ID NO 127
<211> LENGTH: 22
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 127
ccggtatctc ctcgtgggta tt                                                22

<210> SEQ ID NO 128
<211> LENGTH: 18
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 128
ctgcctgagc cacaaatg                                                     18

<210> SEQ ID NO 129
<211> LENGTH: 24
<212> TYPE: DNA
```

```
<213> ORGANISM: Artificial Sequence
<220> FEATURE:
<223> OTHER INFORMATION: PCR primer for amplification from breast cancer
      tumor cDNA

<400> SEQUENCE: 129
ccggaggagg aagctagagg aata                                              24

<210> SEQ ID NO 130
<211> LENGTH: 14
<212> TYPE: DNA
<213> ORGANISM: Artificial Sequence
<220> FEATURE:
<223> OTHER INFORMATION: PCR primer for amplification from breast cancer
      tumor cDNA

<400> SEQUENCE: 130 ttttttttttt ttag                                                        14

<210> SEQ ID NO 131
<211> LENGTH: 18
<212> TYPE: PRT
<213> ORGANISM: Artificial Sequence
<220> FEATURE:
<223> OTHER INFORMATION: Predicited Th Motifs (B-cell epitopes)

<400> SEQUENCE: 131

Ser Ser Gly Gly Arg Thr Phe Asp Asp Phe His Arg Tyr Leu Leu Val
 1               5                  10                  15

Gly Ile

<210> SEQ ID NO 132
<211> LENGTH: 22
<212> TYPE: PRT
<213> ORGANISM: Artificial Sequence
<220> FEATURE:
<223> OTHER INFORMATION: Predicited Th Motifs (B-cell epitopes)
<221> NAME/KEY: VARIANT
<222> LOCATION: 13
<223> OTHER INFORMATION: Xaa = Any Amino Acid

<400> SEQUENCE: 132

Gln Gly Ala Ala Gln Lys Pro Ile Asn Leu Ser Lys Xaa Ile Glu Val
 1               5                  10                  15

Val Gln Gly His Asp Glu
                 20

<210> SEQ ID NO 133
<211> LENGTH: 23
<212> TYPE: PRT
<213> ORGANISM: Artificial Sequence
<220> FEATURE:
<223> OTHER INFORMATION: Predicited Th Motifs (B-cell epitopes)

<400> SEQUENCE: 133

Ser Pro Gly Val Phe Leu Glu His Leu Gln Glu Ala Tyr Arg Ile Tyr
 1               5                  10                  15

Thr Pro Phe Asp Leu Ser Ala
                 20

<210> SEQ ID NO 134
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)
```

<400> SEQUENCE: 134

Tyr Leu Leu Val Gly Ile Gln Gly Ala
1               5

<210> SEQ ID NO 135
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 135

Gly Ala Ala Gln Lys Pro Ile Asn Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)
<221> NAME/KEY: VARIANT
<222> LOCATION: 5
<223> OTHER INFORMATION: Xaa = Any Amino Acid

<400> SEQUENCE: 136

Asn Leu Ser Lys Xaa Ile Glu Val Val
1               5

<210> SEQ ID NO 137
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 137

Glu Val Val Gln Gly His Asp Glu Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 138

His Leu Gln Glu Ala Tyr Arg Ile Tyr
1               5

<210> SEQ ID NO 139
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 139

Asn Leu Ala Phe Val Ala Gln Ala Ala
1               5

<210> SEQ ID NO 140
<211> LENGTH: 9
<212> TYPE: PRT
<213> ORGANISM: Artificial Sequence

```
<220> FEATURE:
<223> OTHER INFORMATION: Predicited HLA A2.1 Motifs (T-cell epitopes)

<400> SEQUENCE: 140

Phe Val Ala Gln Ala Ala Pro Asp Ser
 1               5

<210> SEQ ID NO 141
<211> LENGTH: 9388
<212> TYPE: DNA
<213> ORGANISM: Homo sapiens

<400> SEQUENCE: 141
gctcgcggcc gcgagctcaa ttaaccctca ctaaagggag tcgactcgat cagactgtta      60
ctgtgtctat gtagaaagaa gtagacataa gagattccat tttgttctgt actaagaaaa     120
attcttctgc cttgagatgc tgttaatctg taaccctagc cccaaccctg tgctcacaga     180
gacatgtgct gtgttgactc aaggttcaat ggatttaggg ctatgctttg ttaaaaaagt     240
gcttgaagat aatatgcttg ttaaaagtca tcaccattct ctaatctcaa gtacccaggg     300
acacaataca ctgcggaagg ccgcagggac ctctgtctag aaagccagg tattgtccaa      360 gatttctccc catgtgatag cctgagatat ggcctcatgg aagggtaag acctgactgt      420 cccccagccc gacatccccc agcccgacat ccccagccc gacacccgaa aagggtctgt      480
gctgaggagg attagtaaaa gaggaaggcc tctttgcagt tgaggtaaga ggaaggcatc     540
tgtctcctgc tcgtccctgg gcaatagaat gtcttggtgt aaaacccgat tgtatgttct     600
acttactgag ataggagaaa acatccttag ggctggaggt gagacacgct ggcggcaata     660
ctgctcttta atgcaccgag atgtttgtat aagtgcacat caaggcacag caccttttcct    720 taaacttatt tatgacacag agacctttgt tcacgttttc ctgctgaccc tctccccact     780
attaccctat tggcctgcca catccccctc tccgagatgg tagagataat gatcaataaa     840
tactgaggga actcagagac cagtgtccct gtaggtcctc cgtgtgctga gcgccggtcc     900
cttgggctca cttttctttc tctatacttt gtctctgtgt ctctttcttt tctcagtctc     960
tcgttccacc tgacgagaaa tacccacagg tgtggagggg caggccaccc cttcaataat    1020
ttactagcct gttcgctgac aacaagactg gtggtgcaga aggttgggtc ttggtgttca    1080
ccgggtggca ggcatgggcc aggtgggagg gtctccagcg cctggtgcaa atctccaaga    1140
aagtgcagga acagcacca agggtgattg taaatttga tttggcgcgg caggtagcca      1200
ttccagcgca aaaatgcgca ggaaagcttt tgctgtgctt gtaggcaggt aggccccaag    1260
cacttcttat tggctaatgt ggagggaacc tgcacatcca ttggctgaaa tctccgtcta    1320
tttgaggctg actgagcgcg ttcctttctt ctgtgttgcc tggaaacgga ctgtctgcct    1380
agtaacatct gatcacgttt cccattggcc gccgtttccg gaagcccgcc ctcccatttc    1440
cggaagcctg gcgcaaggtt ggtctgcagg tggcctccag gtgcaaagtg ggaagtgtga    1500
gtcctcagtc ttgggctatt cggccacgtg cctgccggac atgggacgct ggagggtcag    1560
cagcgtggag tcctggcctt ttgcgtccac gggtgggaaa ttggccattg ccacggcggg    1620
aactgggact caggctgccc cccggccgtt tctcatccgt ccaccggact cgtgggcgct    1680
cgcactggcg ctgatgtagt ttcctgacct ctgacccgta ttgtctccag attaaaggta    1740
aaaacggggc tttttcagcc cactcgggta aaacgccttt tgatttctag gcaggtgttt    1800
tgttgcacgc ctgggaggga gtgacccgca ggttgaggtt tattaaaata cattcctggt    1860
ttatgttatg tttataataa agcaccccaa cctttacaaa atctcacttt ttgccagttg    1920
```

```
tattatttag tggactgtct ctgataagga cagccagtta aaatggaatt ttgttgttgc      1980
taattaaacc aattttttagt tttggtgttt gtcctaatag caacaacttc tcaggcttta     2040
taaaaccata tttcttgggg gaaatttctg tgtaaggcac agcgagttag tttggaattg      2100
ttttaaagga agtaagttcc tggttttgat atcttagtag tgtaatgccc aacctggttt      2160
ttactaaccc tgttttaga ctctcccttt ccttaaatca cctagccttg tttccacctg       2220
aattgactct cccttagcta agagcgccag atggactcca tcttggctct ttcactggca     2280
gccccttcct caaggactta acttgtgcaa gctgactccc agcacatcca agaatgcaat     2340
taactgttaa gatactgtgg caagctatat ccgcagttcc gaggaattca tccgattgat     2400
tatgcccaaa agccccgcgt ctatcacctt gtaataatct aaagcccct gcacctggaa      2460 ctattaactt tcctgtaacc atttatcctt ttaactttt tgcttacttt atttctgtaa      2520
aattgtttta actagacctc ccctccccttt tctaaaccaa agtataaaag aagatctagc    2580
cccttcttca gagcggagag aattttgagc attagccatc tcttggcggc cagctaaata    2640
aatggacttt taatttgtct caaagtgtgg cgttttctct aactcgctca ggtacgacat    2700
ttggaggccc cagcgagaaa cgtcaccggg agaaacgtca ccgggcgaga gccgggcccg    2760
ctgtgtgctc ccccggaagg acagccagct tgtaggggg agtgccacct gaaaaaaaaa     2820
tttccaggtc cccaaagggt gaccgtcttc cggaggacag cggatcgact accatgcggg    2880 tgccccaccaa aattccacct ctgagtcctc aactgctgac cccggggtca ggtaggtcag   2940
atttgacttt ggttctggca gagggaagcg accctgatga gggtgtccct cttttgactc    3000 tgcccattc tctaggatgc tagagggtag agccctggtt ttctgttaga cgcctctgtg     3060
tctctgtctg ggagggaagt ggccctgaca ggggccatcc cttgagtcag tccacatccc    3120
aggatgctgg gggactgagt cctggtttct ggcagactgg tctctctctc tctctttttc    3180
tatctctaat ctttccttgt tcaggtttct tggagaatct ctgggaaaga aaaagaaaa     3240 actgttataa actctgtgtg aatggtgaat gaatggggga ggacaagggc ttgcgcttgt    3300
cctccagttt gtagctccac ggcgaaagct acggagttca agtgggccct cacctgcggt    3360
tccgtggcga cctcataagg cttaaggcag catccggcat agctcgatcc gagccggggg    3420
tttataccgg cctgtcaatg ctaagaggag cccaagtccc ctaaggggga gcggccaggc    3480
gggcatctga ctgatcccat cacgggaccc cctcccctttg tttgtctaaa aaaaaaaaaa   3540
gaagaaactg tcataactgt ttacatgccc tagggtcaac tgtttgtttt atgtttattg    3600
ttctgttcgg tgtctattgt cttgtttagt ggttgtcaag gttttgcatg tcaggacgtc    3660
gatattgccc aagacgtctg ggtaagaact tctgcaaggt ccttagtgct gattttttgt    3720
cacaggaggt taaatttctc atcaatcatt taggctggcc accacagtcc tgtctttttct   3780 gccagaagca agtcaggtgt tgttacggga atgagtgtaa aaaaacattc gcctgattgg    3840
gatttctggc accatgatgg ttgtatttag attgtcatac cccacatcca ggttgattgg    3900
acctcctcta aactaaactg gtggtgggtt caaaacagcc accctgcaga tttccttgct    3960
cacctctttg gtcattctgt aacttttcct gtgcccttaa atagcacact gtgtagggaa    4020
acctaccctc gtactgcttt acttcgttta gattcttact ctgttcctct gtggctactc    4080
tcccatctta aaaacgatcc aagtggtcct tttcctcctc cctgccccct accccacaca    4140
tctcgttttc cagtgcgaca gcaagttcag cgtctccagg acttggctct gctctcactc    4200 cttgaacccct taaagaaaa agctgggttt gagctatttg cctttgagtc atggagacac    4260
```

-continued

```
aaaaggtatt tagggtacag atctagaaga agagagagaa cacctagatc caactgaccc      4320
aggagatctc gggctggcct ctagtcctcc tccctcaatc ttaaagctac agtgatgtgg      4380
caagtggtat ttagctgttg tggttttcct gctctttctg gtcatgttga ttctgttctt      4440
tcgatactcc agccccccag ggagtgagtt tctctgtctg tgctgggttt gatatctatg      4500
ttcaaatctt attaaattgc cttcaaaaaa aaaaaaaaa gggaaacact tcctcccagc       4560
cttgtaaggg ttggagccct ctccagtata tgctgcagaa tttttctctc ggtttctcag      4620
aggattatgg agtccgcctt aaaaaaggca agctctggac actctgcaaa gtagaatggc      4680
caaagtttgg agttgagtgg ccccttgaag ggtcactgaa cctcacaatt gttcaagctg      4740
tgtggcgggt tgttactgaa actcccggcc tccctgatca gtttccctac attgatcaat      4800
ggctgagttt ggtcaggagc accccttcca tggctccact catgcaccat tcataatttt      4860
acctccaagg tcctcctgag ccagaccgtg ttttcgcctc gaccctcagc cggttcagct      4920
cgccctgtac tgcctctctc tgaagaagag gagagtctcc ctcacccagt cccaccgcct      4980
taaaaccagc ctactccctt agggtcatcc catgtctcct cggctatgtc ccctgtaggc      5040
tcatcaccca ttgcctcttg gttgcaaccg tggtgggagg aagtagcccc tctactacca      5100
ctgagagagg cacaagtccc tctgggtgat gagtgctcca ccccttcct ggtttatgtc       5160 ccttcttct acttctgact tgtataattg gaaaacccat aatcctccct tctctgaaaa       5220
gccccaggct ttgacctcac tgatggagtc tgtactctgg acacattggc ccacctggga     5280
tgactgtcaa cagctccttt tgacccttt cacctctgaa gagagggaaa gtatccaaag       5340
agaggccaaa aagtacaacc tcacatcaac caataggccg gaggaggaag ctagaggaat      5400
agtgattaga gacccaattg ggacctaatt gggacccaaa tttctcaagt ggagggagaa      5460
cttttgacga tttccaccgg tatctcctcg tgggtattca gggagctgct cagaaaccta     5520
taaacttgtc taaggcgact gaagtcgtcc aggggcatga tgagtcacca ggagtgtttt      5580
tagagcacct ccaggaggct tatcggattt acacccctt tgacctggca gccccgaaa       5640 atagccatgc tcttaatttg gcatttgtgg ctcaggcagc cccagatagt aaaaggaaac      5700
tccaaaaact agagggattt tgctggaatg aataccagtc agcttttaga gatagcctaa      5760 aaggttttg acagtcaaga ggttgaaaaa caaaaacaag cagctcaggc agctgaaaaa       5820
agccactgat aaagcatcct ggagtatcag agtttactgt tagatcagcc tcatttgact     5880 tccctcca catggtgttt aaatccagct cactacttc ctgactcaaa ctccactatt        5940
cctgttcatg actgtcagga actgttgaa actactgaaa ctggccgacc tgatcttcaa      6000
aatgtgcccc taggaaaggt ggatgccacc gtgttcacag acagtagcag cttcctcgag      6060
aagggactac gaaaggccgg tgcagctgtt accatggaga cagatgtgtt gtgggctcag      6120
gctttaccag caaacacctc agcacaaaag gctgaattga tcgccctcac tcaggctctc     6180
cgatggggta aggatattaa cgttaacact gacagcaggt acgcctttgc tactgtgcat      6240
gtacgtggag ccatctacca ggagcgtggg ctactcacct cagcaggtgg ctgtaatcca     6300
ctgtaaagga catcaaaagg aaaacacggc tgttgcccgt ggtaaccaga agctgattc      6360 agcagctcaa gatgcagtgt gactttcagt cacgcctcta aacttgctgc ccacagtctc     6420 cttccacag ccagatctgc ctgacaatcc cgcatactca acagaagaag aaaactggcc     6480
tcagaactca gagccaataa aaatcaggaa ggttggtgga ttcttcctga ctctagaatc      6540
ttcatacccc gaactcttgg gaaaacttta atcagtcacc tacagtctac cacccattta      6600
ggaggagcaa agctacctca gctcctccgg agccgtttta agatccccca tcttcaaagc      6660
```

-continued

```
ctaacagatc aagcagctct ccggtgcaca acctgcgccc aggtaaatgc caaaaaggt    6720
cctaaaccca gcccaggcca ccgtctccaa gaaaactcac caggagaaaa gtgggaaatt   6780
gactttacag aagtaaaacc acaccgggct gggtacaaat accttctagt actggtagac   6840
accttctctg gatggactga agcatttgct accaaaaacg aaactgtcaa tatggtagtt   6900
aagttttac tcaatgaaat catccctcga cgtgggctgc ctgttgccat agggtctgat    6960
aatggaccgg ccttcgcctt gtctatagtt tagtcagtca gtaaggcgtt aaacattcaa   7020
tggaagctcc attgtgccta tcgacccag agctctgggc aagtagaacg catgaactgc    7080
accctaaaaa acactcttac aaaattaatc ttagaaaccg gtgtaaattg tgtaagtctc   7140
cttcctttag ccctacttag agtaaggtgc acccttact gggctgggtt cttacctttt    7200
gaaatcatgt atgggagggc gctgcctatc ttgcctaagc taagagatgc ccaattggca   7260
aaaatatcac aaactaattt attacagtac ctacagtctc cccaacaggt acaagatatc   7320
atcctgccac ttgttcgagg aacccatccc aatccaattc ctgaacagac agggccctgc   7380
cattcattcc cgccaggtga cctgttgttt gttaaaaagt tccagagaga aggactccct   7440
cctgcttgga agagacctca caccgtcatc acgatgccaa cggctctgaa ggtggatggc   7500
attcctgcgt ggattcatca ctcccgcatc aaaaaggcca acggagccca actagaaaca   7560
tgggtcccca gggctgggtc aggcccctta aaactgcacc taagttgggt gaagccatta   7620
gattaattct ttttcttaat tttgtaaaac aatgcatagc ttctgtcaaa cttatgtatc   7680
ttaagactca atataacccc cttgttataa ctgaggaatc aatgatttga ttcccccaaa   7740
acacaagtgg ggaatgtagt gtccaacctg gttttacta accctgtttt tagactctcc    7800
cttttcctta atcactcagc cttgtttcca cctgaattga ctctcctta gctaagagcg    7860
ccagatggac tccatcttgg ctctttcact ggcagccgct tcctcaagga cttaacttgt   7920
gcaagctgac tcccagcaca tccaagaatg caattaactg ataagatact gtggcaagct   7980
atatccgcag ttcccaggaa ttcgtccaat tgattacacc caaaagcccc gcgtctatca   8040
ccttgtaata atcttaaagc ccctgcacct ggaactatta acgttcctgt aaccatttat   8100
cctttaact tttttgccta ctttatttct gtaaaattgt tttaactaga cccccctct    8160
cctttctaaa ccaaagtata aaagcaaatc tagccccttc ttcaggccga gagaatttcg   8220
agcgttagcc gtctcttggc caccagctaa ataaacggat tcttcatgtg tctcaaagtg   8280
tggcgttttc tctaactcgc tcaggtacga ccgtggtagt attttcccca acgtcttatt   8340
tttagggcac gtatgtagag taactttat gaaagaaacc agttaaggag gttttgggat    8400
ttcctttatc aactgtaata ctggttttga ttatttattt atttatttat ttttttgag   8460
aaggagtttc actcttgttg cccaggctgg agtgcaatgg tgcgatcttg gctcactgca   8520
acttccgcct cccaggttca gcgattctc ctgcctcagc ctcgagagta gctgggatta    8580
taggcatgcg ccaccacacc cagctaattt tgtattttta gtaaagatgg ggtttcttca   8640
tgttggtcaa gctggtctgg aactcccgc ctcgggtgat ctgccgcct cggcctccga     8700
aagtgctggg attacaggtg tgatccacca cacccagccg atttatatgt atataaatca   8760
cattcctcta accaaaatgt agtgtttcct tccatcttga atataggctg tagacccgt    8820
gggtatggga cattgttaac agtgagacca cagcagtttt tatgtcatct gacagcatct   8880
ccaaatagcc ttcatggttg tcactgcttc ccaagacaat tccaaataac acttcccagt   8940
gatgacttgc tacttgctat tgttacttaa tgtgttaagg tggctgttac agacactatt   9000
```

```
agtatgtcag gaattacacc aaaatttagt ggctcaaaca atcattttat tatgtatgtg      9060
gattctcatg gtcaggtcag gatttcagac agggcacaag ggtagcccac ttgtctctgt      9120
ctatgatgtc tggcctcagc acaggagact caacagctgg ggtctgggac catttggagg      9180
cttgttccct cacatctgat acctggcttg ggatgttgga agaggggtg agctgagact       9240 gagtgcctat atgtagtgtt tccatatggc cttgacttcc ttacagcctg gcagcctcag      9300
ggtagtcaga attcttagga ggcacagggc tccagggcag atgctgaggg gtcttttatg      9360
aggtagcaca gcaaatccac ccaggatc                                         9388
```

```
<210> SEQ ID NO 142
<211> LENGTH: 419
<212> TYPE: DNA
<213> ORGANISM: Homo sapiens

<400> SEQUENCE: 142
tgtaagtcga gcagtgtgat ggaaggaatg gtctttggag agagcatatc catctcctcc      60
tcactgcctc ctaatgtcat gaggtacact gagcagaatt aaacagggta gtcttaacca     120
cactattttt agctaccttg tcaagctaat ggttaaagaa cacttttggt ttacacttgt     180
tgggtcatag aagttgcttt ccgccatcac gcaataagtt tgtgtgtaat cagaaggagt     240
taccttatgg tttcagtgtc attctttagt taacttggga gctgtgtaat ttaggctttg     300
cgtattattt cacttctgtt ctccacttat gaagtgattg tgtgttcgcg tgtgtgtgcg     360
tgcgcatgtg cttccggcag ttaacataag caaatacccca acatcacact gctcgactt     419
```

```
<210> SEQ ID NO 143
<211> LENGTH: 402
<212> TYPE: DNA
<213> ORGANISM: Homo sapiens

<400> SEQUENCE: 143
tgtaagtcga gcagtgtgat gtccactgca gtgtgttgct gggaacagtt aatgagcaaa      60
ttgtatacaa tggctagtac attgaccggg atttgttgaa gctggtgagt gttatgactt     120
agcctgttag actagtctat gcacatggct ctggtcaact accgctctct catttctcca     180
gataaatccc ccatgcttta tattctcttc caaacatact atcctcatca ccacatagtt     240
cctttgttaa tgctttgttc tagactttcc cttttctgtt ttcttattca aacctatatc     300
tctttgcata gattgtaaat tcaaatgccc tcagggtgca ggcagttcat gtaagggagg     360
gaggctagcc agtgagatct gcatcacact gctcgactta ca                        402
```

```
<210> SEQ ID NO 144
<211> LENGTH: 224
<212> TYPE: DNA
<213> ORGANISM: Homo sapiens

<400> SEQUENCE: 144
tcgggtgatg cctcctcagg ccaagaagat aaagcttcag acccctaaca catttccaaa      60
aaggaagaaa ggagaaaaaa gggcatcatc cccgttccga agggtcaggg aggaggaaat     120
tgaggtggat tcacgagttg cggacaactc ctttgatgcc aagcgaggtg cagccggaga     180
ctggggagag cgagccaatc aggttttgaa gttcctctca gtgc                      224
```

```
<210> SEQ ID NO 145
<211> LENGTH: 111
<212> TYPE: DNA
<213> ORGANISM: Homo sapiens
```

```
<400> SEQUENCE: 145
agccatttac cacccatcca caaaaaaaaa aaaaaaaag aaaatatca aggaataaaa        60 atagactttg aacaaaaagg aacatttgct ggcctgagga ggcatcaccc g              111

<210> SEQ ID NO 146
<211> LENGTH: 585
<212> TYPE: DNA
<213> ORGANISM: Homo sapiens

<400> SEQUENCE: 146
tagcatgttg agcccagaca cttgtagaga gaggaggaca gttagaagaa gaagaaaagt     60
ttttaaatgc tgaaagttac tataagaaag ctttggcttt ggatgagact tttaaagatg    120
cagaggatgc tttgcagaaa cttcataaat atatgcaggt gattccttat ttcctcctag    180
aaatttagtg atatttgaaa taatgcccaa acttaattt ctcctgagga aaactattct    240
acattactta agtaaggcat tatgaaaagt ttcttttttag gtatagtttt tcctaattgg    300
gtttgacatt gcttcatagt gcctctgttt ttgtccataa tcgaaagtaa agatagctgt    360
gagaaaacta ttacctaaat ttggtatgtt gttttgagaa atgtccttat agggagctca    420
cctggtggtt tttaaattat tgttgctact ataattgagc taattataaa aaccttttg    480 agacatattt taaattgtct tttcctgtaa tactgatgat gatgttttct catgcattt    540 cttctgaatt gggaccattg ctgctgtgtc tgggctcaca tgcta                    585

<210> SEQ ID NO 147
<211> LENGTH: 579
<212> TYPE: DNA
<213> ORGANISM: Homo sapiens
<220> FEATURE:
<221> NAME/KEY: misc_feature
<222> LOCATION: 383, 453, 465, 501
<223> OTHER INFORMATION: n = A,T,C or G

<400> SEQUENCE: 147
tagcatgttg agcccagaca ctgggcagcg ggggtggcca cggcagctcc tgccgagccc     60
aagcgtgttt gtctgtgaag gaccctgacg tcacctgcca ggctagggag gggtcaatgt    120
ggagtgaatg ttcaccgact tcgcaggag tgtgcagaag ccaggtgcaa cttggtttgc    180
ttgtgttcat caccctcaa gatatgcaca ctgctttcca aataaagcat caactgtcat    240
ctccagatgg ggaagacttt ttctccaacc agcaggcagg tccccatcca ctcagacacc    300
agcacgtcca ccttctcggg cagcaccacg tcctccacct tctgctggta cacggtgatg    360
atgtcagcaa agccgttctg cangaccagc tgccccgtgt gctgtgccat ctcactggcc    420
tccaccgcgt acaccgctct aggccgcgca tantgtgcac agaanaaatg atgatccagt    480
cccacagccc acgtccaaga ngactttatc cgtcagggat tctttattct gcaggatgac    540
ctgtggtatt aattgttcgt gtctgggctc aacatgcta                           579

<210> SEQ ID NO 148
<211> LENGTH: 249
<212> TYPE: DNA
<213> ORGANISM: Homo sapiens

<400> SEQUENCE: 148
tgacaccttg tccagcatct gcaagccagg aagagagtcc tcaccaagat cccaccccg      60 ttggcaccag gatcttggac ttccaatctc cagaactgtg agaaataagt atttgtcgct    120
```

```
aaataaatct ttgtggtttc agatatttag ctatagcaga tcaggctgac taagagaaac      180
cccataagag ttacatactc attaatctcc gtctctatcc ccaggtctca gatgctggac      240
aaggtgtca                                                              249
```

<210> SEQ ID NO 149
<211> LENGTH: 255
<212> TYPE: DNA
<213> ORGANISM: Homo sapiens

<400> SEQUENCE: 149

```
tgacaccttg tccagcatct gctattttgt gacttttaa taatagccat tctgactggt       60
gtgagatggt aactcattgt gggtttggtc tgcatttctc taatgatcag tgatattaag     120 cttttttaa atatgcttgt tgaccacatg tatatcatct tttgagaagt gtctgttcat     180
atcctttgcc cacttttaa ttttttatc ttgtaaattt gtttaatttc cttacagatg     240
ctggacaagg tgtca                                                      255
```

<210> SEQ ID NO 150
<211> LENGTH: 318
<212> TYPE: DNA
<213> ORGANISM: Homo sapiens

<400> SEQUENCE: 150

```
ttacgctgca acactgtgga ggccaagctg ggatcacttc ttcattctaa ctggagagga      60
gggaagttca agtccagcag agggtgggtg ggtagacagt ggcactcaga aatgtcagct    120
ggacccctgt ccccgcatag gcaggacagc aaggctgtgg ctctccaggg ccagctgaag    180
aacaggacac tgtctccgct gccacaaagc gtcagagact cccatctttg aagcacggcc    240
ttcttggtct tcctgcactt ccctgttctg ttagagacct ggttatagac aaggcttctc    300
cacagtgttg cagcgtaa                                                   318
```

<210> SEQ ID NO 151
<211> LENGTH: 323
<212> TYPE: DNA
<213> ORGANISM: Homo sapiens
<220> FEATURE:
<221> NAME/KEY: misc_feature
<222> LOCATION: 2, 7, 10, 13, 14, 23, 26, 32, 44, 54, 56, 67, 74, 75,
      81, 87, 104, 105, 109, 111, 120, 123, 124, 136, 137, 138, 151,
      155, 162, 168, 171, 176, 184, 186, 196, 215, 231, 239, 252,
      265, 288, 318
<223> OTHER INFORMATION: n = A,T,C or G

<400> SEQUENCE: 151

```
tnacgcngcn acnntgtaga ganggnaagg cnttccccac attncccctt catnanagaa      60
ttattcnacc aagnntgacc natgccnttt atgacttaca tgcnnactnc ntaatctgtn    120
tcnngcctta aaagcnnntc cactacatgc ntcancactg tntgtgtnac ntcatnaact    180
gtcngnaata ggggcncata actacagaaa tgcanttcat actgcttcca ntgccatcng    240
cgtgtggcct tncctactct tcttntattc caagtagcat ctctggantg cttccccact    300
ctccacattg ttgcagcnat aat                                             323
```

<210> SEQ ID NO 152
<211> LENGTH: 311
<212> TYPE: DNA
<213> ORGANISM: Homo sapiens

<400> SEQUENCE: 152

```
tcaagattcc ataggctgac cagtccaagg agagttgaaa tcatgaagga gagtctatct      60
ggagagagct gtagttttga gggttgcaaa gacttaggat ggagttggtg ggtgtggtta     120
gtctctaagg ttgattttgt tcataaattt catgccctga atgccttgct tgcctcaccc     180
tggtccaagc cttagtgaac acctaaaagt ctctgtcttc ttgctctcca aacttctcct     240
gaggatttcc tcagattgtc tacattcaga tcgaagccag ttggcaaaca agatgcagtc     300
cagagggtca g                                                          311
```

<210> SEQ ID NO 153
<211> LENGTH: 332
<212> TYPE: DNA
<213> ORGANISM: Homo sapiens

<400> SEQUENCE: 153

```
caagattcca taggctgacc aggaggctat tcaagatctc tggcagttga ggaagtctct      60
ttaagaaaat agtttaaaca atttgttaaa atttttctgt cttacttcat ttctgtagca     120
gttgatatct ggctgtcctt tttataatgc agagtgggaa cttccctac catgtttgat     180 aaatgttgtc caggctccat tgccaataat gtgttgtcca aaatgcctgt ttagtttta     240 aagacggaac tccacccttt gcttggtctt aagtatgtat ggaatgttat gataggacat     300
agtagtagcg gtggtcagcc tatggaatct tg                                   332
```

<210> SEQ ID NO 154
<211> LENGTH: 345
<212> TYPE: DNA
<213> ORGANISM: Homo sapiens
<220> FEATURE:
<221> NAME/KEY: misc_feature
<222> LOCATION: 154, 224, 297, 330
<223> OTHER INFORMATION: n = A,T,C or G

<400> SEQUENCE: 154

```
tcaagattcc ataggctgac ctggacagag atctcctggg tctggcccag gacagcaggc      60
tcaagctcag tggagaaggt ttccatgacc ctcagattcc cccaaacctt ggattgggtg     120
acattgcatc tcctcagaga gggaggagat gtangtctgg gcttccacag ggacctggta     180
ttttaggatc agggtaccgc tggcctgagg cttggatcat tcanagcctg ggggtggaat     240
ggctggcagc ctgtggcccc attgaaatag gctctggggc actccctctg ttcctanttg     300
aacttgggta aggaacagga atgtggtcan cctatggaat cttga                     345
```

<210> SEQ ID NO 155
<211> LENGTH: 295
<212> TYPE: DNA
<213> ORGANISM: Homo sapiens
<220> FEATURE:
<221> NAME/KEY: misc_feature
<222> LOCATION: 46, 199, 252, 266
<223> OTHER INFORMATION: n = A,T,C or G

<400> SEQUENCE: 155

```
gacgcttggc cacttgacac attaaacagt tttgcataat cactancatg tatttctagt      60
ttgctgtctg ctgtgatgcc ctgccctgat tctctggcgt taatgatggc aagcataatc     120
aaacgctgtt ctgttaattc caagttataa ctggcattga ttaaagcatt atctttcaca     180
actaaactgt tcttcatana acagcccata ttattatcaa attaagagac aatgtattcc     240
aatatccttt anggccaata tatttnatgt cccttaatta agagctactg tccgt          295
```

<210> SEQ ID NO 156
<211> LENGTH: 406
<212> TYPE: DNA
<213> ORGANISM: Homo sapiens
<220> FEATURE:
<221> NAME/KEY: misc_feature
<222> LOCATION: 172, 178, 332, 338, 342, 381, 400, 402
<223> OTHER INFORMATION: n = A,T,C or G

<400> SEQUENCE: 156
gacgcttggc cacttgacac tgcagtggga aaaccagcat gagccgctgc ccccaaggaa    60
cctcgaagcc caggcagagg accagccatc ccagcctgca ggtaaagtgt gtcacctgtc   120
aggtgggctt ggggtgagtg ggtgggggaa gtgtgtgtgc aaaggggGtg tnaatgtnta   180
tgcgtgtgag catgagtgat ggctagtgtg actgcatgtc agggagtgtg aacaagcgtg   240
cgggggtgtg tgtgcaagtg cgtatgcata tgagaatatg tgtctgtgga tgagtgcatt   300
tgaaagtctg tgtgtgtgcg tgtggtcatg anggtaantt antgactgcg caggatgtgt   360
gagtgtgcat ggaacactca ntgtgtgtgt caagtggccn ancgtc               406

<210> SEQ ID NO 157
<211> LENGTH: 208
<212> TYPE: DNA
<213> ORGANISM: Homo sapiens
<220> FEATURE:
<221> NAME/KEY: misc_feature
<222> LOCATION: 115, 119, 182, 187
<223> OTHER INFORMATION: n = A,T,C or G

<400> SEQUENCE: 157
tgacgcttgg ccacttgaca cactaaaggg tgttactcat cactttcttc tctcctcggt    60
ggcatgtgag tgcatctatt cacttggcac tcatttgttt ggcagtgact gtaanccana   120
tctgatgcat acaccagctt gtaaattgaa taaatgtctc taatactatg tgctcacaat   180
anggtanggg tgaggagaag gggagaga                                      208

<210> SEQ ID NO 158
<211> LENGTH: 547
<212> TYPE: DNA
<213> ORGANISM: Homo sapiens
<220> FEATURE:
<221> NAME/KEY: misc_feature
<222> LOCATION: 235
<223> OTHER INFORMATION: n = A,T,C or G

<400> SEQUENCE: 158
cttcaacctc cttcaacctc cttcaacctc ctggattcaa acaatcatcc cacctcagac    60
tccttagtag ctgagactac agactcacgc cactacatct ggctaaattt ttgtagagat   120
agggtttcat catgttgccc tggctggtct caaactcctg acctcaagca atgtgcccac   180
ctcagcctcc caaagtgctg ggattacagg cataagccac catgcccagt ccatntttaa   240
tctttcctac cacattctta ccacactttc ttttatgttt agatacataa atgcttacca   300
ttatgataca attgcccaca gtattaagac agtaacatgc tgcacaggtt tgtagcctag   360
gaacagtagg caataccaca tagcttaggt gtgtggtaga ctataccatc taggtttgtg   420
taagttacac tttatgctgt ttacacaatg acaaaaccat ctaatgatgc atttctcaga   480
atgtatcctt gtcagtaagc tatgatgtac agggaacact gcccaaggac acagatattg   540
tacctgt                                                             547

<210> SEQ ID NO 159

```
<211> LENGTH: 203
<212> TYPE: DNA
<213> ORGANISM: Homo sapiens

<400> SEQUENCE: 159
gctcctcttg ccttaccaac tcacccagta tgtcagcaat tttatcrgct ttacctacga    60
aacagcctgt atccaaacac ttaacacact cacctgaaaa gttcaggcaa caatcgcctt   120
ctcatgggtc tctctgctcc agttctgaac ctttctcttt cctagaaca tgcatttarg    180 tcgatagaag ttcctctcag tgc                                           203

<210> SEQ ID NO 160
<211> LENGTH: 402
<212> TYPE: DNA
<213> ORGANISM: Homo sapiens

<400> SEQUENCE: 160
tgtaagtcga gcagtgtgat gggtggaaca gggttgtaag cagtaattgc aaactgtatt    60
taaacaataa taataatatt tagcatttat agagcacttt atatcttcaa agtacttgca   120
aacattayct aattaaatac cctctctgat tataatctgg atacaaatgc acttaaactc   180
aggacagggt catgagaraa gtatgcattt gaaagttggt gctagctatg ctttaaaaac   240
ctatacaatg atgggraagt tagagttcag attctgttgg actgttttg tgcatttcag    300 ttcagcctga tggcagaatt agatcatatc tgcactcgat gactytgctt gataacttat   360
cactgaaatc tgagtgttga tcatcacact gctcgactta ca                      402

<210> SEQ ID NO 161
<211> LENGTH: 193
<212> TYPE: DNA
<213> ORGANISM: Homo sapiens

<400> SEQUENCE: 161
agcatgttga gcccagacac tgaccaggag aaaaaccaac caatagaaac acgcccagac    60
actgaccagg agaaaaacca accaataaaa acaggcccgg acataagaca ataataaaa    120 ttagcggaca aggacatgaa aacagctatt gtaagagcgg atatagtggt gtgtgtctgg   180
gctcaacatg cta                                                      193

<210> SEQ ID NO 162
<211> LENGTH: 147
<212> TYPE: DNA
<213> ORGANISM: Homo sapiens

<400> SEQUENCE: 162
tgttgagccc agacactgac caggagaaaa accaaccaat aaaaacaggc ccggacataa    60
gacaaataat aaaattagcg gacaaggaca tgaaaacagc tattgtaaga gcggatatag   120
tggtgtgtgt ctgggctcaa catgcta                                       147

<210> SEQ ID NO 163
<211> LENGTH: 294
<212> TYPE: DNA
<213> ORGANISM: Homo sapiens

<400> SEQUENCE: 163
tagcatgttg agcccagaca caaatctttc cttaagcaat aaatcatttc tgcatatgtt    60
tttaaaacca cagctaagcc atgattattc aaaaggacta ttgtattggg tattttgatt   120
tgggttctta tctccctcac attatcttca tttctatcat tgacctctta tcccagagac   180
```

```
tctcaaactt ttatgttata caaatcacat tctgtctcaa aaaatatctc acccacttct      240
cttctgtttc tgcgtgtgta tgtgtgtgtg tgtgtgtctg ggctcaacat gcta            294
```

<210> SEQ ID NO 164
<211> LENGTH: 412
<212> TYPE: DNA
<213> ORGANISM: Homo sapiens
<220> FEATURE:
<221> NAME/KEY: misc_feature
<222> LOCATION: 292
<223> OTHER INFORMATION: n = A,T,C or G

<400> SEQUENCE: 164

```
cgggattggc tttgagctgc agatgctgcc tgtgaccgca cccggcgtgg aacagaaagc      60
cacctggctg caagtgcgcc agagccgccc tgactacgtg ctgctgtggg gctggggcgt     120
gatgaactcc accgccctga aggaagccca ggccaccgga taccccgcg acaagatgta     180 cggcgtgtgg tgggccggtg cggagcccga tgtgcgtgac gtgggcgaag gcgccaaggg     240
ctacaacgcg ctggctctga acggctacgg cacgcagtcc aaggtgatcc angacatcct     300
gaaacacgtg cacgacaagg gccagggcac ggggcccaaa gacgaagtgg gctcggtgct     360
gtacacccgc ggcgtgatca tccagatgct ggacaaggtg tcaatcacta at             412
```

<210> SEQ ID NO 165
<211> LENGTH: 361
<212> TYPE: DNA
<213> ORGANISM: Homo sapiens

<400> SEQUENCE: 165

```
ttgacacctt gtccagcatc tgcatctgat gagagcctca gatggctacc actaatggca      60
gaaggcaaag gagaacaggc attgtatggc aagaaaggaa gaaagagaga ggggagaaag     120
gtgctaggtt cttttcaaca accagttctt gatggaactg agagtaagag ctcaaggcca     180
ggtgtggtga ctccaaccag taatcccaac attttaggag gctgaggcag gcagatgtct     240
tgaccccatg agtttgtgac cagcctgaac aacatcatga gactccatct ctacaataat     300
tacaaaaatt aatcaggcat tgtggtatgc cctgtagtcc cagatgctgg acaaggtgtc     360
a                                                                     361
```

<210> SEQ ID NO 166
<211> LENGTH: 427
<212> TYPE: DNA
<213> ORGANISM: Homo sapiens

<400> SEQUENCE: 166

```
twgactgact catgtcccct cacccaact atcttctcca ggtggccagg catgatagaa      60
tctgatcctg acttagggga atattttctt tttacttccc atcttgattc cctgccggtg     120
agtttcctgg ttcagggtaa gaaggagct caggccaaag taatgaacaa atccatcctc     180
acagacgtac agaataagag aacwtggacw tagccagcag aacmcaaktg aaamcagaac     240
mcttamctag gatracaamc mcrraratar ktgcycmcmc wtataataga aaccaaactt     300
gtatctaatt aaatatttat ccacygtcag ggcattagtg gttttgataa atacgctttg     360
gctaggattc ctgaggttag aatggaaraa caattgcamc gagggtaggg gacatgagtc     420 aktctaa                                                              427
```

<210> SEQ ID NO 167

```
<211> LENGTH: 500
<212> TYPE: DNA
<213> ORGANISM: Homo sapiens
<220> FEATURE:
<221> NAME/KEY: misc_feature
<222> LOCATION: 288, 303, 318, 326
<223> OTHER INFORMATION: n = A,T,C or G

<400> SEQUENCE: 167
aacgtcgcat gctcccggcc gccatggccg cgggatagac tgactcatgt cccctaagat    60
agaggagaca cctgctaggt gtaaggagaa gatggttagg tctacggagg ctccagggtg   120
ggagtagttc cctgctaagg gagggtagac tgttcaacct gttcctgctc cggcctccac   180
tatagcagat gcgagcagga gtaggagaga gggaggtaag agtcagaagc ttatgttgtt   240
tatgcgggga aacgccrtat cggggcagc cragttatta gggacantr tagwyartcw    300 agntagcatc caaagcgngg gagttntccc atatggttgg acctgcaggc ggccgcatta   360
gtgattagca tgtgagcccc agacacgcat agcaacaagg acctaaactc agatcctgtg   420
ctgattactt aacatgaatt attgtattta tttaacaact ttgagttatg aggcatatta   480
ttaggtccat attacctgga                                              500

<210> SEQ ID NO 168
<211> LENGTH: 358
<212> TYPE: DNA
<213> ORGANISM: Homo sapiens

<400> SEQUENCE: 168
ttcatcgctc ggtgactcaa gcctgtaatc ccagaacttt gggaggccga ggggagcaga    60
tcacctgagg ttgggagttt gagaccagcc tggccaacat ggtgacaacc cgtctctgct   120
aaaaatacaa aaattagcca agcatggtgg catgcacttg taatcccagc tactcgggag   180
gctgaggcag gagaatcact tgaggccagg aggcagaggt tgcagtgagg cagaggttga   240
gatcatgcca ctgcactcca gcctgggcaa cagagtaaga ctccatctca aaaaaaaaaa   300 aaaaaagaa tgatcagagc cacaaataca gaaaaccttg agtcaccgag cgatgaaa     358

<210> SEQ ID NO 169
<211> LENGTH: 1265
<212> TYPE: DNA
<213> ORGANISM: Homo sapiens

<400> SEQUENCE: 169
ttctgtccac accaatctta gagctctgaa agaatttgtc tttaaatatc ttttaatagt    60
aacatgtatt ttatggacca aattgacatt ttcgactatt ttttcccaaa aaaagtcagg   120
tgaatttcag cacactgagt tgggaatttc ttatcccaga agwcggcacg agcaatttca   180
tatttattta agattgattc catactccgt tttcaaggag aatccctgca gtctccttaa   240
aggtagaaca aatactttct attttttttt caccattgtg ggattggact ttaagaggtg   300
actctaaaaa aacagagaac aaatatgtct cagttgtatt aagcacggac ccatattatc   360
atattcactt aaaaaaatga tttcctgtgc acctttggc aacttctctt ttcaatgtag    420
ggaaaaactt agtcaccctg aaaacccaca aataaataa aacttgtaga tgtgggcaga    480
argtttgggg gtggacattg tatgtgttta aattaaaccc tgtatcactg agaagctgtt   540
gtatgggtca gagaaaatga atgcttagaa gctgttcaca tcttcaagag cagaagcaaa   600
ccacatgtct cagctatatt attatttatt tttatgcat aaagtgaatc atttcttctg    660
tattaatttc caagggtttt taccctctat ttaaatgctt tgaaaaacag tgcattgaca   720
```

```
atgggttgat attttctttt aaagaaaaa tataattatg aaagccaaga taatctgaag      780
cctgttttat tttaaaactt tttatgttct gtggttgatg ttgtttgttt gtttgtttct      840
attttgttgg ttttttactt tgttttttgt tttgttttgt tttggtttdg catactacat      900
gcagtttctt taaccaatgt ctgtttggct aatgtaatta aagttgttaa tttatatgag      960
tgcatttcaa ctatgtcaat ggtttcttaa tatttattgt gtagaagtac tggtaattt     1020 tttatttaca atatgtttaa agagataaca gtttgatatg ttttcatgtg tttatagcag     1080
aagttattta tttctatggc attccagcgg atattttggt gtttgcgagg catgcagtca     1140
atattttgta cagttagtgg acagtattca gcaacgcctg atagcttctt tggccttatg     1200
ttaaataaaa agacctgttt gggatgtaaa aaaaaaaaa aaaaaaaaa aaaaaaaaa       1260 aaaaa                                                                1265

<210> SEQ ID NO 170
<211> LENGTH: 383
<212> TYPE: DNA
<213> ORGANISM: Homo sapiens

<400> SEQUENCE: 170
tgtaagtcga gcagtgtgat gacgatattc ttcttattaa tgtggtaatt gaacaaatga       60
tctgtgatac tgatcctgag ctaggaggcg ctgttcagtt aatgggactt cttcgtactc      120
taattgatcc agagaacatg ctggctacaa ctaataaaac cgaaaaaagt gaatttctaa      180
attttttcta caaccattgt atgcatgttc tcacagcacc acttttgacc aatacttcag      240
aagacaaatg tgaaaaggat aatatagttg gatcaaacaa aaacaacaca atttgtcccg      300
ataattatca aacagcacag ctacttgcct taattttaga gttactcaca ttttgtgtgg      360
aacatcacac tgctcgactt aca                                              383

<210> SEQ ID NO 171
<211> LENGTH: 383
<212> TYPE: DNA
<213> ORGANISM: Homo sapiens

<400> SEQUENCE: 171
tgggcacctt caatatcgca agttaaaaat aatgttgagt ttattatact tttgacctgt       60
ttagctcaac agggtgaagg catgtaaaga atgtggactt ctgaggaatt ttcttttaaa      120
aagaacataa tgaagtaaca ttttaattac tcaaggacta cttttggttg aagtttataa      180
tctagatacc tctacttttt gttttgctg ttcgacagtt cacaaagacc ttcagcaatt       240
tacagggtaa aatcgttgaa gtagtggagg tgaaactgaa atttaaaatt attctgtaaa      300
tactataggg aaagaggctg agcttagaat cttttggttg ttcatgtgtt ctgtgctctt      360
atcatcacac tgctcgactt aca                                              383

<210> SEQ ID NO 172
<211> LENGTH: 699
<212> TYPE: DNA
<213> ORGANISM: Homo sapiens
<220> FEATURE:
<221> NAME/KEY: misc_feature
<222> LOCATION: 641
<223> OTHER INFORMATION: n = A,T,C or G

<400> SEQUENCE: 172
tcgggtgatg cctcctcagg cttgtcgtta gtgtacacag agctgctcat gaagcgacag       60
```

-continued

| | |
|---|---|
| cggctgcccc tggcacttca gaacctcttc ctctacactt ttggtgcgct tctgaatcta | 120 |
| ggtctgcatg ctggcggcgg ctctggccca ggcctcctgg aaagtttctc aggatgggca | 180 |
| gcactcgtgg tgctgagcca ggcactaaat ggactgctca tgtctgctgt catggagcat | 240 |
| ggcagcagca tcacacgcct ctttgtggtg tcctgctcgc tggtggtcaa cgccgtgctc | 300 |
| tcagcagtcc tgctacggct gcagctcaca gccgccttct tcctggccac attgctcatt | 360 |
| ggcctggcca tgcgcctgta ctatggcagc cgctagtccc tgacaacttc caccctgatt | 420 |
| ccggaccctg tagattgggc gccaccacca gatcccccct ccaggccttc ctccctctcc | 480 |
| catcagcggc cctgtaacaa gtgccttgtg agaaaagctg gagaagtgag ggcagccagg | 540 |
| ttattctctg gaggttggtg gatgaagggg taccccctagg agatgtgaag tgtgggtttg | 600 |
| gttaaggaaa tgcttaccat ccccccaccccc caaccaagtt nttccagact aaagaattaa | 660 |
| ggtaacatca ataccctaggc ctgaggaggc atcacccga | 699 |

<210> SEQ ID NO 173
<211> LENGTH: 701
<212> TYPE: DNA
<213> ORGANISM: Homo sapiens

<400> SEQUENCE: 173

| | |
|---|---|
| tcgggtgatg cctcctcagg ccagatcaaa cttggggttg aaaactgtgc aaagaaatca | 60 |
| atgtcggaga agaattttg caaaagaaaa atgcctaatc agtactaatt taataggtca | 120 |
| cattagcagt ggaagaagaa atgttgatat tttatgtcag ctattttata atcaccagag | 180 |
| tgcttagctt catgtaagcc atctcgtatt cattagaaat aagaacaatt ttattcgtcg | 240 |
| gaaagaactt ttcaattat agcatcttaa ttgctcagga ttttaaattt tgataaagaa | 300 |
| agctccactt ttggcaggag tagggggcag ggagagagga ggctccatcc acaaggacag | 360 |
| agacaccagg gccagtaggg tagctggtgg ctggatcagt cacaacggac tgacttatgc | 420 |
| catgagaaga aacaacctcc aaatctcagt tgcttaatac aacacaagct catttcttgc | 480 |
| tcacgttaca tgtcctatgt agatcaacag caggtgactc agggacccag gctccatctc | 540 |
| catatgagct tccatagtca ccaggacacg ggctctgaaa gtgtcctcca tgcagggaca | 600 |
| catgcctctt ccttcattg ggcagagcaa gtcacttatg ccagaagtc acactgcagg | 660 |
| gcagtgccat cctgctgtat gcctgaggag gcatcacccg a | 701 |

<210> SEQ ID NO 174
<211> LENGTH: 700
<212> TYPE: DNA
<213> ORGANISM: Homo sapiens
<220> FEATURE:
<221> NAME/KEY: misc_feature
<222> LOCATION: 19
<223> OTHER INFORMATION: n = A,T,C or G

<400> SEQUENCE: 174

| | |
|---|---|
| tcgggtgatg cctcctcang ccctaaatc agagtccagg gtcagagcca caggagacag | 60 |
| ggaaagacat agattttaac cggccccctt caggagattc tgaggctcag ttcactttgt | 120 |
| tgcagtttga acagaggcag caaggctagt ggttaggggc acggtctcta aagctgcact | 180 |
| gcctggatct gcctcccagc tctgccagga accagctgcg tggccttgag ctgctgacac | 240 |
| gcagaaagcc ccctgtggac ccagtctcct cgtctgtaag atgaggacag gactctagga | 300 |
| acccttcccc ttggttttggc ctcactttca caggctccca tcttgaactc tatctactct | 360 |
| tttcctgaaa ccttgtaaaa gaaaaaagtg ctagcctggg caacatggca aaaccctgtc | 420 |

```
tctacaaaaa atacaaaaat tagttgggtg tggtggcatg tgcctgtagt cccagccact    480
tgggaggtgc tgaggtggga ggatcacttg agcccgggag gtggaggttg cagtgagcca    540
agatcatgcc actgcactcc agcctgagta atagagtaag actctgtctc aaaaacaaca    600
acaacaacag tgagtgtgcc tctgtttccg ggttggatgg ggcaccacat ttatgcatct    660
ctcagatttg gacgctgcag cctgaggagg catcacccga                          700
```

<210> SEQ ID NO 175
<211> LENGTH: 484
<212> TYPE: DNA
<213> ORGANISM: Homo sapiens
<220> FEATURE:
<221> NAME/KEY: misc_feature
<222> LOCATION: 30
<223> OTHER INFORMATION: n = A,T,C or G

<400> SEQUENCE: 175

```
tatagggcga attgggcccg agttgcatgn tcccggccgc catggccgcg ggattcgggt    60
gatgcctcct caggcttgtc tgccacaagc tacttctctg agctcagaaa gtgcccctttg   120 atgagggaaa atgtcctact gcactgcgaa tttctcagtt ccattttacc tcccagtcct   180
ccttctaaac cagttaataa attcattcca caagtattta ctgattacct gcttgtgcca   240
gggactattc tcaggctgaa gaaggtggga ggggagggcg gaacctgagg agccacctga   300
gccagcttta tatttcaacc atggctggcc catctgagag catctcccca ctctcgccaa   360
cctatcgggg catagcccag ggatgccccc aggcggccca ggttagatgc gtccctttgg   420
cttgtcagtg atgacataca ccttagctgc ttagctggtg ctggcctgag gaggcatcac   480
ccga                                                                484
```

<210> SEQ ID NO 176
<211> LENGTH: 432
<212> TYPE: DNA
<213> ORGANISM: Homo sapiens

<400> SEQUENCE: 176

```
tcgggtgatg cctcctcagg gctcaaggga tgagaagtga cttctttctg gagggaccgt    60
tcatgccacc caggatgaaa atggataggg acccacttgg aggacttgct gatatgtttg   120
gacaaatgcc aggtagcgga attggtactg gtccaggagt tatccaggat agatttttcac 180 ccaccatggg acgtcatcgt tcaaatcaac tcttcaatgg ccatggggga cacatcatgc   240
ctcccacaca atcgcagttt ggagagatgg gaggcaagtt tatgaaaagc cagggctaa    300 gccagctcta ccataaccag agtcaggac tcttatccca gctgcaagga cagtcgaagg    360
atatgccacc tcggttttct aagaaaggac agcttaatgc agatgagatt agcctgagga   420
ggcatcaccc ga                                                       432
```

<210> SEQ ID NO 177
<211> LENGTH: 788
<212> TYPE: DNA
<213> ORGANISM: Homo sapiens

<400> SEQUENCE: 177

```
tagcatgttg agcccagaca cagtagcatt tgtgccaatt tctggttgga atggtgacaa    60
catgctggag ccaagtgcta acatgccttg gttcaaggga tggaaagtca cccgtaagga   120
tggcaatgcc agtggaacca cgctgcttga ggctctggac tgcatcctac caccaactcg   180
```

```
cccaactgac aagcccttgc gcctgcctct ccaggatgtc tacaaaattg gtggtattgg      240
tactgttcct gttggccgag tggagactgg tgttctcaaa cccggtatgg tggtcacctt      300
tgctccagtc aacgttacaa cggaagtaaa atctgtcgaa atgcaccatg aagctttgag      360
tgaagctctt cctggggaca atgtgggctt caatgtcaag aatgtgtctg tcaaggatgt      420
tcgtcgtggc aacgttgctg gtgacagcaa aaatgaccca ccaatggaag cagctggctt      480
cactgctcag gtgattatcc tgaaccatcc aggccaaata agtgccggct atgcccctgt      540
attggattgc cacacggctc acattgcatg caagtttgct gagctgaagg aaaagattga      600
tcgccgttct ggtaaaaagc tggaagatgg ccctaaattc ttgaagtctg gtgatgctgc      660
cattgttgat atggttcctg gcaagcccat gtgtgttgag agcttctcag actatccacc      720
tttgggtcgc tttgctgttc gtgatatgag acagacagtt gcggtgggtg tctgggctca      780
acatgcta                                                              788
```

`<210> SEQ ID NO 178`
`<211> LENGTH: 786`
`<212> TYPE: DNA`
`<213> ORGANISM: Homo sapiens`

`<400> SEQUENCE: 178`

```
tagcatgttg agcccagaca cctgtgtttc tgggagctct ggcagtggcg gattcatagg       60
cacttgggct gcactttgaa tgacacactt ggctttatta gattcactag tttttaaaaa      120
attgttgttc gtttcttttc attaaaggtt taatcagaca gatcagacag cataattttg      180
tatttaatga cagaaacgtt ggtacatttc ttcatgaatg agcttgcatt ctgaagcaag      240
agcctacaaa aggcacttgt tataaatgaa agttctggct ctagaggcca gtactctgga      300
gtttcagagc agccagtgat tgttccagtc agtgatgcct agttatatag aggaggagta      360
cactgtgcac tcttctaggt gtaagggtat gcaactttgg atcttaaaat tctgtacaca      420
tacacacttt atatatatgt atgtatgtat gaaaacatga aattagtttg tcaaatatgt      480
gtgtgtttag tattttagct tagtgcaact atttccacat tatttattaa attgatctaa      540
gacactttct tgttgacacc ttgaatatta atgttcaagg gtgcaatgtg tattccttta      600
gattgttaaa gcttaattac tatgatttgt agtaaattaa cttttaaaat gtatttgagc      660
ccttctgtag tgtcgtaggg ctcttacagg gtgggaaaga ttttaatttt ccagttgcta      720
attgaacagt atggcctcat tatatatttt gatttatagg agtttgtgtc tgggctcaac      780
atgcta                                                                786
```

`<210> SEQ ID NO 179`
`<211> LENGTH: 796`
`<212> TYPE: DNA`
`<213> ORGANISM: Homo sapiens`

`<400> SEQUENCE: 179`

```
tagcatgttg agcccagaca ctggttacaa gaccagacct gcttcctcca tatgtaaaca       60
gcttttaaaa agccagtgaa ccttttttaat actttgcaa ccttctttca caggcaaaga      120
acacccccat ccgccccttg tttggagtgc agagtttggc tttggttctt tgccttgcct      180
ggagtatact tctaattcct gttgtcctgc acaagctgaa taccgagcta cccaccgcca      240
cccaggccag gtttccactc atttattact ttatgtttct gttccattgc tggtccacag      300
aaataagttt tccttgggag gaatgtgatt atacccctttt aatttcctcc ttttgctttt      360
ttttaatatc attggtatgt gtttggccca gaggaaactg aaattcacca tcatcttgac      420
```

-continued

```
tggcaatccc attaccatgc ttttttaaa aaacgtaatt tttcttgcct tacattggca      480
gagtagccct tcctggctac tggcttaatg tagtcactca gtttctaggt ggcattaggc      540
atgagacctg aagcacagac tgtcttacca caaaaggtga caagatctca aaccttagcc      600
aaagggctat gtcaggtttc aatgctatct gcttctgttc ctgctcactg ttctggattt      660
tgtccttctt catccctagc accagaattt cccagtctcc ctccctacct tcccttgttt      720
taattctaat ctatcagcaa ataaactttt caaatgtttt aaccggtatc tccatgtgtc      780
tgggctcaac atgcta                                                      796
```

<210> SEQ ID NO 180
<211> LENGTH: 488
<212> TYPE: DNA
<213> ORGANISM: Homo sapiens

<400> SEQUENCE: 180

```
ggatgtgctg caaggcgatt aagttgggta acgccagggt tttcccagtc acgacgttgt      60
aaaacgacgg ccagtgaatt gtaatacgac tcactatagg gcgaattggg cccgacgtcg      120
catgctcccg gccgccatgg ccgcgggata gcatgttgag cccagacacc tgcaggtcat      180
ttggagagat ttttcacgtt accagcttga tggtcttttt caggaggaga gacactgagc      240
actcccaagg tgaggttgaa gatttcctct agatagccgg ataagaagac taggagggat      300
gcctagaaaa tgattagcat gcaaatttct acctgccatt tcagaactgt gtgtcagccc      360
acattcagct gcttcttgtg aactgaaaag agagaggtat tgagacttt ctgatggccg      420 ctctaacatt gtaacacagt aatctgtgtg tgtgtgggtg tgtgtgtgtg tctgggctca      480
acatgcta                                                              488
```

<210> SEQ ID NO 181
<211> LENGTH: 317
<212> TYPE: DNA
<213> ORGANISM: Homo sapiens

<400> SEQUENCE: 181

```
tagcatgttg agcccagaca cggcgacggt acctgatgag tggggtgatg gcacctgtga      60
aaaggaggaa cgtcatcccc catgatattg gggacccaga tgatgaacca tggctccgcg      120
tcaatgcata tttaatccat gatactgctg attggaagga cctgaacctg aagtttgtgc      180
tgcaggttta tcgggactat tacctcacgg gtgatcaaaa cttcctgaag gacatgtggc      240
ctgtgtgtct agtaagggat gcacatgcag tggccagtgt gccagggta tggttggtgt      300 ctgggctcaa catgcta                                                    317
```

<210> SEQ ID NO 182
<211> LENGTH: 507
<212> TYPE: DNA
<213> ORGANISM: Homo sapiens
<220> FEATURE:
<221> NAME/KEY: misc_feature
<222> LOCATION: 493
<223> OTHER INFORMATION: n = A,T,C or G

<400> SEQUENCE: 182

```
tagcatgttg agcccagaca ctggctgtta gccaaatcct ctctcagctg ctccctgtgg      60
tttggtgact caggattaca gaggcatcct gtttcaggga acaaaaagat tttagctgcc     120
agcagagagc accacataca ttagaatggt aaggactgcc acctccttca agaacaggag     180
```

```
tgagggtggt ggtgaatggg aatggaagcc tgcattccct gatgcatttg tgctctctca      240
aatcctgtct tagtcttagg aaaggaagta agtttcaag  gacggttccg aactgctttt      300
tgtgtctggg ctcaacatgc tatcccgcgg ccatggcggc cgggagcatg cgacgtcggg      360
cccaattcgc cctatagtga gtcgtattac aattcactgg ccgtcgtttt acaacgtcgt      420
gactgggaaa accctggcgt tacccaactt aatcgccttg cagcacatcc cctttccca       480 gctggcgtaa tancgaaaag gcccgca                                          507

<210> SEQ ID NO 183
<211> LENGTH: 227
<212> TYPE: DNA
<213> ORGANISM: Homo sapiens

<400> SEQUENCE: 183
gatttacgct gcaacactgt ggaggtagcc ctggagcaag gcaggcatgg atgcttctgc       60
aatccccaaa tggagcctgg tatttcagcc aggaatctga gcagcccc  ctctaattgt      120 agcaatgata agttattctc tttgttcttc aaccttccaa tagccttgag cttccagggg      180
agtgtcgtta atcattacag cctggtctcc acagtgttgc agcgtaa                    227

<210> SEQ ID NO 184
<211> LENGTH: 225
<212> TYPE: DNA
<213> ORGANISM: Homo sapiens

<400> SEQUENCE: 184
ttacgctgca acactgtgga gcagattaac atcagacttt ctatcaaca tgactggggt       60 tactaaaaag acaacaaatc aatggcttca aaagtctaag gaataatttc gatacttcaa      120
cttttataaa cctgacaaaa ctatcaatca agcataaaga cagatgaaga acatttccag      180
attttggcca atcagatatt ttacctccac agtgttgcag cgtaa                      225

<210> SEQ ID NO 185
<211> LENGTH: 597
<212> TYPE: DNA
<213> ORGANISM: Homo sapiens

<400> SEQUENCE: 185
ggcccgacgt cgcatgctcc cggccgccat ggccgcggga ttcgttaggg tctctatcca       60
ctgggaccca taggctagtc agagtattta gagttgagtt cctttctgct tcccagaatt      120
tgaaagaaaa ggagtgaggt gatagagctg agagatcaga tttgcctctg aagcctgttc      180
aagatgtatg tgctcagacc ccaccactgg ggcctgtggg tgaggtcctg ggcatctatt      240
tgaatgaatt gctgaagggg agcactatgc caaggaaggg gaacccatcc tggcactggc      300 acagggtca  ccttatccag tgctcagtgc ttctttgctg ctacctggtt ttctctcata      360
tgtgaggggc aggtaagaag aagtgcccrg tgttgtgcga gttttagaac atctaccagt      420
aagtggggaa gtttcacaaa gcagcagctt tgttttgtgt attttcacct tcagttagaa      480
gaggaaggct gtgagatgaa tgttagttga gtggaaaaga cgggtaagct tagtggatag      540
agaccctaac gaatcactag tgcggccgcc ttgcaggtcg accatatggg agagctc         597

<210> SEQ ID NO 186
<211> LENGTH: 597
<212> TYPE: DNA
<213> ORGANISM: Homo sapiens

<400> SEQUENCE: 186
```

```
ggcccgaagt tgcatgttcc cggccgccat ggccgcggga ttcgttaggg tctctatcca    60
ctacctaaaa atcccaaac atataactga actcctcaca cccaattgga ccaatccatc   120
accccagagg cctacagatc ctcctttgat acataagaaa atttccccaa actacctaac   180
tatatcattt tgcaagattt gttttaccaa attttgatgg cctttctgag cttgtcagtg   240
tgaaccacta ttacgaacga tcggatatta actgcccctc accgtccagg tgtagctggc   300
aacatcaagt gcagtaaata ttcattaagt tttcacctac taaggtgctt aaacacccta   360
gggtgccatg tcggtagcag atctttgat ttgtttttat ttcccataag ggtcctgttc    420
aaggtcaatc atacatgtag tgtgagcagc tagtcactat cgcatgactt ggagggtgat   480
aatagaggcc tcctttgctg ttaaagaact cttgtcccag cctgtcaaag tggatagaga   540
ccctaacgaa tcactagtgc ggccgcctgc aggtcgacca tatgggagag ctcccaa      597

<210> SEQ ID NO 187
<211> LENGTH: 324
<212> TYPE: DNA
<213> ORGANISM: Homo sapiens

<400> SEQUENCE: 187
tcgttagggt ctctatccac ttgcaggtaa aatccaatcc tgtgtatatc ttatagtctt    60
ccatatgtag tggttcaaga gactgcagtt ccagaaagac tagccgagcc catccatgtc   120
ttccacttaa ccctgctttg ggttacacat cttaactttt ctgttcaagt ttctctgtgt   180
agtttatagc atgagtattg ggawaatgcc ctgaaacctg acatgagatc tgggaaacac   240
aaacttactc aataagaatt ctcccatat ttttatgatg gaaaaatttc acatgcacag    300
aggagtggat agagaccct aacga                                           324

<210> SEQ ID NO 188
<211> LENGTH: 178
<212> TYPE: DNA
<213> ORGANISM: Homo sapiens
<220> FEATURE:
<221> NAME/KEY: misc_feature
<222> LOCATION: 46
<223> OTHER INFORMATION: n = A,T,C or G

<400> SEQUENCE: 188
gcgcggggat tcgggtgat acctcctcat gccaaaatac aacgtntaat ttcacaactt     60
gccttccaat ttacgcattt tcaatttgct ctccccattt gttgagtcac aacaaacacc   120
attgcccaga aacatgtatt acctaacatg cacatactct taaaactact catcccctt    178

<210> SEQ ID NO 189
<211> LENGTH: 367
<212> TYPE: DNA
<213> ORGANISM: Homo sapiens

<400> SEQUENCE: 189
tgacaccttg tccagcatct gacacagtct tggctcttgg aaaatattgg ataaatgaaa    60
atgaatttct ttagcaagtg gtataagctg agaatatacg tatcacatat cctcattcta   120
agacacattc agtgtccctg aaattagaat aggacttaca ataagtgtgt tcactttctc   180
aatagctgtt attcaattga tggtaggcct taaaagtcaa agaaatgaga gggcatgtga   240 aaaaagctc aacatcactg atcattagaa aacttccatt caaacccccaa atgagatacc   300 atctcatacc agtcagaatg gctattatta aaaagtcaaa aataacaga tgctggacaa    360
``` ggtgtca 367

<210> SEQ ID NO 190
<211> LENGTH: 369
<212> TYPE: DNA
<213> ORGANISM: Homo sapiens
<220> FEATURE:
<221> NAME/KEY: misc_feature
<222> LOCATION: 323
<223> OTHER INFORMATION: n = A,T,C or G

<400> SEQUENCE: 190
gacaccttgt ccagcatctg acaacgctaa cagcctgagg agatctttat ttatttattt     60
agttttact ctggctaggc agatggtggc taaaacattc atttacccat ttattcattt    120
aattgttcct gcaaggccta tggatagagt attgtccagc actgctctgg aagctaggag    180
catggggatg aacaagatag gctacatcct gttcccacag aacttccact ttagtctggg    240
aaacagatga tatatacaaa tatataaatg aattcaggta gttttaagta cgaaaagaat    300
aagaaagcag agtcatgatt tanaatgctg gaaacagggg ctattgcttg agatattgaa    360
ggtgcccaa                                                             369

<210> SEQ ID NO 191
<211> LENGTH: 369
<212> TYPE: DNA
<213> ORGANISM: Homo sapiens

<400> SEQUENCE: 191
tgacaccttg tccagcatct gcacagggaa aagaaactat tatcagagtg aacaggcaac     60
ctacagaatg ggagaaaatt tttgcaatct atccatctga caagggcta atatccagaa     120
tctacaaaga acttatacaa atttacaaga aacaaacaaa caaacaactc ctcaaaaagt    180
gggtgaagga tgtgaacaga cacttctcaa aagaagacat ttatgggggcc aacaaacata    240
tgaaaaaaag ctcatcatca ctggtcacta gataaatgca aatcaaaacc acaatgagat    300
accatctcat tccagttaga atggcaatca ttaaaaagtc aggaaacaac agatgctgga    360
caaggtgtc                                                             369

<210> SEQ ID NO 192
<211> LENGTH: 449
<212> TYPE: DNA
<213> ORGANISM: Homo sapiens

<400> SEQUENCE: 192
tgacgcttgg ccacttgaca cttcatcttt gcacagaaaa acttctttac agatttaatt     60
caagactggt ctagtgacag tcctccagac attttttcat ttgttccata tacgtggaat    120
tttaaaatca tgtttcatca gtttgaaatg atttgggctg ctaatcaaca caattggatc    180
gactgttcta ctaaacaaca ggaaaatgtg tatctggcag cctgtggaga acactaaac    240
attgattttt ctttgccttt tacggacttt gttccagcta catgtaatac caagttctct    300
ttaagaggag aagatgttga tcttcatttg tttctaccag actgccaccc tagtaaatat    360
tcttttattta tgctggtaaa aaattgccat ccaaataaga tgattcatga tactggtatt    420
cctgctgagt gtcaagtggc caagcgtca                                       449

<210> SEQ ID NO 193
<211> LENGTH: 372
<212> TYPE: DNA
<213> ORGANISM: Homo sapiens

<400> SEQUENCE: 193

| tgacgcttgg ccacttgaca ccagggatgt akcagttgaa tataatcctg caattgtaca | 60 |
| tattggcaat ttcccatcaa acattctaga aagagacaac caggattgct aggccataaa | 120 |
| agctgcaata aataactggt aattgcagta atcatttcag gccaattcaa tccagtttgg | 180 |
| ctcagaggtg cctttggctg agagaagagg tgagatataa tgtgttttct tgcaacttct | 240 |
| tggaagaata actccacaat agtctgagga ctagatacaa acctatttgc cattaaagca | 300 |
| ccagagtctg ttaattccag tactgataag tgttggagat tagactccag tgtgtcaagt | 360 |
| ggccaagcgt ca | 372 |

<210> SEQ ID NO 194
<211> LENGTH: 309
<212> TYPE: DNA
<213> ORGANISM: Homo sapiens
<220> FEATURE:
<221> NAME/KEY: misc_feature
<222> LOCATION: 140, 205
<223> OTHER INFORMATION: n = A,T,C or G

<400> SEQUENCE: 194

| tgacgcttgg ccacttgaca cttatgtaga atccatcgtg ggctgatgca agcccttat | 60 |
| ttaggcttag tgttgtgggc accttcaata tcacactaga gacaaacgcc acaagatctg | 120 |
| cagaaacatt cagttctgan cactcgaatg gcaggataac ttttttgtgtt gtaatccttc | 180 |
| acatatacaa aaacaaactc tgcantctca cgttacaaaa aaacgtactg ctgtaaaata | 240 |
| ttaagaaggg gtaaaggata ccatctataa caaagtaact tacaactagt gtcaagtggc | 300 |
| caagcgtca | 309 |

<210> SEQ ID NO 195
<211> LENGTH: 312
<212> TYPE: DNA
<213> ORGANISM: Homo sapiens
<220> FEATURE:
<221> NAME/KEY: misc_feature
<222> LOCATION: 100, 270
<223> OTHER INFORMATION: n = A,T,C or G

<400> SEQUENCE: 195

| tgacgcttgg ccacttgaca cccaatctcg cacttcatcc tcccagcacc tgatgaagta | 60 |
| ggactgcaac tatccccact tcccagatga ggggaccaan gtacacatta ggacccggat | 120 |
| gggagcacag atttgtccga tcccagactc caagcactca gcgtcactcc aggacagcgg | 180 |
| ctttcagata aggtcacaaa catgaatggc tccgacaacc ggagtcagtc cgtgctgagt | 240 |
| taaggcaatg gtgacacgga tgcacgtgtn acctgtaatg gttcatcgta agtgtcaagt | 300 |
| ggccaagcgt ca | 312 |

<210> SEQ ID NO 196
<211> LENGTH: 288
<212> TYPE: DNA
<213> ORGANISM: Homo sapiens

<400> SEQUENCE: 196

| tgtatcgacg tagtggtctc ctcagccatg cagaactgtg actcaattaa acctctttcc | 60 |
| tttatgaatt acccaatctc gggtagtgtc tttatagtag tgtgagaatg gactaataca | 120 |
| agtacatttt acttagtaat aataataaac aaatatatta catttttgtg tatttactac | 180 |

| | |
|---|---|
| accatatttt ttattgttat tgtagtgtac accttctact tattaaaaga aataggcccg | 240 |
| aggcgggcag atcacgaggt caggagatgg agaccactac gtcgatac | 288 |

<210> SEQ ID NO 197
<211> LENGTH: 289
<212> TYPE: DNA
<213> ORGANISM: Homo sapiens

<400> SEQUENCE: 197

| | |
|---|---|
| ttgggcacct tcaatatcat gacaggtgat gtgataacca agaaggctac taagtgatta | 60 |
| atgggtgggt aatgtataca gagtaggtac actggacaga ggggtaattc atagccaagg | 120 |
| caggagaagc agaatggcaa acatttcat cacactactc aggatagcat gcagtttaaa | 180 |
| acctataagt agtttatttt tggaattttc cacttaatat tttcagactg caggtaacta | 240 |
| aactgtggaa cacaagaaca tagataaggg gagaccacta cgtcgatac | 289 |

<210> SEQ ID NO 198
<211> LENGTH: 288
<212> TYPE: DNA
<213> ORGANISM: Homo sapiens

<400> SEQUENCE: 198

| | |
|---|---|
| gtatcgacgt agtggtctcc caagcagtgg gaagaaaacg tgaaccaatt aaaatgtatc | 60 |
| agataccccca agaaaggcg cttgagtaaa gattccaagt gggtcacaat ctcagatctt | 120 |
| aaaattcagg ctgtcaaaga gatttgctat gaggttgctc tcaatgactt caggcacagt | 180 |
| cggcaggaga ttgaagccct ggccattgtc aagatgaagg agctttgtgc catgtatggc | 240 |
| aagaaagacc ccaatgagcg ggactcctgg agaccactac gtcgatac | 288 |

<210> SEQ ID NO 199
<211> LENGTH: 1027
<212> TYPE: DNA
<213> ORGANISM: Homo sapiens
<220> FEATURE:
<221> NAME/KEY: misc_feature
<222> LOCATION: 17, 21, 36, 39, 40, 42, 63, 98, 116, 145, 162, 173, 865,
      885, 891, 916, 924, 927, 929, 934, 942, 949, 976, 983, 988,
      989, 1009, 1014
<223> OTHER INFORMATION: n = A,T,C or G

<400> SEQUENCE: 199

| | |
|---|---|
| gcttttggg aaaaacncaa ntggggaaa ggggnttnn tngcaagggg ataaaggggg | 60 |
| aancccaggg tttccccatt cagggaggtg taaaaagncg gccaggggat tgtaanagga | 120 |
| ttcaataata gggggaatgg gcccngaagt tgcaaggttc cngcccgcca tgnccgcggg | 180 |
| atttagtgac attacgacgs tggtaataaa gtgggsccaa waaatatttg tgatgtgatt | 240 |
| tttsgaccag tgaacccatt gwacaggacc tcatttccty tgagatgrta gccataatca | 300 |
| gataaaagrt tagaagtytt tctgcacgtt aacagcatca ttaaatggag tggcatcacc | 360 |
| aatttcaccc tttgttagcc gataccttcc ccttgaaggc attcaattaa gtgaccaatc | 420 |
| gtcatacgag aggggatggc atggggattg atgatgatat caggggtgat accttcacag | 480 |
| gtgaaaggca tatcctcttg tctatactga ataccacaag tacccttttg accatgtcga | 540 |
| ctagcaaatt tgtctccaat ctgtgtwatc cctaacagag cgtacccta ttttacaaaa | 600 |
| tttatatcct tcctgattga gagttaccat aacctgatcc acaatgcccg tctcgctwgt | 660 |
| tctgagaaaa gtgctacagt ctctcttggt atagcgtcta ttggtgctct ccaattcatc | 720 |
| ttcatttttc aggcaaggtg aactgttttg cctataataa cmtcatctcc tgatacmcga | 780 |

```
aacccckgga rctatcaaac catcatcatc cagcgttckt watgtymcta aatccctatt    840
gcggccgcct gcaggtcaac atatnggaaa acccccccacc ccttnggagc ntaccttgaa    900
ttttccatat gtcccntaaa ttanctngnc ttanccctggc cntaacctnt tccggtttaa    960
attgtttccg ccccnttcc ccnccttnna accggaaacc ttaattttna accngggggtt   1020 cctatcc                                                             1027
```

<210> SEQ ID NO 200
<211> LENGTH: 207
<212> TYPE: DNA
<213> ORGANISM: Homo sapiens

<400> SEQUENCE: 200

```
agtgacatta cgacgctggc catcttgaat cctagggcat gaagttgccc caaagttcag     60
cacttggtta agcctgatcc ctctggttta tcacaaagaa taggatggga taagaaagt    120 ggacacttaa ataagctata aattatatgg tccttgtcta gcaggagaca actgcacagg   180
tatactacca gcgtcgtaat gtcacta                                        207
```

<210> SEQ ID NO 201
<211> LENGTH: 209
<212> TYPE: DNA
<213> ORGANISM: Homo sapiens

<400> SEQUENCE: 201

```
tgggcaccttt caatatctat taaaagcaca aatactgaag aacacaccaa gactatcaat    60
gaggttacat ctggagtcct cgatatatca ggaaaaaatg aagtgaacat tcacagagtt   120
ttacttcttt gggaactcaa atgctagaaa agaaaagggg ccctctttc tctggcttcc    180 tggtcctatc cagcgtcgta atgtcacta                                      209
```

<210> SEQ ID NO 202
<211> LENGTH: 349
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 202

```
ntacgctgca acactgtgga gccactggtt tttattcccg gcaggttatc cagcaaacag     60
tcactgaaca caccgaagac cgtggtatgg taaccgttca cagtaatcgt tccagtcgtc    120
tgcgggaccc cgacgagcgt cactgggtac agaccagatt cagccggaag agaaagcgcc   180
gcagggagag actcgaactc cactccgctg gtgagcagcc ccatgttttc aactcgaagt   240
tcaaacggca ttgggttata taccatcagc tgaacttcac acacatctcc ttgaacccac   300
tggaaatcta ttttcttgtt ccgctcttct ccacagtgtt gcagcgtaa                349
```

<210> SEQ ID NO 203
<211> LENGTH: 241
<212> TYPE: DNA
<213> ORGANISM: Homo sapiens

<400> SEQUENCE: 203

```
tgctcctctt gccttaccaa cccaaagccc actgtgaaat atgaagtgaa tgacaaaatt     60
cagttttcaa cgcaatatag tatagtttat ctgattcttt tgatctccag gacacttaa    120
```

| acaactgcta | ccaccaccac | caacctaggg | atttaggatt | ctccacagac | cagaaattat | 180 |
| ttctcctttg | agtttcaggc | tcctctggga | ctcctgttca | tcaatgggtg | gtaaatggct | 240 |
| a | | | | | | 241 |

<210> SEQ ID NO 204
<211> LENGTH: 248
<212> TYPE: DNA
<213> ORGANISM: Homo sapiens

<400> SEQUENCE: 204

| tagccattta | ccacccatct | gcaaaccswg | acmwwcargr | cywgwackya | ggcgatttga | 60 |
| agtactggta | atgctctgat | catgttagtt | acataagtgt | ggtcagttta | caaaaattca | 120 |
| cagaactaaa | tactcaatgc | tatgtgttca | tgtctgtgtt | tatgtgtgtg | taatgtttca | 180 |
| attaagtttt | tttaaaaaaa | agagatgatt | tccaaataag | aaagccgtgt | tggtaaggca | 240 |
| agaggagc | | | | | | 248 |

<210> SEQ ID NO 205
<211> LENGTH: 505
<212> TYPE: DNA
<213> ORGANISM: Homo sapiens
<220> FEATURE:
<221> NAME/KEY: misc_feature
<222> LOCATION: 447
<223> OTHER INFORMATION: n = A,T,C or G

<400> SEQUENCE: 205

| tacgctgcaa | cactgtggag | ccattcatac | aggtccctaa | ttaaggaaca | agtgattatg | 60 |
| ctacctttgc | acggttaggg | taccgcggcc | gttaaacatg | tgtcactggg | caggcggtgc | 120 |
| ctctaatact | ggtgatgcta | gaggtgatgt | ttttggtaaa | caggcggggt | aagatttgcc | 180 |
| gagttccttt | tactttttt | aacctttcct | tatgagcatg | cctgtgttgg | gttgacagtg | 240 |
| ggggtaataa | tgacttgttg | gttgattgta | gatattgggc | tgttaattgt | cagttcagtg | 300 |
| ttttaatctg | acgcaggctt | atgcggagga | gaatgttttc | atgttactta | tactaacatt | 360 |
| agttcttcta | tagggtgata | gattggtcca | attgggtgtg | aggagttcag | ttatatgttt | 420 |
| gggattttt | aggtagtggg | tgttganctt | gaacgctttc | ttaattggtg | gctgcttta | 480 |
| rgcctactat | gggtggtaaa | tggct | | | | 505 |

<210> SEQ ID NO 206
<211> LENGTH: 179
<212> TYPE: DNA
<213> ORGANISM: Homo sapiens

<400> SEQUENCE: 206

| tagactgact | catgtcccct | accaaagccc | atgtaaggag | ctgagttctt | aaagactgaa | 60 |
| gacagactat | tctctggaga | aaataaaat | ggaaattgta | ctttaaaaaa | aaaaaaaatc | 120 |
| ggccgggcat | ggtagcacac | acctgtaatc | ccagctacta | ggggacatga | gtcagtcta | 179 |

<210> SEQ ID NO 207
<211> LENGTH: 176
<212> TYPE: DNA
<213> ORGANISM: Homo sapiens

<400> SEQUENCE: 207

| agactgactc | atgtccccta | ccccaccttc | tgctgtgctg | ccgtgttcct | aacaggtcac | 60 |
| agactggtac | tggtcagtgg | cctgggggtt | ggggacctct | attatatggg | atacaaattt | 120 |

```
aggagttgga attgacacga tttagtgact gatgggatat gggtggtaaa tggcta        176

<210> SEQ ID NO 208
<211> LENGTH: 196
<212> TYPE: DNA
<213> ORGANISM: Homo sapiens

<400> SEQUENCE: 208
agactgactc atgtcccta tttaacaggg tctctagtgc tgtgaaaaaa aaaaatgctg     60
aacattgcat ataacttata ttgtaagaaa tactgtacaa tgactttatt gcatctgggt   120
agctgtaagg catgaaggat gccaagaagt ttaaggaata tgggtggtaa atggctaggg   180
gacatgagtc agtcta                                                   196

<210> SEQ ID NO 209
<211> LENGTH: 345
<212> TYPE: DNA
<213> ORGANISM: Homo sapiens
<220> FEATURE:
<221> NAME/KEY: misc_feature
<222> LOCATION: 53, 56
<223> OTHER INFORMATION: n = A,T,C or G

<400> SEQUENCE: 209
gacgcttggc cacttgacac cttttatttt ttaaggattc ttaagtcatt tangtnactt    60
tgtaagtttt tcctgtgccc ccataagaat gatagcttta aaaattatgc tggggtagca  120
aagaagatac ttctagcttt agaatgtgta ggtatagcca ggattcttgt gaggagggggt 180 gatttagagc aaatttctta ttctccttgc ctcatctgta acatgggat aataatagaa   240 ctggcttgac aaggttggaa ttagtattac atggtaaata catgtaaaat gtttagaatg  300
gtgccaagta tctaggaagt acttgggcat gggtggtaaa tggct                  345

<210> SEQ ID NO 210
<211> LENGTH: 178
<212> TYPE: DNA
<213> ORGANISM: Homo sapiens

<400> SEQUENCE: 210
gacgcttggc cacttgacac tagagtaggg tttggccaac tttttctata aaggaccaga   60
gagtaaatat ttcaggcttt gtgggttgtg cagtctctct tgcaactact cagctctgcc  120
attgtagcat agaaatcagc catagacagg acagaaatga atgggtggta aatggcta    178

<210> SEQ ID NO 211
<211> LENGTH: 454
<212> TYPE: DNA
<213> ORGANISM: Homo sapiens

<400> SEQUENCE: 211
tgggcacctt caatatctat ccagcgcatc taaattcgct ttttcttga ttaaaaattt    60 caccacttgc tgttttgct catgtatacc aagtagcagt ggtgtgaggc catgcttgtt  120
ttttgattcg atatcagcac cgtataagag cagtgctttg gccattaatt tatcttcatt  180
gtagacagca tagtgtagag tggtatctcc atactcatct ggaatatttg gatcagtgcc  240
atgttccagc aacattaacg cacattcatc ttcctggcat tgtacggcct ttgtcagagc  300
tgtcctcttt ttgttgtcaa ggacattaag ttgacatcgt ctgtccagca cgagttttac  360
tacttctgaa ttcccattgg cagaggccag atgtagagca gtcctcttt gcttgtccct   420
```

```
cttgttcaca tcagtgtccc tgagcataac ggaa                                454
```

<210> SEQ ID NO 212
<211> LENGTH: 337
<212> TYPE: DNA
<213> ORGANISM: Homo sapiens

<400> SEQUENCE: 212

```
tccgttatgc acccagaaa acctactgga gttacttatt aacatcaagg ctggaaccta     60
tttgcctcag tcctatctga ttcatgagca catggttatt actgatcgca ttgaaaacat   120
tgatcacctg ggtttctta tttatcgact gtgtcatgac aaggaaactt acaaactgca    180
acgcagagaa actattaaag gtattcagaa acgtgaagcc agcaattgtt tcgcaattcg   240
gcattttgaa aacaaatttg ccgtggaaac tttaatttgt tcttgaacag tcaagaaaaa   300
cattattgag gaaaattaat atcacagcat aacggaa                            337
```

<210> SEQ ID NO 213
<211> LENGTH: 715
<212> TYPE: DNA
<213> ORGANISM: Homo sapiens
<220> FEATURE:
<221> NAME/KEY: misc_feature
<222> LOCATION: 552, 630, 649, 657, 691, 693, 697
<223> OTHER INFORMATION: n = A,T,C or G

<400> SEQUENCE: 213

```
tcgggtgatg cctcctcagg catcttccat ccatctcttc aagattagct gtcccaaatg    60
ttttccttc tcttctttac tgataaattt ggactccttc ttgacactga tgacagcttt   120
agtatccttc ttgtcaccttt gcagacttta aacataaaaa tactcattgg ttttaaaagg  180
aaaaaagtat acattagcac tattaagctt ggccttgaaa cattttctat cttttattaa   240
atgtcggtta gctgaacaga attcatttta caatgcagag tgagaaaaga agggagctat   300
atgcatttga gaatgcaagc attgtcaaat aaacatttta aatgctttct taaagtgagc   360
acatacagaa atacattaag atattagaaa gtgttttgc ttgtgtacta ctaattaggg    420
aagcaccttg tatagttcct cttctaaaat tgaagtagat tttaaaaacc catgtaattt   480
aattgagctc tcagttcaga ttttaggaga attttaacag ggatttggtt ttgtctaaat   540
tttgtcaatt tntttagtta atctgtataa ttttataaat gtcaaactgt atttagtccg   600
ttttcatgct gctatgaaag aaatacccan gacagggtta tttataaang gaaagangtt   660
aatttgactc ccagttcaca ggcctgagga ngnatcnccc gaaatcctta ttgcg         715
```

<210> SEQ ID NO 214
<211> LENGTH: 345
<212> TYPE: DNA
<213> ORGANISM: Homo sapiens
<220> FEATURE:
<221> NAME/KEY: misc_feature
<222> LOCATION: 6, 8, 15
<223> OTHER INFORMATION: n = A,T,C or G

<400> SEQUENCE: 214

```
ggtaangngc atacntcggt gctccggccg ccggagtcgg gggattcggg tgatgcctcc    60
tcaggcccac ttgggcctgc ttttcccaaa tggcagctcc tctggacatg ccattccttc   120
tcccacctgc ctgattcttc atatgttggg tgtccctgtt tttctggtgc tatttcctga   180
ctgctgttca gctgccactg tcctgcaaag cctgcctttt taaatgcctc accattcctt   240
catttgtttc ttaaatatgg gaagtgaaag tgccacctga ggccgggcac agtggctcac   300
```

```
gcctgtaatc ccagcacttt gggagcctga ggaggcatca cccga              345

<210> SEQ ID NO 215
<211> LENGTH: 429
<212> TYPE: DNA
<213> ORGANISM: Homo sapiens

<400> SEQUENCE: 215
ggtgatgcct cctcaggcga agctcaggga ggacagaaac ctcccgtgga gcagaagggc    60
aaaagctcgc ttgatcttga ttttcagtac gaatacagac cgtgaaagcg gggcctcacg   120
atccttctga cctttttgggt tttaagcagg aggtgtcaga aaagttacca cagggataac   180
tggcttgtgg cggccaagcg ttcatagcga cgtcgctttt tgatccttcg atgtcggctc   240
ttcctatcat tgtgaagcag aattcaccaa gcgttggatt gttcacccac taatagggaa   300
cgtgagctgg gtttagaccg tcgtgagaca ggttagtttt accctactga tgatgtgtkg   360
ttgccatggt aatcctgctc agtacgagag gaaccgcagg ttcasacatt tggtgtatgt   420
gcttgcctt                                                           429

<210> SEQ ID NO 216
<211> LENGTH: 593
<212> TYPE: DNA
<213> ORGANISM: Homo sapiens
<220> FEATURE:
<221> NAME/KEY: misc_feature
<222> LOCATION: 15, 429, 446, 498, 512, 538, 543, 557
<223> OTHER INFORMATION: n = A,T,C or G

<400> SEQUENCE: 216
tgacacctat gtccngcatc tgttcacagt ttccacaaat agccagcctt tggccacctc    60
tctgtcctga ggtatacaag tatatcagga ggtgtatacc ttctcttctc ttccccacca   120
aagagaacat gcaggctctg gaagctgtct taggagcctt tgggctcaga atttcagagt   180
cttgggtacc ttggatgtgg tctggaagga gaaacattgg ctctggataa ggagtacagc   240
cggaggaggg tcacagagcc ctcagctcaa gccectgtgc cttagtctaa aagcagcttt   300
ggatgaggaa gcaggttaag taacatacgt aagcgtacac aggtagaaag tgctgggagt   360
cagaattgca cagtgtgtag gagtagtacc tcaatcaatg agggcaaatc aactgaaaga   420
agaagaccna ttaatgaatt gcttangggg aaggatcaag gctatcatgg agatctttct   480
aggaagatta ttgtttanaa ttatgaaagg antagggcag ggacagggcc agaagtanaa   540
ganaacattg cctatanccc ttgtcttgca cccagatgct ggacaaggtg tca          593

<210> SEQ ID NO 217
<211> LENGTH: 335
<212> TYPE: DNA
<213> ORGANISM: Homo sapiens

<400> SEQUENCE: 217
tgacaccttg tccagcatct gacgtgaaga tgagcagctc agaggaggtg tcctggattt    60
cctggttctg tgggctccgt ggcaatgaat tcttctgtga agtggatgaa gactacatcc   120
aggacaaatt taatcttact ggactcaatg agcaggtccc tcactatcga caagctctag   180
acatgatctt ggacctggag cctgatgaag aactggaaga caaccccaac cagagtgacc   240
tgattgagca ggcagccgag atgctttatg gattgatcca cgcccgctac atccttacca   300
accgtggcat cgcccagatg ctggacaagg tgtca                              335
```

```
<210> SEQ ID NO 218
<211> LENGTH: 248
<212> TYPE: DNA
<213> ORGANISM: Homo sapiens

<400> SEQUENCE: 218
tacgtactgg tcttgaaggt cttaggtaga gaaaaaatgt gaatatttaa tcaaagacta      60
tgtatgaaat gggactgtaa gtacagaggg aagggtggcc cttatcgcca gaagttggta     120
gatgcgtccc cgtcatgaaa tgttgtgtca ctgcccgaca tttgccgaat tactgaaatt     180
ccgtagaatt agtgcaaatt ctaacgttgt tcatctaaga ttatggttcc atgtttctag     240
tacttttta                                                              248

<210> SEQ ID NO 219
<211> LENGTH: 530
<212> TYPE: DNA
<213> ORGANISM: Homo sapiens
<220> FEATURE:
<221> NAME/KEY: misc_feature
<222> LOCATION: 49, 216, 265, 275, 281, 296, 371, 407, 424, 429, 454,
      456, 458, 464, 474, 476, 506, 509, 527, 530
<223> OTHER INFORMATION: n = A,T,C or G

<400> SEQUENCE: 219
tgacgcttgg ccacttgaca caagtagggg ataaggacaa agacccatna ggtggcctgt      60
cagccttttg ttactgttgc ttccctgtca ccacggcccc ctctgtaggg gtgtgctgtg     120
ctctgtggac attggtgcat tttcacacat accattctct ttctgcttca cagcagtcct     180
gaggcgggag cacacaggac taccttgtca gatgangata atgatgtctg gccaactcac     240
cccccaacct tctcactagt tatangaaga gccangccta naaccttcta tcctgncccc     300
ttgccctatg acctcatccc tgttccatgc cctattctga tttctggtga actttggagc     360
agcctggttt ntcctcctca ctccagcctc tctccatacc atggtangggg ggtgctgttc     420 cacncaaang gtcaggtgtg tctggggaat cctnananct gccnggagtt tccnangcat     480
tcttaaaaac cttcttgcct aatcanatng tgtccagtgg ccaaccntcn              530

<210> SEQ ID NO 220
<211> LENGTH: 531
<212> TYPE: DNA
<213> ORGANISM: Homo sapiens

<400> SEQUENCE: 220
tgacgcttgg ccacttgaca ctaaatagca tcttctaaag gcctgattca gagttgtgga      60
aaattctccc agtgtcaggg attgtcagga acagggctgc tcctgtgctc actttacctg     120
ctgtgtttct gctggaaaag gagggaagag gaatggctga ttttaccta atgtctccca     180 gttttttcata ttcttcttgg atcctcttct ctgacaactg ttcccttttg gtcttcttct     240
tcttgctcag agagcaggtc tctttaaaac tgagaaggga gaatgagcaa atgattaaag     300
aaaacacact tctgaggccc agagatcaaa tattaggtaa atactaaacc gcttgcctgc     360
tgtggtcact tttctcctct ttcacatgct ctatccctct atccccacc tattcatatg      420 gcttttatct gccaagttat ccggcctctc atcaaccttc tccctagcc tactggggga     480 tatccatctg ggtctgtctc tggtgtattg gtgtcaagtg gccaagcgtc a              531

<210> SEQ ID NO 221
<211> LENGTH: 530
<212> TYPE: DNA
```

<213> ORGANISM: Homo sapiens

<400> SEQUENCE: 221

```
attgacgctt ggccacttga cacccgcctg cctgcaatac tggggcaagg gccttcactg      60
ctttcctgcc accagctgcc actgcacaca gagatcagaa atgctaccaa ccaagactgt     120
tggtcctcag cctctctgag gagaaagagc agaagcctgg aagtcagaag agaagctaga     180
tcggctacgg ccttggcagc cagcttcccc acctgtggca taaagtcgt gcatggctta      240
acaatggggg cacctcctga gaaacacatt gttaggcaat cggcgtgtg ttcatcagag       300
catatttaca caaacctcga tagtgcagcc tactatccac tattgctcct acgctgcaaa     360
cctgaacagc atgggactgt actgaatact ggaagcagct ggtgatggta cttatttgtg     420
tatctaaaca cagagaaggt acagtaagaa tatggtatca taaacttaca gggaccgcca     480
tcctatatgc agtctgttgt gaccaaaatg tgtcaagtgg ccaagcgtca               530
```

<210> SEQ ID NO 222
<211> LENGTH: 578
<212> TYPE: DNA
<213> ORGANISM: Homo sapiens
<220> FEATURE:
<221> NAME/KEY: misc_feature
<222> LOCATION: 308, 381, 561, 570, 573
<223> OTHER INFORMATION: n = A,T,C or G

<400> SEQUENCE: 222

```
tgtatcgacg tagtggtctc cgggctacta ggccgttgtg tgctggtagt acctggttca      60
ctgaaaggcg catctccctc cccgcgtcgc cctgaagcag ggggaggact tcgcccagcc     120
aaggcagttg tatgagtttt agctgcggca cttcgagacc tctgagccca cctccttcag     180
gagccttccc cgattaagga agccagggta aggattcctt cctcccccag acaccacgaa     240
caaaccacca cccccctat tctggcagcc catatacatc agaacgaaac aaaaataaca      300
aataaacnaa aaccaaaaaa aaaagagaag gggaaatgta tatgtctgtc catcctgttg     360
ctttagcctg tcagctccta nagggcaggg accgtgtctt ccgaatggtc tgtgcagcgc     420
cgactgcggg aagtatcgga ggaggaagca gagtcagcag aagttgaacg gtgggcccgg     480
cggctcttgg gggctggtgt tgtacttcga gaccgctttc gcttttgtc ttagatttac       540
gtttgctctt tggagtggga naccactacn tcnataca                             578
```

<210> SEQ ID NO 223
<211> LENGTH: 578
<212> TYPE: DNA
<213> ORGANISM: Homo sapiens

<400> SEQUENCE: 223

```
tgtatcgacg tagtggtctc ctcttgcaaa ggactggctg gtgaatggtt tccctgaatt      60
atggacttac cctaaacata tcttatcatc attaccagtt gcaaatatt agaatgtgtt      120
gtcactgttt catttgattc ctagaaggtt agtcttagat atgttacttt aacctgtatg     180
ctgtagtgct ttgaatgcat ttttttgtttg cattttttgtt tgcccaacct gtcaattata   240
gctgcttagg tctggactgt cctggataaa gctgttaaaa tattcaccag tccagccatc     300
ttacaagcta attaagtcaa ctaaatgctt ccttgttttg ccagacttgt tatgtcaatc     360
ctcaatttct gggttcattt tgggtgccct aaatcttagg gtgtgacttt cttagcatcc     420
tgtaacatcc attcccaagc aagcacaact tcacataata ctttccagaa gttcattgct     480
gaagcctttc cttcacccag cggagcaact tgattttcta caacttccct catcagagcc     540
```

```
<210> SEQ ID NO 224
<211> LENGTH: 345
<212> TYPE: DNA
<213> ORGANISM: Homo sapiens
<220> FEATURE:
<221> NAME/KEY: misc_feature
<222> LOCATION: 13
<223> OTHER INFORMATION: n = A,T,C or G

<400> SEQUENCE: 224
tgtatcgacg tantggtctc ccaaggtgct gggattgcag gcatgagcca ccactcccag    60
gtggatcttt ttctttatac ttacttcatt aggtttctgt tattcaagaa gtgtagtggt   120
aaaagtcttt tcaatctaca tggttaaata atgatagcct gggaaataaa tagaaatttt   180
ttctttcatc tttaggttga ataaagaaac agaaaaaata gaacatactg aaaataatct   240
aagttccaac catagaagaa ctgcagaaga aatgaagaaa gtgatgatga tttagatttt   300
gatattgatt tagaagacac aggaggagac cactacgtcg ataca                   345

<210> SEQ ID NO 225
<211> LENGTH: 347
<212> TYPE: DNA
<213> ORGANISM: Homo sapiens

<400> SEQUENCE: 225
tgtatcgacg tagtggtctc caaactgagg tatgtgtgcc actagcacac aaagccttcc    60
aacagggacg caggcacagg cagtttaaag ggaatctgtt tctaaattaa tttccacctt   120
ctctaagtat tctttcctaa aactgatcaa ggtgtgaagc ctgtgctctt tcccaactcc   180
cctttgacaa cagccttcaa ctaacacaag aaaaggcatg tctgacactc ttcctgagtc   240
tgactctgat acgttgttct gatgtctaaa gagctccaga acaccaaagg gacaattcag   300
aatgctggtg tataacagac tccaatggag accactacgt cgataca                 347

<210> SEQ ID NO 226
<211> LENGTH: 281
<212> TYPE: DNA
<213> ORGANISM: Homo sapiens
<220> FEATURE:
<221> NAME/KEY: misc_feature
<222> LOCATION: 4, 6, 11
<223> OTHER INFORMATION: n = A,T,C or G

<400> SEQUENCE: 226
aggngnggga ntgtatcgac gtagtggtct cccaacagtc tgtcattcag tctgcaggtg    60
tcagtgtttt ggacaatgag gcaccattgt cacttattga ctcctcagct ctaaatgctg   120
aaattaaatc ttgtcatgac aagtctggaa ttcctgatga ggttttacaa agtattttgg   180
atcaatactc caacaaatca gaaagccaga aagaggatcc tttcaatatt gcagaaccac   240
gagtggattt acacacctca ggagaccact acgtcgatac a                       281

<210> SEQ ID NO 227
<211> LENGTH: 3646
<212> TYPE: DNA
<213> ORGANISM: Homo sapiens

<400> SEQUENCE: 227
gggaaacact tcctcccagc cttgtaaggg ttggagccct ctccagtata tgctgcagaa    60
```
acaagagtat gggatatgga gaccactacg tcgataca    578

-continued

```
tttttctctc ggtttctcag aggattatgg agtccgcctt aaaaaaggca agctctggac      120
actctgcaaa gtagaatggc caaagttkgg agttgagtgg cccctkgaag ggtcactgaa      180
cctcacaatt gttcaagctg tgtggcgggt tgttactgaa actcccggcc tccctgatca      240
gtttccctac attgatcaat ggctgagttt ggtcaggagc acccckkccg tggctccact      300
catgcaccat tcataatttt acctccaagg tcctcctgag ccagaccgtg ttttcgcctc      360
gaccctcagc cggttcggct cgccctgtac tgcctctctc tgaagaagag gagagtctcc      420
ctcacccagt cccaccgcct taaaaccagc ctactccctt agggtcatcc catgtctcct      480
cggctatgtc cctgtaggc tcatcaccca ttgcctcttg gttgcaaccg tggtgggagg      540
aagtagcccc tctactacca ctgagagagg cacaagtccc tctgggtgat gagtgctcca      600
ccccckkcct ggtttatgtc ccktcttkct actkckgact tgtataatkg gaaaacccat      660
aatcctccct tctctgaaaa gccccaggct ttgacctcac tgatggagtc tgtactctgg      720
acacattggc ccacctggga tgactgtcaa cagctccttt tgacccttkk cacctctgaa      780
gagagggaaa gtatccaaag agaggccaaa aagtacaacc tcacatcaac caataggccg      840
gaggaggaag ctagaggaat agtgattaga acccccaatkg ggacctaatt gggacccaaa      900
tttctcaagt ggagggagaa cttttgacga tttccaccgg tatctcctcg tgggtattca      960
gggagctgct cagaaaccta taaacttgtc taaggcgact gaagtcgtcc aggggcatga     1020
tgagtcacca ggagtgtttt tagagcacct ccaggaggct tatcagattt acccccctkk     1080
tgacctggca gcccccgaaa atagccatgc tctkaattkg gcattkgtgg ctcaggcagc     1140
cccagatagt aaaaggaaac tccaaaaact agagggatttt tgctggaatg aataccagtc     1200
agctttkaga gatagcctaa aaggtkktkg acagtcaaga ggttgaaaaa caaaacaag     1260
cagctcaggc agctgaaaaa agccactgat aaagcatcct ggagtatcag agtttactgt     1320
tagatcagcc tcatttgact tcccctccca catggtgttt aaatccagct acactacttc     1380
ctgactcaaa ctccactatt cctgttcatg actgtcagga actgttggaa actactgaaa     1440
ctggccgacc tgatcttcaa aatgtgcccc taggaaaggt ggatgccacc atgttcacag     1500
acagtagcag cttcctcgag aagggactac gaaaggccgg tgcagctgtt accatggaga     1560
cagatgtgtt gtgggctcag gctttaccag caaacacctc agcacaaaag gctgaattga     1620
tcgccctcac tcaggctctc cgatggggta aggatattaa cgttaacact gacagcaggt     1680
acgcctttgc tactgtgcat gtacgtggag ccatctacca ggagcgtggg ctactcacct     1740
cagcaggtgg ctgtaatcca ctgtaaagga catcaaaagg aaaacacggc tgttgcccgt     1800
ggtaaccaga aagctgattc agcagctcaa gatgcagtgt gactttcagt cacgcctcta     1860
aacttgctgc ccacagtctc cttkccacag ccagatctgc ctgacaatcc cgcatactca     1920
acagaagaag aaaactggcc tcagaactca gagccaataa aaatcaggaa ggttggtgga     1980
ttcttcctga ctctagaatc ttcatacccc gaactctkgg gaaaacttta atcagtcacc     2040
tacagtctac cacccattta ggaggagcaa agctacctca gctcctccgg agccgtttta     2100
agatccccca tcttcaaagc ctaacagatc aagcagctct ccggtgcaca acctgcgccc     2160
aggtaaatgc caaaaaaggt cctaaaccca gcccaggcca ccgtctccaa gaaaactcac     2220
caggagaaaa gtgggaaatt gactttacag aagtaaaacc acaccgggct gggtacaaat     2280
accttctagt actggtagac accttctctg gatggactga agcatttgct accaaaaacg     2340
aaactgtcaa tatggtagtt aagtttttac tcaatgaaat catccctcga catgggctgc     2400
ctgtttgcca tagggtctga taatggaccg gccttcgcct tgtctatagt ttagtcagtc     2460
```

-continued

```
agtaaggcgt taaacattca atggaagctc cattgtgcct atcgacccca gagctctggg    2520
caagtagaac gcatgaactg caccctaaaa aacactctta caaaattaat cttagaaacc    2580
ggtgtaaatt gtgtaagtct ccttccttta gccctactta gagtaaggtg caccccttac    2640
tgggctgggt tcttaccttt tgaaatcatg tatgggaggg tgctgcctat cttgcctaag    2700
ctaagagatg cccaattggc aaaaatatca caaactaatt tattacagta cctacagtct    2760
ccccaacagg tacaagatat catcctgcca cttgttcgag gaacccatcc caatccaatt    2820
cctgaacaga cagggccctg ccattcattc ccgccaggtg acctgttgtt tgttaaaaag    2880
ttccagagag aaggactccc tcctgcttgg aagagacctc acaccgtcat cacgatgcca    2940
acggctctga aggtggatgg cattcctgcg tggattcatc actcccgcat caaaaaggcc    3000
aacagagccc aactagaaac atgggtcccc agggctgggt caggcccctt aaaactgcac    3060
ctaagttggg tgaagccatt agattaattc tttttcttaa ttttgtaaaa caatgcatag    3120
cttctgtcaa acttatgtat cttaagactc aatataaccc ccttgttata actgaggaat    3180
caatgatttg attcccccaa aaacacaagt ggggaatgta gtgtccaacc tggtttttac    3240
taaccctgtt tttagactct ccctttcctt taatcactca gcttgtttcc acctgaattg    3300
actctccctt agctaagagc gccagatgga ctccatcttg gctctttcac tggcagccgc    3360
ttcctcaagg acttaacttg tgcaagctga ctcccagcac atccaagaat gcaattaact    3420
gataagatac tgtggcaagc tatatccgca gttcccagga attcgtccaa ttgatcacag    3480
cccctctacc cttcagcaac caccaccctg atcagtcagc agccatcagc accgaggcaa    3540
ggccctccac cagcaaaaag attctgactc actgaagact tggatgatca ttagtatttt    3600
tagcagtaaa gttttttttt ctttttcttt ctttttttct cgtgcc                   3646
```

<210> SEQ ID NO 228
<211> LENGTH: 419
<212> TYPE: DNA
<213> ORGANISM: Homo sapiens
<220> FEATURE:
<221> NAME/KEY: misc_feature
<222> LOCATION: 402
<223> OTHER INFORMATION: n = A,T,C or G

<400> SEQUENCE: 228

```
taagagggta caagatctaa gcacagccgt caatgcagaa cacagaacgt agcctggtaa     60
gtgtgttaag agtgggaatt tttggagtac agagtaaggc acctaaccct agctggggtt    120
tggtgacggt cccagatggc ttacagaaga agtgtcctg agatgagttt ttaagaatga    180
ataaggatag acacaagtga ggactgactt ggcagtggtg aatggtgggt ggcaaaaaac    240
ttcgcatgta tggaaactgc acgtacagga atgaagaatg agactgtgtg gtgtttaatg    300
agctgcaaat actaatttta tcctgaaagt tttgaagagt taactaaaaa gtatttttta    360
gtaaggaaat aaccctacat ttcagggtta ttgtttgttt anatattgaa ggtgcccaa     419
```

<210> SEQ ID NO 229
<211> LENGTH: 148
<212> TYPE: DNA
<213> ORGANISM: Homo sapiens

<400> SEQUENCE: 229

```
aagagggtac tgtatgtag ccatggtggc aatgagagac tgattactac ctgctggaga     60
ttgtttaagt gagttaatat attaaggata aagggagcca ggtttttga ctgttggaga    120
```

```
aggaaattac agatattgaa ggtcccaa                                              148

<210> SEQ ID NO 230
<211> LENGTH: 257
<212> TYPE: DNA
<213> ORGANISM: Homo sapiens

<400> SEQUENCE: 230
taagagggta cmaaaaaaaa aaaatagaac gaatgagtaa gacctactat ttgatagtac            60
aacagggtga ctatagtcaa tgataactta attatacatt taacatagag tgtaattgga          120
ttgtttgtaa ctcgaaggat aaatgcttga gaggatggat accccattct ccatgatgta          180
cttatttcac attacatgcc tgtatcaaag catctcatat accctataaa tatgtacacc          240
tactatgtac cctctta                                                         257

<210> SEQ ID NO 231
<211> LENGTH: 260
<212> TYPE: DNA
<213> ORGANISM: Homo sapiens

<400> SEQUENCE: 231
taagagggta cgggtatttg ctgatgggat ttttttttct ttcttttttct ttggaaaaca          60 aaatgaaagc cagaacaaaa ttattgaaca aaagacaggg actaaatctg agaaatgaa          120 gtcccctcac ctgactgcca tttcattcta tctgaccttc cagtctaggt taggagaata        180
gggggtggag gggattaatc tgatacaggt atatttaaag caactctgca tgtgtgccag        240
aagtccatgg taccctctta                                                      260

<210> SEQ ID NO 232
<211> LENGTH: 596
<212> TYPE: DNA
<213> ORGANISM: Homo sapiens
<220> FEATURE:
<221> NAME/KEY: misc_feature
<222> LOCATION: 437, 440, 461, 536, 541, 565, 580, 587, 590, 595
<223> OTHER INFORMATION: n = A,T,C or G

<400> SEQUENCE: 232
tgctcctctt gccttaccaa ccacaaatta gaaccataat gagatgtcac ctcatacctg          60
gtgggattaa cattatttaa aaaatcagaa gtattgacaa ggatgtgaag aaattagaac        120
atctgtgcac tgttggtggg aatgtaaaaa aggtgtggcc actatgggta acagcatgaa        180
ggttcctcaa aaaaattttt ttttaatcta ctctatgatc gatcttgagg ttgtttatgc        240
aaaagaactg aaatcaggat tttgaggaaa tattcacatt cccacatcca tttctgcttt        300
attcataata ctcaagagat ggaaacaacc taaatgtcca tcccgggatg aatggataaa        360
cacagtgtgg tatatgcata caatggaata ttatttagtc tttaaaaaga aaattctat          420 catatactac aacttanatn aaccttgagg acacaatgct nagtgaaata agccacggaa         480
ggacgaatac tgcattattc ccttatatga agtatctaaa gtggtcaaac tcttanagca        540
naaagtaaaa atgggtggtt gccanacagt tggttaggcn agaaganaan cctant            596

<210> SEQ ID NO 233
<211> LENGTH: 96
<212> TYPE: DNA
<213> ORGANISM: Homo sapiens

<400> SEQUENCE: 233
tcttctgaag acctttcgcg actcttaagc tcgtggttgg taaggcaaga ggagcgttgg          60
```

<210> SEQ ID NO 234
<211> LENGTH: 313
<212> TYPE: DNA
<213> ORGANISM: Homo sapiens

<400> SEQUENCE: 234

```
tgtaagtcga gcagtgtgat gataaaactt gaatggatca atagttgctt cttatggatg    60
agcaaagaaa gtagtttctt gtgatggaat ctgctcctgg caaaaatgct gtgaacgttg   120
ttgaaaagac aacaaagagt ttagagtagt acataaattt agaatagtac ataaacttag   180
aatagtacat aaacttagta cataaataat gcacgaagca ggggcagggc ttgagagaat   240
tgacttcaat ttggaaagag tatctactgt aggttagatg ctctcaaaca gcatcacact   300
gctcgactta caa                                                      313
```

<210> SEQ ID NO 235
<211> LENGTH: 550
<212> TYPE: DNA
<213> ORGANISM: Homo sapiens

<400> SEQUENCE: 235

```
aacgaggaca gatccttaaa aagaatgttg agtgaaaaaa gtagaaaata agataatctc    60
caaagtccag tagcattatt taaacatttt taaaaaatac actgataaaa attttgtaca   120
tttcccaaaa atacatatgg aagcacagca gcatgaatgc ctatgggrtt gaggataggg   180
gttgggagta gggatgggga taaaggggga aaataaaacc agagaggagt cttacacatt   240
tcatgaacca aggagtataa ttatttcaac tatttgtacc wgaagtccag aaagagtgga   300
ggcagaaggg ggagaagagg gcgaagaaac gttttttggga gaggggtccc asaagagaga   360
ttttcgcgat gtggcgctac atacgttttt ccaggatgcc ttaagctctg caccctattt   420
ttctcatcac taatattaga ttaaacccctt tgaagacagc gtctgtggtt tctctacttc   480
agctttccct ccgtgtcttg cacacagtag ctgttttaca agggttgaac tgactgaagt   540
gagattattc                                                          550
```

<210> SEQ ID NO 236
<211> LENGTH: 325
<212> TYPE: DNA
<213> ORGANISM: Homo sapiens

<400> SEQUENCE: 236

```
tagactgact catgtcccct accagagtag ctagaattaa tagcacaagc ctctacaccc    60
aggaactcac tattgaatac ataaatggaa tttattcagc cttaaaaagt ttggaaggaa   120
attctgacat atgctaaaac atggatgaac cttgaagact ttatgataag taaaagaagc   180
cagtcataaa aggaaaaata ttgcatgatt ccacttatat gaggtaccta gagtagtcaa   240
tttcatagaa acacaaaata gaatggtgtt tgccagggct tttgaggaaa agggaatgac   300
aagttagggg acatgagtca gtcta                                         325
```

<210> SEQ ID NO 237
<211> LENGTH: 373
<212> TYPE: DNA
<213> ORGANISM: Homo sapiens
<220> FEATURE:
<221> NAME/KEY: misc_feature
<222> LOCATION: 355

<223> OTHER INFORMATION: n = A,T,C or G

<400> SEQUENCE: 237

```
tagactgact catgtccct atctactcaa catttccact tgaagtctga taggcatctc      60
agacttatct tgtcccaaag caaactcttt atttctttc atcctagtct ttatttcttg     120
tgctgtctta cccatctcaa aagagtgcca aaatccacca agttgctgaa acagaaatct    180
aagaaatatc cttgattctt cttttcccca tctacttcac ttctaattca ttagtaaata    240
atctgtttca gaaaaccaaa cacctcatgt tctcactcat aagggggagt tgaacaatga    300
gaacacacag acagggag gggaacatca cacaccacgg cccgtcaggg agtangggac      360
atgagtcagt cta                                                       373
```

<210> SEQ ID NO 238
<211> LENGTH: 492
<212> TYPE: DNA
<213> ORGANISM: Homo sapiens
<220> FEATURE:
<221> NAME/KEY: misc_feature
<222> LOCATION: 272, 310, 380, 435, 474, 484, 488
<223> OTHER INFORMATION: n = A,T,C or G

<400> SEQUENCE: 238

```
tagactgact catgtccct ataatgctcc caggcatcag aaagcatctc aaactggagc      60
tgacaccatg gcagaggttt caggtaagtc acaaagggg tcctaaagaa tttgccctca     120
atatcagagt gattagaaga agtggacaga gctacccaag ttaaacatat gcgagataaa    180
aaaaatatgg cacttgtgaa cacacactac aggaggaaaa taaggaacat aatagcatat    240
tgtgctatta tgatgatgaa gaacctctct anaagaaaac ataaccaaag aaacaaagaa    300
aattcctgcn aatgtttaat gctatagaag aaattaacaa aaacatatat tcaatgaatt    360
cagaaaagtt agcaggtcan aagaaaacaa atcaaagacc agaataatcc cattttagat    420
tgtcgagtaa actanaacag aaagaatacc actggaaatt gaattcctac gtangggaca    480
tgantcantc ta                                                         492
```

<210> SEQ ID NO 239
<211> LENGTH: 482
<212> TYPE: DNA
<213> ORGANISM: Homo sapiens
<220> FEATURE:
<221> NAME/KEY: misc_feature
<222> LOCATION: 245
<223> OTHER INFORMATION: n = A,T,C or G

<400> SEQUENCE: 239

```
tggaaagtat ttaatgatgg gcaacttgct gtttacttcc tacatatccc atcatcttct     60
gtatttttt aaataacttt ttttggatt tttaaagtaa ccttattctg agaggtaaca     120
tggattacat acttctaagc cattaggaga ctctatgtta aaccaaaagg aaatgttact    180
agatcttcat ttgatcaata ggatgtgata atcatcatct ttctgctcta atggaaaagt    240
actanaaaca tggaaccata atcttagatg aacaacgtta gaatttgcac taattctacg    300
gaatttcagt aattcggcaa atgtcgggca gtgacacaac atttcatgac ggggacgcat    360
ctaccaactt ctggcgataa gggccaccct tccctctgta cttacagtcc catttctac    420
acagtctttg attaaatatt cacatttttt ctctacctaa agaccttcaa gaccagtacg    480
ta                                                                    482
```

<210> SEQ ID NO 240
<211> LENGTH: 519
<212> TYPE: DNA
<213> ORGANISM: Homo sapiens
<220> FEATURE:
<221> NAME/KEY: misc_feature
<222> LOCATION: 491
<223> OTHER INFORMATION: n = A,T,C or G

<400> SEQUENCE: 240

```
tgtatcgacg tagtggtctc cccatgtgat agtctgaaat atagcctcat gggatgagag      60
gctgtgcccc agcccgacac ccgtaaaggg tctgtgctga ggtggattag taaaagagga     120
aagccttgca gttgagatag aggaagggca ctgtctcctg cctgcccctg ggaactgaat     180
gtctcggtat aaaacccgat tgtacatttg ttcaattctg agataggaga aaaaccaccc     240
tatggcggga ggcgagacat gttggcagca atgctgcctt gttatgcttt actccacaga     300
tgtttgggcg gagggaaaca taaatctggc ctacgtgcac atccaggcat agtacctccc     360
tttgaactta attatgacac agattccttt gctcacatgt ttttttgctg accttctcct     420
tattatcacc ctgctctcct accgcattcc ttgtgctgag ataatgaaaa taatatcaat     480
aaaaacttga nggaactcgg agaccactac gtcgataca                            519
```

<210> SEQ ID NO 241
<211> LENGTH: 771
<212> TYPE: DNA
<213> ORGANISM: Homo sapiens
<220> FEATURE:
<221> NAME/KEY: misc_feature
<222> LOCATION: 304, 402, 442, 463, 510, 541, 550, 567, 571, 596, 617,
      624, 644, 648, 652, 667, 682, 686, 719, 722, 729, 732, 751, 752,
      757, 758, 760, 763, 766, 769
<223> OTHER INFORMATION: n = A,T,C or G

<400> SEQUENCE: 241

```
tgtatcgacg tagtggtctc cactcccgcc ttgacggggc tgctatctgc cttccaggcc      60
actgtcacgg ctcccgggta gaagtcactt atgagacaca ccagtgtggc cttgttggct     120
tgaagctcct cagaggaggg tgggaacaga gtgaccgagg gggcagcctt gggctgacct     180
aggacggtca gcttggtccc tccgccaaac acgagagtgc tgctgcttgt atatgagctg     240
cagtaataat cagcctcgtc ctcagcctgg agcccagaga tggtcaggga ggccgtgttg     300
ccanacttgg agccagagaa gcgattagaa accoctgagg gccgattacc gacctcataa     360
atcatgaatt tgggggcttt gcctgggtgc tgttggtacc angagacatt attataacca     420
ccaacgtcac tgctggttcc antgcaggga aaatggttga tcnaactgtc caagaaaacc     480
actacgtcca taccaatcca ctaattgccn gccgcctgca ggttcaacca tattggggaa     540
naactccccn ccgccgtttg ggattgncat naacctttga aatttttttcc tattanttgt     600
cccccctaaaa taaaccnttg ggcnttaatc cattgggtcc atancttntt tncccggttt     660
ttaaaanttg tttatcccgc cnccnnattt ccccccaac tttccaaaac ccgaaaccnt     720
tnaaatttnt tnaaaccctg gggggttccc nnaattnnan ttnaanctnc c             771
```

<210> SEQ ID NO 242
<211> LENGTH: 167
<212> TYPE: DNA
<213> ORGANISM: Homo sapiens

<400> SEQUENCE: 242

```
tgggcacctt caatatcggg ctcatcgata acatcacgct gctgatgctg ctgttgctgg      60
```

| | |
|---|---|
| tcctctctag gaacctctgg attttcaaat tctttgagga attcatccaa attatctgcc | 120 |
| tctcctcctt tcctccttt tctaaggtct tctggtacaa gcggtca | 167 |

<210> SEQ ID NO 243
<211> LENGTH: 338
<212> TYPE: DNA
<213> ORGANISM: Homo sapiens

<400> SEQUENCE: 243

| | |
|---|---|
| ttgggcacct tcaatatcta ctgatctaaa tagtgtggtt tgaggcctct tgttcctggc | 60 |
| taaaatcct tggcaagagt caatctccac tttacaatag aggtaaaaat cttacaatgg | 120 |
| atattcttga caaagctagc atagagacag caattttaca caaggtatt ttcacctgtt | 180 |
| taataacagt ggttttccta cacccatagg gtgccaccaa gggaggagtg cacagttgca | 240 |
| gaaacaaatt aagatactga agacaacact acttaccatt tcccgtatag ctaaccacca | 300 |
| gttcaactgt acatgtatgt tcttatgggc aatcaaga | 338 |

<210> SEQ ID NO 244
<211> LENGTH: 346
<212> TYPE: DNA
<213> ORGANISM: Homo sapiens

<400> SEQUENCE: 244

| | |
|---|---|
| tttttggctc ccatacagca cactctcatg ggaaatgtct gttctaaggt caacccataa | 60 |
| tgcaaaaatc atcaatatac ttgaagatcc ccgtgtaagg tacaatgtat ttaatattat | 120 |
| cactgataca attgatccaa taccagtttt agtctggcat tgaatcaaat cactgttttt | 180 |
| gttgtataaa aagagaaata tttagcttat atttaagtac catattgtaa gaaaaaagat | 240 |
| gcttatcttt acatgctaaa atcatgatct gtacattggt gcagtgaata ttactgtaaa | 300 |
| agggaagaag gaatgaagac gagctaagga tattgaaggt gcccaa | 346 |

<210> SEQ ID NO 245
<211> LENGTH: 521
<212> TYPE: DNA
<213> ORGANISM: Homo sapiens
<220> FEATURE:
<221> NAME/KEY: misc_feature
<222> LOCATION: 252, 337, 434, 455, 466, 478, 494, 510, 516
<223> OTHER INFORMATION: n = A,T,C or G

<400> SEQUENCE: 245

| | |
|---|---|
| accaatccca cacggatact gagggacaag tatatcatcc catttcatcc ctacagcagc | 60 |
| aacttcatga ggcaggagtt attagtccca ttttacagaa gaggaaactg agacttaggg | 120 |
| agatcaagta atttgcccag gtcgcacaat tagtgataga gccagggctt gaagcgacgt | 180 |
| ctgtcttaag ccaatgaccc ctgcagatta ttagagcaac tgttctccac aacagtgtaa | 240 |
| gcctcttgct anaagctcag gtccacaagg gcagagattt ttgtctgttt tgctcattgc | 300 |
| tccttcccca ttgcttagag cagggtctgc cacgaancag gttctcaatg catagttatt | 360 |
| aaatgtatat aagagcaaac atatgttaca gagaactttc tgtatgcttg tcacttacat | 420 |
| gaatcacctg tganatgggt atgcttgttc cccantgttg cagatnaaga tattgaangt | 480 |
| gcccaaatca ctanttgcgg gcgcctgcan gtccancata t | 521 |

<210> SEQ ID NO 246
<211> LENGTH: 482
<212> TYPE: DNA
<213> ORGANISM: Homo sapiens
<220> FEATURE:
<221> NAME/KEY: misc_feature
<222> LOCATION: 464
<223> OTHER INFORMATION: n = A,T,C or G

<400> SEQUENCE: 246

| | | |
|---|---|---|
| tggaaccaat ccaaataccc atcaatgata gactggataa agaaaatttg gcacatgttc | 60 |
| accatgaaat actatgcagc cataaaaaag gatgagttca tatcctttgc agggacatgg | 120 |
| atgaagctgg agaccatcat tctcagcaaa ctaacaaggg aacagaaaac caaacactgc | 180 |
| atgttctcac tcttaagtgg gagctgaaca atgagaacac atggacacag ggaggggaac | 240 |
| atcacacagt ggggcctgct ggtgggtagg ggtctagggg agggatagca ttaggagaaa | 300 |
| tacctaatgt agatgacggg ttgatgggtg cagcaaacca ccatgacacg tgtataccta | 360 |
| tgtaacaaac ctgcatgttc tgcacatgta ccccagaact taaagtgtta ataaaaaaat | 420 |
| taagaaaaaa gttaagtatg tcatagatac ataaaatatt gtanatattg aaggtgccca | 480 |
| aa | 482 |

<210> SEQ ID NO 247
<211> LENGTH: 474
<212> TYPE: DNA
<213> ORGANISM: Homo sapiens
<220> FEATURE:
<221> NAME/KEY: misc_feature
<222> LOCATION: 220, 255, 287, 312, 339, 374, 382, 403, 414, 426, 427,
      428, 432, 433, 434, 435, 436, 465
<223> OTHER INFORMATION: n = A,T,C or G

<400> SEQUENCE: 247

| | | |
|---|---|---|
| ttcgatacag gcacagagta agcagaaaaa tggctgtggt ttaaccaagt gagtacagtt | 60 |
| aagtgagaga ggggcagaga agacaagggc atatgcaggg ggtgattata acaggtggtt | 120 |
| gtgctgggaa gtgagggtac tcggggatga ggaacagtga aaaagtggca aaaagtggta | 180 |
| agatcagtga attgtacttc tccagaattt gatttctggn ggagtcaaat aactatccag | 240 |
| tttgggtat catanggcaa cagttgaggt ataggaggta gaagtcncag tgggataatt | 300 |
| gaggttatga anggtttggt actgactggt actgacaang tctgggttat gaccatggga | 360 |
| atgaatgact gtanaagcgt anaggatgaa actattccac ganaaagggg tccnaaaact | 420 |
| aaaaannnaa gnnnnngggg aatattattt atgtggatat tgaangtgcc caaa | 474 |

<210> SEQ ID NO 248
<211> LENGTH: 355
<212> TYPE: DNA
<213> ORGANISM: Homo sapiens
<220> FEATURE:
<221> NAME/KEY: misc_feature
<222> LOCATION: 69, 87, 186, 192, 220, 227, 251, 278, 339, 346, 350
<223> OTHER INFORMATION: n = A,T,C or G

<400> SEQUENCE: 248

| | | |
|---|---|---|
| ttcgatacag gcaaacatga actgcaggag ggtggtgacg atcatgatgt tgccgatggt | 60 |
| ccggatggnc acgaagacgc actggancac gtgcttacgt ccttttgctc tgttgatggc | 120 |
| cctgagggga cgcaggaccc ttatgaccct cagaatcttc acaacgggag atggcactgg | 180 |
| attgantccc antgacacca gagacacccc aaccaccagn atatcantat attgatgtag | 240 |
| ttcctgtaga nggccccctt gtggaggaaa gctccatnag ttggtcatct tcaacaggat | 300 |
| ctcaacagtt tccgatggct gtgatgggca tagtcatant taaccntgtn tcgaa | 355 |

```
<210> SEQ ID NO 249
<211> LENGTH: 434
<212> TYPE: DNA
<213> ORGANISM: Homo sapiens

<400> SEQUENCE: 249
ttggattggt cctccaggag aacaagggga aaaaggtgac cgagggctcc ctggaactca       60
aggatctcca ggagcaaaag gggatggggg aattcctggt cctgctggtc ccttaggtcc      120
acctggtcct ccaggcttac caggtcctca aggcccaaag ggtaacaaag gctctactgg      180
acccgctggc cagaaaggtg acagtggtct tccaggggcct cctgggcctc caggtccacc     240
tggtgaagtc attcagcctt taccaatctt gtcctccaaa aaaacgagaa gacatactga      300
aggcatgcaa gcagatgcag atgataatat tcttgattac tcggatggaa tggaagaaat      360
atttggttcc ctcaattccc tgaaacaaga catcgagcat atgaaatttc caatgggtac      420
tcagaccaat ccaa                                                        434

<210> SEQ ID NO 250
<211> LENGTH: 430
<212> TYPE: DNA
<213> ORGANISM: Homo sapiens
<220> FEATURE:
<221> NAME/KEY: misc_feature
<222> LOCATION: 301, 430
<223> OTHER INFORMATION: n = A,T,C or G

<400> SEQUENCE: 250
tggattggtc acatggcaga gacaggattc caaggcagtg agaggaggat acaatgcttc       60
tcactagtta ttattattta ttttattttt gagatgaagt ctcgctttgt ctcccaggct      120
ggagagcggt ggtgcgatct ggctctctg caaccccgc ctcaagcaat tctcctgtct        180
tagcctcgcg ggtagatgga attacaggcg cccaccgcca tgcccaacta atttttttgt      240
gtcttcagta gagacagggt ttcgccatgt tgggcaggct ggtcttgaac tcctgacctc      300
nagtgatctg ccctcctcgg cctcacaaag tgctggaatt acaggcatgg gctgctgcac      360
ccagtcaact tctcactagt tatggcctta tcattttcac cacattctat tggcccaaaa      420 aaaaaaaaan                                                             430

<210> SEQ ID NO 251
<211> LENGTH: 329
<212> TYPE: DNA
<213> ORGANISM: Homo sapiens

<400> SEQUENCE: 251
tggtactcca ccatyatggg gtcaaccgcc atcctcgccc tcctcctggc tgttctccaa       60
ggagtctgtg ccgaggtgca gctgrtgcag tctggagcag aggtgaaaaa gtccggggag      120
tctctgaaga tctcctgtaa gggttctgga tacacccttta agatctactg gatcgcctgg      180
gtgcgccagt tgcccgggaa aggcctggag tggatggggc tcatcttcc tgatgactct       240 gataccagat acagcccgtc cttccaaggc caggtcacca tctcagtcga taagtccatc      300
agcaccgcct atctgcagtg gagtaccaa                                        329

<210> SEQ ID NO 252
<211> LENGTH: 536
<212> TYPE: DNA
<213> ORGANISM: Homo sapiens

<400> SEQUENCE: 252
```

```
tggtactcca ctcagcccaa ccttaattaa gaattaagag ggaacctatt actattctcc      60
caggctcctc tgctctaacc aggcttctgg gacagtatta gaaaggatg tctcaacaag      120 tatgtagatc ctgtactggc ctaagaagtt aaactgagaa tagcataaat cagaccaaac    180
ttaatggtcg ttgagacttg tgtcctggag cagctgggat aggaaaactt ttgggcagca    240
agaggaagaa ctgcctggaa gggggcatca tgttaaaaat tacaagggga acccacacca    300 ggccccttc ccagctctca gcctagagta ttagcatttc tcagctagag actcacaact      360
tccttgctta gaatgtgcca ccggggggag tccctgtggg tgatgaggct ctcaagagtg    420
agagtggcat cctatcttct gtgtgcccac aggagcctgg cccgagactt agcaggtgaa    480
gtttctggtc caggctttgc ccttgactca ctatgtgacc tctggtggag taccaa        536
```

<210> SEQ ID NO 253
<211> LENGTH: 507
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 253

```
ntgttgcgat cccagtaact cgggaagctg aggcgggagg atcacctgag ctcaggaggt     60
tgaggccgca gtgagccggg accacgccac tacactccag cctgggcat agagtgagac      120 cctccaagac agaaaagaaa agaaaggaag ggaaagggaa agggaaaagg aaaaggaaaa    180
ggaaaaggaa aaggaaaaga caagacaaaa caagacttga atttggatct cctgacttca    240
attttatgtt ctttctacac cacaattcct ctgcttacta agatgataat ttagaaaccc    300
ctcgttccat tctttacagc aagctggaag tttggtcaag taattacaat aatagtaaca    360
aatttgaata ttatatgcca ggtgtttttc attcctgctc tcacttaatt ctcaccactc    420
tgatataaat acaattgctg ccgggtgtgg tggctcatgc ctgtaatccc ggcactttgg    480
gagaccgagg tgggcggats gcaacaa                                         507
```

<210> SEQ ID NO 254
<211> LENGTH: 222
<212> TYPE: DNA
<213> ORGANISM: Homo sapiens
<220> FEATURE:
<221> NAME/KEY: misc_feature
<222> LOCATION: 167
<223> OTHER INFORMATION: n = A,T,C or G

<400> SEQUENCE: 254

```
ttggattggt cactgtgagg aagccaaatc ggatccgaga gtcttttct aaaggccagt      60 actggccaca ctttctcctg ccgccttcct caaagctgaa gacacacaga gcaaggcgct    120
tctgttttac tccccaatgg taactccaaa ccatagatgt ttagctnccc tgctcatctt    180
tccacatccc tgctattcag tatagtccgt ggaccaatcc aa                        222
```

<210> SEQ ID NO 255
<211> LENGTH: 463
<212> TYPE: DNA
<213> ORGANISM: Homo sapiens

<400> SEQUENCE: 255

```
tgttgcgatc cataaatgct gaaatggaaa taaacaacat gatgagggag gattaagttg      60
gggagggagc acattaaggt ggccatgaag tttgttggaa gaagtgactt ttgaacaagg    120
```

```
ccttggtgtt aagagctgat gagagtgtcc cagacagagg ggccactggt acaatagacg      180
agatgggaga gggcttggaa ggtgtgcgaa ataggaagga gtttgttctg gtatgagtct      240
agtgaacaca gaggcgagag gccctggtgg gtgcagctgg agagttatgc agaataacat      300
taggccctgt gggggactgt agactgtcag caataatcca cagtttggat tttattctaa      360
gagtgatggg aagccgtgga aaggggtta agcaaggagt gaaattatca gatttacagt       420
gataaaaata aattggtctg gctactgggg aaaaaaaaaa aaa                         463

<210> SEQ ID NO 256
<211> LENGTH: 262
<212> TYPE: DNA
<213> ORGANISM: Homo sapiens

<400> SEQUENCE: 256
ttggattggt caacctgctc aactctacyt ttcctccttc ttcctaaaaa attaatgaat       60
ccaatacatt aatgccaaaa cccttgggtt ttatcaatat ttctgttaaa aagtattatc     120
cagaactgga cataatacta cataataata cataacaacc ccttcatctg gatgcaaaca    180
tctattaata tagcttaaga tcactttcac tttacagaag caacatcctg ttgatgttat    240
tttgatgttt ggaccaatcc aa                                              262

<210> SEQ ID NO 257
<211> LENGTH: 461
<212> TYPE: DNA
<213> ORGANISM: Homo sapiens
<220> FEATURE:
<221> NAME/KEY: misc_feature
<222> LOCATION: 2, 5, 6, 7, 8, 9, 10, 11, 12, 13, 25, 32, 38, 71, 72
<223> OTHER INFORMATION: n = A,T,C or G

<400> SEQUENCE: 257
gnggnnnnnn nnncaattcg actcngttcc cntggtancc ggtcgacatg gccgcgggat      60
taccgcttgt nnctgggggt gtatgggga ctatgaccgc ttgtagctgg gggtgtatgg     120
gggactatga ccgcttgtag mtggkggtgt atgggggact atgaccgctt gtcgggtggt    180
cggataaacc gacgcaaggg acgtgatcga agctgcgttc ccgctctttc gcatcggtag    240
ggatcatgga cagcaatatc cgcattcgyc tgaaggcgtt cgaccatcgc gtgctcgatc    300
aggcgaccgg cgacatcgcc gacaccgcac gccgtaccgg cgcgctcatc cgcggtccga    360
tcccgcttcc cacgcgcatc gagaagttca cggtcaaccg tggcccgcac gtcgacaaga    420
agtcgcgcga gcagttcgag gtgcgtacct acaagcggtc a                        461

<210> SEQ ID NO 258
<211> LENGTH: 332
<212> TYPE: DNA
<213> ORGANISM: Homo sapiens
<220> FEATURE:
<221> NAME/KEY: misc_feature
<222> LOCATION: 251
<223> OTHER INFORMATION: n = A,T,C or G

<400> SEQUENCE: 258
tgaccgcttg tagctggggg tgtatggggg actacgaccg cttgtagctg ggggtgtatg      60
ggggactatg accgcttgta gctggggtg tatgggggac tatgaccgct tgtagctggg     120
ggtgtatggg ggactaggac cgcttgtagc tgggggtgta tggggactg tgaccgcttg     180 tagctggggg tgtatggggg actacgaccg cttgtagctg ggggtgtatg gggactatg     240
```

| | | |
|---|---|---|
| accgcttgta nctggggtg tatgggggac tatgaccgct tgtgctgcct gggggatggg | 300 | |
| aggagagttg tggttgggga aaaaaaaaaa aa | 332 | |

<210> SEQ ID NO 259
<211> LENGTH: 291
<212> TYPE: DNA
<213> ORGANISM: Homo sapiens
<220> FEATURE:
<221> NAME/KEY: misc_feature
<222> LOCATION: 141, 144, 167, 168, 171, 175, 194, 201, 202, 205, 209,
    212, 235, 236, 245, 246, 258, 266, 268, 270, 273, 277, 285, 290
<223> OTHER INFORMATION: n = A,T,C or G

<400> SEQUENCE: 259

| | |
|---|---|
| taccgcttgt gaccgcttgt gaccgcttgt gaccgcttgt gaccgcttgt gaccgcttgt | 60 |
| gaccgcttgt gaccgcttgt gaccgcttgt gaccgcttgt gaccgcttgt gaccgcttgt | 120 |
| gaccgcttgt gaccgcttgt nacnggggt gtctggggga ctatgannga ntgtnactgg | 180 |
| gggtgtctgg gggnctatga nngantgtna cnggggtgt ctgggggact atganngact | 240 |
| gtgcnncctg ggggatcnga ggagantngn ggntagngat ggttngggan a | 291 |

<210> SEQ ID NO 260
<211> LENGTH: 238
<212> TYPE: DNA
<213> ORGANISM: Homo sapiens

<400> SEQUENCE: 260

| | |
|---|---|
| taagagggta ctggttaaaa tacaggaaat ctggggtaat gaggcagaga accaggatac | 60 |
| tttgaggtca gggatgaaaa ctagaatttt tttcttttt tttgcctgag aaacttgctg | 120 |
| ctctgaagag gcccatgtat taattgcttt gatcttcctt tcttacagc cctttcaagg | 180 |
| gcagagccct ccttatcctg aaggaatctt atccttagct atagtatgta ccctctta | 238 |

<210> SEQ ID NO 261
<211> LENGTH: 746
<212> TYPE: DNA
<213> ORGANISM: Homo sapiens
<220> FEATURE:
<221> NAME/KEY: misc_feature
<222> LOCATION: 662, 680, 685, 698, 707, 709, 734, 740, 741
<223> OTHER INFORMATION: n = A,T,C or G

<400> SEQUENCE: 261

| | |
|---|---|
| ttgggcacct tcaatatcaa tagctaacat ttattgagtg tttatcgtat cataaaacac | 60 |
| tgttctaagc cttaaacgt actaattcat ttaatgctca taatcacttt agaaggtggg | 120 |
| tactagtatt agtctcattt acagatgcaa catgcaggca cagagaggtt aattaacttg | 180 |
| cccaaggtaa cacagctaag aaatagaaaa atatattgaat ctggaaagtt gggcttctgg | 240 |
| gtaacccaca gagtcttcaa tgagcctggg gcctcactca gtttgctttt acaaagcgaa | 300 |
| tgagtaacat cacttaattc agtgagtagg ccaaatggag gtcagctacg agtttctgct | 360 |
| gttcttgcag tggactgaca gatgtttaca acgtctggcc atcagtwaat ggactgatta | 420 |
| tcattgggaw gtgggtgggc tgaatgttgg ccagtgaagt ttattcawgc catattttta | 480 |
| tgtttaggat gacttttggc tggtcctagg gcaagctctg tctgscacgg aacacagaat | 540 |
| wacacaggga cccctcaat ttctggtgtg gctagaacca tgaaccactg gttggggaa | 600 |
| caagcggtca aaacctaagt gcggccggct ggcagggtcc acccatatgg ggaaaactcc | 660 |
| cnacgcgttt ggaatgcctn agctngaatt attctaaanag ttgtccncnt aaaattagcc | 720 |

-continued

```
tgggcgttaa tcangggtcn naagcc                                           746
```

<210> SEQ ID NO 262
<211> LENGTH: 588
<212> TYPE: DNA
<213> ORGANISM: Homo sapiens
<220> FEATURE:
<221> NAME/KEY: misc_feature
<222> LOCATION: 485, 488, 489, 492, 493, 494, 496, 497, 498, 499, 502,
      503, 504, 506, 521, 537, 550, 564
<223> OTHER INFORMATION: n = A,T,C or G

<400> SEQUENCE: 262

```
tgaccgcttg tcatctcaca tggggtcctg cacgcttttg cctttgtagg aaacctgaca     60
tttgtctgtt tcttctttct cttttccttc ccatatcctc ctaatttacg tttgacttgt    120
ttgctgagga ggcaggagct agagactgct gtgagctcat aggggtggga agtttatcct    180
tcaagtcccg cccactcatc actgcttctc accttcccct gaccaggctt acaagtgggt    240
tcttgcctgc tttcccttttg gacccaacaa gccctgtaa tgagtgtgca tgactctgac    300
agctgtggac tcagggtcct tggctacagc tgccatgtaa aatatctcat ccagttctcg    360
caaattgtta aaataaccac atttcttaga ttccagtacc caaatcatgt ctttacgaac    420
tgctcctcac acccagaagt ggcacaataa ttcttgggga attattactt ttttttttct    480
ctctnttnnc gnnngnnnng gnnngnccag gaattaccac nttggaagac ctggccngaa    540
tttattatan aggggagccg attnttttc ctaacacaaa gcgggtca                  588
```

<210> SEQ ID NO 263
<211> LENGTH: 730
<212> TYPE: DNA
<213> ORGANISM: Homo sapiens
<220> FEATURE:
<221> NAME/KEY: misc_feature
<222> LOCATION: 124, 510, 534, 559, 604, 605, 635, 711, 729
<223> OTHER INFORMATION: n = A,T,C or G

<400> SEQUENCE: 263

```
tttttttttt tttggcctga gcaactgaaa ttatgaaatt tccatatact caaagagta      60
agactgcaaa aagattaaat gtaaagttg tcttgtatac agtaatgttt aagataccta     120
ttanatttat aaatgaaaaa ttagggcatt tggatataca agttgaaaat tcaggagtga    180
ggttgggctg gctgggtata tactgaaaac tgtcagtaca cagatgacat ctaaaaccac    240
aaatctggtt ttattttagc agtgatatgt gtcactccca caaagccttt cccaattggc    300
ctcagcatac acaacaagtc acctccccac agccctctac acataaacaa attccttagt    360
ttagttcagg aggaaatgcg cccttttcct tccgctctag gtgaccgcaa ggcccagttc    420
tcgtcaccaa gatgttaagg gaagtctgcc aaagaggcat ctgaaaggaa ataaggggaa    480
tgggagtgac cacaaaggaa agccaaggan aaactttgga gaccgtttct aganccctgg    540
catttcacaa caaaactcng gaacaaacct tgtctcatca atcatttaag cccttcgttt    600
ggannagact ttctgaactg ggcgctgaac ataanccctca ttgaatgtct tcacagtctc    660
ccagctgaag gcacaccttg ggccagaagg ggaatcttcc aggtcctcaa nacagggctc    720
gcccttttgnc                                                          730
```

<210> SEQ ID NO 264
<211> LENGTH: 715
<212> TYPE: DNA
<213> ORGANISM: Homo sapiens
<220> FEATURE:

```
<221> NAME/KEY: misc_feature
<222> LOCATION: 364, 451, 476, 494, 495, 515, 519, 524, 633, 635, 636,
      645, 647, 649, 657, 692, 695, 701, 707, 710, 713
<223> OTHER INFORMATION: n = A,T,C or G

<400> SEQUENCE: 264 ttttttttttt tttggccagt atgatagtct ctaccactat attgaagctc ttaggtcatt    60
tacacttaat gtggttatag atgctgttga gcttacttct accaccttgc tatttctccc   120
gtctcttttt tgttcctttt ctcttctttt cctcccttat tttataattg aattttttag   180
gattctattt tatatagatt tatcagctat aacactttgt attcttttgt tttgtggttc   240
ttctgtcatt tcaatgtgca tcttaaactc atcacaatct attttcaaat aatatcatat   300
aaccttacat ataatgtaag aatctaccac catatatttc catttctccc ttccatccta   360
tgtntgtcat attttttcct ttatatatgt tttaaagaca taatagtata tgggaggttt   420
ttgcttaaaa tgtgatcaat attccttcaa ngaaacgtaa aaattcaaaa taaatntctg   480
tttattctca aatnnaccta atatttccta ccatntctna tacntttcaa gaatctgaag   540
gcattggttt tttccggctt aagaacctcc tctaaagcac tctaagcaga attaagtctt   600
ctgggagagg aattctccca agcttgggcc ttnanntgta ctccntnang gttaaanttt   660
ggccgggaaa tagaaattcc aagttaacag gntantttt nttttntttn tcncc          715

<210> SEQ ID NO 265
<211> LENGTH: 152
<212> TYPE: DNA
<213> ORGANISM: Homo sapiens

<400> SEQUENCE: 265 ttttttttttt tttcccaaca caaagcacca ttatctttcc tcacaatttt caacatagtt    60
tgattcccat gaagaggtta tgatttctaa agaaaacatg gctactatac tatcaatcag   120 ggttaaaatct ttttttttttg agacggagtt ta                               152

<210> SEQ ID NO 266
<211> LENGTH: 193
<212> TYPE: DNA
<213> ORGANISM: Homo sapiens
<220> FEATURE:
<221> NAME/KEY: misc_feature
<222> LOCATION: 180
<223> OTHER INFORMATION: n = A,T,C or G

<400> SEQUENCE: 266
taaactccgt ccccttctta atcaatatgg aggctaccca ctccacatta ccttcttttc    60
aagggactgt ttccgtaact gttgtgggta ttcacgacca ggcttctaaa cctcttaaaa   120
ctccccaatt ctggtgccaa cttggacaac atgctttttt ttttttttttt tttttttttn   180 gagacggagt tta                                                      193

<210> SEQ ID NO 267
<211> LENGTH: 460
<212> TYPE: DNA
<213> ORGANISM: Homo sapiens

<400> SEQUENCE: 267
tgttgcgatc ccttaagcat gggtgctatt aaaaaaatgg tggagaagaa aatacctgga    60
atttacgtct tatctttaga gattgggaag accctgatgg aggacgtgga gaacagcttc   120
ttcttgaatg tcaattccca agtaacaaca gtgtgtcagg cacttgctaa ggatcctaaa   180
```

-continued

| | |
|---|---|
| ttgcagcaag gctacaatgc tatgggattc tcccagggag gccaatttct gagggcagtg | 240 |
| gctcagagat gcccttcacc tcccatgatc aatctgatct cggttggggg acaacatcaa | 300 |
| ggtgttttg gactcctcg atgcccagga gagagctctc acatctgtga cttcatccga | 360 |
| aaaacactga atgctgggc gtactccaaa gttgttcagg aacgcctcgt gcaagccgaa | 420 |
| tactggcatg acccataaaa ggaggatgtg gatcgcaaca | 460 |

<210> SEQ ID NO 268
<211> LENGTH: 533
<212> TYPE: DNA
<213> ORGANISM: Homo sapiens
<220> FEATURE:
<221> NAME/KEY: misc_feature
<222> LOCATION: 450, 470
<223> OTHER INFORMATION: n = A,T,C or G

<400> SEQUENCE: 268

| | |
|---|---|
| tgttgcgatc cgttgataga atagcgacgt ggtaatgagt gcatggcacg cctccgactt | 60 |
| accttcgccc gtggggaccc cgagtacgtc tacggcgtcg tcacttagag taccctctgg | 120 |
| acgcccgggc gcgttcgatt taccggaagc gcgagctgca gtgggcttgc gccccggcc | 180 |
| aaattctttg gggggtttaa ggccgcgggg aatttgaggt atctctatca gtatgtagcc | 240 |
| aagttggaac agtcgccatt cccgaaatcg ctttctttga atccgcaccg cctccagcat | 300 |
| tgcctcattc atcaacctga aggcacgcat aagtgacggt tgtgtcttca gcagctccac | 360 |
| tccataacta gcgcgctcga cctcgtcttc gtacgcgcca ggtccgtgcg tgcgaattcc | 420 |
| caactccggt gagttgcgca tttcaagttn cgaaactgtt cgcctccacn atttggcatg | 480 |
| ttcacgcatg acacggaata aactcgtcca gtaccgggaa tgggatcgca aca | 533 |

<210> SEQ ID NO 269
<211> LENGTH: 50
<212> TYPE: DNA
<213> ORGANISM: Homo sapiens

<400> SEQUENCE: 269

| | |
|---|---|
| tttttttttt ttcgcctgaa ttagctacag atcctcctca caagcggtca | 50 |

<210> SEQ ID NO 270
<211> LENGTH: 519
<212> TYPE: DNA
<213> ORGANISM: Homo sapiens

<400> SEQUENCE: 270

| | |
|---|---|
| tgttgcgatc caaataaccc accagcttct tgcacacttc gcagaagcca ccgtcctttg | 60 |
| gctgagtcac gtgaacggtc agtgcaagca gccgcgtgcc agagcagagg tgcagcatgc | 120 |
| tgcacaccag ctcagggctg acctcctcca gcaggatgga caggatggag ctgccgtacg | 180 |
| tgtccaccac ctcctggcac tcttccgaca gggacttcgg cagcttcgag cacattttgt | 240 |
| caaaagcgtc gagtatttct ttctcagtct tgttgttgtc aatcagcttg gtcacctcct | 300 |
| tcaccaggaa ttcacacacc tcacagtaaa catcagactt tgctgggacc tcgtgcttct | 360 |
| taatgggctc caccagttcc agggcaggga tgacattctt ggaggccact ttggcgggga | 420 |
| ccagagtctg catgggcatc tctttcacct catcacagaa cccaaccagc gcacagatct | 480 |
| ccttgggttg catgtgcatc atcatctggg atcgcaaca | 519 |

<210> SEQ ID NO 271
<211> LENGTH: 457

```
<212> TYPE: DNA
<213> ORGANISM: Homo sapiens

<400> SEQUENCE: 271
tttttttttt ttcgggcggc gaccggacgt gcactcctcc agtagcggct gcacgtcgtg    60
ccaatggccc gctatgagga ggtgagcgtg tccggcttcg aggagttcca ccgggccgtg   120
gaacagcaca atggcaagac cattttcgcc tactttacgg gttctaagga cgccgggggg   180
aaaagctggt gccccgactg cgtgcaggct gaaccagtcg tacgagaggg gctgaagcac   240
attagtgaag gatgtgtgtt catctactgc caagtaggaa agagcctta ttggaaagat    300
ccaaataatg acttcagaaa aaacttgaaa gtaacagcag tgcctacact acttaagtat   360
ggaacacctc aaaaactggt agaatctgag tgtcttcagg ccaacctggt ggaaatgttg   420
ttctctgaag attaagattt taggatggca atcaaga                             457

<210> SEQ ID NO 272
<211> LENGTH: 102
<212> TYPE: DNA
<213> ORGANISM: Homo sapiens

<400> SEQUENCE: 272
tttttttttt ttgggcaaca acctgaatac cttttcaagg ctctggcttg ggctcaagcc    60
cgcaggggaa atgcaactgg ccaggtcaca gggcaatcaa ga                      102

<210> SEQ ID NO 273
<211> LENGTH: 455
<212> TYPE: DNA
<213> ORGANISM: Homo sapiens
<220> FEATURE:
<221> NAME/KEY: misc_feature
<222> LOCATION: 380, 415, 454
<223> OTHER INFORMATION: n = A,T,C or G

<400> SEQUENCE: 273
tttttttttt ttggcaatca acaggtttaa gtcttcggcc gaagttaatc tcgtgttttt    60
ggcaatcaac aggtttaagt cttcggccga agttaatctc gtgttttggg caatcaacag   120
gtttaagtct tcggccgaag ttaatctcgt gttttggca atcaacaggt ttaagtcttc    180
ggccgaagtt aatctcgtgt tttggcaat caacaggttt aagtcttcgg ccgaagttaa    240
tctcgtgttt ttggcaatca acaggtttaa gtcttcggcc gaagttaatc tcgtgttttt    300
ggcaatcaag aggtttaagt cttcggccga agttaatctc gtgttttggg caatcaacag   360
gtttaagtct tcggccgaan ttaatctcgt gttttggca atcaacaggt ttaantcttc    420
ggccgaagtt aatctcgtgt ttttggcaat caana                              455

<210> SEQ ID NO 274
<211> LENGTH: 461
<212> TYPE: DNA
<213> ORGANISM: Homo sapiens

<400> SEQUENCE: 274
tttttttttt ttggccaata cccttgatga acatcaatgt gaaaatcctc ggtaaaatac    60
tggcaaacca atccagcag cacatcaaaa agcttatcca ccatgatcaa gtgggcttca   120
tccctgggat gcaaggctgg ttcaacataa gaaaatcaat aaatgtaatc catcacataa   180
acagaaccaa agacaaaaac cacatgatta tctcaataga tgcagaaaag gccttggaca   240
aattcaacag cccttcatgc taaacactct taataaacta gatattgatg gaatgtatct   300
```

| caaaataata agagctattt atgacaaacc cacagccaat atcatactga atgggcaaag | 360 |
|---|---|
| actggaagca ttccctttga aaactggcac aagacaagga tgccctctct caccgctcct | 420 |
| attcaacata gtattggaag ttctggccag ggcaatcaag a | 461 |

<210> SEQ ID NO 275
<211> LENGTH: 729
<212> TYPE: DNA
<213> ORGANISM: Homo sapiens
<220> FEATURE:
<221> NAME/KEY: misc_feature
<222> LOCATION: 164, 193, 207, 215, 216, 220, 223, 241, 244, 254, 269,
271, 275, 290, 295, 298, 309, 318, 325, 326, 331, 352, 380, 401,
411, 420, 424, 426, 431, 433, 435, 438, 440, 442, 443, 448,
453, 464, 465, 468, 474, 475, 481, 487, 491, 503, 516
<223> OTHER INFORMATION: n = A,T,C or G
<221> NAME/KEY: misc_feature
<222> LOCATION: 519, 530, 531, 542, 547, 549, 559, 561, 564, 582, 586,
587, 588, 589, 592, 595, 612, 614, 620, 631, 632, 635, 636, 644,
646, 649, 650, 651, 655, 657, 660, 661, 662, 663, 666, 672,
673, 674, 682, 687, 691, 693, 697, 700, 701, 704, 705
<223> OTHER INFORMATION: n = A,T,C or G
<221> NAME/KEY: misc_feature
<222> LOCATION: 713, 715, 717, 718, 722, 726, 727
<223> OTHER INFORMATION: n = A,T,C or G

<400> SEQUENCE: 275

| ttttttttt ttggccaaca ccaagtcttc cacgtgggag gttttattat gttttacaac | 60 |
|---|---|
| catgaaaaca taggaaggtg gctgttacag caaacatttc agatagacga atcggccaag | 120 |
| ctccccaaac cccaccttca cagcctcttc cacacgtctc ccanagattg ttgtccttca | 180 |
| cttgcaaatt canggatgtt ggaagtngac atttnnagtn gcnggaaccc catcagtgaa | 240 |
| ncantaagca gaantacgat gactttgana nacanctgat gaagaacacn ctacngaaaa | 300 |
| cccctttctnt cgtgttanga tctcnngtcc ntcactaatg cggcccnctg cnggtccacc | 360 |
| atttgggaga actcccccn cgttggatcc ccccttgagt ntccattct ngtcccccan | 420 |
| accngncttg ngngncantn cnncctcnca ccntgtttcc ctgnngtnaa aatnngtttt | 480 |
| nccgccncccc naattcccac ccnaatcaca gcgaanccng aaggccttcn naagtgttta | 540 |
| angcccngng gtttcctcnt ntanttgcag cctaccctcc cncttnnnnt tncgngttgg | 600 |
| tcgcgccctg gncncgcctn gttcctcttt nnggnnacaa cctngntcnn nggcncntcn | 660 |
| nnnctnttcc tnnnactagc tngcctntcc ncnccgnggn ncanngcaca ttncncnnac | 720 |
| tntgtnncc | 729 |

<210> SEQ ID NO 276
<211> LENGTH: 339
<212> TYPE: DNA
<213> ORGANISM: Homo sapiens

<400> SEQUENCE: 276

| tgacctgaca tgtagtagat acttaataaa tatttgtgga atgaatggat gaagtggagt | 60 |
|---|---|
| tacagagaaa aatagaaaag tacaaattgt tgtcagtgtt ttgaaggaaa attatgatct | 120 |
| ttcccaaagt tctgacttca ttctaagaca gggttagtat ctccatacat aattttactt | 180 |
| gcttttgaaa atcaaatgag ataatctatt tagattgata atttatttag actggctata | 240 |
| aactattaag tgctagcaaa tatacatttt aatctcattt tccacctctt gtgatatagc | 300 |
| tatgtaggtg ttgactttaa tggatgtcag gtcaatccc | 339 |

<210> SEQ ID NO 277
<211> LENGTH: 664

```
<212> TYPE: DNA
<213> ORGANISM: Homo sapiens
<220> FEATURE:
<221> NAME/KEY: misc_feature
<222> LOCATION: 267, 534, 590, 601, 646, 657
<223> OTHER INFORMATION: n = A,T,C or G

<400> SEQUENCE: 277
tgacctgaca tccataacaa aatctttctc cattatattc ttctagggga atttcttgaa      60
aagcatccaa aggaaacaaa tgatggtaag accgtgccaa gtggggagca gacaccaaag     120
taagaccaca gattttacat tcaacaggta gctcacagta ctttgcccga cactgtgggc     180
agaaatagcc tcctaatgta agccctggct cagtattgcc atccaaatgc gccatgctga     240
aagagggttt tgcatcctgg tcagatnaag aagcaatggt gtgctgagga atcccatac     300 gaataagtga gcattcagaa cttgagctag caggaggagg actaagatga tgtgtgagca     360
actctttgta atggctttca tctaaaataa catggtacgt gccaccagtt tcacgagcaa     420
gtacagtgca aacgcgaact tctgcagaca atccaataac agatactcta attttagctg     480
cctttagggt cttgattaaa tcataaatat tagatggatc gcaagttgta aggntgctaa     540
aagatgatta gtacttctcg acttgtatgt ccaggcatgt tgttttaaan tctgccttag     600
nccctgctta ggggaatttt taaagaagat ggctctccat gttcanggtc aatcacnaat     660
tgcc                                                                  664

<210> SEQ ID NO 278
<211> LENGTH: 452
<212> TYPE: DNA
<213> ORGANISM: Homo sapiens
<220> FEATURE:
<221> NAME/KEY: misc_feature
<222> LOCATION: 430
<223> OTHER INFORMATION: n = A,T,C or G

<400> SEQUENCE: 278
tgacctgaca ttgaggaaga gcacacacct ctgaaattcc ttaggttcag aagggcattt      60
gacacagagt gggcctctga taattcatga aatgcattct gaagtcatcc agaatggagg     120
ctgcaatctg ctgtgctttg ggggttgcct cactgtgctc ctggatatca cacaaaagct     180
gcaatccttc ttcttcaact aacatttttgc agtatttgct gggattttta ctgcagacat     240
gatacatagc ccatagtgcc cagagctgaa cctctggttg agagaagttg ccaaggagcg     300
ggaaaaatgt cttgaaagat ctataggtca ccaatgctgt catcttacaa cttgaacttg     360
gccaattctg tatggttgca tgcagatctt ggagaagagt acgcctctgg aagtcacggg     420
atatccaaan ctgtctgtca gatgtcaggt ca                                   452

<210> SEQ ID NO 279
<211> LENGTH: 274
<212> TYPE: DNA
<213> ORGANISM: Homo sapiens

<400> SEQUENCE: 279
tttttttttt ttcggcaagg caaatttact tctgcaaaag ggtgctgctt gcacttttgg      60
ccactgcgag agcacaccaa acaaagtagg aagggtttt ttatccctaa cgcggttatt     120
ccctggttct gtgtcgtgtc cccattggct ggagtcagac tgcacaatct acactgaccc     180
aactggctac tgtttaaaat tgaatatgaa taattaggta ggaagggga ggctgtttgt     240 tacggtacaa gacgtgtttg ggcatgtcag gtca                                 274
```

<210> SEQ ID NO 280
<211> LENGTH: 272
<212> TYPE: DNA
<213> ORGANISM: Homo sapiens

<400> SEQUENCE: 280
tacctgacat ggagaaataa cttgtagtat tttgcgtgca atggaatact atatgagggt      60
gaaaatgaat gaactagcaa tgcgtgtatc aacatgaata aatccccaaa acataataat     120
gttgaatgga aaggtgagt ttcagaagga tatatatgcc ctctaaatcc atttatgtaa     180
acctttaaaa aactacatta tttatggtca taagtccatc cagaaaatat ttaaaaacct     240
acatgggatt gataactact gatgtcaggt ca                                   272

<210> SEQ ID NO 281
<211> LENGTH: 431
<212> TYPE: DNA
<213> ORGANISM: Homo sapiens
<220> FEATURE:
<221> NAME/KEY: misc_feature
<222> LOCATION: 339, 420, 430, 431
<223> OTHER INFORMATION: n = A,T,C or G

<400> SEQUENCE: 281
tttttttttt ttggccaata gcatgattta aacattggaa aaagtcaaat gagcaatgcg      60
aatttttatg ttctcttgaa taatcaaaag agtaggcaac attggttcct cattcttgaa     120
tagcattaat cagaaaatat tgcatagcct ctagcctcct tagagtaggt gtgctctctc     180
aaatatatca tagtcccaca gtttatttca tgtatatttt ctgcctgaat cacatagaca     240
tttgaatttg caacgcctga tgtaaatata taaattctta ccaatcagaa acatagcaag     300
aaattcaggg acttggtcat yatcagggta tgacagcana tccctgtara aacactgata     360
cacactcaca cacgtatgca acgtggagat gtcgcyttww kkktwywcwm rmrycrwcgn     420
aatcacttan n                                                         431

<210> SEQ ID NO 282
<211> LENGTH: 98
<212> TYPE: DNA
<213> ORGANISM: Homo sapiens

<400> SEQUENCE: 282
attcgattcg atgcttgagc ccaggagttc aagactgcag tgagccactg cacttcaggc      60
tggacaacag agcgagtccc tgtgccaaaa aaaaaaaa                              98

<210> SEQ ID NO 283
<211> LENGTH: 764
<212> TYPE: DNA
<213> ORGANISM: Homo sapiens
<220> FEATURE:
<221> NAME/KEY: misc_feature
<222> LOCATION: 372, 374, 379, 380, 381, 382, 384, 387, 389, 392, 402,
      409, 411, 419, 421, 432, 440, 447, 452, 457, 466, 470, 471, 480,
      483, 492, 503, 506, 510, 512, 518, 520, 521, 524, 531, 534,
      536, 542, 545, 547, 550, 552, 553, 562, 566, 567, 575
<223> OTHER INFORMATION: n = A,T,C or G
<221> NAME/KEY: misc_feature
<222> LOCATION: 580, 581, 584, 586, 587, 595, 598, 601, 603, 604, 606,
      624, 629, 630, 646, 651, 652, 653, 656, 659, 664, 665, 681, 691,
      700, 706, 709, 721, 724, 731, 732, 737, 741, 744, 745, 750,
      753, 754, 758
<223> OTHER INFORMATION: n = A,T,C or G

<400> SEQUENCE: 283

```
tttttttttt tcgcaagca cgtgcacttt attgaatgac actgtagaca ggtgtgtggg      60
tataaactgc tgtatctagg ggcaggacca aggggggcagg ggcaacagcc ccagcgtgca    120
gggccascat tgcacagtgg astgcaaagg ttgcaggcta tgggcggcta ctavtaaccc    180 cgttttcct gtattatctg taacataata tggtagactg tcacagagcc gaatwccart     240
hacasgatga atccaawggt caygaggatg cccasaatca gggcccasat sttcaggcac    300
ttggcggtgg gggcatasgc ctgkgccccg gtcacgtcsc caaccwtcty cctgtcccta   360
cmcttgawtc cncnccttnn nntnccntna tntgcccgcc cncctcctng ngtcaaccng   420
natctgcact anctccctcn ccccttntgg antctcntcc ttcaantaan nttatccttn   480 acnccccct cnccttccc ctnccnccn tnatcccngn nccntatca ntcntnccct       540 cnctntnctn cnnatcgttc cncctnntaa ctacncttn nacnanncct cactnatncc   600
ngnnanttct ttccttccct cccnacgcnn tgcgtgcgcc cgtctngcct nnnctncgna   660
cccnnacttt atttacctt ncaccctagc nctctacttn acccanccnc tcctacctcc    720
nggnccaccc nnccctnatc nctnnctctn tcnnctcntt cccc                    764

<210> SEQ ID NO 284
<211> LENGTH: 157
<212> TYPE: DNA
<213> ORGANISM: Homo sapiens

<400> SEQUENCE: 284
caagtgtagg cacagtgatg aaagcctgga gcaaacacaa tctgtgggta attaacgttt   60
atttctcccc ttccaggaac gtcttgcatg gatgatcaaa gatcagctcc tggtcaacat  120
aaataagcta gtttaagata cgttcccta cacttga                           157

<210> SEQ ID NO 285
<211> LENGTH: 150
<212> TYPE: DNA
<213> ORGANISM: Homo sapiens

<400> SEQUENCE: 285
attcgattgt actcagacaa caatatgcta agtggaagaa gtcagtcaca aaagaccaca   60
tactgtatga cttcatttac attaagtgtc cagaataggc aaatccgtag agacagaaag  120
tagatgagca gctgcctagg tctgagtaca                                  150

<210> SEQ ID NO 286
<211> LENGTH: 219
<212> TYPE: DNA
<213> ORGANISM: Homo sapiens

<400> SEQUENCE: 286
attcgatttt ttttttttg gccatgatga aattcttact ccctcagatt ttttgtctgg    60
ataaatgcaa gtctcaccac cagatgtgaa attacagtaa actttgaagg aatctcctga  120
gcaaccttgg ttaggatcaa tccaatattc accatctggg aagtcaggat ggctgagttg  180 caggtctta caagttcggg ctggattggt ctgagtaca                         219

<210> SEQ ID NO 287
<211> LENGTH: 196
<212> TYPE: DNA
<213> ORGANISM: Homo sapiens

<400> SEQUENCE: 287
attcgattct tgaggctacc aggagctagg agaagaggca tggaacaaat tttccctcat   60
```

```
atccatactc agaaggaacc aaccctgctg acaccttaat ttcagcttct ggcctctaga      120
actgtgagag agtacatttc tcttggttta agccaagaga atctgtcttt ggtacttta      180 tatcatagcc tcaaga                                                     196

<210> SEQ ID NO 288
<211> LENGTH: 199
<212> TYPE: DNA
<213> ORGANISM: Homo sapiens

<400> SEQUENCE: 288
attcgatttc agtccagtcc cagaacccac attgtcaatt actactctgt araagattca      60
tttgttgaaa ttcattgagt aaaacattta tgatcccctta atatatgcca attaccatgc   120
taggtactga agattcaagt gaccgagatg ctagcccttg ggttcaagtg atccctctcc   180
cagagtgcac tggactgaa                                                  199

<210> SEQ ID NO 289
<211> LENGTH: 182
<212> TYPE: DNA
<213> ORGANISM: Homo sapiens

<400> SEQUENCE: 289
attcgattct tgaggctaca aacctgtaca gtatgttact ctactgaata ctgtaggcaa      60
tagtaataca gaagcaagta tctgtatatg taaacattaa aaaggtacag tgaaacttca    120
gtattataat cttagggacc accattatat atgtggtcca tcattggcca aaaaaaaaa    180 aa                                                                    182

<210> SEQ ID NO 290
<211> LENGTH: 1646
<212> TYPE: DNA
<213> ORGANISM: Homo sapiens

<400> SEQUENCE: 290
ggcacgagga gaaatgtaat tccatatttt atttgaaact tattccatat tttaattgga      60
tattgagtga ttgggttatc aaacacccac aaactttaat tttgttaaat ttatatggct   120
ttgaaataga agtataagtt gctaccattt tttgataaca ttgaaagata gtattttacc   180
atctttaatc atcttggaaa atacaagtcc tgtgaacaac cactctttca cctagcagca   240
tgaggccaaa agtaaaggct ttaaattata acatatggga ttcttagtag tatgttttt    300 tcttgaaact cagtggctct atctaacctt actatctcct cactctttct ctaagactaa   360
actctaggct cttaaaaatc tgcccacacc aatcttagaa gctctgaaaa gaatttgtct   420
ttaaatatct tttaatagta acatgtattt tatggaccaa attgacattt tcgactattt   480
tttccaaaaa agtcaggtga atttcagcac actgagttgg gaatttctta tcccagaaga   540
ccaaccaatt tcatatttat ttaagattga ttccatactc cgttttcaag agaatccct    600 gcagtctcct taaaggtaga acaaatactt tctattttt tttcaccatt gtgggattgg   660
actttaagag gtgactctaa aaaaacagag aacaaatatg tctcagttgt attaagcacg   720
gacccatatt atcatattca cttaaaaaaa tgatttcctg tgcacctttt ggcaacttct   780
cttttcaatg tagggaaaaa cttagtcacc ctgaaaaccc acaaaataaa taaaacttgt   840
agatgtgggc agaaggtttg ggggtggaca ttgtatgtgt ttaaattaaa ccctgtatca   900
ctgagaagct gttgtatggg tcagagaaaa tgaatgctta gaagctgttc acatcttcaa   960
```

```
gagcagaagc aaaccacatg tctcagctat attattattt attttttatg cataaagtga      1020
atcatttctt ctgtattaat ttccaaaggg ttttaccctc tatttaaatg ctttgaaaaa      1080
cagtgcattg acaatggggtt gatattttc tttaaaagaa aaatataatt atgaaagcca      1140
agataatctg aagcctgttt tattttaaaa cttttatgt tctgtggttg atgttgtttg      1200
tttgtttgtt tctatttttgt tggttttta ctttgttttt tgttttgttt tgttttgttt      1260
kgcatactac atgcagttct ttaaccaatg tctgtttggc taatgtaatt aaagttgtta      1320
atttatatga gtgcatttca actatgtcaa tggtttctta atatttattg tgtagaagta      1380
ctggtaattt tttatttac aatatgttta aagagataac agtttgatat gtttcatgt        1440 gtttatagca gaagttattt atttctatgg cattccagcg gatattttgg tgtttgcgag      1500
gcatgcagtc aatattttgt acagttagtg gacagtattc agcaacgcct gatagcttct      1560
ttggccttat gttaaataaa aagacctgtt tgggatgtat tttttatttt taaaaaaaaa      1620
aaaaaaaaaa aaaaaaaaaa aaaaaa                                            1646

<210> SEQ ID NO 291
<211> LENGTH: 1851
<212> TYPE: DNA
<213> ORGANISM: Homo sapiens

<400> SEQUENCE: 291
tcatcaccat tgccagcagc ggcaccgtta gtcaggtttt ctgggaatcc cacatgagta        60
cttccgtgtt cttcattctt ttcaatagc cataaatctt ctagctctgg ctggctgttt       120
tcacttcctt taagccttg tgactcttcc tctgatgtca gctttaagtc ttgttctgga       180
ttgctgtttt cagaagagat ttttaacatc tgttttcctt tgtagtcaga aagtaactgg      240
caaattacat gatgatgact agaaacagca tactctctgg ccgtctttcc agatcttgag      300
aagatacatc aacattttgc tcaagtagag ggctgactat acttgctgat ccacaacata      360
cagcaagtat gagagcagtt cttccatatc tatccagcgc atttaaattc gcttttttct      420
tgattaaaaa tttccaccact tgctgttttt gctcatgtat accaagtagc agtggtgtga      480
ggccatgctt gttttttgat tcgatatcag caccgtataa gagcagtgct ttggccatta      540
atttatcttc attgtagaca gcatagtgta gagtggtatt tccatactca tctggaatat      600
ttggatcagt gccatgttcc agcaacatta acgcacattc atcttcctgg cattgtacgg      660
cctttgtcag agctgtcctc ttttttgttgt caaggacatt aagttgacat cgtctgtcca      720
gcacgagttt tactacttct gaattcccat tggcagaggc cagatgtaga gcagtcctct      780
tttgcttgtc cctcttgttc acatccgtgt ccctgagcat gacgatgaga tcctttctgg      840
ggactttacc ccaccaggca gctctgtgga gcttgtccag atcttctcca tggacgtggt      900
acctgggatc catgaaggcg ctgtcatcgt agtctcccca agcgaccacg ttgctcttgc      960
cgctcccctg cagcagggga agcagtggca gcaccacttg cacctcttgc tcccaagcgt     1020
cttcacagag gagtcgttgt ggtctccaga agtgcccacg ttgctcttgc cgctccccct     1080
gtccatccag ggaggaagaa atgcaggaaa tgaaagatgc atgcacgatg gtatactcct     1140
cagccatcaa acttctggac agcaggtcac ttccagcaag gtggagaaag ctgtccaccc     1200
acagaggatg agatccagaa accacaatat ccattcacaa acaaacactt ttcagccaga     1260
cacaggtact gaaatcatgt catctgcggc aacatggtgg aacctaccca atcacacatc     1320
aagagatgaa gacactgcag tatatctgca acgtaata ctcttcatcc ataacaaaat       1380
aatataattt tcctctggag ccatatggat gaactatgaa ggaagaactc cccgaagaag     1440
```

```
ccagtcgcag agaagccaca ctgaagctct gtcctcagcc atcagcgcca cggacaggar    1500
tgtgtttctt ccccagtgat gcagcctcaa gttatcccga agctgccgca gcacacggtg    1560
gctcctgaga acaccccag ctcttccggt ctaacacagg caagtcaata aatgtgataa     1620
tcacataaac agaattaaaa gcaaagtcac ataagcatct caacagacac agaaaaggca    1680
tttgacaaaa tccagcatcc ttgtatttat tgttgcagtt ctcagaggaa atgcttctaa    1740
cttttcccca tttagtatta tgttggctgt gggcttgtca taggtggttt ttattacttt    1800
aaggtatgtc ccttctatgc ctgttttgct gagggtttta attctcgtgc c             1851

<210> SEQ ID NO 292
<211> LENGTH: 1851
<212> TYPE: DNA
<213> ORGANISM: Homo sapiens

<400> SEQUENCE: 292
tcatcaccat tgccagcagc ggcaccgtta gtcaggtttt ctgggaatcc cacatgagta     60
cttccgtgtt cttcattctt cttcaatagc cataaatctt ctagctctgg ctggctgttt    120
tcacttcctt taagcctttg tgactcttcc tctgatgtca gctttaagtc ttgttctgga    180
ttgctgtttt cagaagagat ttttaacatc tgttttttct tgtagtcaga aagtaactgg    240
caaattacat gatgatgact agaaacagca tactctctgg ccgtctttcc agatcttgag    300
aagatacatc aacattttgc tcaagtagag ggctgactat acttgctgat ccacaacata    360
cagcaagtat gagagcagtt cttccatatc tatccagcgc atttaaattc gcttttttct    420
tgattaaaaa tttcaccact tgctgttttt gctcatgtat accaagtagc agtggtgtga    480
ggccatgctt gttttttgat tcgatatcag caccgtataa gagcagtgct ttggccatta    540
atttatcttc attgtagaca gcatagtgta gagtggtatt tccatactca tctggaatat    600
ttggatcagt gccatgttcc agcaacatta acgcacattc atcttcctgg cattgtacgg    660
cctttgtcag agctgtcctc ttttttgttgt caaggacatt aagttgacat cgtctgtcca    720
gcacgagttt tactacttct gaattcccat tggcagaggc cagatgtaga gcagtcctct    780
tttgcttgtc cctcttgttc acatccgtgt ccctgagcat gacgatgaga tcctttctgg    840
ggactttacc ccaccaggca gctctgtgga gcttgtccag atcttctcca tggacgtggt    900
acctgggatc catgaaggcg ctgtcatcgt agtctcccca agcgaccacg ttgctcttgc    960
cgctcccctg cagcagggga agcagtggca gcaccacttg cacctcttgc tcccaagcgt   1020
cttcacagag gagtcgttgt ggtctccaga agtgcccacg ttgctcttgc cgctcccct    1080 gtccatccag ggaggaagaa atgcaggaaa tgaaagatgc atgcacgatg gtatactcct   1140
cagccatcaa acttctggac agcaggtcac ttccagcaag gtggagaaag ctgtccaccc   1200
acagaggatg agatccagaa accacaatat ccattcacaa acaaacactt ttcagccaga   1260
cacaggtact gaaatcatgt catctgcggc aacatggtgg aacctaccca atcacacatc   1320
aagagatgaa gacactgcag tatatctgca acgtaata ctcttcatcc ataacaaaat    1380
aatataattt tcctctggag ccatatggat gaactatgaa ggaagaactc cccgaagaag   1440
ccagtcgcag agaagccaca ctgaagctct gtcctcagcc atcagcgcca cggacaggar   1500
tgtgtttctt ccccagtgat gcagcctcaa gttatcccga agctgccgca gcacacggtg   1560
gctcctgaga acaccccag ctcttccggt ctaacacagg caagtcaata aatgtgataa    1620
tcacataaac agaattaaaa gcaaagtcac ataagcatct caacagacac agaaaaggca   1680
```

| | |
|---|---|
| tttgacaaaa tccagcatcc ttgtatttat tgttgcagtt ctcagaggaa atgcttctaa | 1740 |
| cttttcccca tttagtatta tgttggctgt gggcttgtca taggtggttt ttattacttt | 1800 |
| aaggtatgtc ccttctatgc ctgttttgct gagggtttta attctcgtgc c | 1851 |

<210> SEQ ID NO 293
<211> LENGTH: 668
<212> TYPE: DNA
<213> ORGANISM: Homo sapiens

<400> SEQUENCE: 293

| | |
|---|---|
| cttgagcttc caaataygga agactggccc ttacacasgt caatgttaaa atgaatgcat | 60 |
| ttcagtattt tgaagataaa attrgtagat ctataccttg ttttttgatt cgatatcagc | 120 |
| accrtataag agcagtgctt tggccattaa tttatcttc attrtagaca gcrtagtgya | 180 |
| gagtggtatt tccatactca tctggaatat ttggatcagt gccatgttcc agcaacatta | 240 |
| acgcacatta atcttcctgg cattgtacgg cctgtcagta ttagacccaa aaacaaatta | 300 |
| catatcttag gaattcaaaa taacattcca cagctttcac caactagtta tatttaaagg | 360 |
| agaaaactca tttttatgcc atgtattgaa atcaaaccca cctcatgctg atatagttgg | 420 |
| ctactgcata cctttatcag agctgtcctc tttttgttgt caaggacatt aagttgacat | 480 |
| cgtctgtcca gcaggagttt tactacttct gaattcccat tggcagaggc cagatgtaga | 540 |
| gcagtcctat gagagtgaga agactttta ggaaattgta gtgcactagc tacagccata | 600 |
| gcaatgattc atgtaactgc aaacactgaa tagcctgcta ttactctgcc ttcaaaaaaa | 660 |
| aaaaaaaa | 668 |

<210> SEQ ID NO 294
<211> LENGTH: 1512
<212> TYPE: DNA
<213> ORGANISM: Homo sapiens

<400> SEQUENCE: 294

| | |
|---|---|
| gggtcgccca gggggsgcgt ggctttcct cggtgggtg tgggttttcc ctgggtgggg | 60 |
| tgggctgggc trgaatcccc tgctggggtt ggcaggtttt ggctgggatt gactttytc | 120 |
| ttcaaacaga ttggaaaccc ggagttacct gctagttggt gaaactggtt ggtagacgcg | 180 |
| atctgttggc tactactggc ttctcctggc tgttaaaagc agatggtggt tgaggttgat | 240 |
| tccatgccgg ctgcttcttc tgtgaagaag ccatttggtc tcaggagcaa gatgggcaag | 300 |
| tggtgctgcc gttgcttccc ctgctgcagg gagagcggca agagcaacgt gggcacttct | 360 |
| ggagaccacg acgactctgc tatgaagaca ctcaggagca agatgggcaa gtggtgccgc | 420 |
| cactgcttcc cctgctgcag ggggagtggc aagagcaacg tgggcgcttc tggagaccac | 480 |
| gacgaytctg ctatgaagac actcaggaac aagatgggca agtggtgctg ccactgcttc | 540 |
| ccctgctgca gggggagcrg caagagcaag gtgggcgctt ggggagacta cgatgacagt | 600 |
| gccttcatgg agcccaggta ccacgtccgt ggagaagatc tggacaagct ccacagagct | 660 |
| gcctggtggg gtaaagtccc cagaaaggat ctcatcgtca tgctcaggga cactgacgtg | 720 |
| aacaagaagg acaagcaaaa gaggactgct ctacatctgg cctctgccaa tgggaattca | 780 |
| gaagtagtaa aactcstgct ggacagacga tgtcaactta atgtccttga caacaaaaag | 840 |
| aggacagctc tgayaaaggc cgtacaatgc caggaagatg aatgtgcgtt aatgttgctg | 900 |
| gaacatggca ctgatccaaa tattccagat gagtatggaa ataccactct rcactaygct | 960 |
| rtctayaatg aagataaatt aatggccaaa gcactgctct tatayggtgc tgatatcgaa | 1020 |

```
tcaaaaaaca aggtatagat ctactaattt tatcttcaaa atactgaaat gcattcattt    1080
taacattgac gtgtgtaagg gccagtcttc cgtatttgga agctcaagca taacttgaat    1140
gaaaatattt tgaaatgacc taattatctm agactttatt ttaaatattg ttattttcaa    1200
agaagcatta gagggtacag ttttttttt ttaaatgcac ttctggtaaa tacttttgtt     1260
gaaaacactg aatttgtaaa aggtaatact tactatttt caatttttcc ctcctaggat     1320
ttttttcccc taatgaatgt aagatggcaa aatttgccct gaaataggtt ttacatgaaa    1380
actccaagaa aagttaaaca tgtttcagtg aatagagatc ctgctccttt ggcaagttcc    1440
taaaaaacag taatagatac gaggtgatgc gcctgtcagt ggcaaggttt aagatatttc    1500
tgatctcgtg cc                                                        1512

<210> SEQ ID NO 295
<211> LENGTH: 1853
<212> TYPE: DNA
<213> ORGANISM: Homo sapiens

<400> SEQUENCE: 295
gggtcgccca gggggsgcgt gggctttcct cgggtgggtg tgggttttcc ctgggtgggg    60
tgggctgggc trgaatcccc tgctggggtt ggcaggtttt ggctgggatt gactttytc    120 ttcaaacaga ttggaaaccc ggagttacct gctagttggt gaaactggtt ggtagacgcg    180
atctgttggc tactactggc ttctcctggc tgttaaaagc agatggtggt tgaggttgat    240
tccatgccgg ctgcttcttc tgtgaagaag ccatttggtc tcaggagcaa gatgggcaag    300
tggtgctgcc gttgcttccc ctgctgcagg gagagcggca agagcaacgt gggcacttct    360
ggagaccacg acgactctgc tatgaagaca ctcaggagca gatgggcaa gtggtgccgc     420 cactgcttcc cctgctgcag ggggagtggc aagagcaacg tgggcgcttc tggagaccac    480
gacgaytctg ctatgaagac actcaggaac aagatgggca gtggtgctg ccactgcttc     540 ccctgctgca gggggagcrg caagagcaag gtgggcgctt ggggagacta cgatgacagy    600
gccttcatgg akcccaggta ccacgtccrt ggagaagatc tggacaagct ccacagagct    660
gcctggtggg gtaaagtccc cagaaaggat ctcatcgtca tgctcaggga cackgaygtg    720
aacaagargg acaagcaaaa gaggactgct ctacatctgg cctctgccaa tgggaattca    780
gaagtagtaa aactcstgct ggacagacga tgtcaactta atgtccttga caacaaaaag    840
aggacagctc tgayaaaggc cgtacaatgc caggaagatg aatgtgcgtt aatgttgctg    900
gaacatggca ctgatccaaa tattccagat gagtatggaa ataccactct rcactaygct    960
rtctayaatg aagataaatt aatggccaaa gcactgctct tataygtgc tgatatcgaa     1020 tcaaaaaaca agcatggcct cacaccactg ytacttggtr tacatgagca aaaacagcaa    1080
gtsgtgaaat tttaatyaa gaaaaaagcg aatttaaaat gcrctggata gatatggaag    1140
ractgctctc atacttgctg tatgttgtgg atcagcaagt atagtcagcc ytctacttga    1200
gcaaaatrtt gatgtatctt ctcaagatct ggaaagacgg ccagagagta tgctgtttct    1260
agtcatcatc atgtaatttg ccagttactt tctgactaca agaaaaaaca gatgttaaaa    1320
atctcttctg aaaacagcaa tccagaacaa gacttaaagc tgacatcaga ggaagagtca    1380
caaaggctta aaggaagtga aaacagccag ccagaggcat ggaaactttt aaatttaaac    1440
ttttggttta atgtttttt ttttgcctt aataatatta gatagtccca aatgaaatwa      1500
cctatgagac taggctttga gaatcaatag attcttttt taagaatctt ttggctagga    1560
```

| | |
|---|---:|
| gcggtgtctc acgcctgtaa ttccagcacc ttgagaggct gaggtgggca gatcacgaga | 1620 |
| tcaggagatc gagaccatcc tggctaacac ggtgaaaccc catctctact aaaaatacaa | 1680 |
| aaacttagct gggtgtggtg gcgggtgcct gtagtcccag ctactcagga rgctgaggca | 1740 |
| ggagaatggc atgaacccgg gaggtggagg ttgcagtgag ccgagatccg ccactacact | 1800 |
| ccagcctggg tgacagagca agactctgtc tcaaaaaaaa aaaaaaaaaa aaa | 1853 |

<210> SEQ ID NO 296
<211> LENGTH: 2184
<212> TYPE: DNA
<213> ORGANISM: Homo sapiens

<400> SEQUENCE: 296

| | |
|---|---:|
| ggcacgagaa ttaaaaccct cagcaaaaca ggcatagaag ggacatacct taaagtaata | 60 |
| aaaaccacct atgacaagcc cacagccaac ataatactaa atggggaaaa gttagaagca | 120 |
| tttcctctga gaactgcaac aataaataca aggatgctgg attttgtcaa atgccttttc | 180 |
| tgtgtctgtt gagatgctta tgtgactttg cttttaattc tgtttatgtg attatcacat | 240 |
| ttattgactt gcctgtgtta gaccggaaga gctggggtgt ttctcaggag ccaccgtgtg | 300 |
| ctgcggcagc ttcgggataa cttgaggctg catcactggg gaagaaacac aytcctgtcc | 360 |
| gtggcgctga tggctgagga cagagcttca gtgtggcttc tctgcgactg gcttcttcgg | 420 |
| ggagttcttc cttcatagtt catccatatg gctccagagg aaaattatat tattttgtta | 480 |
| tggatgaaga gtattacgtt gtgcagatat actgcagtgt cttcatctct tgatgtgtga | 540 |
| ttgggtaggt tccaccatgt tgccgcagat gacatgattt cagtacctgt gtctggctga | 600 |
| aaagtgtttg tttgtgaatg gatattgtgg tttctggatc tcatcctctg tgggtggaca | 660 |
| gctttctcca ccttgctgga agtgacctgc tgtccagaag tttgatggct gaggagtata | 720 |
| ccatcgtgca tgcatctttc atttcctgca tttcttcctc cctggatgga caggggagc | 780 |
| ggcaagagca acgtgggcac ttctggagac cacaacgact cctctgtgaa gacgcttggg | 840 |
| agcaagaggt gcaagtggtg ctgccactgc ttcccctgct gcaggggagc ggcaagagca | 900 |
| acgtggtcgc ttggggagac tacgatgaca gcgccttcat ggatcccagg taccacgtcc | 960 |
| atggagaaga tctggacaag ctccacagag ctgcctggtg gggtaaagtc cccagaaagg | 1020 |
| atctcatcgt catgctcagg gacacggatg tgaacaagag ggacaagcaa agaggactg | 1080 |
| ctctacatct ggcctctgcc aatgggaatt cagaagtagt aaaactcgtg ctggacagac | 1140 |
| gatgtcaact taatgtcctt gacaacaaaa agaggacagc tctgacaaag gccgtacaat | 1200 |
| gccaggaaga tgaatgtgcg ttaatgttgc tggaacatgg cactgatcca atattccag | 1260 |
| atgagtatgg aaataccact ctacactatg ctgtctacaa tgaagataaa ttaatggcca | 1320 |
| aagcactgct cttatacggt gctgatatcg aatcaaaaaa caagcatggc ctcacaccac | 1380 |
| tgctacttgg tatacatgag caaaacagc aagtggtgaa attttttaatc aagaaaaaag | 1440 |
| cgaatttaaa tgcgctggat agatatggaa gaactgctct catacttgct gtatgttgtg | 1500 |
| gatcagcaag tatagtcagc cctctacttg agcaaaatgt tgatgtatct tctcaagatc | 1560 |
| tggaaagacg gccagagagt atgctgtttc tagtcatcat catgtaattt gccagttact | 1620 |
| ttctgactac aaagaaaaac agatgttaaa aatctcttct gaaacagca atccagaaca | 1680 |
| agacttaaag ctgacatcag aggaagagtc acaaaggctt aaaggaagtg aaaacagcca | 1740 |
| gccagaggca tggaaacttt taaatttaaa cttttggttt aatgtttttt ttttttgcct | 1800 |
| taataatatt agatagtccc aaatgaaatw acctatgaga ctaggctttg agaatcaata | 1860 |

```
gattctttt   ttaagaatct  tttggctagg  agcggtgtct  cacgcctgta  attccagcac   1920
cttgagaggc  tgaggtgggc  agatcacgag  atcaggagat  cgagaccatc  ctggctaaca   1980
cggtgaaacc  ccatctctac  taaaaataca  aaaacttagc  tgggtgtggt  ggcgggtgcc   2040
tgtagtccca  gctactcagg  argctgaggc  aggagaatgg  catgaacccg  ggaggtggag   2100
gttgcagtga  gccgagatcc  gccactacac  tccagcctgg  gtgacagagc  aagactctgt   2160
ctcaaaaaaa  aaaaaaaaaa  aaaa                                            2184
```

<210> SEQ ID NO 297
<211> LENGTH: 1855
<212> TYPE: DNA
<213> ORGANISM: Homo sapiens
<220> FEATURE:
<221> NAME/KEY: misc_feature
<222> LOCATION: 606
<223> OTHER INFORMATION: n = A,T,C or G

<400> SEQUENCE: 297

```
tgcacgcatc  ggccagtgtc  tgtgccacgt  acactgacgc  ccctgagat   gtgcacgccg   60 cacgcgcacg  ttgcacgcgc  ggcagcggct  tggctggctt  gtaacggctt  gcacgcgcac  120 gccgccccg   cataaccgtc  agactggcct  gtaacggctt  gcaggcgcac  gccgcacgcg  180
cgtaacggct  tggctgccct  gtaacggctt  gcacgtgcat  gctgcacgcg  cgttaacggc  240
ttggctggca  tgtagccgct  tggcttggct  ttgcattytt  tgctkggctk  ggcgttgkty  300
tcttggattg  acgcttcctc  cttggatkga  cgtttcctcc  ttggatkgac  gtttcytyty  360
tcgcgttcct  ttgctggact  tgacctttty  tctgctgggt  ttggcattcc  tttggggtgg  420 gctggtgtt   ttctccgggg  gggktkgccc  ttcctgggt   gggcgtgggk  cgccccagg   480 gggcgtgggc  tttccccggg  tgggtgtggg  ttttcctggg  gtggggtggg  ctgtgctggg  540 atcccctgc   tggggttggc  agggattgac  ttttttcttc  aaacagattg  gaaacccgga  600
gtaacntgct  agttggtgaa  actggttggt  agacgcgatc  tgctggtact  actgtttctc  660
ctggctgtta  aaagcagatg  gtggctgagg  ttgattcaat  gccggctgct  tcttctgtga  720
agaagccatt  tggtctcagg  agcaagatgg  gcaagtggtg  cgccactgct  tcccctgctg  780 caggggagc   ggcaagagca  acgtgggcac  ttctggagac  cacaacgact  cctctgtgaa  840
gacgcttggg  agcaagaggt  gcaagtggtg  ctgcccactg  cttcccctgc  tgcaggggag  900
cggcaagagc  aacgtggkcg  cttggggaga  ctacgatgac  agcgccttca  tggakcccag  960
gtaccacgtc  crtggagaag  atctggacaa  gctccacaga  gctgcctggt  ggggtaaagt  1020
ccccagaaag  gatctcatcg  tcatgctcag  ggacactgay  gtgaacaaga  rggacaagca  1080
aaagaggact  gctctacatc  tggcctctgc  caatgggaat  tcagaagtag  taaaactcgt  1140
gctggacaga  cgatgtcaac  ttaatgtcct  tgacaacaaa  agaggacag   ctctgacaaa  1200 ggccgtacaa  tgcaggaag   atgaatgtgc  gttaatgttg  ctggaacatg  gcactgatcc  1260
aaatattcca  gatgagtatg  gaaataccac  tctacactat  gctgtctaca  atgaagataa  1320
attaatggcc  aaagcactgc  tcttatacgg  tgctgatatc  gaatcaaaaa  acaaggtata  1380
gatctactaa  ttttatcttc  aaaatactga  aatgcattca  ttttaacatt  gacgtgtgta  1440
agggccagtc  ttccgtattt  ggaagctcaa  gcataacttg  aatgaaaata  ttttgaaatg  1500
acctaattat  ctaagacttt  attttaaata  ttgttatttt  caagaagca   ttagagggta  1560 cagtttttt   ttttaaatg   cacttctggt  aaatactttt  gttgaaaaca  ctgaatttgt  1620
```

-continued

| | |
|---|---|
| aaaaggtaat acttactatt tttcaatttt tccctcctag gatttttttc ccctaatgaa | 1680 |
| tgtaagatgg caaaatttgc cctgaaatag gtttttacatg aaaactccaa gaaaagttaa | 1740 |
| acatgtttca gtgaatagag atcctgctcc tttggcaagt tcctaaaaaa cagtaataga | 1800 |
| tacgaggtga tgcgcctgtc agtggcaagg tttaagatat ttctgatctc gtgcc | 1855 |

<210> SEQ ID NO 298
<211> LENGTH: 1059
<212> TYPE: DNA
<213> ORGANISM: Homo sapiens

<400> SEQUENCE: 298

| | |
|---|---|
| gcaacgtggg cacttctgga gaccacaacg actcctctgt gaagacgctt gggagcaaga | 60 |
| ggtgcaagtg gtgctgccca ctgcttcccc tgctgcaggg gagcggcaag agcaacgtgg | 120 |
| gcgcttgrgg agactmcgat gacagygcct tcatggagcc caggtaccac gtccgtggag | 180 |
| aagatctgga caagctccac agagctgccc tggtggggta agtcccccag aaaggatctc | 240 |
| atcgtcatgc tcagggacac tgaygtgaac aagarggaca agcaaaagag gactgctcta | 300 |
| catctggcct ctgccaatgg gaattcagaa gtagtaaaac tcstgctgga cagacgatgt | 360 |
| caacttaatg tccttgacaa caaaaagagg acagctctga yaaaggccgt acaatgccag | 420 |
| gaagatgaat gtgcgttaat gttgctggaa catggcactg atccaaatat tccagatgag | 480 |
| tatggaaata ccactctrca ctaygctrtc tayaatgaag ataaattaat ggccaaagca | 540 |
| ctgctcttat ayggtgctga tatcgaatca aaaaacaagg tatagatcta ctaattttat | 600 |
| cttcaaaata ctgaaatgca ttcattttaa cattgacgtg tgtaagggcc agtcttccgt | 660 |
| atttggaagc tcaagcataa cttgaatgaa aatattttga aatgacctaa ttatctaaga | 720 |
| cttttatttta aatattgtta ttttcaaaga agcattagag ggtacagttt tttttttta | 780 |
| aatgcacttc tggtaaatac ttttgttgaa aacactgaat ttgtaaaagg taatacttac | 840 |
| tattttcaa ttttccctc ctaggattt ttcccctaa tgaatgtaag atggcaaaat | 900 |
| ttgccctgaa ataggtttta catgaaaact ccaagaaaag ttaaacatgt ttcagtgaat | 960 |
| agagatcctg ctcctttggc aagttcctaa aaaacagtaa tagatacgag gtgatgcgcc | 1020 |
| tgtcagtggc aaggtttaag atatttctga tctcgtgcc | 1059 |

<210> SEQ ID NO 299
<211> LENGTH: 329
<212> TYPE: PRT
<213> ORGANISM: Homo sapiens

<400> SEQUENCE: 299

```
Met Asp Ile Val Val Ser Gly Ser His Pro Leu Trp Val Asp Ser Phe
 1               5                  10                  15

Leu His Leu Ala Gly Ser Asp Leu Leu Ser Arg Ser Leu Met Ala Glu
            20                  25                  30

Glu Tyr Thr Ile Val His Ala Ser Phe Ile Ser Cys Ile Ser Ser Ser
        35                  40                  45

Leu Asp Gly Gln Gly Glu Arg Gln Glu Gln Arg Gly His Phe Trp Arg
    50                  55                  60

Pro Gln Arg Leu Leu Cys Glu Asp Ala Trp Glu Gln Glu Val Gln Val
65                  70                  75                  80

Val Leu Pro Leu Leu Pro Leu Leu Gln Gly Ser Gly Lys Ser Asn Val
                85                  90                  95

Val Ala Trp Gly Asp Tyr Asp Asp Ser Ala Phe Met Asp Pro Arg Tyr
```

```
               100                 105                 110
His Val His Gly Glu Asp Leu Asp Lys Leu His Arg Ala Ala Trp Trp
        115                 120                 125

Gly Lys Val Pro Arg Lys Asp Leu Ile Val Met Leu Arg Asp Thr Asp
130                 135                 140

Val Asn Lys Arg Asp Lys Gln Lys Arg Thr Ala Leu His Leu Ala Ser
145                 150                 155                 160

Ala Asn Gly Asn Ser Glu Val Val Lys Leu Val Leu Asp Arg Arg Cys
                165                 170                 175

Gln Leu Asn Val Leu Asp Asn Lys Lys Arg Thr Ala Leu Thr Lys Ala
            180                 185                 190

Val Gln Cys Gln Glu Asp Glu Cys Ala Leu Met Leu Leu Glu His Gly
        195                 200                 205

Thr Asp Pro Asn Ile Pro Asp Glu Tyr Gly Asn Thr Thr Leu His Tyr
    210                 215                 220

Ala Val Tyr Asn Glu Asp Lys Leu Met Ala Lys Ala Leu Leu Leu Tyr
225                 230                 235                 240

Gly Ala Asp Ile Glu Ser Lys Asn Lys His Gly Leu Thr Pro Leu Leu
                245                 250                 255

Leu Gly Ile His Glu Gln Lys Gln Gln Val Val Lys Phe Leu Ile Lys
            260                 265                 270

Lys Lys Ala Asn Leu Asn Ala Leu Asp Arg Tyr Gly Arg Thr Ala Leu
        275                 280                 285

Ile Leu Ala Val Cys Cys Gly Ser Ala Ser Ile Val Ser Pro Leu Leu
    290                 295                 300

Glu Gln Asn Val Asp Val Ser Ser Gln Asp Leu Glu Arg Arg Pro Glu
305                 310                 315                 320

Ser Met Leu Phe Leu Val Ile Ile Met
                325

<210> SEQ ID NO 300
<211> LENGTH: 148
<212> TYPE: PRT
<213> ORGANISM: Homo sapiens
<220> FEATURE:
<221> NAME/KEY: VARIANT
<222> LOCATION: 3, 46, 69, 88, 124
<223> OTHER INFORMATION: Xaa = Any Amino Acid

<400> SEQUENCE: 300

Met Thr Xaa Pro Ser Trp Ser Pro Gly Thr Thr Ser Val Glu Lys Ile
1               5                   10                  15

Trp Thr Ser Ser Thr Glu Leu Pro Trp Trp Gly Lys Val Pro Arg Lys
            20                  25                  30

Asp Leu Ile Val Met Leu Arg Asp Thr Asp Val Asn Lys Xaa Asp Lys
        35                  40                  45

Gln Lys Arg Thr Ala Leu His Leu Ala Ser Ala Asn Gly Asn Ser Glu
    50                  55                  60

Val Val Lys Leu Xaa Leu Asp Arg Arg Cys Gln Leu Asn Val Leu Asp
65                  70                  75                  80

Asn Lys Lys Arg Thr Ala Leu Xaa Lys Ala Val Gln Cys Gln Glu Asp
                85                  90                  95

Glu Cys Ala Leu Met Leu Leu Glu His Gly Thr Asp Pro Asn Ile Pro
            100                 105                 110

Asp Glu Tyr Gly Asn Thr Thr Leu His Tyr Ala Xaa Tyr Asn Glu Asp
        115                 120                 125
```

Lys Leu Met Ala Lys Ala Leu Leu Leu Tyr Gly Ala Asp Ile Glu Ser
    130                 135                 140

Lys Asn Lys Val
145

<210> SEQ ID NO 301
<211> LENGTH: 1155
<212> TYPE: DNA
<213> ORGANISM: Homo sapiens

<400> SEQUENCE: 301

| | |
|---|---|
| atggtggttg aggttgattc catgccggct gcctcttctg tgaagaagcc atttggtctc | 60 |
| aggagcaaga tgggcaagtg gtgctgccgt tgcttcccct gctgcaggga gagcggcaag | 120 |
| agcaacgtgg gcacttctgg agaccacgac gactctgcta tgaagacact caggagcaag | 180 |
| atgggcaagt ggtgccgcca ctgcttcccc tgctgcaggg ggagtggcaa gagcaacgtg | 240 |
| ggcgcttctg gagaccacga cgactctgct atgaagacac tcaggaacaa gatgggcaag | 300 |
| tggtgctgcc actgcttccc ctgctgcagg gggagcggca gagcaaggt gggcgcttgg | 360 |
| ggagactacg atgacagtgc cttcatggag cccaggtacc acgtccgtgg agaagatctg | 420 |
| gacaagctcc acagagctgc ctggtggggt aaagtcccca gaaaggatct catcgtcatg | 480 |
| ctcagggaca ctgacgtgaa caagaaggac aagcaaaaga ggactgctct acatctggcc | 540 |
| tctgccaatg gaattcaga agtagtaaaa ctcctgctgg acagacgatg tcaacttaat | 600 |
| gtccttgaca caaaaagag gacagctctg ataaaggccg tacaatgcca ggaagatgaa | 660 |
| tgtgcgttaa tgttgctgga acatggcact gatccaaata ttccagatga gtatggaaat | 720 |
| accactctgc actacgctat ctataatgaa gataaattaa tggccaaagc actgctctta | 780 |
| tatggtgctg atatcgaatc aaaaaacaag catggcctca caccactgtt acttggtgta | 840 |
| catgagcaaa acagcaagt cgtgaaattt ttaatcaaga aaaagcgaa tttaaatgca | 900 |
| ctggatagat atggaaggac tgctctcata cttgctgtat gttgtggatc agcaagtata | 960 |
| gtcagccttc tacttgagca aaatattgat gtatcttctc aagatctatc tggacagacg | 1020 |
| gccagagagt atgctgtttc tagtcatcat catgtaattt gccagttact ttctgactac | 1080 |
| aaagaaaaac agatgctaaa aatctcttct gaaaacagca tccagaaaaa tgtctcaaga | 1140 |
| accagaaata aataa | 1155 |

<210> SEQ ID NO 302
<211> LENGTH: 2000
<212> TYPE: DNA
<213> ORGANISM: Homo sapiens

<400> SEQUENCE: 302

| | |
|---|---|
| atggtggttg aggttgattc catgccggct gcctcttctg tgaagaagcc atttggtctc | 60 |
| aggagcaaga tgggcaagtg gtgctgccgt tgcttcccct gctgcaggga gagcggcaag | 120 |
| agcaacgtgg gcacttctgg agaccacgac gactctgcta tgaagacact caggagcaag | 180 |
| atgggcaagt ggtgccgcca ctgcttcccc tgctgcaggg ggagtggcaa gagcaacgtg | 240 |
| ggcgcttctg gagaccacga cgactctgct atgaagacac tcaggaacaa gatgggcaag | 300 |
| tggtgctgcc actgcttccc ctgctgcagg gggagcggca gagcaaggt gggcgcttgg | 360 |
| ggagactacg atgacagtgc cttcatggag cccaggtacc acgtccgtgg agaagatctg | 420 |
| gacaagctcc acagagctgc ctggtggggt aaagtcccca gaaaggatct catcgtcatg | 480 |

```
ctcagggaca ctgacgtgaa caagaaggac aagcaaaaga ggactgctct acatctggcc      540
tctgccaatg ggaattcaga agtagtaaaa ctcctgctgg acagacgatg tcaacttaat      600
gtccttgaca acaaaaagag gacagctctg ataaaggccg tacaatgcca ggaagatgaa      660
tgtgcgttaa tgttgctgga acatggcact gatccaaata ttccagatga gtatggaaat      720
accactctgc actacgctat ctataatgaa gataaattaa tggccaaagc actgctctta      780
tatggtgctg atatcgaatc aaaaaacaag catggcctca ccactgtt acttggtgta       840 catgagcaaa aacagcaagt cgtgaaattt ttaatcaaga aaaagcgaa tttaaatgca      900 ctggatagat atggaaggac tgctctcata cttgctgtat gttgtggatc agcaagtata      960
gtcagccttc tacttgagca aaatattgat gtatcttctc aagatctatc tggacagacg      1020
gccagagagt atgctgtttc tagtcatcat catgtaattt gccagttact ttctgactac      1080
aaagaaaaac agatgctaaa aatctcttct gaaacagca atccagaaca agacttaaag      1140
ctgacatcag aggaagagtc acaaaggttc aaaggcagtg aaaatagcca gccagagaaa      1200
atgtctcaag aaccagaaat aaataaggat ggtgatagag aggttgaaga agaaatgaag      1260
aagcatgaaa gtaataatgt gggattacta gaaaacctga ctaatggtgt cactgctggc      1320
aatggtgata atggattaat tcctcaaagg aagagcagaa cacctgaaaa tcagcaattt      1380
cctgacaacg aaagtgaaga gtatcacaga atttgcgaat tagtttctga ctacaaagaa      1440
aaacagatgc caaaatactc ttctgaaaac agcaacccag aacaagactt aaagctgaca      1500
tcagaggaag agtcacaaag gcttgagggc agtgaaaatg ccagccaga gctagaaaat      1560 tttatggcta tcgaagaaat gaagaagcac ggaagtactc atgtcggatt cccagaaaac      1620
ctgactaatg gtgccactgc tggcaatggt gatgatggat taattcctcc aaggaagagc      1680
agaacacctg aaagccagca atttcctgac actgagaatg aagagtatca cagtgacgaa      1740
caaaatgata ctcagaagca attttgtgaa gaacagaaca ctggaatatt acacgatgag      1800
attctgattc atgaagaaaa gcagatagaa gtggttgaaa aaatgaattc tgagctttct      1860
cttagttgta agaagaaaa agacatcttg catgaaaata gtacgttgcg ggaagaaatt      1920
gccatgctaa gactggagct agacacaatg aaacatcaga gccagctaaa aaaaaaaaa      1980 aaaaaaaaaa aaaaaaaaa                                                  2000
```

<210> SEQ ID NO 303
<211> LENGTH: 2040
<212> TYPE: DNA
<213> ORGANISM: Homo sapiens

<400> SEQUENCE: 303

```
atggtggttg aggttgattc catgccggct gcctcttctg tgaagaagcc atttggtctc       60
aggagcaaga tgggcaagtg gtgctgccgt tgcttcccct gctgcaggga gagcggcaag      120
agcaacgtgg gcacttctgg agaccacgac gactctgcta tgaagacact caggagcaag      180
atgggcaagt ggtgccgcca ctgcttcccc tgctgcaggg ggagtggcaa gagcaacgtg      240
ggcgcttctg gagaccacga cgactctgct atgaagacac tcaggaacaa gatgggcaag      300
tggtgctgcc actgcttccc ctgctgcagg gggagcggca gagcaaggt gggcgcttgg      360 ggagactacg atgacagtgc cttcatggag cccaggtacc acgtccgtgg agaagatctg      420
gacaagctcc acagagctgc ctggtgggt aaagtcccca gaaggatct catcgtcatg      480 ctcagggaca ctgacgtgaa caagaaggac aagcaaaaga ggactgctct acatctggcc      540
tctgccaatg ggaattcaga agtagtaaaa ctcctgctgg acagacgatg tcaacttaat      600
```

-continued

```
gtccttgaca acaaaaagag gacagctctg ataaaggccg tacaatgcca ggaagatgaa    660
tgtgcgttaa tgttgctgga acatggcact gatccaaata ttccagatga gtatggaaat    720
accactctgc actacgctat ctataatgaa gataaattaa tggccaaagc actgctctta    780
tatggtgctg atatcgaatc aaaaaacaag catggcctca caccactgtt acttggtgta    840
catgagcaaa acagcaagt cgtgaaattt ttaatcaaga aaaagcgaa tttaaatgca    900 ctggatagat atggaaggac tgctctcata cttgctgtat gttgtggatc agcaagtata    960
gtcagccttc tacttgagca aaatattgat gtatcttctc aagatctatc tggacagacg   1020
gccagagagt atgctgtttc tagtcatcat catgtaattt gccagttact ttctgactac   1080
aaagaaaaac agatgctaaa aatctcttct gaaacagca atccagaaca agacttaaag   1140
ctgacatcag aggaagagtc acaaaggttc aaaggcagtg aaaatagcca gccagagaaa   1200
atgtctcaag aaccagaaat aaataaggat ggtgatagag aggttgaaga agaaatgaag   1260
aagcatgaaa gtaataatgt gggattacta gaaaacctga ctaatggtgt cactgctggc   1320
aatggtgata atggattaat tcctcaaagg aagagcagaa cacctgaaaa tcagcaattt   1380
cctgacaacg aaagtgaaga gtatcacaga atttgcgaat tagtttctga ctacaaagaa   1440
aaacagatgc caaatactc ttctgaaaac agcaacccag aacaagactt aaagctgaca   1500
tcagaggaag agtcacaaag gcttgagggc agtgaaaatg gccagccaga gaaaagatct   1560
caagaaccag aataaataa ggatggtgat agagagctag aaaatttat ggctatcgaa   1620 gaaatgaaga agcacggaag tactcatgtc ggattcccag aaaacctgac taatggtgcc   1680
actgctggca atggtgatga tggattaatt cctccaagga agagcagaac acctgaaagc   1740
cagcaatttc ctgacactga gaatgaagag tatcacagtg acgaacaaaa tgatactcag   1800
aagcaatttt gtgaagaaca gaacactgga atattacacg atgagattct gattcatgaa   1860
gaaaagcaga tagaagtggt tgaaaaaatg aattctgagc tttctcttag ttgtaagaaa   1920
gaaaaagaca tcttgcatga aaatagtacg ttgcgggaag aaattgccat gctaagactg   1980
gagctagaca caatgaaaca tcagagccag ctaaaaaaaa aaaaaaaaaa aaaaaaaaa   2040
```

<210> SEQ ID NO 304
<211> LENGTH: 384
<212> TYPE: PRT
<213> ORGANISM: Homo sapiens

<400> SEQUENCE: 304

```
Met Val Val Glu Val Asp Ser Met Pro Ala Ala Ser Ser Val Lys Lys
 1               5                  10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
                85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
```

```
            115                 120                 125
Met Glu Pro Arg Tyr His Val Arg Gly Glu Asp Leu Asp Lys Leu His
        130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380

<210> SEQ ID NO 305
<211> LENGTH: 656
<212> TYPE: PRT
<213> ORGANISM: Homo sapiens

<400> SEQUENCE: 305

Met Val Val Glu Val Asp Ser Met Pro Ala Ala Ser Ser Val Lys Lys
1               5                   10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
            85                  90                  95

Lys Met Gly Lys Trp Cys Cys His Cys Phe Pro Cys Cys Arg Gly Ser
            100                 105                 110
```

```
Gly Lys Ser Lys Val Gly Ala Trp Gly Asp Tyr Asp Ser Ala Phe
            115                 120                 125
Met Glu Pro Arg Tyr His Val Arg Gly Glu Asp Leu Asp Lys Leu His
    130                 135                 140
Arg Ala Ala Trp Trp Gly Lys Val Pro Arg Lys Asp Leu Ile Val Met
145                 150                 155                 160
Leu Arg Asp Thr Asp Val Asn Lys Lys Asp Lys Gln Lys Arg Thr Ala
                165                 170                 175
Leu His Leu Ala Ser Ala Asn Gly Asn Ser Glu Val Val Lys Leu Leu
            180                 185                 190
Leu Asp Arg Arg Cys Gln Leu Asn Val Leu Asp Asn Lys Lys Arg Thr
        195                 200                 205
Ala Leu Ile Lys Ala Val Gln Cys Gln Glu Asp Glu Cys Ala Leu Met
    210                 215                 220
Leu Leu Glu His Gly Thr Asp Pro Asn Ile Pro Asp Glu Tyr Gly Asn
225                 230                 235                 240
Thr Thr Leu His Tyr Ala Ile Tyr Asn Glu Asp Lys Leu Met Ala Lys
                245                 250                 255
Ala Leu Leu Leu Tyr Gly Ala Asp Ile Glu Ser Lys Asn Lys His Gly
            260                 265                 270
Leu Thr Pro Leu Leu Leu Gly Val His Glu Gln Lys Gln Gln Val Val
        275                 280                 285
Lys Phe Leu Ile Lys Lys Lys Ala Asn Leu Asn Ala Leu Asp Arg Tyr
    290                 295                 300
Gly Arg Thr Ala Leu Ile Leu Ala Val Cys Cys Gly Ser Ala Ser Ile
305                 310                 315                 320
Val Ser Leu Leu Leu Glu Gln Asn Ile Asp Val Ser Ser Gln Asp Leu
                325                 330                 335
Ser Gly Gln Thr Ala Arg Glu Tyr Ala Val Ser Ser His His His Val
            340                 345                 350
Ile Cys Gln Leu Leu Ser Asp Tyr Lys Glu Lys Gln Met Leu Lys Ile
        355                 360                 365
Ser Ser Glu Asn Ser Asn Pro Glu Gln Asp Leu Lys Leu Thr Ser Glu
    370                 375                 380
Glu Glu Ser Gln Arg Phe Lys Gly Ser Glu Asn Ser Gln Pro Glu Lys
385                 390                 395                 400
Met Ser Gln Glu Pro Glu Ile Asn Lys Asp Gly Asp Arg Glu Val Glu
                405                 410                 415
Glu Glu Met Lys Lys His Glu Ser Asn Asn Val Gly Leu Leu Glu Asn
            420                 425                 430
Leu Thr Asn Gly Val Thr Ala Gly Asn Gly Asp Asn Gly Leu Ile Pro
        435                 440                 445
Gln Arg Lys Ser Arg Thr Pro Glu Asn Gln Gln Phe Pro Asp Asn Glu
    450                 455                 460
Ser Glu Glu Tyr His Arg Ile Cys Glu Leu Val Ser Asp Tyr Lys Glu
465                 470                 475                 480
Lys Gln Met Pro Lys Tyr Ser Ser Glu Asn Ser Asn Pro Glu Gln Asp
                485                 490                 495
Leu Lys Leu Thr Ser Glu Glu Ser Gln Arg Leu Glu Gly Ser Glu
            500                 505                 510
Asn Gly Gln Pro Glu Leu Glu Asn Phe Met Ala Ile Glu Glu Met Lys
        515                 520                 525
Lys His Gly Ser Thr His Val Gly Phe Pro Glu Asn Leu Thr Asn Gly
```

-continued

```
                530                 535                 540
Ala Thr Ala Gly Asn Gly Asp Asp Gly Leu Ile Pro Pro Arg Lys Ser
545                 550                 555                 560

Arg Thr Pro Glu Ser Gln Gln Phe Pro Asp Thr Glu Asn Glu Glu Tyr
                565                 570                 575

His Ser Asp Glu Gln Asn Asp Thr Gln Lys Gln Phe Cys Glu Glu Gln
                580                 585                 590

Asn Thr Gly Ile Leu His Asp Glu Ile Leu Ile His Glu Lys Gln
            595                 600                 605

Ile Glu Val Val Glu Lys Met Asn Ser Glu Leu Ser Leu Ser Cys Lys
610                 615                 620

Lys Glu Lys Asp Ile Leu His Glu Asn Ser Thr Leu Arg Glu Ile
625                 630                 635                 640

Ala Met Leu Arg Leu Glu Leu Asp Thr Met Lys His Gln Ser Gln Leu
                645                 650                 655

<210> SEQ ID NO 306
<211> LENGTH: 671
<212> TYPE: PRT
<213> ORGANISM: Homo sapiens

<400> SEQUENCE: 306

Met Val Val Glu Val Asp Ser Met Pro Ala Ala Ser Ser Val Lys Lys
1               5                   10                  15

Pro Phe Gly Leu Arg Ser Lys Met Gly Lys Trp Cys Cys Arg Cys Phe
                20                  25                  30

Pro Cys Cys Arg Glu Ser Gly Lys Ser Asn Val Gly Thr Ser Gly Asp
            35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
                85                  90                  95

Lys Met Gly Lys Trp Cys Cys His Cys Phe Pro Cys Cys Arg Gly Ser
                100                 105                 110

Gly Lys Ser Lys Val Gly Ala Trp Gly Asp Tyr Asp Asp Ser Ala Phe
            115                 120                 125

Met Glu Pro Arg Tyr His Val Arg Gly Glu Asp Leu Asp Lys Leu His
130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
                180                 185                 190

Leu Asp Arg Arg Cys Gln Leu Asn Val Leu Asp Asn Lys Lys Arg Thr
            195                 200                 205

Ala Leu Ile Lys Ala Val Gln Cys Gln Glu Asp Glu Cys Ala Leu Met
210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255
```

```
Ala Leu Leu Leu Tyr Gly Ala Asp Ile Glu Ser Lys Asn Lys His Gly
            260                 265                 270

Leu Thr Pro Leu Leu Gly Val His Glu Gln Lys Gln Gln Val Val
        275                 280                 285

Lys Phe Leu Ile Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Gln Asp Leu Lys Leu Thr Ser Glu
    370                 375                 380

Glu Glu Ser Gln Arg Phe Lys Gly Ser Glu Asn Ser Gln Pro Glu Lys
385                 390                 395                 400

Met Ser Gln Glu Pro Glu Ile Asn Lys Asp Gly Asp Arg Glu Val Glu
                405                 410                 415

Glu Glu Met Lys Lys His Glu Ser Asn Asn Val Gly Leu Leu Glu Asn
            420                 425                 430

Leu Thr Asn Gly Val Thr Ala Gly Asn Gly Asp Asn Gly Leu Ile Pro
        435                 440                 445

Gln Arg Lys Ser Arg Thr Pro Glu Asn Gln Gln Phe Pro Asp Asn Glu
    450                 455                 460

Ser Glu Glu Tyr His Arg Ile Cys Glu Leu Val Ser Asp Tyr Lys Glu
465                 470                 475                 480

Lys Gln Met Pro Lys Tyr Ser Ser Glu Asn Ser Asn Pro Glu Gln Asp
                485                 490                 495

Leu Lys Leu Thr Ser Glu Glu Ser Gln Arg Leu Glu Gly Ser Glu
            500                 505                 510

Asn Gly Gln Pro Glu Lys Arg Ser Gln Glu Pro Glu Ile Asn Lys Asp
        515                 520                 525

Gly Asp Arg Glu Leu Glu Asn Phe Met Ala Ile Glu Glu Met Lys Lys
    530                 535                 540

His Gly Ser Thr His Val Gly Phe Pro Glu Asn Leu Thr Asn Gly Ala
545                 550                 555                 560

Thr Ala Gly Asn Gly Asp Asp Gly Leu Ile Pro Pro Arg Lys Ser Arg
                565                 570                 575

Thr Pro Glu Ser Gln Gln Phe Pro Asp Thr Glu Asn Glu Glu Tyr His
            580                 585                 590

Ser Asp Glu Gln Asn Asp Thr Gln Lys Gln Phe Cys Glu Glu Gln Asn
        595                 600                 605

Thr Gly Ile Leu His Asp Glu Ile Leu Ile His Glu Glu Lys Gln Ile
    610                 615                 620

Glu Val Val Glu Lys Met Asn Ser Glu Leu Ser Leu Ser Cys Lys Lys
625                 630                 635                 640

Glu Lys Asp Ile Leu His Glu Asn Ser Thr Leu Arg Glu Glu Ile Ala
                645                 650                 655

Met Leu Arg Leu Glu Leu Asp Thr Met Lys His Gln Ser Gln Leu
            660                 665                 670
```

-continued

```
<210> SEQ ID NO 307
<211> LENGTH: 800
<212> TYPE: DNA
<213> ORGANISM: Homo sapiens

<400> SEQUENCE: 307
atkagcttcc gcttctgaca acactagaga tccctcccct ccctcagggt atggccctcc      60
acttcatttt tggtacataa catctttata ggacaggggt aaaatcccaa tactaacagg     120
agaatgctta ggactctaac aggttttga gaatgtgttg gtaagggcca ctcaatccaa     180
tttttcttgg tcctccttgt ggtctaggag acaggcaag ggtgcagatt ttcaagaatg     240
catcagtaag ggccactaaa tccgaccttc ctcgttcctc cttgtggtct gggaggaaaa     300
ctagtgtttc tgttgctgtg tcagtgagca caactattcc gatcagcagg gtccagggac     360
cactgcaggt tcttgggcag ggggagaaac aaaacaaacc aaaaccatgg gcrgttttgt     420
ctttcagatg ggaaacactc aggcatcaac aggctcacct ttgaaatgca tcctaagcca     480
atgggacaaa tttgacccac aaaccctgga aaagaggtg gctcattttt tttgcactat     540
ggcttggccc caacattctc tctctgatgg ggaaaaatgg ccacctgagg gaagtacaga     600
ttacaatact atcctgcagc ttgaccttt ctgtaagagg gaaggcaaat ggagtgaaat     660
accttatgtc caagctttct tttcattgaa ggagaataca ctatgcaaag cttgaaattt     720
acatcccaca ggaggacctc tcagcttacc cccatatcct agcctcccta tagctcccct     780
tcctattagt gataagcctc                                                  800

<210> SEQ ID NO 308
<211> LENGTH: 102
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Any Amino Acid

<400> SEQUENCE: 308

Met Gly Xaa Phe Val Phe Gln Met Gly Asn Thr Gln Ala Ser Thr Gly
 1               5                  10                  15

Ser Pro Leu Lys Cys Ile Leu Ser Gln Trp Asp Lys Phe Asp Pro Gln
            20                  25                  30

Thr Leu Glu Lys Glu Val Ala His Phe Phe Cys Thr Met Ala Trp Pro
        35                  40                  45

Gln His Ser Leu Ser Asp Gly Glu Lys Trp Pro Pro Glu Gly Ser Thr
    50                  55                  60

Asp Tyr Asn Thr Ile Leu Gln Leu Asp Leu Phe Cys Lys Arg Glu Gly
65                  70                  75                  80

Lys Trp Ser Glu Ile Pro Tyr Val Gln Ala Phe Phe Ser Leu Lys Glu
                85                  90                  95

Asn Thr Leu Cys Lys Ala
            100

<210> SEQ ID NO 309
<211> LENGTH: 9
<212> TYPE: PRT
<213> ORGANISM: Artificial Sequence
<220> FEATURE:
<223> OTHER INFORMATION: Made in the lab

<400> SEQUENCE: 309

Leu Met Ala Glu Glu Tyr Thr Ile Val
```

-continued

<210> SEQ ID NO 310
<211> LENGTH: 9
<212> TYPE: PRT
<213> ORGANISM: Artificial Sequence
<220> FEATURE:
<223> OTHER INFORMATION: Made in the lab

<400> SEQUENCE: 310

Lys Leu Met Ala Lys Ala Leu Leu Leu
 1               5

<210> SEQ ID NO 311
<211> LENGTH: 9
<212> TYPE: PRT
<213> ORGANISM: Artificial Sequence
<220> FEATURE:
<223> OTHER INFORMATION: Made in the lab

<400> SEQUENCE: 311

Gly Leu Thr Pro Leu Leu Leu Gly Ile
 1               5

<210> SEQ ID NO 312
<211> LENGTH: 10
<212> TYPE: PRT
<213> ORGANISM: Artificial Sequence
<220> FEATURE:
<223> OTHER INFORMATION: Made in the lab

<400> SEQUENCE: 312

Lys Leu Val Leu Asp Arg Arg Cys Gln Leu
 1               5                  10

<210> SEQ ID NO 313
<211> LENGTH: 1852
<212> TYPE: DNA
<213> ORGANISM: Homo sapiens

<400> SEQUENCE: 313
ggcacgagaa ttaaaaccct cagcaaaaca ggcatagaag ggacatacct taaagtaata      60 aaaccacct atgacaagcc cacagccaac ataatactaa atggggaaaa gttagaagca     120
tttcctctga gaactgcaac aataaataca aggatgctgg attttgtcaa atgccttttc    180
tgtgtctgtt gagatgctta tgtgactttg cttttaattc tgtttatgtg attatcacat    240
ttattgactt gcctgtgtta gaccggaaga gctggggtgt ttctcaggag ccaccgtgtg    300
ctgcggcagc ttcgggataa cttgaggctg catcactggg gaagaaacac aytcctgtcc    360
gtggcgctga tggctgagga cagagcttca gtgtggcttc tctgcgactg gcttcttcgg    420
ggagttcttc cttcatagtt catccatatg gctccagagg aaaattatat tattttgtta    480
tggatgaaga gtattacgtt gtgcagatat actgcagtgt cttcatctct tgatgtgtga    540
ttgggtaggt tccaccatgt tgccgcagat gacatgattt cagtacctgt gtctggctga    600
aaagtgtttg tttgtgaatg gatattgtgg tttctggatc tcatcctctg tgggtggaca    660
gctttctcca ccttgctgga agtgacctgc tgtccagaag tttgatggct gaggagtata    720
ccatcgtgca tgcatctttc atttcctgca tttcttcctc cctggatgga caggggagc     780 ggcaagagca acgtgggcac ttctggagac acaacgact cctctgtgaa gacgcttggg     840
agcaagaggt gcaagtggtg ctgccactgc ttcccctgct gcaggggag cggcaagagc      900

```
aacgtggtcg cttggggaga ctacgatgac agcgccttca tggatcccag gtaccacgtc    960
catggagaag atctggacaa gctccacaga gctgcctggt ggggtaaagt ccccagaaag   1020
gatctcatcg tcatgctcag ggacacggat gtgaacaaga gggacaagca aaagaggact   1080
gctctacatc tggcctctgc caatgggaat tcagaagtag taaaactcgt gctggacaga   1140
cgatgtcaac ttaatgtcct tgacaacaaa aagaggacag ctctgacaaa ggccgtacaa   1200
tgccaggaag atgaatgtgc gttaatgttg ctggaacatg gcactgatcc aaatattcca   1260
gatgagtatg gaaataccac tctacactat gctgtctaca atgaagataa attaatggcc   1320
aaagcactgc tcttatacgg tgctgatatc gaatcaaaaa acaagcatgg cctcacacca   1380
ctgctacttg gtatacatga gcaaaaacag caagtggtga aatttttaat caagaaaaaa   1440
gcgaatttaa atgcgctgga tagatatgga agaactgctc tcatacttgc tgtatgttgt   1500
ggatcagcaa gtatagtcag ccctctactt gagcaaaatg ttgatgtatc ttctcaagat   1560
ctggaaagac ggccagagag tatgctgttt ctagtcatca tcatgtaatt tgccagttac   1620
tttctgacta caagaaaaa cagatgttaa aaatctcttc tgaaaacagc aatccagaac   1680
aagacttaaa gctgacatca gaggaagagt cacaaaggct taaggaagt gaaaacagcc   1740 agccagagct agaagattta tggctattga agaagaatga agaacacgga agtactcatg   1800
tgggattccc agaaaacctg actaacggtg ccgctgctgg caatggtgat ga           1852

<210> SEQ ID NO 314
<211> LENGTH: 879
<212> TYPE: DNA
<213> ORGANISM: Homo sapiens

<400> SEQUENCE: 314
atgcatcttt catttcctgc atttcttcct ccctggatgg acaggggag cggcaagagc     60 aacgtgggca cttctggaga ccacaacgac tcctctgtga agacgcttgg gagcaagagg   120
tgcaagtggt gctgccactg cttcccctgc tgcaggggga gcggcaagag caacgtggtc   180
gcttggggag actacgatga cagcgccttc atggatccca gtaccacgt ccatggagaa    240 gatctggaca agctccacag agctgcctgg tggggtaaag tccccagaaa ggatctcatc   300
gtcatgctca gggacacgga tgtgaacaag agggacaagc aaaagaggac tgctctacat   360
ctggcctctg ccaatgggaa ttcagaagta gtaaaactcg tgctggacag acgatgtcaa   420
cttaatgtcc ttgacaacaa aaagaggaca gctctgacaa aggccgtaca atgccaggaa   480
gatgaatgtg cgttaatgtt gctggaacat ggcactgatc caaatattcc agatgagtat   540
ggaaatacca ctctacacta tgctgtctac aatgaagata aattaatggc caaagcactg   600
ctcttatacg gtgctgatat cgaatcaaaa acaagcatg gcctcacacc actgctactt    660
ggtatacatg agcaaaaaca gcaagtggtg aaattttaa tcaagaaaaa agcgaattta    720
aatgcgctgg atagatatgg aagaactgct ctcatacttg ctgtatgttg tggatcagca   780
agtatagtca gccctctact tgagcaaaat gttgatgtat cttctcaaga tctggaaaga   840
cggccagaga gtatgctgtt tctagtcatc atcatgtaa                          879

<210> SEQ ID NO 315
<211> LENGTH: 292
<212> TYPE: PRT
<213> ORGANISM: Homo sapiens

<400> SEQUENCE: 315

Met His Leu Ser Phe Pro Ala Phe Leu Pro Pro Trp Met Asp Arg Gly
```

|   |   |   | 5 |   |   |   |   | 10 |   |   |   |   | 15 |   |   |
|---|---|---|---|---|---|---|---|---|---|---|---|---|---|---|---|
| Ser | Gly | Lys | Ser | Asn | Val | Gly | Thr | Ser | Gly | Asp | His | Asn | Asp | Ser | Ser |
|   |   |   | 20 |   |   |   |   | 25 |   |   |   |   | 30 |   |   |
| Val | Lys | Thr | Leu | Gly | Ser | Lys | Arg | Cys | Lys | Trp | Cys | Cys | His | Cys | Phe |
|   |   |   | 35 |   |   |   |   | 40 |   |   |   |   | 45 |   |   |
| Pro | Cys | Cys | Arg | Gly | Ser | Gly | Lys | Ser | Asn | Val | Val | Ala | Trp | Gly | Asp |
|   |   |   | 50 |   |   |   |   | 55 |   |   |   |   | 60 |   |   |
| Tyr | Asp | Asp | Ser | Ala | Phe | Met | Asp | Pro | Arg | Tyr | His | Val | His | Gly | Glu |
| 65 |   |   |   |   | 70 |   |   |   |   | 75 |   |   |   |   | 80 |
| Asp | Leu | Asp | Lys | Leu | His | Arg | Ala | Ala | Trp | Trp | Gly | Lys | Val | Pro | Arg |
|   |   |   |   | 85 |   |   |   |   | 90 |   |   |   |   | 95 |   |
| Lys | Asp | Leu | Ile | Val | Met | Leu | Arg | Asp | Thr | Asp | Val | Asn | Lys | Arg | Asp |
|   |   |   | 100 |   |   |   |   | 105 |   |   |   |   | 110 |   |   |
| Lys | Gln | Lys | Arg | Thr | Ala | Leu | His | Leu | Ala | Ser | Ala | Asn | Gly | Asn | Ser |
|   |   |   | 115 |   |   |   |   | 120 |   |   |   |   | 125 |   |   |
| Glu | Val | Val | Lys | Leu | Val | Leu | Asp | Arg | Arg | Cys | Gln | Leu | Asn | Val | Leu |
|   |   |   | 130 |   |   |   |   | 135 |   |   |   |   | 140 |   |   |
| Asp | Asn | Lys | Lys | Arg | Thr | Ala | Leu | Thr | Lys | Ala | Val | Gln | Cys | Gln | Glu |
| 145 |   |   |   |   | 150 |   |   |   |   | 155 |   |   |   |   | 160 |
| Asp | Glu | Cys | Ala | Leu | Met | Leu | Leu | Glu | His | Gly | Thr | Asp | Pro | Asn | Ile |
|   |   |   |   | 165 |   |   |   |   | 170 |   |   |   |   | 175 |   |
| Pro | Asp | Glu | Tyr | Gly | Asn | Thr | Thr | Leu | His | Tyr | Ala | Val | Tyr | Asn | Glu |
|   |   |   | 180 |   |   |   |   | 185 |   |   |   |   | 190 |   |   |
| Asp | Lys | Leu | Met | Ala | Lys | Ala | Leu | Leu | Leu | Tyr | Gly | Ala | Asp | Ile | Glu |
|   |   |   | 195 |   |   |   |   | 200 |   |   |   |   | 205 |   |   |
| Ser | Lys | Asn | Lys | His | Gly | Leu | Thr | Pro | Leu | Leu | Leu | Gly | Ile | His | Glu |
|   |   |   | 210 |   |   |   |   | 215 |   |   |   |   | 220 |   |   |
| Gln | Lys | Gln | Gln | Val | Val | Lys | Phe | Leu | Ile | Lys | Lys | Ala | Asn | Leu |   |
| 225 |   |   |   |   | 230 |   |   |   |   | 235 |   |   |   |   | 240 |
| Asn | Ala | Leu | Asp | Arg | Tyr | Gly | Arg | Thr | Ala | Leu | Ile | Leu | Ala | Val | Cys |
|   |   |   |   | 245 |   |   |   |   | 250 |   |   |   |   | 255 |   |
| Cys | Gly | Ser | Ala | Ser | Ile | Val | Ser | Pro | Leu | Leu | Glu | Gln | Asn | Val | Asp |
|   |   |   | 260 |   |   |   |   | 265 |   |   |   |   | 270 |   |   |
| Val | Ser | Ser | Gln | Asp | Leu | Glu | Arg | Arg | Pro | Glu | Ser | Met | Leu | Phe | Leu |
|   |   |   | 275 |   |   |   |   | 280 |   |   |   |   | 285 |   |   |
| Val | Ile | Ile | Met |   |   |   |   |   |   |   |   |   |   |   |   |
|   |   |   | 290 |   |   |   |   |   |   |   |   |   |   |   |   |

<210> SEQ ID NO 316
<211> LENGTH: 584
<212> TYPE: DNA
<213> ORGANISM: Homo sapiens

<400> SEQUENCE: 316

```
agttgggcca aattcccctc cccctacagc ttgaagggga cataaccaat agcctggggt      60
ttttttgtgg tcctttggag atttctttgc ttattttctt ctgggtgggg gtgattagag     120
gaggcttatc actaatagga agggagcta tagggaggct aggatatggg ggtaagctga      180
gaggtcctcc tgtgggatgt aaatttcaag ctttgcatag tgtattctcc ttcaatgaaa     240
agaaagcttg gacataaggt atttcactcc atttgccttc cctcttacag aaaaggtcaa     300
gctgcaggat agtattgtaa tctgtacttc cctcaggtgg ccatttttcc ccatcagaga     360
gagaatgttg gggccaagcc atagtgcaga aaaaaaaatg agccacctct ttttccaggg     420
tttgtgggtc aaatttgtcc cattggctta ggatgcattt caaggtgag   cctgttgatg   480
```

```
cctgagtgtt tcccatctga agacaaaac tgcccatggt tttggtttgt tttgtttctc      540
cccctgccca agaactatca aactcctgag ccaacaacta aaaa                      584
```

<210> SEQ ID NO 317
<211> LENGTH: 829
<212> TYPE: DNA
<213> ORGANISM: Homo sapiens

<400> SEQUENCE: 317

```
attagcttcc gcttctgaca acactagaga tccctcccct ccctcagggt atggccctcc      60
acttcatttt tggtacataa catctttata ggacaggggt aaaatcccaa tactaacagg     120
agaatgctta ggactctaac aggttttttga gaatgtgttg gtaagggcca ctcaatccaa     180 ttttttcttgg tcctccttgt ggtctaggag gacaggcaag ggtgcagatt ttcaagaatg     240
catcagtaag ggccactaaa tccgaccttc ctcgttcctc cttgtggtct gggaggaaaa     300
ctagtgtttc tgttgctgtg tcagtgagca caactattcc gatcagcagg gtccagggac     360
cactgcaggt tcttgggcag ggggagaaac aaaacaaacc aaaaccatgg gcagttttgt     420
ctttcagatg ggaaacactc aggcatcaac aggctcacct ttgaaatgca tcctaagcca     480
atgggacaaa tttgacccac aaaccctgga aaaagaggtg gctcattttt tttgcactat     540
ggcttggccc caacattctc tctctgatgg ggaaaaatgg ccacctgagg gaagtacaga     600
ttacaatact atcctgcagc ttgaccttttt ctgtaagagg gaaggcaaat ggagtgaaat     660 acctttatgtc caagctttct tttcattgaa ggagaataca ctatgcaaag cttgaaattt     720
acatcccaca ggaggacctc tcagcttacc cccatatcct agcctcccta tagctcccct     780
tcctattagt gataagcctc ctctaatcac ccccacccag aagaaaata                  829
```

<210> SEQ ID NO 318
<211> LENGTH: 30
<212> TYPE: PRT
<213> ORGANISM: Homo sapien

<400> SEQUENCE: 318

```
Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile
            20                  25                  30
```

<210> SEQ ID NO 319
<211> LENGTH: 41
<212> TYPE: DNA
<213> ORGANISM: Artificial Sequence
<220> FEATURE:
<223> OTHER INFORMATION: PCR primer

<400> SEQUENCE: 319

```
ggcctctgcc aatgggaact cagaagtagt aaaactcctg c                          41
```

<210> SEQ ID NO 320
<211> LENGTH: 41
<212> TYPE: DNA
<213> ORGANISM: Artificial Sequence
<220> FEATURE:
<223> OTHER INFORMATION: PCR primer

<400> SEQUENCE: 320

```
gcaggagttt tactacttct gagttcccat tggcagaggc c                          41
```

-continued

```
<210> SEQ ID NO 321
<211> LENGTH: 60
<212> TYPE: DNA
<213> ORGANISM: Artificial Sequence
<220> FEATURE:
<223> OTHER INFORMATION: PCR primer

<400> SEQUENCE: 321
ggggaattcc cgctggtgcc gcgcggcagc cctatggtgg ttgaggttga          50
ttccatgccg                                                      60

<210> SEQ ID NO 322
<211> LENGTH: 42
<212> TYPE: DNA
<213> ORGANISM: Artificial Sequence
<220> FEATURE:
<223> OTHER INFORMATION: PCR primer

<400> SEQUENCE: 322
cccgaattct tatttatttc tggttcttga gacattttct gg                  42

<210> SEQ ID NO 323
<211> LENGTH: 1590
<212> TYPE: DNA
<213> ORGANISM: Homo sapiens

<400> SEQUENCE: 323
atgcatcacc atcaccatca cacggccgcg tccgataact tccagctgtc ccagggtggg      60
cagggattcg ccattccgat cgggcaggcg atggcgatcg cgggccagat caagcttccc     120
accgttcata tcgggcctac cgccttcctc ggcttgggtg ttgtcgacaa caacggcaac     180
ggcgcacgag tccaacgcgt ggtcgggagc gctccggcgg caagtctcgg catctccacc     240
ggcgacgtga tcaccgcggt cgacggcgct ccgatcaact cggccaccgc gatggcggac     300
gcgcttaacg ggcatcatcc cggtgacgtc atctcggtga cctggcaaac caagtcgggc     360
ggcacgcgta cagggaacgt gacattggcc gagggacccc cggccgaatt cccgctggtg     420
ccgcgcggca gccctatggt ggttgaggtt gattccatgc cggctgcttc ttctgtgaag     480
aagccatttg gtctcaggag caagatgggc aagtggtgct gccgttgctt ccccctgctg     540
agggagagcg gcaagagcaa cgtgggcact tctggagacc acgacgactc tgctatgaag     600
acactcagga gcaagatggg caagtggtgc cgccactgct ccccctgctg caggggagt      660 ggcaagagca acgtgggcgc ttctggagac acgacgactc tgctatgaa gacactcagg     720 aacaagatgg gcaagtggtg ctgccactgc ttccccctgct gcaggggag cggcaagagc     780 aaggtgggcg cttggggaga ctacgatgac agygccttca tggagcccag gtaccacgtc     840
cgtggagaag atctggacaa gctccacaga gctgcctggt ggggtaaagt ccccagaaag     900
gatctcatcg tcatgctcag ggacactgac gtgaacaaga aggacaagca aaagaggact     960
gctctacatc tggcctctgc caatgggaat tcagaagtag taaaactcct gctggacaga    1020
cgatgtcaac ttaatgtcct tgacaacaaa aagaggacag ctctgataaa ggccgtacaa    1080
tgccaggaag atgaatgtgc gttaatgttg ctggaacatg gcactgatcc aaatattcca    1140
gatgagtatg gaaataccac tctgcactac gctatctata tgaagataa attaatggcc    1200 aaagcactgc tcttatatgg tgctgatatc gaatcaaaaa acaagcatgg cctcacacca    1260
ctgttacttg gtgtacatga gcaaaaacag caagtcgtga aatttttaat caagaaaaaa    1320
gcgaatttaa atgcactgga tagatatgga aggactgctc tcatacttgc tgtatgttgt    1380
```

```
ggatcagcaa gtatagtcag ccttctactt gagcaaaata ttgatgtatc ttctcaagat   1440
ctatctggac agacggccag agagtatgct gtttctagtc atcatcatgt aatttgccag   1500
ttactttctg actacaaaga aaaacagatg ctaaaaatct cttctgaaaa cagcaatcca   1560
gaaaatgtct caagaaccag aaataaataa                                    1590
```

<210> SEQ ID NO 324
<211> LENGTH: 529
<212> TYPE: PRT
<213> ORGANISM: Homo sapiens

<400> SEQUENCE: 324

```
Met His His His His His Thr Ala Ala Ser Asp Asn Phe Gln Leu
                 5                  10                  15

Ser Gln Gly Gly Gln Gly Phe Ala Ile Pro Ile Gly Gln Ala Met Ala
                20                  25                  30

Ile Ala Gly Gln Ile Lys Leu Pro Thr Val His Ile Gly Pro Thr Ala
                35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
                100                 105                 110

Val Thr Trp Gln Thr Lys Ser Gly Gly Thr Arg Thr Gly Asn Val Thr
            115                 120                 125

Leu Ala Glu Gly Pro Pro Ala Glu Phe Pro Leu Val Pro Arg Gly Ser
130                 135                 140

Pro Met Val Val Glu Val Asp Ser Met Pro Ala Ala Ser Ser Val Lys
145                 150                 155                 160

Lys Pro Phe Gly Leu Arg Ser Lys Met Gly Lys Trp Cys Cys Arg Cys
                165                 170                 175

Phe Pro Cys Cys Arg Glu Ser Gly Lys Ser Asn Val Gly Thr Ser Gly
                180                 185                 190

Asp His Asp Asp Ser Ala Met Lys Thr Leu Arg Ser Lys Met Gly Lys
            195                 200                 205

Trp Cys Arg His Cys Phe Pro Cys Cys Arg Gly Ser Gly Lys Ser Asn
        210                 215                 220

Val Gly Ala Ser Gly Asp His Asp Asp Ser Ala Met Lys Thr Leu Arg
225                 230                 235                 240

Asn Lys Met Gly Lys Trp Cys Cys His Cys Phe Pro Cys Cys Arg Gly
                245                 250                 255

Ser Gly Lys Ser Lys Val Gly Ala Trp Gly Asp Tyr Asp Asp Ser Ala
                260                 265                 270

Phe Met Glu Pro Arg Tyr His Val Arg Gly Glu Asp Leu Asp Lys Leu
            275                 280                 285

His Arg Ala Ala Trp Trp Gly Lys Val Pro Arg Lys Asp Leu Ile Val
        290                 295                 300

Met Leu Arg Asp Thr Asp Val Asn Lys Lys Asp Lys Gln Lys Arg Thr
305                 310                 315                 320

Ala Leu His Leu Ala Ser Ala Asn Gly Asn Ser Glu Val Val Lys Leu
                325                 330                 335
```

-continued

```
Leu Leu Asp Arg Arg Cys Gln Leu Asn Val Leu Asp Asn Lys Lys Arg
            340                 345                 350

Thr Ala Leu Ile Lys Ala Val Gln Cys Gln Glu Asp Glu Cys Ala Leu
            355                 360                 365

Met Leu Leu Glu His Gly Thr Asp Pro Asn Ile Pro Asp Glu Tyr Gly
            370                 375                 380

Asn Thr Thr Leu His Tyr Ala Ile Tyr Asn Glu Asp Lys Leu Met Ala
385                 390                 395                 400

Lys Ala Leu Leu Leu Tyr Gly Ala Asp Ile Glu Ser Lys Asn Lys His
            405                 410                 415

Gly Leu Thr Pro Leu Leu Leu Gly Val His Glu Gln Lys Gln Gln Val
            420                 425                 430

Val Lys Phe Leu Ile Lys Lys Lys Ala Asn Leu Asn Ala Leu Asp Arg
            435                 440                 445

Tyr Gly Arg Thr Ala Leu Ile Leu Ala Val Cys Cys Gly Ser Ala Ser
            450                 455                 460

Ile Val Ser Leu Leu Leu Glu Gln Asn Ile Asp Val Ser Ser Gln Asp
465                 470                 475                 480

Leu Ser Gly Gln Thr Ala Arg Glu Tyr Ala Val Ser Ser His His His
            485                 490                 495

Val Ile Cys Gln Leu Leu Ser Asp Tyr Lys Glu Lys Gln Met Leu Lys
            500                 505                 510

Ile Ser Ser Glu Asn Ser Asn Pro Glu Asn Val Ser Arg Thr Arg Asn
            515                 520                 525

Lys
```

<210> SEQ ID NO 325
<211> LENGTH: 1155
<212> TYPE: DNA
<213> ORGANISM: Homo sapiens

<400> SEQUENCE: 325

```
atggtggctg aggtttgttc aatgcccact gcctctactg tgaagaagcc atttgatctc      60
aggagcaaga tgggcaagtg gtgccaccac cgcttcccct gctgcagggg gagcggcaag     120
agcaacatgg gcacttctgg agaccacgac gactcccttta tgaagatgct caggagcaag     180
atgggcaagt gttgccgcca ctgcttcccc tgctgcaggg ggagcggcac gagcaacgtg     240
ggcacttctg gagaccatga aaactccttt atgaagatgc tcaggagcaa gatgggcaag     300
tggtgctgtc actgcttccc ctgctgcagg gggagcggca agagcaacgt gggcgcttgg     360
ggagactacg accacagcgc cttcatggag ccgaggtacc acatccgtcg agaagatctg     420
gacaagctcc acagagctgc ctggtggggt aaagtcccca gaaggatct catcgtcatg     480
ctcaggggaca ctgacatgaa caagagggac aaggaaaaga ggactgctct acatttggcc     540
tctgccaatg gaaattcaga agtagtacaa ctcctgctgg acagacgatg tcaacttaat     600
gtccttgaca caaaaaaaag gacagctctg ataaaggcca taatgcca ggaagatgaa     660
tgtgtgttaa tgttgctgga acatggcgct gatcgaaata ttccagatga gtatggaaat     720
accgctctac actatgctat ctacaatgaa gataaattaa tggccaaagc actgcttcta     780
tatggtgctg atattgaatc aaaaaacaag gttggcctca caccacttt gcttggcgta     840
catgaacaaa aacagcaagt ggtgaaattt ttaatcaaga aaaagctaa tttaaatgta     900
cttgatagat atggaaggac tgccctcata cttgctgtat gttgtggatc agcaagtata     960
```

```
gtcaatcttc tacttgagca aaatgttgat gtatcttctc aagatctatc tggacagacg    1020
gccagagagt atgctgtttc tagtcatcat catgtaatt gtgaattact ttctgactat    1080
aaagaaaaac agatgctaaa aatctcttct gaaacagca atccagaaaa tgtctcaaga     1140
accagaaata aataa                                                    1155
```

<210> SEQ ID NO 326
<211> LENGTH: 384
<212> TYPE: PRT
<213> ORGANISM: Homo sapiens

<400> SEQUENCE: 326

```
Met Val Ala Glu Val Cys Ser Met Pro Thr Ala Ser Thr Val Lys Lys
                 5                  10                  15

Pro Phe Asp Leu Arg Ser Lys Met Gly Lys Trp Cys His Arg Phe
             20                  25                  30

Pro Cys Cys Arg Gly Ser Gly Lys Ser Asn Met Gly Thr Ser Gly Asp
         35                  40                  45

His Asp Asp Ser Phe Met Lys Met Leu Arg Ser Lys Met Gly Lys Cys
     50                  55                  60

Cys Arg His Cys Phe Pro Cys Cys Arg Gly Ser Gly Thr Ser Asn Val
 65                  70                  75                  80

Gly Thr Ser Gly Asp His Glu Asn Ser Phe Met Lys Met Leu Arg Ser
                 85                  90                  95

Lys Met Gly Lys Trp Cys Cys His Cys Phe Pro Cys Cys Arg Gly Ser
            100                 105                 110

Gly Lys Ser Asn Val Gly Ala Trp Gly Asp Tyr Asp His Ser Ala Phe
        115                 120                 125

Met Glu Pro Arg Tyr His Ile Arg Arg Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Met Asn Lys Arg Asp Lys Glu Lys Arg Thr Ala
                165                 170                 175

Leu His Leu Ala Ser Ala Asn Gly Asn Ser Glu Val Val Gln Leu Leu
            180                 185                 190

Leu Asp Arg Arg Cys Gln Leu Asn Val Leu Asp Asn Lys Lys Arg Thr
        195                 200                 205

Ala Leu Ile Lys Ala Ile Gln Cys Gln Glu Asp Glu Cys Val Leu Met
    210                 215                 220

Leu Leu Glu His Gly Ala Asp Arg Asn Ile Pro Asp Glu Tyr Gly Asn
225                 230                 235                 240

Thr Ala Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys Val Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Val Leu Asp Arg Tyr
    290                 295                 300

Gly Arg Thr Ala Leu Ile Leu Ala Val Cys Cys Gly Ser Ala Ser Ile
305                 310                 315                 320

Val Asn Leu Leu Leu Glu Gln Asn Val Asp Val Ser Ser Gln Asp Leu
                325                 330                 335
```

```
Ser Gly Gln Thr Ala Arg Glu Tyr Ala Val Ser Ser His His His Val
            340                 345                 350

Ile Cys Glu Leu Leu Ser Asp Tyr Lys Glu Lys Gln Met Leu Lys Ile
            355                 360                 365

Ser Ser Glu Asn Ser Asn Pro Glu Asn Val Ser Arg Thr Arg Asn Lys
            370                 375                 380

<210> SEQ ID NO 327
<211> LENGTH: 634
<212> TYPE: DNA
<213> ORGANISM: Homo sapiens

<400> SEQUENCE: 327
gactgctcta catctggcct ctgccaatgg aaattcagaa gtagtaaaac tcctgctgga      60
cagacgatgt caacttaata tccttgacaa caaaaagagg acagctctga caaaggccgt     120
acaatgccag gaagatgaat gtgcgttaat gttgctggaa catggcactg atccgaatat     180
tccagatgag tatggaaata ccgctctaca ctatgctatc tacaatgaag ataaattaat     240
ggccaaagca ctgctcttat acggtgctga tatcgaatca aaaaacaagc atggcctcac     300
accactgtta cttggtgtac atgagcaaaa acagcaagtg gtgaaatttt taatcaagaa     360
aaaagcaaat ttaaatgcac tggatagata tggaagaact gctctcatac ttgctgtatg     420
ttgtggatcg gcaagtatag tcagccttct acttgagcaa acattgatg tatcttctca      480 agatctatct ggacagacgg ccagagagta tgctgtttct agtcgtcata atgtaatttg     540
ccagttactt tctgactaca agaaaaaaca gatactaaaa gtctcttctg aaaacagcaa     600
tccaggaaat gtctcaagaa ccagaaataa ataa                                 634

<210> SEQ ID NO 328
<211> LENGTH: 1155
<212> TYPE: DNA
<213> ORGANISM: Homo sapiens

<400> SEQUENCE: 328
atggtggttg aggttgattc catgccggct gcctcttctg tgaagaagcc atttggtctc      60
aggagcaaga tgggcaagtg gtgctgccgt tgcttcccct gctgcaggga gagcggcaag     120
agcaacgtgg gcacttctgg agaccacgac gactctgcta tgaagacact caggagcaag     180
atgggcaagt ggtgccgcca ctgcttcccc tgctgcaggg ggagtggcaa gagcaacgtg     240
ggcgcttctg gagaccacga cgactctgct atgaagacac tcaggaacaa gatgggcaag     300
tggtgctgcc actgcttccc ctgctgcagg ggagcagca agagcaaggt gggcgcttgg      360
ggagactacg atgacagtgc cttcatggag cccaggtacc acgtccgtgg agaagatctg     420
gacaagctcc acagagctgc ctggtggggt aaagtcccca gaaggatct catcgtcatg      480 ctcagggaca ctgacgtgaa caagcaggac aagcaaaaga ggactgctct acatctggcc     540
tctgccaatg gaaattcaga agtagtaaaa ctcctgctgg acagacgatg tcaacttaat     600
gtccttgaca caaaaagag acagctctg ataaaggccg tacaatgcca ggaagatgaa       660
tgtgcgttaa tgttgctgga acatggcact gatccaaata ttccagatga gtatggaaat     720
accactctgc actacgctat ctataatgaa gataaattaa tggccaaagc actgctctta     780
tatggtgctg atatcgaatc aaaaaacaag catggcctca caccactgtt acttggtgta     840
catgagcaaa acagcaagt cgtgaaattt ttaattaaga aaaaagcgaa tttaaatgca      900
ctggatagat atggaaggac tgctctcata cttgctgtat gttgtggatc agcaagtata     960
```

-continued

| | |
|---|---|
| gtcagccttc tacttgagca aaatattgat gtatcttctc aagatctatc tggacagacg | 1020 |
| gccagagagt atgctgtttc tagtcatcat catgtaattt gccagttact ttctgactac | 1080 |
| aaagaaaaac agatgctaaa aatctcttct gaaaacagca atccagaaaa tgtctcaaga | 1140 |
| accagaaata aataa | 1155 |

<210> SEQ ID NO 329
<211> LENGTH: 1155
<212> TYPE: DNA
<213> ORGANISM: Homo sapiens

<400> SEQUENCE: 329

| | |
|---|---|
| atggtggctg aggtttgttc aatgcccgct gcctctgctg tgaagaagcc atttgatctc | 60 |
| aggagcaaga tgggcaagtg gtgccaccac cgcttcccct gctgcagggg gagcggcaag | 120 |
| agcaacatgg gcacttctgg agaccacgac gactcccttta tgaagacgct caggagcaag | 180 |
| atgggcaagt gttgccacca ctgcttcccc tgctgcaggg ggagcggcac gagcaatgtg | 240 |
| ggcacttctg gagaccatga caactccttt atgaagacac tcaggagcaa gatgggcaag | 300 |
| tggtgctgtc actgcttccc ctgctgcagg ggagcggca agagcaacgt gggcacttgg | 360 |
| ggagactacg acgacagcgc cttcatggag ccgaggtacc acgtccgtcg agaagatctg | 420 |
| gacaagctcc acagagctgc ctggtggggt aaagtcccca aaaggatct catcgtcatg | 480 |
| ctcagggaca ctgacatgaa caagagggac aagcaaaaga ggactgctct acatttggcc | 540 |
| tctgccaatg gaaattcaga agtagtacaa ctcctgctgg acagacgatg tcaacttaac | 600 |
| gtccttgaca caaaaaaag acagctctg ataaaggccg tacaatgcca ggaagatgaa | 660 |
| tgtgtgttaa tgttgctgga acatggcgct gatggaaata ttcaagatga gtatggaaat | 720 |
| accgctctac actatgctat ctacaatgaa gataaattaa tggccaaagc actgctctta | 780 |
| tatggtgcta atattgaatc aaaaaacaag tgtggcctca caccactttt gcttggcgta | 840 |
| catgaacaaa acagcaagt ggtgaaattt ttaatcaaga aaaagctaa tttaaatgca | 900 |
| cttgatagat atgaagaac tgccctcata cttgctgtat gttgtggatc agcaagtata | 960 |
| gtcaatcttc tacttgagca aaatgttgat gtatcttctc aagatctatc tggacagacg | 1020 |
| gccagagagt atgctgtttc tagtcatcat catgtaattt gtgaattact ttctgactat | 1080 |
| aaagaaaaac agatgctaaa aatctcttct gaaaacagca atccagaaaa tgtctcaaga | 1140 |
| accagaaata aataa | 1155 |

<210> SEQ ID NO 330
<211> LENGTH: 1155
<212> TYPE: DNA
<213> ORGANISM: Homo sapiens

<400> SEQUENCE: 330

| | |
|---|---|
| atggtggctg aggtttgttc aatgcccact gcctctactg tgaagaagcc atttgatctc | 60 |
| aggagcaaga tgggcaagtg gtgccaccac cgcttcccct gctgcagggg gagcggcaag | 120 |
| agcaacatgg gcacttctgg agaccacgac gactcccttta tgaagatgct caggagcaag | 180 |
| atgggcaagt gttgccgcca ctgcttcccc tgctgcaggg ggagcggcac gagcaacgtg | 240 |
| ggcacttctg gagaccatga aaactccttt atgaagatgc tcaggagcaa gatgggcaag | 300 |
| tggtgctgtc actgcttccc ctgctgcagg ggagcggca agagcaacgt gggcgcttgg | 360 |
| ggagactacg accacagcgc cttcatggag ccgaggtacc acatccgtcg agaagatctg | 420 |

```
gacaagctcc acagagctgc ctggtggggt aaagtcccca gaaaggatct catcgtcatg    480
ctcagggaca ctgacatgaa caagagggac aaggaaaaga ggactgctct acatttggcc    540
tctgccaatg gaaattcaga agtagtacaa ctcctgctgg acagacgatg tcaacttaat    600
gtccttgaca acaaaaaaag gacagctctg ataaaggcca tacaatgcca ggaagatgaa    660
tgtgtgttaa tgttgctgga acatggcgct gatcgaaata ttccagatga gtatggaaat    720
accgctctac actatgctat ctacaatgaa gataaattaa tggccaaagc actgctctta    780
tatggtgctg atattgaatc aaaaaacaag tgtggcctca caccactttt gcttggcgta    840
catgaacaaa aacagcaagt ggtgaaattt ttaatcaaga aaaaagctaa tttaaatgta    900
cttgatagat atggaagaac tgccctcata cttgctgtat gttgtggatc agcaagtata    960
gtcaatcttc tacttgagca aaatgttgat gtatcttctc aagatctatc tggacagacg    1020
gccagagagt atgctgtttc tagtcatcat catgtaattt gtgaattact ttctgactat    1080
aaagaaaaac agatgctaaa aatctcttct gaaaacagca atccagaaaa tgtctcaaga    1140
accagaaata aataa                                                    1155
```

<210> SEQ ID NO 331
<211> LENGTH: 210
<212> TYPE: PRT
<213> ORGANISM: Homo sapiens

<400> SEQUENCE: 331

```
Thr Ala Leu His Leu Ala Ser Ala Asn Gly Asn Ser Glu Val Val Lys
              5                  10                  15

Leu Leu Leu Asp Arg Arg Cys Gln Leu Asn Ile Leu Asp Asn Lys Lys
         20                  25                  30

Arg Thr Ala Leu Thr Lys Ala Val Gln Cys Gln Glu Asp Glu Cys Ala
     35                  40                  45

Leu Met Leu Leu Glu His Gly Thr Asp Pro Asn Ile Pro Asp Glu Tyr
 50                  55                  60

Gly Asn Thr Ala Leu His Tyr Ala Ile Tyr Asn Glu Asp Lys Leu Met
 65                  70                  75                  80

Ala Lys Ala Leu Leu Leu Tyr Gly Ala Asp Ile Glu Ser Lys Asn Lys
                 85                  90                  95

His Gly Leu Thr Pro Leu Leu Leu Gly Val His Glu Gln Lys Gln Gln
            100                 105                 110

Val Val Lys Phe Leu Ile Lys Lys Ala Asn Leu Asn Ala Leu Asp
        115                 120                 125

Arg Tyr Gly Arg Thr Ala Leu Ile Leu Ala Val Cys Cys Gly Ser Ala
    130                 135                 140

Ser Ile Val Ser Leu Leu Leu Glu Gln Asn Ile Asp Val Ser Ser Gln
145                 150                 155                 160

Asp Leu Ser Gly Gln Thr Ala Arg Glu Tyr Ala Val Ser Ser Arg His
                165                 170                 175

Asn Val Ile Cys Gln Leu Leu Ser Asp Tyr Lys Glu Lys Gln Ile Leu
            180                 185                 190

Lys Val Ser Ser Glu Asn Ser Asn Pro Gly Asn Val Ser Arg Thr Arg
        195                 200                 205

Asn Lys
    210
```

<210> SEQ ID NO 332
<211> LENGTH: 384

<212> TYPE: PRT
<213> ORGANISM: Homo sapiens

<400> SEQUENCE: 332

Met Val Ala Glu Val Cys Ser Met Pro Thr Ala Ser Thr Val Lys Lys
        1               5                  10                  15

Pro Phe Asp Leu Arg Ser Lys Met Gly Lys Trp Cys His His Arg Phe
                20                  25                  30

Pro Cys Cys Arg Gly Ser Gly Lys Ser Asn Met Gly Thr Ser Gly Asp
            35                  40                  45

His Asp Asp Ser Phe Met Lys Met Leu Arg Ser Lys Met Gly Lys Cys
    50                  55                  60

Cys Arg His Cys Phe Pro Cys Cys Arg Gly Ser Gly Thr Ser Asn Val
65                  70                  75                  80

Gly Thr Ser Gly Asp His Glu Asn Ser Phe Met Lys Met Leu Arg Ser
                85                  90                  95

Lys Met Gly Lys Trp Cys Cys His Cys Phe Pro Cys Cys Arg Gly Ser
            100                 105                 110

Gly Lys Ser Asn Val Gly Ala Trp Gly Asp Tyr Asp His Ser Ala Phe
        115                 120                 125

Met Glu Pro Arg Tyr His Ile Arg Arg Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Met Asn Lys Arg Asp Lys Glu Lys Arg Thr Ala
                165                 170                 175

Leu His Leu Ala Ser Ala Asn Gly Asn Ser Glu Val Val Gln Leu Leu
            180                 185                 190

Leu Asp Arg Arg Cys Gln Leu Asn Val Leu Asp Asn Lys Lys Arg Thr
        195                 200                 205

Ala Leu Ile Lys Ala Ile Gln Cys Gln Glu Asp Glu Cys Val Leu Met
    210                 215                 220

Leu Leu Glu His Gly Ala Asp Arg Asn Ile Pro Asp Glu Tyr Gly Asn
225                 230                 235                 240

Thr Ala Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys Cys Gly
            260                 265                 270

Leu Thr Pro Leu Leu Gly Val His Glu Gln Lys Gln Gln Val Val
        275                 280                 285

Lys Phe Leu Ile Lys Lys Ala Asn Leu Asn Val Leu Asp Arg Tyr
    290                 295                 300

Gly Arg Thr Ala Leu Ile Leu Ala Val Cys Cys Gly Ser Ala Ser Ile
305                 310                 315                 320

Val Asn Leu Leu Leu Glu Gln Asn Val Asp Val Ser Ser Gln Asp Leu
                325                 330                 335

Ser Gly Gln Thr Ala Arg Glu Tyr Ala Val Ser Ser His His His Val
            340                 345                 350

Ile Cys Glu Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380

<210> SEQ ID NO 333

```
<211> LENGTH: 384
<212> TYPE: PRT
<213> ORGANISM: Homo sapiens

<400> SEQUENCE: 333

Met Val Ala Glu Val Cys Ser Met Pro Ala Ser Ala Val Lys Lys
                  5                  10                  15

Pro Phe Asp Leu Arg Ser Lys Met Gly Lys Trp Cys His His Arg Phe
                 20                  25                  30

Pro Cys Cys Arg Gly Ser Gly Lys Ser Asn Met Gly Thr Ser Gly Asp
             35                  40                  45

His Asp Asp Ser Phe Met Lys Thr Leu Arg Ser Lys Met Gly Lys Cys
 50                  55                  60

Cys His His Cys Phe Pro Cys Cys Arg Gly Ser Gly Thr Ser Asn Val
 65                  70                  75                  80

Gly Thr Ser Gly Asp His Asp Asn Ser Phe Met Lys Thr Leu Arg Ser
                 85                  90                  95

Lys Met Gly Lys Trp Cys Cys His Cys Phe Pro Cys Cys Arg Gly Ser
            100                 105                 110

Gly Lys Ser Asn Val Gly Thr Trp Gly Asp Tyr Asp Asp Ser Ala Phe
        115                 120                 125

Met Glu Pro Arg Tyr His Val Arg Arg Glu Asp Leu Asp Lys Leu His
130                 135                 140

Arg Ala Ala Trp Trp Gly Lys Val Pro Arg Lys Asp Leu Ile Val Met
145                 150                 155                 160

Leu Arg Asp Thr Asp Met Asn Lys Arg Asp Lys Gln Lys Arg Thr Ala
                165                 170                 175

Leu His Leu Ala Ser Ala Asn Gly Asn Ser Glu Val Val Gln Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Val Leu Met
    210                 215                 220

Leu Leu Glu His Gly Ala Asp Gly Asn Ile Gln Asp Glu Tyr Gly Asn
225                 230                 235                 240

Thr Ala Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys Cys Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Asn Leu Leu Leu Glu Gln Asn Val Asp Val Ser Ser Gln Asp Leu
                325                 330                 335

Ser Gly Gln Thr Ala Arg Glu Tyr Ala Val Ser Ser His His His Val
            340                 345                 350

Ile Cys Glu Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380
```

<210> SEQ ID NO 334
<211> LENGTH: 384
<212> TYPE: PRT
<213> ORGANISM: Homo sapiens

<400> SEQUENCE: 334

Met Val Val Glu Val Asp Ser Met Pro Ala Ala Ser Val Lys Lys
                 5                  10                  15

Pro Phe Gly Leu Arg Ser Lys Met Gly Lys Trp Cys Cys Arg Cys Phe
                 20                  25                  30

Pro Cys Cys Arg Glu Ser Gly Lys Ser Asn Val Gly Thr Ser Gly Asp
                 35                  40                  45

His Asp Asp Ser Ala Met Lys Thr Leu Arg Ser Lys Met Gly Lys Trp
 50                  55                  60

Cys Arg His Cys Phe Pro Cys Cys Arg Gly Ser Gly Lys Ser Asn Val
 65                  70                  75                  80

Gly Ala Ser Gly Asp His Asp Ser Ala Met Lys Thr Leu Arg Asn
                 85                  90                  95

Lys Met Gly Lys Trp Cys Cys His Cys Phe Pro Cys Cys Arg Gly Ser
                 100                 105                 110

Ser Lys Ser Lys Val Gly Ala Trp Gly Asp Tyr Asp Ser Ala Phe
                 115                 120                 125

Met Glu Pro Arg Tyr His Val Arg Gly Glu Asp Leu Asp Lys Leu His
             130                 135                 140

Arg Ala Ala Trp Trp Gly Lys Val Pro Arg Lys Asp Leu Ile Val Met
145                 150                 155                 160

Leu Arg Asp Thr Asp Val Asn Lys Gln Asp Lys Gln Lys Arg Thr Ala
                 165                 170                 175

Leu His Leu Ala Ser Ala Asn Gly Asn Ser Glu Val Val Lys Leu Leu
                 180                 185                 190

Leu Asp Arg Arg Cys Gln Leu Asn Val Leu Asp Asn Lys Lys Arg Thr
                 195                 200                 205

Ala Leu Ile Lys Ala Val Gln Cys Gln Glu Asp Glu Cys Ala Leu Met
             210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                 245                 250                 255

Ala Leu Leu Leu Tyr Gly Ala Asp Ile Glu Ser Lys Asn Lys His Gly
                 260                 265                 270

Leu Thr Pro Leu Leu Leu Gly Val His Glu Gln Lys Gln Gln Val Val
             275                 280                 285

Lys Phe Leu Ile Lys Lys Lys Ala Asn Leu Asn Ala Leu Asp Arg Tyr
             290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                 325                 330                 335

Ser Gly Gln Thr Ala Arg Glu Tyr Ala Val Ser Ser His His His Val
             340                 345                 350

Ile Cys Gln Leu Leu Ser Asp Tyr Lys Glu Lys Gln Met Leu Lys Ile
             355                 360                 365

Ser Ser Glu Asn Ser Asn Pro Glu Asn Val Ser Arg Thr Arg Asn Lys
370                 375                 380

-continued

<210> SEQ ID NO 335
<211> LENGTH: 1185
<212> TYPE: DNA
<213> ORGANISM: Homo sapiens

<400> SEQUENCE: 335

| | | | | | |
|---|---|---|---|---|---|
| atggtggttg | aggttgattc | catgccggct | gcctcttctg | tgaagaagcc | atttggtctc | 60 |
| aggagcaaga | tgggcaagtg | gtgctgccgt | tgcttcccct | gctgcaggga | gagcggcaag | 120 |
| agcaacgtgg | gcacttctgg | agaccacgac | gactctgcta | tgaagacact | caggagcaag | 180 |
| atgggcaagt | ggtgccgcca | ctgcttcccc | tgctgcaggg | ggagtggcaa | gagcaacgtg | 240 |
| ggcgcttctg | gagaccacga | cgactctgct | atgaagacac | tcaggaacaa | gatgggcaag | 300 |
| tggtgctgcc | actgcttccc | ctgctgcagg | gggagcggca | gagcaaggt | gggcgcttgg | 360 |
| ggagactacg | atgacagtgc | cttcatggag | cccaggtacc | acgtccgtgg | agaagatctg | 420 |
| gacaagctcc | acagagctgc | ctggtggggt | aaagtcccca | gaaaggatct | catcgtcatg | 480 |
| ctcagggaca | ctgacgtgaa | caagaaggac | aagcaaaaga | ggactgctct | acatctggcc | 540 |
| tctgccaatg | ggaattcaga | agtagtaaaa | ctcctgctgg | acagacgatg | tcaacttaat | 600 |
| gtccttgaca | caaaaagag | gacagctctg | ataaaggccg | tacaatgcca | ggaagatgaa | 660 |
| tgtgcgttaa | tgttgctgga | acatggcact | gatccaaata | ttccagatga | gtatggaaat | 720 |
| accactctgc | actacgctat | ctataatgaa | gataaattaa | tggccaaagc | actgctctta | 780 |
| tatggtgctg | atatcgaatc | aaaaaacaag | catggcctca | caccactgtt | acttggtgta | 840 |
| catgagcaaa | acagcaagt | cgtgaaattt | ttaatcaaga | aaaagcgaa | tttaaatgca | 900 |
| ctggatagat | atggaaggac | tgctctcata | cttgctgtat | gttgtggatc | agcaagtata | 960 |
| gtcagccttc | tacttgagca | aaatattgat | gtatcttctc | aagatctatc | tggacagacg | 1020 |
| gccagagagt | atgctgtttc | tagtcatcat | catgtaattt | gccagttact | ttctgactac | 1080 |
| aaagaaaaac | agatgctaaa | aatctcttct | gaaaacagca | atccagaaaa | tgtctcaaga | 1140 |
| accagaaata | acatcatca | ccatcatcat | caccatcacc | attaa | | 1185 |

<210> SEQ ID NO 336
<211> LENGTH: 394
<212> TYPE: PRT
<213> ORGANISM: Homo sapiens

<400> SEQUENCE: 336

Met Val Val Glu Val Asp Ser Met Pro Ala Ala Ser Ser Val Lys Lys
              5                  10                  15

Pro Phe Gly Leu Arg Ser Lys Met Gly Lys Trp Cys Cys Arg Cys Phe
         20                  25                  30

Pro Cys Cys Arg Glu Ser Gly Lys Ser Asn Val Gly Thr Ser Gly Asp
     35                  40                  45

His Asp Asp Ser Ala Met Lys Thr Leu Arg Ser Lys Met Gly Lys Trp
 50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
                 85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
        115                 120                 125

-continued

```
Met Glu Pro Arg Tyr His Val Arg Gly Glu Asp Leu Asp Lys Leu His
130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380

His His His His His His His His
385                 390
```

<210> SEQ ID NO 337
<211> LENGTH: 34
<212> TYPE: DNA
<213> ORGANISM: Artificial Sequence
<220> FEATURE:
<223> OTHER INFORMATION: PCR primer

<400> SEQUENCE: 337
cggcggatcc accatggtgg ttgaggttga ttcc       34

<210> SEQ ID NO 338
<211> LENGTH: 74
<212> TYPE: DNA
<213> ORGANISM: Artificial Sequence
<220> FEATURE:
<223> OTHER INFORMATION: PCR primer

<400> SEQUENCE: 338
cggctctaga ttaatggtga tggtgatgat gatggtgatg atgtttattt ctggttcttg       60
agacattttc tgga       74

-continued

```
<210> SEQ ID NO 339
<211> LENGTH: 1166
<212> TYPE: DNA
<213> ORGANISM: Homo sapiens

<400> SEQUENCE: 339
atggtggctg aggctggttc aatgccggct gcctcctctg tgaagaagcc atttggtctc      60
agaagcaaga tgggcaagtg gtgccgccac tgcttcccct ggtgcagggg gagcggcaag     120
agcaacgtgg gcacttctgg agaccacgac gattctgcta tgaagacact caggagcaag     180
atgggcaagt ggtgccgcca ctgcttcccc tggtgcaggg ggagcagcaa gagcaacgtg     240
ggcacttctg gagaccacga cgactctgct atgaagacac tcaggagcaa gatgggcaag     300
tggtgctgcc actgcttccc ctgctgcagg gggagcggca gagcaaagt gggcccttgg      360 ggagactacg acgacagcgc tttcatggag ccgaggtacc acgtccgtcg agaagatctg     420
gacaagctcc acagagctgc ctggtggggt aaagtcccca gaaaggatct catcgtcatg     480
ctcaaggaca ctgacatgaa caagaaggac aagcaaaaga ggactgctct acatctggcc     540
tctgccaatg gaaattcaga agtagtaaaa ctcctgctgg acagacgatg tcaacttaat     600
atccttgaca caaaaagag gacagctctg acaaaggccg tacaatgccg ggaagatgaa      660
tgtgcgttaa tgttgctgga acatggcact gatccgaata ttccagatga gtatggaaat     720
accgctctac actatgctat ctacaatgaa gataaattaa tggccaaagc actgctctta     780
tacggtgctg atatcgaatc aaaaaacaag catggcctca caccactgtt acttggtgta     840
catgagcaaa acagcaagt ggtgaaattc ttaatcaaga aaaagcaaa tttaaatgca      900 ctggatagat atggaagaac tgctctcata cttgctgtat gttgtggatc ggcaagtata     960
gtcagccttc tacttgagca aaacattgat gtatcttctc aagatctatc tggacagacg    1020
gccagagagt atgctgtttc tagtcatcat aatgtaattt gccagttact ttctgactac    1080
aaagaaaaac agatgctaaa agtctcttct gaaaacagca atccaggaaa tgtctcaaga    1140
accagaaata ataagggtg gtgata                                           1166

<210> SEQ ID NO 340
<211> LENGTH: 384
<212> TYPE: PRT
<213> ORGANISM: Homo sapiens

<400> SEQUENCE: 340

Met Val Ala Glu Ala Gly Ser Met Pro Ala Ala Ser Ser Val Lys Lys
                 5                  10                  15

Pro Phe Gly Leu Arg Ser Lys Met Gly Lys Trp Cys Arg His Cys Phe
             20                  25                  30

Pro Trp Cys Arg Gly Ser Gly Lys Ser Asn Val Gly Thr Ser Gly Asp
         35                  40                  45

His Asp Asp Ser Ala Met Lys Thr Leu Arg Ser Lys Met Gly Lys Trp
     50                  55                  60

Cys Arg His Cys Phe Pro Trp Cys Arg Gly Ser Ser Lys Ser Asn Val
 65                  70                  75                  80

Gly Thr Ser Gly Asp His Asp Ser Ala Met Lys Thr Leu Arg Ser
                 85                  90                  95

Lys Met Gly Lys Trp Cys Cys His Cys Phe Pro Cys Cys Arg Gly Ser
            100                 105                 110

Gly Lys Ser Lys Val Gly Pro Trp Gly Asp Tyr Asp Asp Ser Ala Phe
        115                 120                 125
```

```
                                      -continued
Met Glu Pro Arg Tyr His Val Arg Arg Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Lys Asp Thr Asp Met Asn Lys Lys Asp Lys Gln Lys Arg Thr Ala
                165                 170                 175

Leu His Leu Ala Ser Ala Asn Gly Asn Ser Glu Val Val Lys Leu Leu
                180                 185                 190

Leu Asp Arg Arg Cys Gln Leu Asn Ile Leu Asp Asn Lys Lys Arg Thr
            195                 200                 205

Ala Leu Thr Lys Ala Val Gln Cys Arg Glu Asp Glu Cys Ala Leu Met
        210                 215                 220

Leu Leu Glu His Gly Thr Asp Pro Asn Ile Pro Asp Glu Tyr Gly Asn
225                 230                 235                 240

Thr Ala Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
                260                 265                 270

Leu Thr Pro Leu Leu Leu Gly Val His Glu Gln Lys Gln Gln Val Val
            275                 280                 285

Lys Phe Leu Ile Lys Lys Lys Ala Asn Leu Asn Ala Leu Asp Arg Tyr
        290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His Asn Val
                340                 345                 350

Ile Cys Gln Leu Leu Ser Asp Tyr Lys Glu Lys Gln Met Leu Lys Val
            355                 360                 365

Ser Ser Glu Asn Ser Asn Pro Gly Asn Val Ser Arg Thr Arg Asn Lys
        370                 375                 380
```

COMPOSITIONS AND METHODS FOR THE THERAPY AND DIAGNOSIS OF BREAST CANCER

CROSS REFERENCE TO RELATED APPLICATIONS

This application is a continuation-in-part of U.S. patent application Ser. No. 09/810,936, filed Mar. 16, 2001, now abandoned, which is a continuation-in-part of U.S. patent application Ser. No. 09/699,295, filed Oct. 26, 2000, now U.S. Pat. No. 6,828,431, which is a continuation-in-part of U.S. patent application Ser. No. 09/590,583, filed Jun. 8, 2000, now abandoned, which is a continuation-in-part of U.S. patent application Ser. No. 09/577,505, filed May 24, 2000, now abandoned, which is a continuation-in-part of U.S. patent application Ser. No. 09/534,825, filed Mar. 23, 2000, which is a continuation-in-part of U.S. patent application Ser. No. 09/429,755, filed Oct. 28, 1999, now U.S. Pat. No. 6,656,480, which is a continuation-in-part of U.S. patent application Ser. No. 09/289,198, filed Apr. 9, 1999, now U.S. Pat. No. 6,586,570.

BACKGROUND OF THE INVENTION

1. Field of the Invention

The present invention relates generally to therapy and diagnosis of cancer, such as breast cancer. The invention is more specifically related to polypeptides, comprising at least a portion of a breast tumor protein, and to polynucleotides encoding such polypeptides. Such polypeptides and polynucleotides are useful in pharmaceutical compositions, e.g., vaccines, and other compositions for the diagnosis and treatment of breast cancer.

2. Description of the Related Art

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

BRIEF SUMMARY OF THE INVENTION

In one aspect, the present invention provides polynucleotide compositions comprising a sequence selected from the group consisting of:

(a) sequences provided in SEQ ID NOs:1, 3–86, 142–298, 301–303, 307, 313, 314, 316, 317, 323, 325, 327–330, 335, and 339;

(b) complements of the sequences provided in SEQ ID NOs:1, 3–86, 142–298, 301–303, 307, 313, 314, 316, 317, 323, 325, 327–330, 335, and 339;

(c) sequences consisting of at least 20 contiguous residues of a sequence provided in SEQ ID NOs:1, 3–86, 142–298, 301–303, 307, 313, 314, 316, 317, 323, 325, 327–330, 335, and 339;

(d) sequences that hybridize to a sequence provided in SEQ ID NOs:1, 3–86, 142–298, 301–303, 307, 313, 314, 316, 317, 323, 325, 327–330, 335, and 339, under moderately stringent conditions;

(e) sequences having at least 75% identity to a sequence of SEQ ID NOs:1, 3–86, 142–298, 301–303, 307, 313, 314, 316, 317, 323, 325, 327–330, 335, and 339;

(f) sequences having at least 90% identity to a sequence of SEQ ID NOs:1, 3–86, 142–298, 301–303, 307, 313, 314, 316, 317, 323, 325, 327–330, 335, and 339; and (g) degenerate variants of a sequence provided in SEQ ID NOs:1, 3–86, 142–298, 301–303, 307, 313, 314, 316, 317, 323, 325, 327–330, 335, and 339.

In one preferred embodiment, the polynucleotide compositions of the invention are expressed in at least about 20%, more preferably in at least about 30%, and most preferably in at least about 50% of breast tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NOs: 131–140, 299, 300, 304–306, 308–312, 315, 318, 324, 326, 331–334, 336, and 340.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NOs:131–140, 299, 300, 304–306, 308–312, 315, 318, 324, 326, 331–334, 336, and 340 or a polypeptide sequence encoded by a polynucleotide sequence set forth in SEQ ID NOs:1, 3–86, 142–298, 301–303, 307, 313, 314, 316, 317, 323, 325, 327–330, 335, and 339.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with breast cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably a breast cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6 shows the nucleotide sequence of the representative breast tumor-specific cDNA B18Ag1.

FIG. 7 shows the nucleotide sequence of the representative breast tumor-specific cDNA B17Ag1.

FIG. 8 shows the nucleotide sequence of the representative breast tumor-specific cDNA B17Ag2.

FIG. 9 shows the nucleotide sequence of the representative breast tumor-specific cDNA B13Ag2a.

FIG. 10 shows the nucleotide sequence of the representative breast tumor-specific cDNA B13Ag1b.

FIG. 11 shows the nucleotide sequence of the representative breast tumor-specific cDNA B13Ag1a.

FIG. 12 shows the nucleotide sequence of the representative breast tumor-specific cDNA B11Ag1.

FIG. 13 shows the nucleotide sequence of the representative breast tumor-specific cDNA B3CA3c.

FIG. 14 shows the nucleotide sequence of the representative breast tumor-specific cDNA B9CG1.

FIG. 15 shows the nucleotide sequence of the representative breast tumor-specific cDNA B9CG3.

FIG. 16 shows the nucleotide sequence of the representative breast tumor-specific cDNA B2CA2.

FIG. 17 shows the nucleotide sequence of the representative breast tumor-specific cDNA B3CA1.

FIG. 18 shows the nucleotide sequence of the representative breast tumor-specific cDNA B3CA2.

FIG. 19 shows the nucleotide sequence of the representative breast tumor-specific cDNA B3CA3.

FIG. 20 shows the nucleotide sequence of the representative breast tumor-specific cDNA B4CA1.

DETAILED DESCRIPTION OF THE INVENTION

Figure 1:
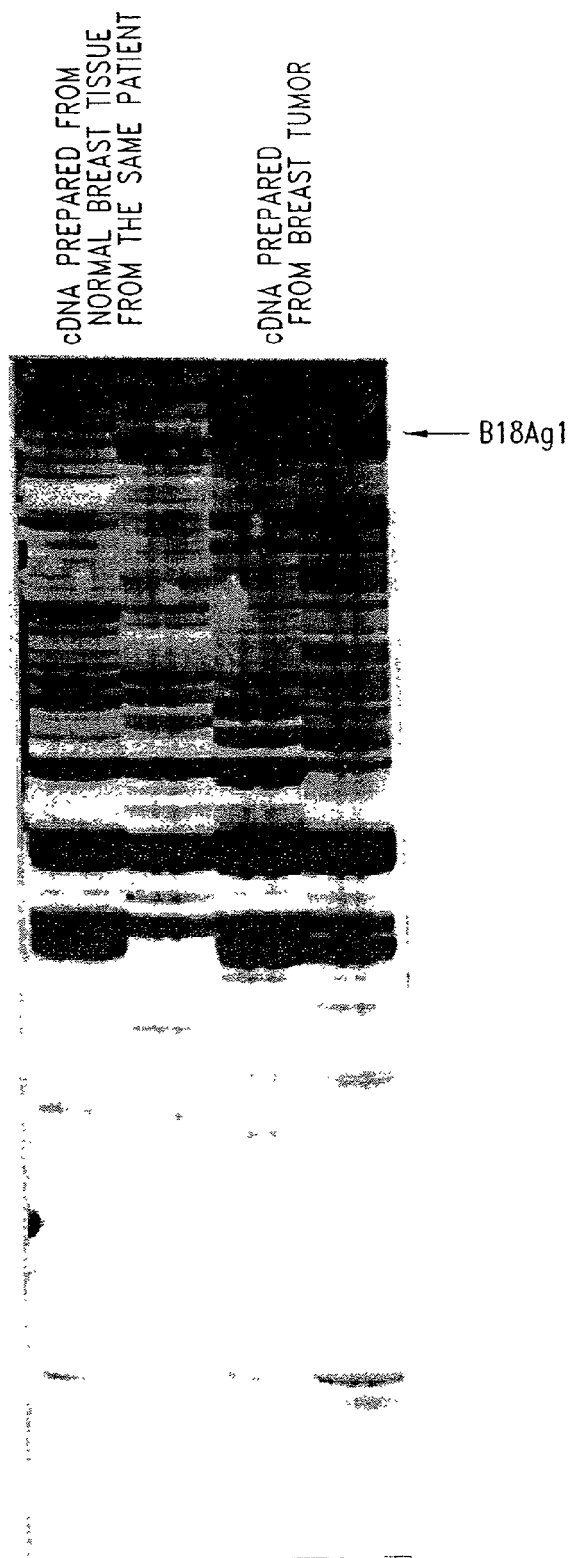
FIG. 1 shows the differential display PCR products, separated by gel electrophoresis, obtained from cDNA prepared from normal breast tissue (lanes 1 and 2) and from cDNA prepared from breast tumor tissue from the same patient (lanes 3 and 4). The arrow indicates the band corresponding to B18Ag1.

The present invention is directed generally to compositions and their use in the therapy and diagnosis of cancer, particularly breast cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs:1, 3–86, 142–298, 301–303, 307, 313, 314, 316, 317, 323, 325, 327–330, 335, and 339, or a sequence that hybridizes under moderately stringent conditions, or, alternatively, under highly stringent conditions, to a polynucleotide sequence set forth in any one of SEQ ID NOs:1, 3–86, 142–298, 301–303, 307, 313, 314, 316, 317, 323, 325, 327–330, 335, and 339. Certain other illustrative polypeptides of the invention comprise amino acid sequences as set forth in any one of SEQ ID NOs: 131–140, 299, 300, 304–306, 308–312, 315, 318, 324, 326, 331–334, 336, and 340.

The polypeptides of the present invention are sometimes herein referred to as breast tumor proteins or breast tumor polypeptides, as an indication that their identification has been based at least in part upon their increased levels of expression in breast tumor samples. Thus, a "breast tumor polypeptide" or "breast tumor protein," refers generally to a polypeptide sequence of the present invention, or a polynucleotide sequence encoding such a polypeptide, that is expressed in a substantial proportion of breast tumor samples, for example preferably greater than about 20%, more preferably greater than about 30%, and most preferably greater than about 50% or more of breast tumor samples tested, at a level that is at least two fold, and preferably at least five fold, greater than the level of expression in normal tissues, as determined using a representative assay provided herein. A breast tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with breast cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs: 131–140, 299, 300, 304–306, 308–312, 315, 318, 324, 326, 331–334, 336, and 340, or those encoded by a polynucleotide sequence set forth in a sequence of SEQ ID NOs:1, 3–86, 142–298, 301–303, 307, 313, 314, 316, 317, 323, 325, 327–330, 335, and 339.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1–30 amino acids, preferably 5–15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |

TABLE 1-continued

| Amino Acids | | | Codons | | | | | |
|---|---|---|---|---|---|---|---|---|
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 Methods in Enzymology vol. 183, Academic Press, Inc., San Diego, Calif.; Higgins, D. G. and Sharp, P. M. (1989) CABIOS 5:151–153; Myers, E. W. and Muller W. (1988) CABIOS 4:11–17; Robinson, E. D. (1971) Comb. Theor 11:105; Santou, N. Nes, M. (1987) Mol. Biol. Evol. 4:406–425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726–730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) Nucl. Acids Res. 25:3389–3402 and Altschul et al. (1990) J. Mol. Biol. 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes.

Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86–91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. patent application Ser. No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. patent application Ser. No. 60/158,585; see also, Skeiky et al., *Infection and Immun.* (1999) 67:3998–4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4$^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs:1, 3–86, 142–298, 301–303, 307, 313, 314, 316, 317, 323, 325, 327–330, 335, and 339, complements of a polynucleotide sequence set forth in any one of SEQ ID NOs:1, 3–86, 142–298, 301–303, 307, 313, 314, 316, 317, 323, 325, 327–330, 335, and 339, and degenerate variants of a polynucleotide sequence set forth in any one of SEQ ID NOs:1, 3–86, 142–298, 301–303, 307, 313, 314, 316, 317, 323, 325, 327–330, 335, and 339. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NOs:1, 3–86, 142–298, 301–303, 307, 313, 314, 316, 317, 323, 325, 327–330, 335, and 339, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60–65° C. or 65–70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15–25 nucleotides in length up to and including the fall length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739, 119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. Jun. 10, 1988;240(4858):1544–6; Vasanthakumar and Ahmed, Cancer Commun. 1989;1(4):225–32; Peris et al., Brain Res Mol Brain Res. Jun. 15, 1998;57(2):310–20; U.S. Pat. No. 5,801, 154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389–402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. Jul. 15, 1997;25(14):2730–6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December; 84(24):8788–92; Forster and Symons, Cell. 1987 Apr. 24;49(2):211–20). For example, a large number of ribozymes accelerate phosphoester transfer reactions with a high degree of specificity, often cleaving only one of several phosphoesters in an oligonucleotide substrate (Cech et al., Cell. 1981 Dec.;27(3 Pt 2):487–96; Michel and Westhof, J Mol Biol. 1990 Dec. 5;216(3):585–610; Reinhold-Hurek and Shub, Nature. 1992 May 14;357(6374):173–6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci U.S.A. 1992 Aug. 15;89(16):7305–9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11;20(17):4559–65. Examples of hairpin motifs are described by Hampel et al. (Eur. Pat. appl. Publ. No. EP 0360257), Hampel and Tritz, Biochemistry 1989 Jun. 13;28 (12):4929–33; Hampel et al., Nucleic Acids Res. 1990 Jan. 25;18(2):299–304 and U.S. Pat. No. 5,631,359. An example of the hepatitis δ virus motif is described by Perrotta and Been, Biochemistry. 1992 Dec. 1;31(47):11843–52; an example of the RNaseP motif is described by Guerrier-Takada et al., Cell. 1983 December; 35(3 Pt 2):849–57; Neurospora VS RNA ribozyme motif is described by Collins (Saville and Collins, Cell. 1990 May 18;61(4):685–96; Saville and Collins, Proc Natl Acad Sci USA. 1991 Oct. 1;88(19):8826–30; Collins and Olive, Biochemistry. 1993 Mar. 23;32(11):2795–9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. appl. Publ. No. WO 93/23569 and Int. Pat. appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. appl. Publ. No. WO 92/07065; Int. Pat. appl. Publ. No. WO 93/15187; Int. Pat. appl. Publ. No. WO 91/03162; Eur. Pat. appl. Publ. No. 92110298.4; U.S. Pat. No. 5,334,711; and Int. Pat. appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. appl. Publ. No. WO 94/02595 and Int. Pat. appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431–37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June ;15(6):224–9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6;254(5037):1497–500; Hanvey et al., Science. 1992 Nov. 27;258(5087):1481–5; Hyrup and Nielsen, Bioorg Med Chem. 1996 Jan. ;4(1):5–23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 Apr. ;3(4):437–45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 Apr. ;3(4):437–45; Petersen et al., J Pept Sci. 1995 May–Jun. ;1(3):175–83; Orum et al., Biotechniques. 1995 Sep. ;19(3):472–80; Footer et al., Biochemistry. 1996 Aug. 20;35(33):10673–9; Griffith et al., Nucleic Acids Res. 1995 Aug. 11;23(15):3003–8; Pardridge et al., Proc Natl Acad Sci U.S.A. 1995 Jun. 6;92(12): 5592–6; Boffa et al, Proc Natl Acad Sci U.S.A. 1995 Mar. 14;92(6):1901–5; Gambacorti-Passerini et al., Blood. 1996 Aug. 15;88(4):1411–7; Armitage et al., Proc Natl Acad Sci U.S.A. 1997 Nov. 11;94(23):12320–5; Seeger et al., Biotechniques. 1997 Sep. ;23(3):512–7). U.S. Pat. No. 5,700, 922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15;65(24):3545–9) and Jensen et al. (Biochemistry. 1997 Apr. 22;36(16):5072–7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. appl. Publ. No. 320,308 and U.S. Pat. No. 4,883,750; Qbeta Replicase, described in PCT Intl. Pat. appl. Publ. No. PCT/US87/00880; Strand Displacement Amplification (SDA) and Repair Chain Reaction (RCR). Still other amplification methods are described in Great Britain Pat. appl. No. 2 202 328, and in PCT Intl. Pat. appl. Publ. No. PCT/US89/01025. Other nucleic acid amplification procedures include transcription-based amplification systems (TAS) (PCT Intl. Pat. appl. Publ. No. WO 88/10315), including nucleic acid sequence based amplification (NASBA) and 3SR. Eur. Pat. appl. Publ. No. 329,822 describes a nucleic acid amplification process involving cyclically synthesizing single-stranded RNA ("ssRNA"), ssDNA, and double-stranded DNA (dsDNA). PCT Intl. Pat. appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (Ac-NPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St. Paul. Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using applied Biosystems 431A Peptide Synthesizer (Perkin Elmer). Alternatively, various fragments may be chemically synthesized separately and combined using chemical methods to produce the full length molecule.

Antibody Compositions, Fragments thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439–473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as breast cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659–2662; Hochman et al. (1976) Biochem 15:2706–2710; and Ehrlich et al. (1980) Biochem 19:4091–4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1, " "CDR2, " and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293–299; Lobuglio et al. (1989) Proc. Nat. Acad. Sci. USA 86:4220–4224; Shaw et al. (1987) J Immunol. 138:4534–4538; and Brown et al. (1987) Cancer Res. 47:3577–3583), rodent CDRs grafted into a human supporting FR prior to fusion with an appropriate human antibody constant domain (Riechmann et al. (1988) Nature 332:323–327; Verhoeyen et al. (1988) Science 239:1534–1536; and Jones et al. (1986) Nature 321:522–525), and rodent CDRs supported by recombinantly veneered rodent FRs (European patent Publication Ser. No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml–100 μg/ml, preferably 200 ng/ml–25 μg/ml) for 3–7 days will typically result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be CD4$^+$ and/or CD8$^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, CD4$^+$ or CD8$^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more inununostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as *Bacillus-Calmette-Guerrin*) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980–990; Miller, A. D. (1990) Human Gene Therapy 1:5–14; Scarpa et al. (1991) Virology 180:849–852; Burns et al. (1993) Proc. Natl. Acad. Sci. USA 90:8033–8037; and Boris-Lawrie and Temin (1993) Cur. Opin. Genet. Develop. 3:102–109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; and Rich et al. (1993) Human Gene Therapy 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Ser. Nos. WO 92/01070 and WO 93/03769; Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158: 97–129; Kotin, R. M. (1994) Human Gene Therapy 5:793–801; Shelling and Smith (1994) Gene Therapy 1:165–169; and Zhou et al. (1994) J. Exp. Med. 179: 1867–1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743–6747; Fuerst et al. Proc. Natl. Acad. Sci. USA (1986) 83:8122–8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866–6869 and Wagner et al. Proc. Natl. Acad. Sci. USA (1992) 89:6099–6103, can also be used for gene delivery under the invention.

Additional illustrative information on these and other known viral-based delivery systems can be found, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., Cir. Res. 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865, 796; 5,584,807; and EP patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312, 335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffinan, *Ann. Rev. Immunol.* 7:145–173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877, 611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{—}A\text{—}R, \quad (I)$$

wherein, n is 1–50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12th edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation.

Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature Mar. 27, 1997;386(6623):410–4; Hwang et al., Crit Rev Ther Drug Carrier Syst 1998;15(3):243–84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both.

Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2;52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 Jul. ;16(7):307–21; Takakura, Nippon Rinsho 1998 March ;56(3):691–5; Chandran et al., Indian J Exp Biol. 1997 August ;35(8):801–9; Margalit, Crit Rev Ther Drug Carrier Syst. 1995;12(2–3):233–61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25;265(27):16337–42; Muller et al., DNA Cell Biol. 1990 Apr. ;9(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 Dec. ;24(12): 1113–28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988;5(1): 1–20; zur Muhlen et al., Eur J Pharm Biopharm. 1998 March ;45(2):149–55; Zambaux et al. J Controlled Release. 1998 Jan. 2;50(1–3):31–40; and U. S. Pat. No. 5,145,684.

Cancer Therapeutic Methods

In further aspects of the present invention, the pharmaceutical compositions described herein may be used for the treatment of cancer, particularly for the immunotherapy of breast cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be strict administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally.

Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 µg/ml). It may be desirable to incubate another aliquot of a T cell sample in the absence of tumor polypeptide to serve as a control. For $CD4^+$ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLE 1

Preparation of Breast Tumor-specific cDNAs Using Differential Display RT-PCR

This Example illustrates the preparation of cDNA molecules encoding breast tumor-specific polypeptides using a differential display screen.

A. Preparation of B18Ag1 cDNA and Characterization of mRNA Expression

Tissue samples were prepared from breast tumor and normal tissue of a patient with breast cancer that was confirmed by pathology after removal from the patient. Normal RNA and tumor RNA was extracted from the samples and mRNA was isolated and converted into cDNA using a $(dT)_{12}AG$ (SEQ ID NO:130) anchored 3' primer. Differential display PCR was then executed using a randomly chosen primer (CTTCAACCTC) (SEQ ID NO:103). Amplification conditions were standard buffer containing 1.5 mM MgCl$_2$, 20 pmol of primer, 500 pmol dNTP, and 1 unit of Taq DNA polymerase (Perkin-Elmer, Branchburg, N.J.). Forty cycles of amplification were performed using 94° C. denaturation for 30 seconds, 42° C. annealing for 1 minute, and 72° C. extension for 30 seconds. An RNA fingerprint containing 76 amplified products was obtained. Although the RNA fingerprint of breast tumor tissue was over 98% identical to that of the normal breast tissue, a band was repeatedly observed to be specific to the RNA fingerprint pattern of the tumor. This band was cut out of a silver stained gel, subcloned into the T-vector (Novagen, Madison, Wis.) and sequenced.

The sequence of the cDNA, referred to as B18Ag1, is provided in SEQ ID NO:1. A database search of GENBANK and EMBL revealed that the B18Ag1 fragment initially cloned is 77% identical to the endogenous human retroviral element S71, which is a truncated retroviral element homologous to the Simian Sarcoma Virus (SSV). S71 contains an incomplete gag gene, a portion of the pol gene and an LTR-like structure at the 3' terminus (see Werner et al., *Virology* 174:225–238 (1990)). B18Ag1 is also 64% identical to SSV in the region corresponding to the P30 (gag) locus. B18Ag1 contains three separate and incomplete reading frames covering a region which shares considerable homology to a wide variety of gag proteins of retroviruses which infect mammals. In addition, the homology to S71 is not just within the gag gene, but spans several kb of sequence including an LTR.

Figure 2:
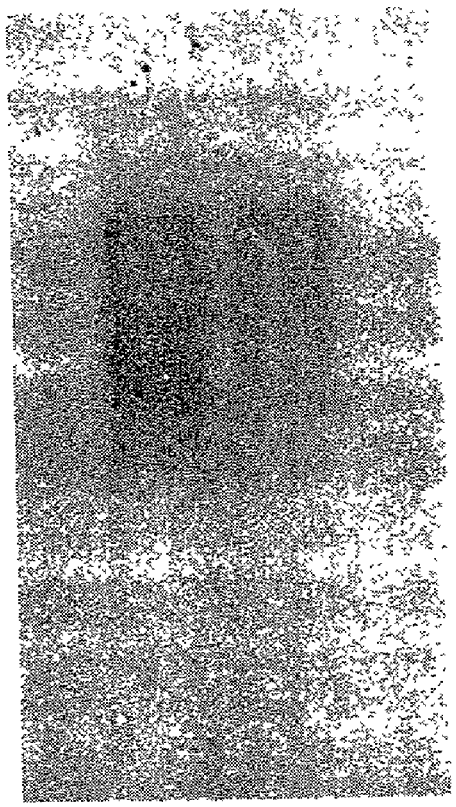
FIG. 2 is a northern blot comparing the level of B18Ag1 mRNA in breast tumor tissue (lane 1) with the level in normal breast tissue.

B18Ag1-specific PCR primers were synthesized using computer analysis guidelines. RT-PCR amplification (94° C., 30 seconds; 60° C.→42° C., 30 seconds; 72° C., 30 seconds for 40 cycles) confirmed that B18Ag1 represents an actual mRNA sequence present at relatively high levels in the patient's breast tumor tissue. The primers used in amplification were B18Ag1-1 (CTG CCT GAG CCA CAA ATG) (SEQ ID NO:128) and B18Ag1-4 (CCG GAG GAG GAA GCT AGA GGA ATA) (SEQ ID NO:129) at a 3.5 mM magnesium concentration and a pH of 8.5, and B18Ag1-2 (ATG GCT ATT TTC GGG GCC TGA CA) (SEQ ID NO:126) and B18Ag1-3 (CCG GTA TCT CCT CGT GGG TAT T) (SEQ ID NO:127) at 2 mM magnesium at pH 9.5. The same experiments showed exceedingly low to nonexistent levels of expression in this patient's normal breast tissue (see FIG. 1). RT-PCR experiments were then used to show that B18Ag1 mRNA is present in nine other breast tumor samples (from Brazilian and American patients) but absent in, or at exceedingly low levels in, the normal breast tissue corresponding to each cancer patient. RT-PCR analysis has also shown that the B18Ag1 transcript is not present in various normal tissues (including lymph node, myocardium and liver) and present at relatively low levels in PBMC and lung tissue. The presence of B18Ag1 mRNA in breast tumor samples, and its absence from normal breast tissue, has been confirmed by Northern blot analysis, as shown in FIG. 2.

Figure 3:
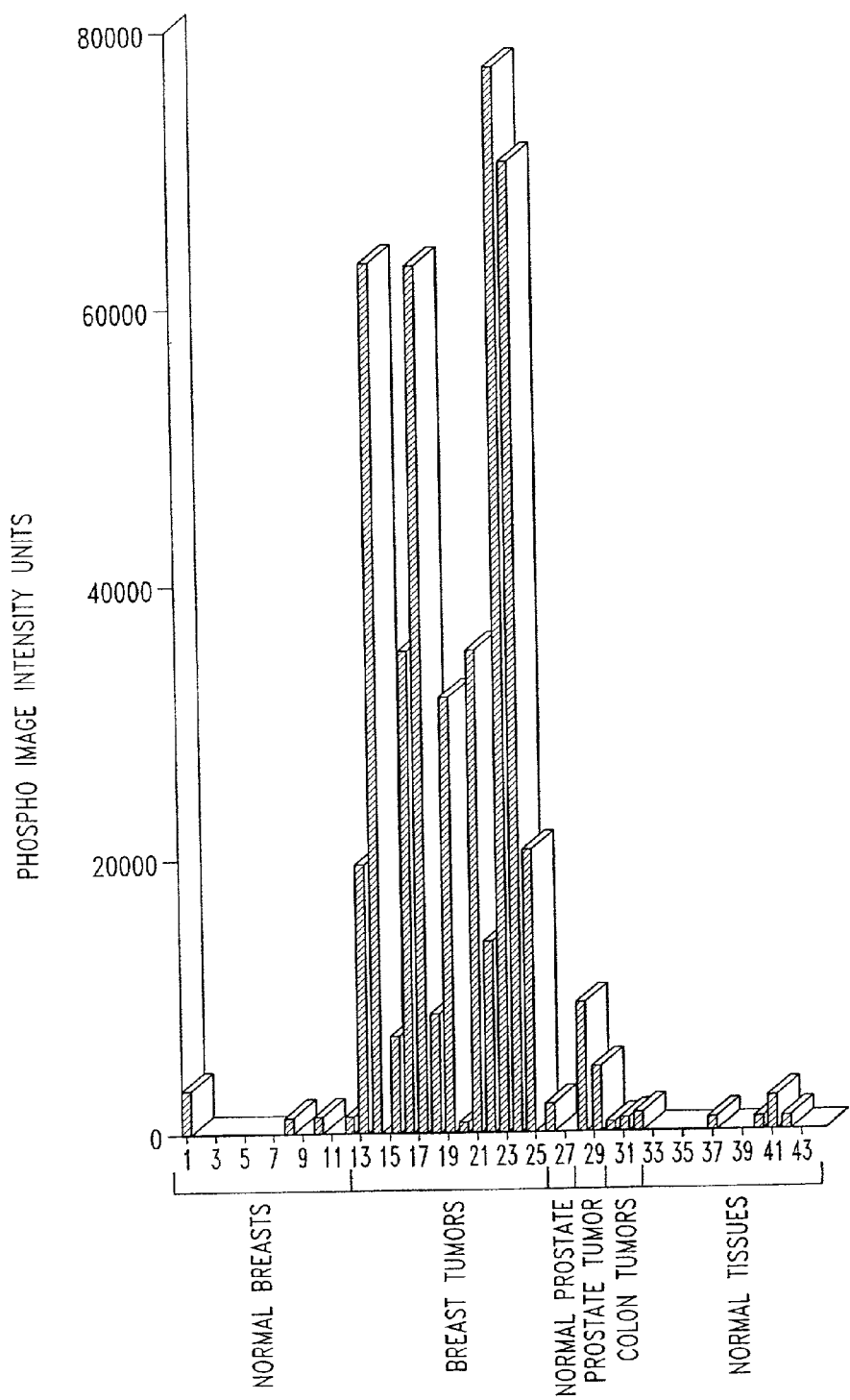
FIG. 3 shows the level of B18Ag1 mRNA in breast tumor tissue compared to that in various normal and non-breast tumor tissues as determined by RNase protection assays.

The differential expression of B18Ag1 in breast tumor tissue was also confirmed by RNase protection assays. FIG. 3 shows the level of B18Ag1 mRNA in various tissue types as determined in four different RNase protection assays. Lanes 1–12 represent various normal breast tissue samples, lanes 13–25 represent various breast tumor samples; lanes 26–27 represent normal prostate samples; lanes 28–29 represent prostate tumor samples; lanes 30–32 represent colon tumor samples; lane 33 represents normal small intestine; lane 34 represents normal small intestine; lane 35 represents normal skin, lane 36 represents normal lymph node; lane 37 represents normal ovary; lane 38 represents normal liver; lane 39 represents normal skeletal muscle; lane 40 represents a first normal stomach sample, lane 41 represents a second normal stomach sample; lane 42 represents a normal lung; lane 43 represents normal kidney; and lane 44 represents normal pancreas. Interexperimental comparison was facilitated by including a positive control RNA of known β-actin message abundance in each assay and normalizing the results of the different assays with respect to this positive control.

Figure 4:
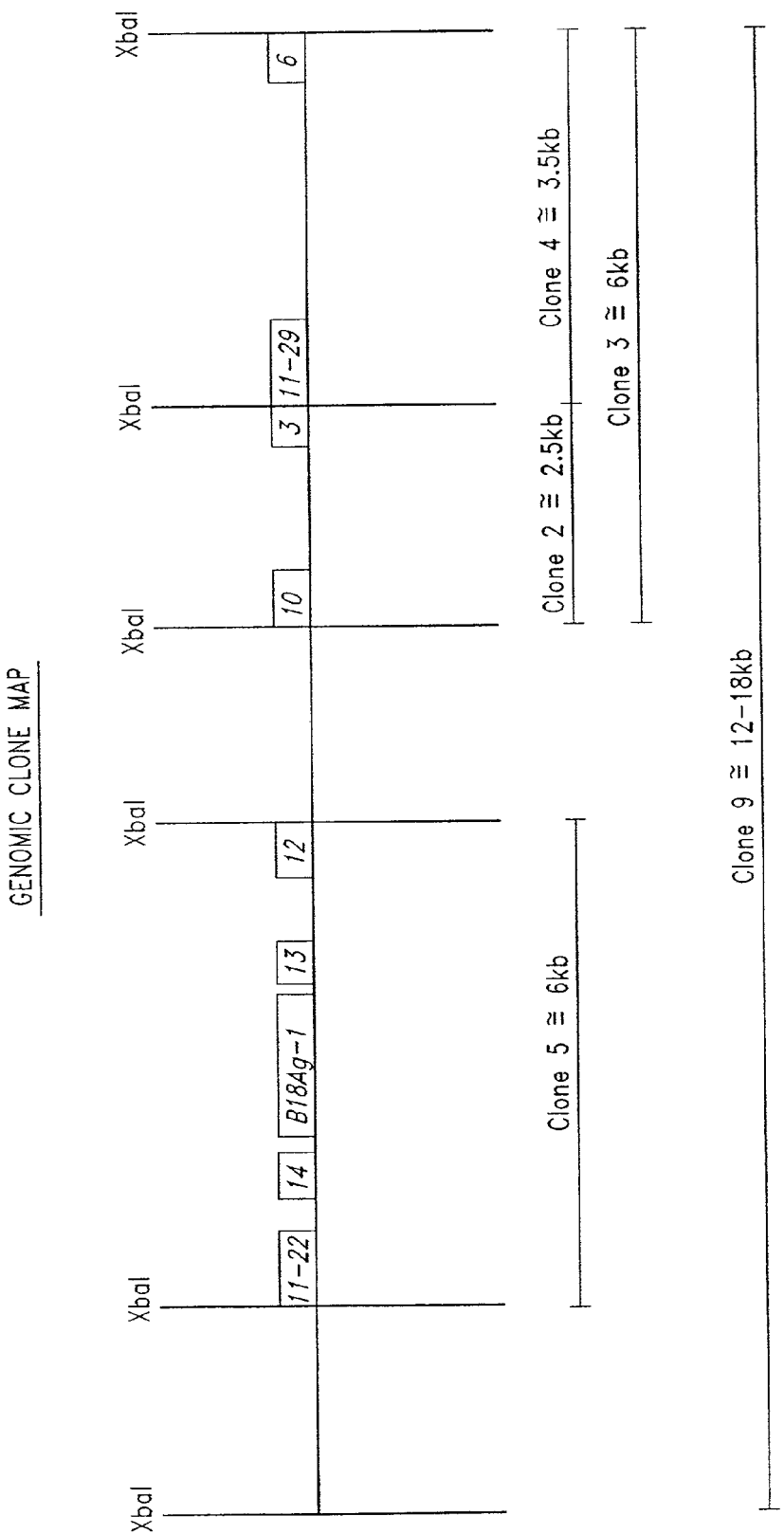
FIG. 4 is a genomic clone map showing the location of additional retroviral sequences obtained from ends of XbaI restriction digests (provided in SEQ ID NO:3–SEQ ID NO:10) relative to B18Ag1.

RT-PCR and Southern Blot analysis has shown the B18Ag1 locus to be present in human genomic DNA as a single copy endogenous retroviral element. A genomic clone of approximately 12–18 kb was isolated using the initial B18Ag1 sequence as a probe. Four additional subclones were also isolated by XbaI digestion. Additional retroviral sequences obtained from the ends of the XbaI digests of these clones (located as shown in FIG. 4) are shown as SEQ ID NO:3 –SEQ ID NO:10, where SEQ ID NO:3 shows the location of the sequence labeled 10 in FIG. 4, SEQ ID NO:4 shows the location of the sequence labeled 11–29, SEQ ID NO:5 shows the location of the sequence labeled 3, SEQ ID NO:6 shows the location of the sequence labeled 6, SEQ ID NO:7 shows the location of the sequence labeled 12, SEQ ID NO:8 shows the location of the sequence labeled 13, SEQ ID NO:9 shows the location of the sequence labeled 14 and SEQ ID NO:10 shows the location of the sequence labeled 11 –22.

Figures 5A, 5B:
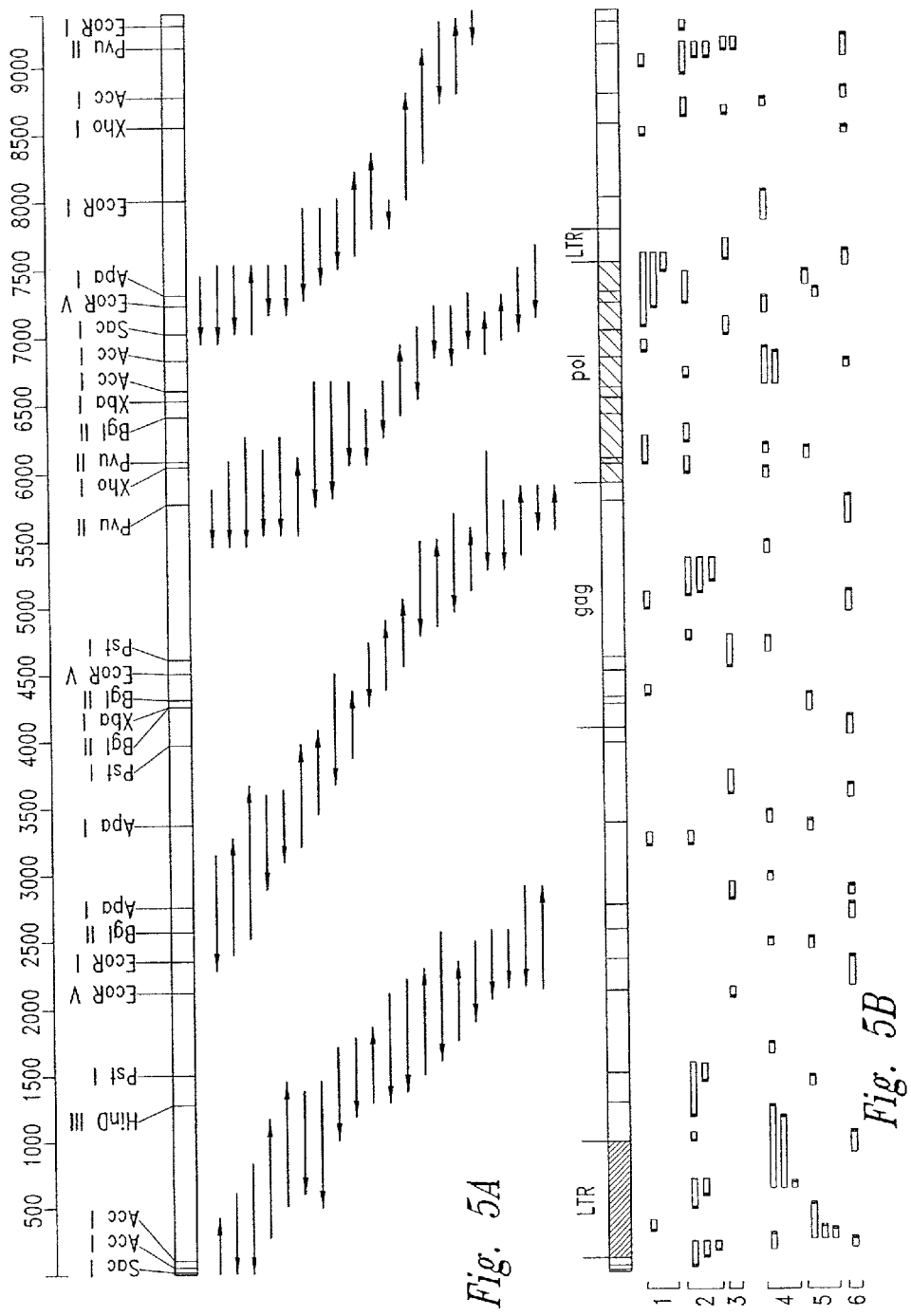
FIGS. 5A and 5B show the sequencing strategy, genomic organization and predicted open reading frame for the retroviral element containing B18Ag1.

Subsequent studies demonstrated that the 12–18 kb genomic clone contains a retroviral element of about 7.75 kb, as shown in FIGS. 5A and 5B. The sequence of this retroviral element is shown in SEQ ID NO:141. The numbered line at the top of FIG. 5A represents the sense strand sequence of the retroviral genomic clone. The box below this line shows the position of selected restriction sites. The arrows depict the different overlapping clones used to sequence the retroviral element. The direction of the arrow shows whether the single-pass subcloned sequence corresponded to the sense or anti-sense strand. FIG. 5B is a schematic diagram of the retroviral element containing B18Ag1 depicting the organization of viral genes within the element. The open boxes correspond to predicted reading frames, starting with a methionine, found throughout the element. Each of the six likely reading frames is shown, as indicated to the left of the boxes, with frames 1–3 corresponding to those found on the sense strand.

Using the cDNA of SEQ ID NO:1 as a probe, a longer cDNA was obtained (SEQ ID NO:227) which contains minor nucleotide differences (less than 1%) compared to the genomic sequence shown in SEQ ID NO:141.

B. Preparation of cDNA Molecules Encoding Other Breast Tumor-Specific Polypeptides Normal RNA and tumor RNA was prepared and mRNA was isolated and converted into cDNA using a (dT)$_{12}$AG anchored 3' primer, as described above. Differential display PCR was then executed using the randomly chosen primers of SEQ ID NOs:87–125. Amplification conditions were as noted above, and bands observed to be specific to the RNA fingerprint pattern of the tumor were cut out of a silver stained gel, subcloned into either the T-vector (Novagen, Madison, Wis.) or the pCRII vector (Invitrogen, San Diego, Calif.) and sequenced. The sequences are provided in SEQ ID NO:11–SEQ ID NO:86. Of the 79 sequences isolated, 67 were found to be novel (SEQ ID NOs:11–26 and 28–77) (see also FIGS. 6–20).

An extended DNA sequence (SEQ ID NO:290) for the antigen B15Ag1 (originally identified partial sequence provided in SEQ ID NO:27) was obtained in further studies.

Comparison of the sequence of SEQ ID NO:290 with those in the gene bank as described above, revealed homology to the known human β-A activin gene. Further studies led to the isolation of the full-length cDNA sequence for the antigen B21GT2 (also referred to as B311D; originally identified partial cDNA sequence provided in SEQ ID NOs:56). The full-length sequence is provided in SEQ ID NO:307, with the corresponding amino acid sequence being provided in SEQ ID NO:308. Further studies led to the isolation of a splice variant of B311D. The B311D clone of SEQ ID NO:316 was sequenced and a XhoI/NotI fragment from this clone was gel purified and 32P-cDTP labeled by random priming for use as a probe for further screening to obtain additional B311D gene sequence. Two fractions of a human breast tumor cDNA bacterial library were screened using standard techniques. One of the clones isolated in this manner yielded additional sequence which includes a poly A+ tail. The determined cDNA sequence of this clone (referred to as B311D_BT1_1A) is provided in SEQ ID NO:317. The sequences of SEQ ID NOs:316 and 317 were found to share identity over a 464 bp region, with the sequences diverging near the poly A+ sequence of SEQ ID NO:317.

Subsequent studies identified an additional 146 sequences (SEQ ID NOs:142–289), of which 115 appeared to be novel (SEQ ID NOs:142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291). To the best of the inventors' knowledge none of the previously identified sequences have heretofore been shown to be expressed at a greater level in human breast tumor tissue than in normal breast tissue.

In further studies, several different splice forms of the antigen B 11Ag1 (also referred to as B305D) were isolated, with each of the various splice forms containing slightly different versions of the B11Ag1 coding frame. Splice junction sequences define individual exons which, in various patterns and arrangements, make up the various splice forms. Primers were designed to examine the expression pattern of each of the exons using RT-PCR as described below. Each exon was found to show the same expression pattern as the original B11Ag1 clone, with expression being breast tumor-, normal prostate- and normal testis-specific. The determined cDNA sequences for the isolated protein coding exons are provided in SEQ ID NOs:292–298, respectively. The predicted amino acid sequences corresponding to the sequences of SEQ ID NOs:292 and 298 are provided in SEQ ID NOs:299 and 300. Additional studies using rapid amplification of cDNA ends (RACE), a 5' specific primer to one of the splice forms of B11Ag1 provided above and a breast adenocarcinoma, led to the isolation of three additional, related, splice forms referred to as isoforms B11C-15, B11C-8 and B11C-9,16. The determined cDNA sequences for these isoforms are provided in SEQ ID NO: 301–303, with the corresponding predicted amino acid sequences being provided in SEQ ID NOs:304–306.

The protein coding region of B11C-15 (SEQ ID NO: 301; also referred to as B305D isoform C) was used as a query sequence in a BLASTN search of the Genbank DNA database. A match was found to a genomic clone from chromosome 21 (Accessson no. AP001465). The pairwise alignments provided in the BLASTN output were used to identify the putative exon, or coding, sequence of the chromosome 21 sequence that corresponds to the B305D sequence. Based on the BlastN pairwise alignments, the following pieces of GenBank record AP001465 were put together: base pairs 67978–68499, 72870–72987, 73144–73335, 76085–76206, 77905–78085, 80520–80624, 87602–87633. This sequence was then aligned with the B305D isoform C sequence using the DNA Star Seqman program and excess sequence was deleted in such a way as to maintain the sequence most similar to B305D. The final edited form of the chromosome 21 sequence was 96.5% identical to B305D. This resulting edited sequence from chromosome 21 was then translated and found to contain no stop codons other than the final stop codon in the same position as that for B305D. As with B305D, the chromosome 21 sequence (provided in SEQ ID NO: 325) encoded a protein (SEQ ID NO: 326) with 384 amino acids. An alignment of this protein with the B305D isoform C protein (SEQ ID NO: 304) showed 90% amino acid identity.

The cDNA sequence of B305D isoform C (SEQ ID NO: 301) was used to identify homologs by searching the High Throughput Genome Sequencing (HTGS) database (NCBI, National Institutes for Health, Bethesda, Md.). Homologs were identified on Chromosome 2 (Clone ID 9838181), Chromosome 10 (Clone ID 10933022), Chromosome 15 (Clone ID 11560284). These homologs shared greater than 90% identity with B305D isoform C at the nucleic acid level. All three of these homologs encode 384 amino acid ORFs that share greater than 90% identity with the amino acid sequence of SEQ ID NO: 304. Further searching of the GenBank database with the sequence of SEQ ID NO: 301 yielded a partial sequence homolog on Chromosome 22 (Clone ID 5931507). cDNA sequences for the Chromosome 2, 10, 15 and 22 homologs were constructed based on the homology with B305D isoform C and the conserved sequences at intron-exon junctions. The cDNA sequences for the Chromosome 22, 2, 15 and 10 homologs are provided in SEQ ID NO: 327–330, respectively, with the corresponding amino acid sequences being provided in SEQ ID NO: 331, 334, 333 and 332, respectively.

In subsequent studies on B305D isoform A (cDNA sequence provided in SEQ ID NO:292), the cDNA sequence (provided in SEQ ID NO:313) was found to contain an additional guanine residue at position 884, leading to a frameshift in the open reading frame. The determined DNA sequence of this ORF is provided in SEQ ID NO:314. This frameshift generates a protein sequence (provided in SEQ ID NO:315) of 293 amino acids that contains the C-terminal domain common to the other isoforms of B305D but that differs in the N-terminal region.

EXAMPLE 2

Preparation of B18Ag1 DNA from Human Genomic DNA

This Example illustrates the preparation of B18Ag1 DNA by amplification from human genomic DNA.

B18Ag1 DNA may be prepared from 250 ng human genomic DNA using 20 pmol of B18Ag1 specific primers, 500 pmol dNTPS and 1 unit of Taq DNA polymerase (Perkin Elmer, Branchburg, N.J.) using the following amplification parameters: 94° C. for 30 seconds denaturing, 30 seconds 60° C. to 42° C. touchdown annealing in 2° C. increments every two cycles and 72° C. extension for 30 seconds. The last increment (a 42° C. annealing temperature) should cycle 25 times. Primers were selected using computer analysis. Primers synthesized were B18Ag1-1, B18Ag1-2, B18Ag1-3, and B18Ag1-4. Primer pairs that may be used are 1+3, 1+4, 2+3, and 2+4.

Following gel electrophoresis, the band corresponding to B18Ag1 DNA may be excised and cloned into a suitable vector.

EXAMPLE 3

Preparation of B18Ag1 DNA from Breast Tumor cDNA

This Example illustrates the preparation of B18Ag1 DNA by amplification from human breast tumor cDNA.

First strand cDNA is synthesized from RNA prepared from human breast tumor tissue in a reaction mixture containing 500 ng poly A+ RNA, 200 pmol of the primer $(T)_{12}AG$ (i.e., TTT TTT TTT TTT AG) (SEQ ID NO:130), 1×first strand reverse transcriptase buffer, 6.7 mM DTT, 500 mnmol dNTPs, and 1 unit AMV or MMLV reverse transcriptase (from any supplier, such as Gibco-BRL (Grand Island, N.Y.)) in a final volume of 30 µl. After first strand synthesis, the cDNA is diluted approximately 25 fold and 1 µl is used for amplification as described in Example 2. While some primer pairs can result in a heterogeneous population of transcripts, the primers B18Ag1-2 (5'ATG GCT ATT TTC GGG GGC TGA CA) (SEQ ID NO:126) and B18Ag1-3 (5'CCG GTA TCT CCT CGT GGG TAT T) (SEQ ID NO:127) yield a single 151 bp amplification product.

EXAMPLE 4

Identification of B-cell and T-cell Epitopes of B18Ag1

This Example illustrates the identification of B18Ag1 epitopes.

The B18Ag1 sequence can be screened using a variety of computer algorithms. To determine B-cell epitopes, the sequence can be screened for hydrophobicity and hydrophilicity values using the method of Hopp, *Prog. Clin. Biol. Res.* 172B:367–77 (1985) or, alternatively, Cease et al., *J. Exp. Med.* 164:1779–84 (1986) or Spouge et al., *J. Immunol.* 138:204–12 (1987). Additional Class II MHC (antibody or B-cell) epitopes can be predicted using programs such as AMPHI (e.g., Margalit et al., *J. Immunol.* 138:2213 (1987)) or the methods of Rothbard and Taylor (e.g., *EMBO J.* 7:93 (1988)).

Once peptides (15–20 amino acids long) are identified using these techniques, individual peptides can be synthesized using automated peptide synthesis equipment (available from manufacturers such as Perkin Elmer/applied Biosystems Division, Foster City, Calif.) and techniques such as Merrifield synthesis. Following synthesis, the peptides can used to screen sera harvested from either normal or breast cancer patients to determine whether patients with breast cancer possess antibodies reactive with the peptides. Presence of such antibodies in breast cancer patient would confirm the immunogenicity of the specific B-cell epitope in question. The peptides can also be tested for their ability to generate a serologic or humoral immune in animals (mice, rats, rabbits, chimps etc.) following immunization in vivo. Generation of a peptide-specific antiserum following such immunization further confirms the immunogenicity of the specific B-cell epitope in question.

To identify T-cell epitopes, the B18Ag1 sequence can be screened using different computer algorithms which are useful in identifying 8–10 amino acid motifs within the B18Ag1 sequence which are capable of binding to HLA Class I MHC molecules. (see, e.g., Rammensee et al., *Immunogenetics* 41:178–228 (1995)). Following synthesis such peptides can be tested for their ability to bind to class I MHC using standard binding assays (e.g., Sette et al., *J. Immunol.* 153:5586–92 (1994)) and more importantly can be tested for their ability to generate antigen reactive cytotoxic T-cells following in vitro stimulation of patient or normal peripheral mononuclear cells using, for example, the methods of Bakker et al., *Cancer Res.* 55:5330–34 (1995); Visseren et al., *J. Immunol.* 154:3991–98 (1995); Kawakami et al., *J. Immunol.* 154:3961–68 (1995); and Kast et al., *J. Immunol.* 152:3904–12 (1994). Successful in vitro generation of T-cells capable of killing autologous (bearing the same Class I MHC molecules) tumor cells following in vitro peptide stimulation further confirms the immunogenicity of the B18Ag1 antigen. Furthermore, such peptides may be used to generate murine peptide and B18Ag1 reactive cytotoxic T-cells following in vivo immunization in mice rendered transgenic for expression of a particular human MHC Class I haplotype (Vitiello et al., *J. Exp. Med.* 173:1007–15 (1991).

A representative list of predicted B18Ag1 B-cell and T-cell epitopes, broken down according to predicted HLA Class I MHC binding antigen, is shown below:

| Predicted Th Motifs (B–cell epitopes) | |
|---|---|
| SSGGRTFDDFHRYLLVGI | (SEQ ID NOS.: 131–133) |
| QGAAQKPINLSKXIEVVQGHDE | |
| SPGVFLEHLQEAYRIYTPFDLSA | |

| Predicted HLA A2.1 Motifs (T–cell epitopes) | |
|---|---|
| YLLVGIQGA | (SEQ ID NOS.: 134–140) |
| GAAQKPINL | |
| NLSKXIEVV | |
| EVVQGHDES | |
| HLQEAYRIY | |
| NLAFVAQAA | |
| FVAQAAPDS | |

EXAMPLE 5

Identification of T-cell Epitopes of B11 AG1

This Example illustrates the identification of B11Ag1 (also referred to as B305D) epitopes. Four peptides, referred to as B11-8, B11-1, B11-5 and B11-12 (SEQ ID NOs: 309–312, respectfully) were derived from the B11Ag1 gene.

Figure 22:
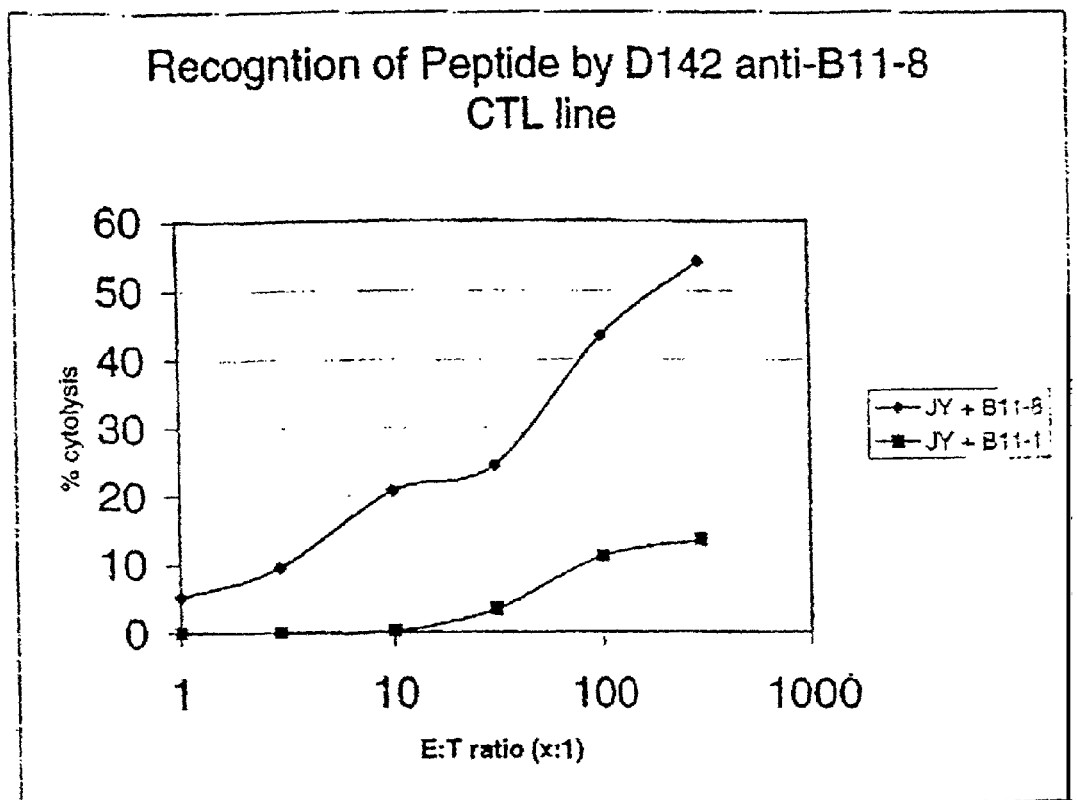
FIG. 22 shows the recognition of a B11Ag1 peptide (referred to as B11-8) by an anti-B11-8 CTL line.

Human CD8 T cells were primed in vitro to the peptide B11-8 using dendritic cells according to the protocol of Van Tsai et al. (*Critical Reviews in Immunology* 18:65–75, 1998). The resulting CD8 T cell cultures were tested for their ability to recognize the B11-8 peptide or a negative control peptide, presented by the B-LCL line, JY. Briefly, T cells were incubated with autologous monocytes in the presence of 10 ug/ml peptide, 10 ng/ml IL-7 and 10 ug/ml IL-2, and assayed for their ability to specifically lyse target cells in a standard 51-Cr release assay. As shown in FIG. 22, the bulk culture line demonstrated strong recognition of the B11-8 peptide with weaker recognition of the peptide B11-1.

Figure 23:
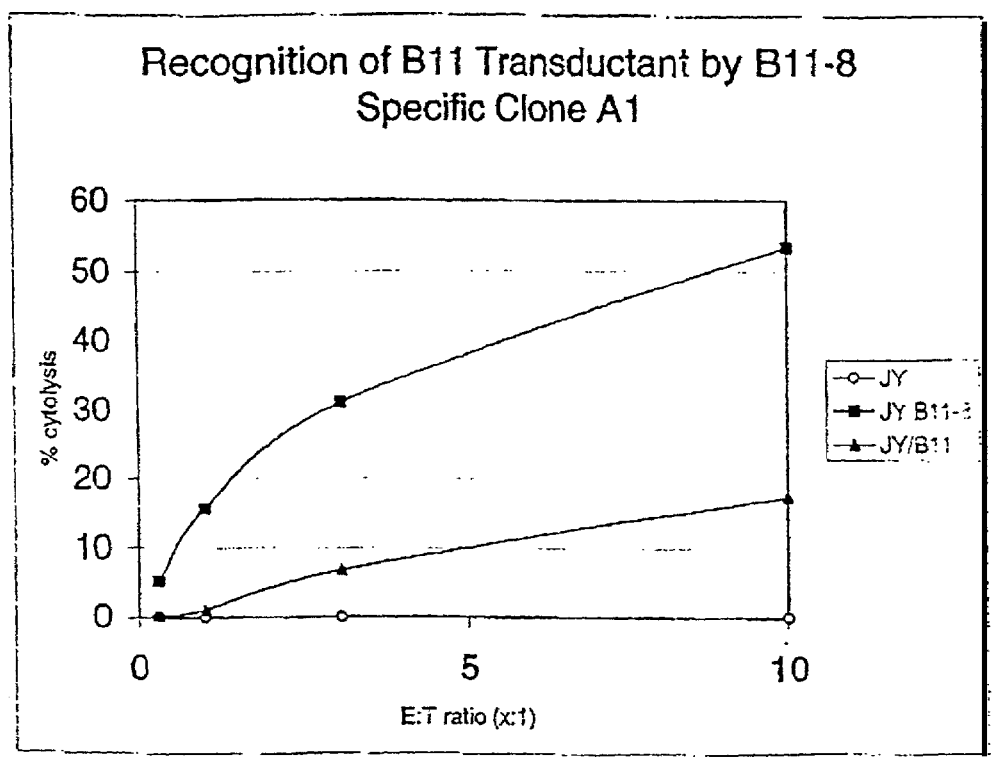
FIG. 23 shows the recognition of a cell line transduced with the antigen B11Ag1 by the B11-8 specific clone A1.
Figure 24:
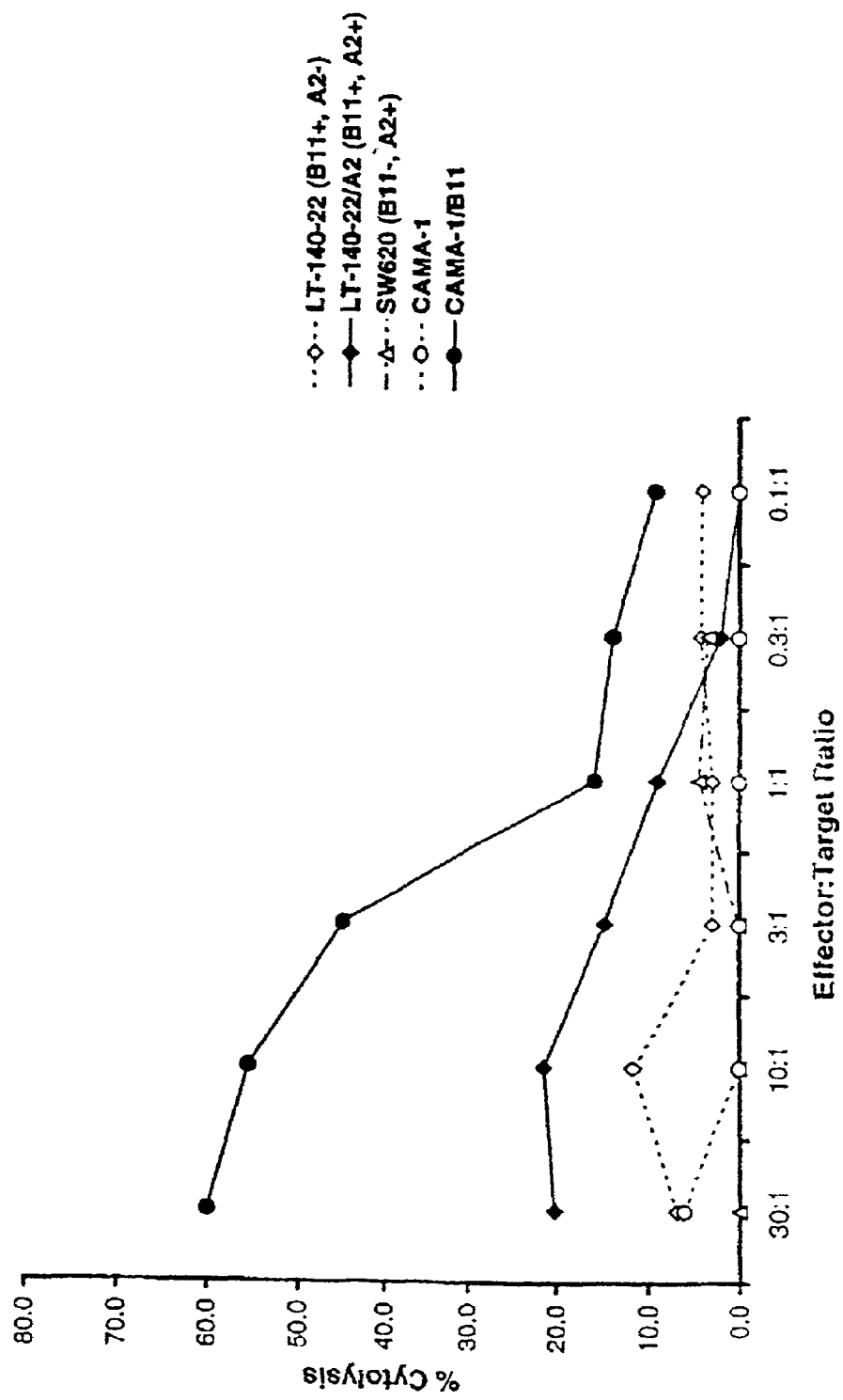
FIG. 24 shows recognition of a lung adenocarcinoma line (LT-11-22) and a breast adenocarcinoma line (CAMA-1) by the B11-8 specific clone A1.

A clone from this CTL line was isolated following rapid expansion using the monoclonal antibody OKT3 and human IL-2. As shown in FIG. 23, this clone (referred to as A1), in addition to being able to recognize specific peptide, recognized JY LCL transduced with the B11Ag1 gene. This data demonstrates that B11-8 is a naturally processed epitope of the B11Ag1 gene. In addition these T cells were further found to recognize and lyse, in an HLA-A2 restricted manner, an established tumor cell line naturally expressing B11Ag1 (FIG. 24). The T cells strongly recognize a lung adenocarcinoma (LT-140-22) naturally expressing B11Ag1 transduced with HLA-A2, as well as an A2+ breast carcinoma (CAMA-1) transduced with B11Ag1, but not untransduced lines or another negative tumor line (SW620).

These data clearly demonstrate that these human T cells recognize not only B11-specific peptides but also transduced cells, as well as naturally expressing tumor lines.

CTL lines raised against the antigens B11-5 and B11-12, using the procedures described above, were found to recognize corresponding peptide-coated targets.

EXAMPLE 6

Characterization of Breast Tumor Genes Discovered by Differential Display PCR

The specificity and sensitivity of the breast tumor genes discovered by differential display PCR were determined using RT-PCR. This procedure enabled the rapid evaluation of breast tumor gene mRNA expression semiquantitatively without using large amounts of RNA. Using gene specific primers, mRNA expression levels in a variety of tissues were examined, including 8 breast tumors, 5 normal breasts, 2 prostate tumors, 2 colon tumors, 1 lung tumor, and 14 other normal adult human tissues, including normal prostate, colon, kidney, liver, lung, ovary, pancreas, skeletal muscle, skin, stomach and testes.

To ensure the semiquantitative nature of the RT-PCR, β-actin was used as internal control for each of the tissues examined. Serial dilutions of the first strand cDNAs were prepared and RT-PCR assays performed using β-actin specific primers. A dilution was then selected that enabled the linear range amplification of β-actin template, and which was sensitive enough to reflect the difference in the initial copy number. Using this condition, the β-actin levels were determined for each reverse transcription reaction from each tissue. DNA contamination was minimized by DNase treatment and by assuring a negative result when using first strand cDNA that was prepared without adding reverse transcriptase.

Figure 21A:
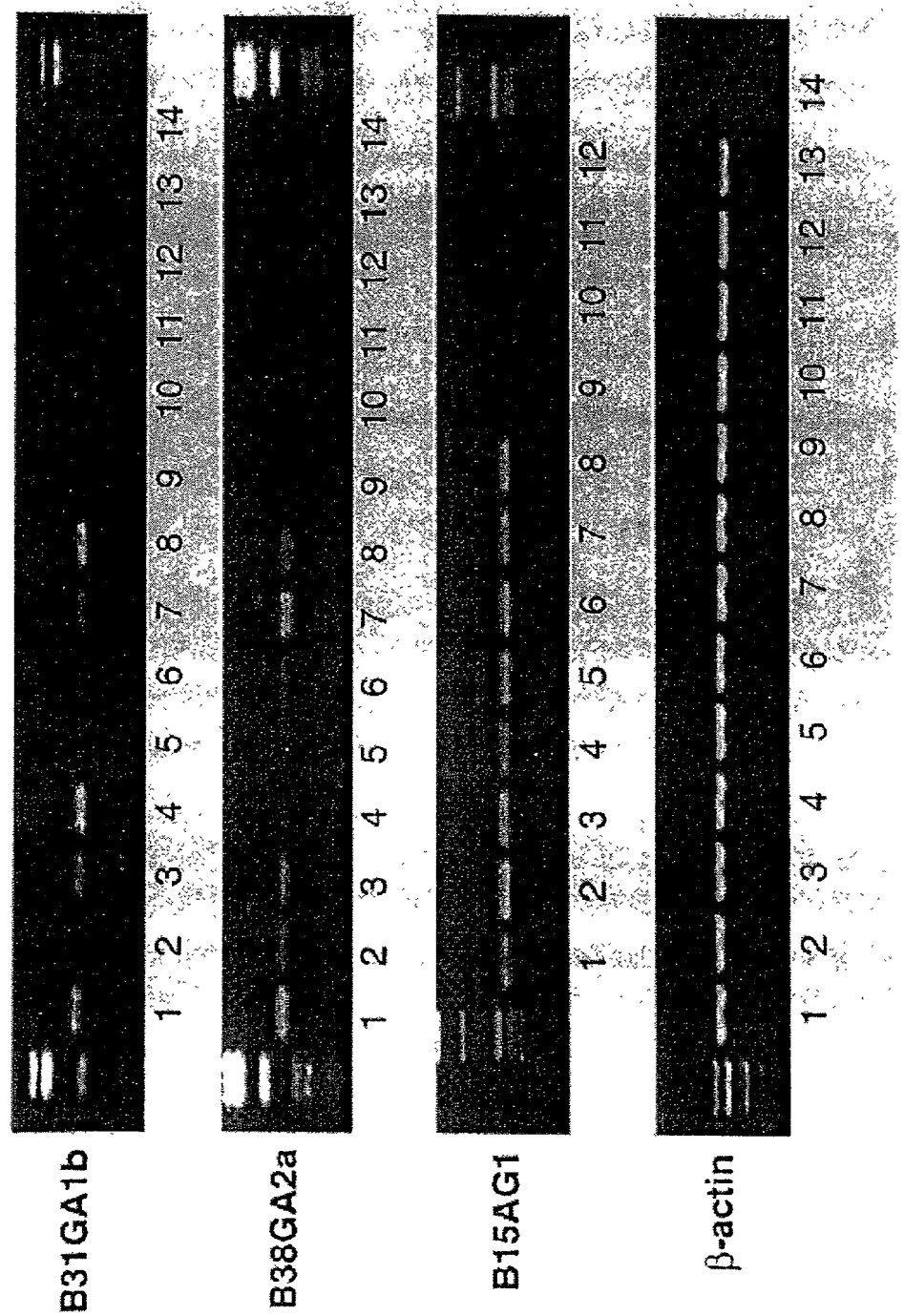
FIG. 21A depicts RT-PCR analysis of breast tumor genes in breast tumor tissues (lanes 1–8) and normal breast tissues (lanes 9–13) and $H_2O$ (lane 14).
Figure 21B:
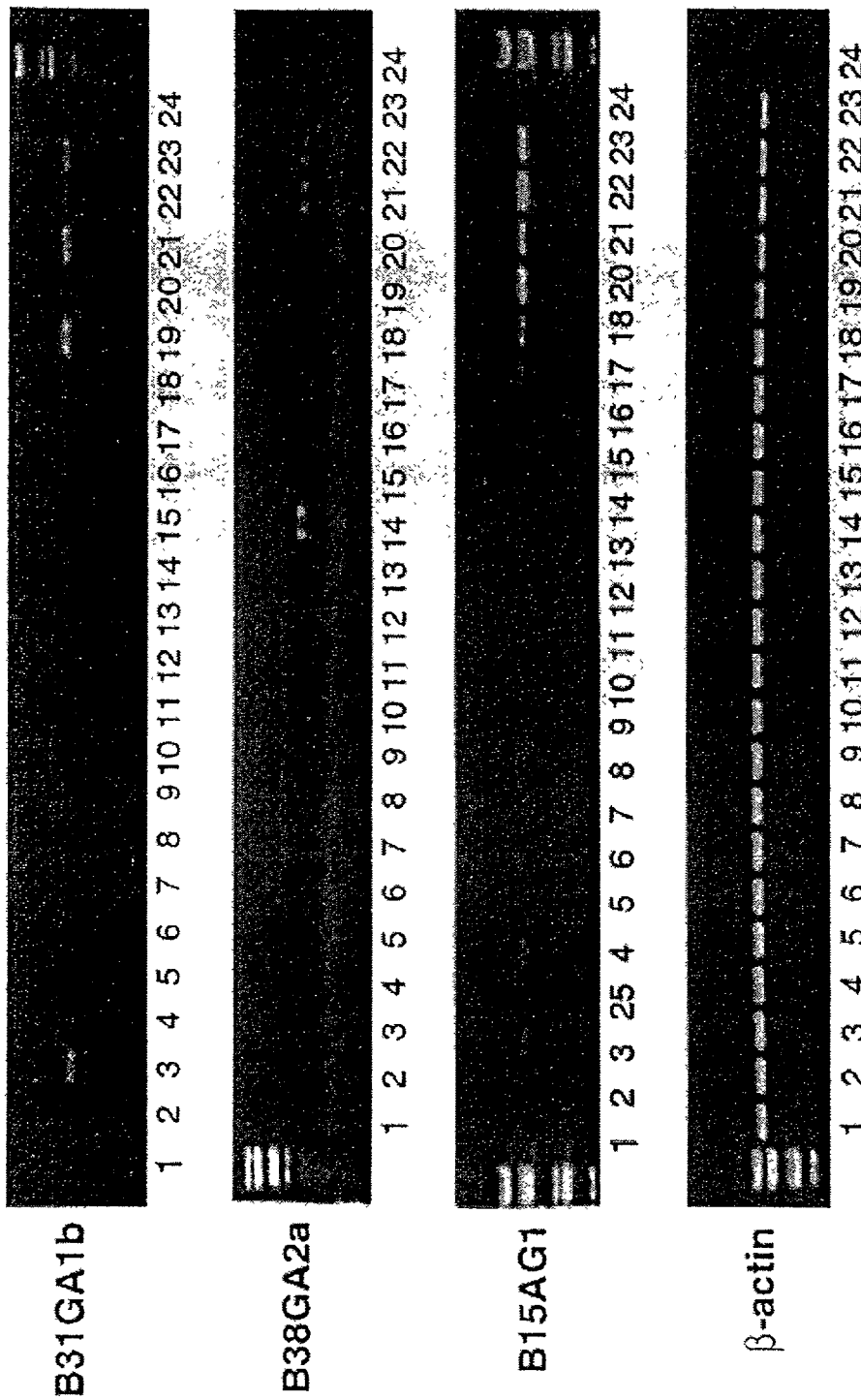
FIG. 21B depicts RT-PCR analysis of breast tumor genes in prostate tumors (lane 1, 2), colon tumors (lane 3), lung tumor (lane 4), normal prostate (lane 5), normal colon (lane 6), normal kidney (lane 7), normal liver (lane 8), normal lung (lane 9), normal ovary (lanes 10, 18), normal pancreases (lanes 11, 12), normal skeletal muscle (lane 13), normal skin (lane 14), normal stomach (lane 15), normal testes (lane 16), normal small intestine (lane 17), HBL-100 (lane 19), MCF-12A (lane 20), breast tumors (lanes 21–23), $H_2O$ (lane 24), and colon tumor (lane 25).

Using gene specific primers, the mRNA expression levels were determined in a variety of tissues. To date, 38 genes have been successfully examined by RT-PCR, five of which exhibit good specificity and sensitivity for breast tumors (B15AG-1, B31GA1b, B38GA2a, B11A1a and B18AG1a). FIGS. 21A and 21B depict the results for three of these genes: B15AG-1 (SEQ ID NO:27), B31GA1b (SEQ ID NO:148) and B38GA2a (SEQ ID NO:157). Table I summarizes the expression level of all the genes tested in normal breast tissue and breast tumors, and also in other tissues.

TABLE I

Percentage of Breast Cancer Antigens that are Expressed in Various Tissues

| Breast Tissues | Over-expressed in Breast Tumors | 84% |
|---|---|---|
| | Equally Expressed in Normals and Tumor | 16% |
| Other Tissues | Over-expressed in Breast Tumors but not in any Normal Tissues | 9% |
| | Over-expressed in Breast Tumors but Expressed in Some Normal Tissues | 30% |
| | Over-expressed in Breast Tumors but Equally Expressed in All Other Tissues | 61% |

EXAMPLE 7

Preparation and Characterization of Antibodies Against Breast Tumor Polypeptides Polyclonal antibodies against the breast tumor antigen B305D were prepared as follows.

The breast tumor antigen expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2L-baffled Erlenmeyer flask. When the Optical Density (at 560 nm) of the culture reached 0.4–0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin such as HiPrepQ (Biorad) was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of B305D antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12–24 hours followed by centrifugation.

Ninety-six well plates were coated with B305D antigen by incubating with 50 microliters (typically 1 microgram) of recombinant protein at 4° C. for 20 hours. 250 microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the calorimetric reaction was stopped with 100 microliters of 1N $H_2SO_4$ and read immediately at 450 nm. The polyclonal antibodies showed immunoreactivity to B305D.

Immunohistochemical (IHC) analysis of B305D expression in breast cancer and normal breast specimens was performed as follows. Paraffin-embedded formal fixed tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody was added to each section for 25 min at indicated concentrations followed by a 25 min incubation with either an anti-rabbit or anti-mouse biotinylated antibody. Endogenous peroxidase activity was blocked by three 1.5 min incubations with hydrogen peroxide. The avidin biotin complex/horseradish peroxidase (ABC/HRP) systems was used along with DAB chromagen to visualize antigen expression. Slides were counterstained with hematoxylin. B305D expression was detected in both breast tumor and normal breast tissue. However, the intensity of staining was much less in normal samples than in tumor samples and surface expression of B305D was observed only in breast tumor tissues.

A summary of real-time PCR and immunohistochemical analysis of B305D expression in an extensive panel of normal tissues is presented in Table II below. These results demonstrate minimal expression of B305D in testis, inconclusive results in gall bladder, and no detection in all other tissues tested.

TABLE II

| mRNA | IHC staining | Tissue type | Summary |
| --- | --- | --- | --- |
| Moderately positive | Positive | Testis | Nuclear staining of small minority of spermatids; spermatozoa negative; siminoma negative |
| Negative | Negative | Thymus | No expression |
| N/A | Negative | Artery | No expression |
| Negative | Negative | Skeletal muscle | No expression |
| Negative | Positive (weak staining) | Small bowel | No expression |
| Negative | Positive (weak staining) | Ovary | No expression |
| Negative | | Pituitary | No expression |
| Negative | Positive (weak staining) | Stomach | No expression |
| Negative | Negative | Spinal cord | No expression |
| Negative | Negative | Spleen | No expression |
| Negative | Negative | Ureter | No expression |
| N/A | Negative | Gall bladder | Inconclusive |
| N/A | Negative | Placenta | No expression |
| Negative | Negative | Thyroid | No expression |
| Negative | Negative | Heart | No expression |
| Negative | Negative | Kidney | No expression |
| Negative | Negative | Liver | No expression |
| Negative | Negative | Brain-cerebellum | No expression |
| Negative | Negative | Colon | No expression |
| Negative | Negative | Skin | No expression |
| Negative | Negative | Bone marrow | No expression |
| N/A | Negative | Parathyroid | No expression |
| Negative | Negative | Lung | No expression |
| Negative | Negative | Esophagus | No expression |
| Negative | Positive (weak staining) | Uterus | No expression |
| Negative | Negative | Adrenal | No expression |
| Negative | Negative | Pancreas | No expression |
| N/A | Negative | Lymph node | No expression |
| Negative | Negative | Brain-cortex | No expression |
| N/A | Negative | Fallopian tube | No expression |
| Negative | Positive (weak staining) | Bladder | No expression |
| Negative | N/A | Bone | No expression |
| Negative | N/A | Salivary gland | No expression |
| Negative | N/A | Activated PBMC | No expression |
| Negative | N/A | Resting PBMC | No expression |
| Negative | N/A | Trachea | No expression |
| Negative | N/A | Vena cava | No expression |
| Negative | N/A | Retina | No expression |
| Negative | N/A | Cartilage | No expression |

EXAMPLE 8

Protein Expression of Breast Tumor Antigens

This example describes the expression and purification of the breast tumor antigen B305D in *E. coli* and in mammalian cells.

Expression of B305D isoform C-15 (SEQ ID NO:301; translated to 384 amino acids) in *E. coli* was achieved by cloning the open reading frame of B305D isoform C-15 downstream of the first 30 amino acids of the *M. tuberculosis* antigen Ra12 (SEQ ID NO:318) in pET17b. First, the internal EcoRI site in the B305D ORF was mutated without changing the protein sequence so that the gene could be cloned at the EcoRI site with Ra12. The PCR primers used for site-directed mutagenesis are shown in SEQ ID NO:319 (referred to as AW012) and SEQ ID NO:320 (referred to as AW013). The ORF of EcoRI site-modified B305D was then amplified by PCR using the primers AW014 (SEQ ID NO:321) and AW015 (SEQ ID NO:322). The PCR product was digested with EcoRI and ligated to the Ra12/pET17b vector at the EcoRI site. The sequence of the resulting fusion construct (referred to as Ra12mB11C) was confirmed by DNA sequencing. The determined cDNA sequence for the fusion construct is provided in SEQ ID NO:323, with the amino acid sequence being provided in SEQ ID NO:324.

The fusion construct was transformed into BL21(DE3) CodonPlus-RIL *E. coli* (Stratagene) and grown overnight in LB broth with kanamycin. The resulting culture was induced with IPTG. Protein was transferred to PVDF membrane and blocked with 5% non-fat milk (in PBS-Tween buffer), washed three times and incubated with mouse anti-His tag antibody (Clontech) for 1 hour. The membrane was washed 3 times and probed with HRP-Protein A (Zymed) for 30 min. Finally, the membrane was washed 3 times and developed with ECL (Amersham). Expression was detected by Western blot.

For recombinant expression in mammalian cells, B305D isoform C-15 (SEQ ID NO:301; translated to 384 amino acids) was subcloned into the mammalian expression vectors pCEP4 and pcDNA3.1 (Invitrogen). These constructs were transfected into HEK293 cells (ATCC) using Fugene 6 reagent (Roche). Briefly, the HEK cells were plated at a density of 100,000 cells/ml in DMEM (Gibco) containing 10% FBS (Hyclone) and grown overnight. The following day, 2 ul of Fugene 6 was added to 100 ul of DMEM containing no FBS and incubated for 15 minutes at room temperature. The Fugene 6/DMEM mixture was added to 1 ug of B305D/pCEP4 or B305D/pcDNA plasmid DNA and incubated for 15 minutes at room temperature. The Fugene/DNA mix was then added to the HEK293 cells and incubated for 48–72 hours at 37° C. with 7% $CO_2$. Cells were rinsed with PBS, the collected and pelleted by centrifugation.

For Western blot analysis, whole cell lysates were generated by incubating the cells in Triton-X100 containing lysis buffer for 30 minutes on ice. Lysates were then cleared by centrifugation at 10,000 rpm for 5 minutes at 4° C. Samples were diluted with SDS-PAGE loading buffer containing beta-mercaptoethanol, and boiled for 10 minutes prior to loading the SDS-PAGE gel. Proteins were transferred to nitrocellulose and probed using Protein A purified anti-B305D rabbit polyclonal sera (prepared as described above) at a concentration of 1 ug/ml. The blot was revealed with a goat anti-rabbit Ig coupled to HRP followed by incubation in ECL substrate. Expression of B305D was detected in the the HEK293 lysates transfected with B305D, but not in control HEK293 cells transfected with vector alone.

For FACS analysis, cells were washed further with ice cold staining buffer and then incubated with a 1:100 dilution of a goat anti-rabbit Ig (H+L)-FITC reagent (Southern Biotechnology) for 30 minutes on ice. Following 3 washes, the cells were resuspended in staining buffer containing Propidium Iodide (PI), a vital stain that allows for identification of permeable cells, and then analyzed by FACS. The FACS analysis showed surface expression of B305D protein.

EXAMPLE 9

Expression of Full-Length B305D in Insect Cells Using a Baculovirus Expression System The cDNA for the full-length breast tumor antigen, B305D isoform C (SEQ ID NO:301), with a C-terminal His Tag was made by PCR using B11C15/pBib as a template and the following primers:

```
B305DF1  (SEQ ID NO: 337):

5'CGGCGGATCCACCATGGTGGTTGAGGTTGATTCC

B305DRV1 (SEQ ID NO: 338):

5'CGGCTCTAGATTAATGGTGATGGTGATGATGATGGTGATGATGT

TTATTTCTGGTTCTTGAGACATTTTCTGGA.
```

The PCR product with the expected size was recovered from an agarose gel, digested with the Bam HI and Xba I restriction enzymes, and ligated into the transfer plasmid pFastBac1 which was digested with the same restriction enzymes. The sequence of the insert was confirmed by DNA sequencing and is set forth in SEQ ID NO:335. The predicted amino acid sequence of B305D with the C-terminal His tag is set forth in SEQ ID NO:336. The recombinant transfer plasmid pFBB305D was used to make recombinant bacmid DNA and virus by the Bac-To-Bac baculovirus expression system (Invitrogen Life Technologies, Carlsbad, Calif.). The recombinant BVB305D virus was amplified in Sf9 insect cells and used to infect High Five insect cells. Infected cells were harvested at 24–30 hours post-infection. The identity of the recombinant protein was confirmed by Western blot with a rabbit polyclonal antibody against B305D. Recombinant protein was further analyzed by SDS-PAGE followed by Coomassie blue staining.

EXAMPLE 10

Identification of an Additional B305D Homolog Discovered by Bioinformatic Search The High Throughput Genome Sequencing (HTGS) database was searched with the B305D C form sequence (SEQ ID NO:301) and revealed another highly related copy of the B305D gene, tentatively localized to Chromosome 14. The sequences identified were spliced together based on the B305D C form sequence and exon-intron splice sites. This predicted cDNA sequence (SEQ ID NO:339) was translated to generate the predicted amino acid sequence (SEQ ID NO:340). The B305D gene family members have been shown to be overexpressed in breast cancer, prostate cancer, and ovarian cancer.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated polynucleotide comprising a sequence selected from the group consisting of:
   (a) the contiguous nucleotide sequence provided in SEQ ID NO:302, or a contiguous nucleotide sequence encoding the polypeptide of SEQ ID NO:305;
   (b) the contiguous nucleotide sequence provided in SEQ ID NO:303, or a contiguous nucleotide sequence encoding the polypeptide of SEQ ID NO:306; and
   (c) the full length complement of a sequence according to (a) or (b).

2. An expression vector comprising a polynucleotide of claim 1 operably linked to an expression control sequence.

3. A host cell transformed or transfected with an expression vector according to claim 2.

4. A composition comprising a first component selected from the group consisting of physiologically acceptable carriers and immunostimulants, and a second component consisting of a polynucleotide according to claim 1.

* * * * *